United States Patent
Procko et al.

(10) Patent No.: US 9,750,814 B2
(45) Date of Patent: Sep. 5, 2017

(54) POLYPEPTIDES TO INHIBIT EPSTEIN BARR VIRAL PROTEIN BHRF1 AND B CELL LYMPHOMA FAMILY PROTEINS

(71) Applicant: University of Washington, Seattle, WA (US)

(72) Inventors: Erik Procko, Seattle, WA (US); David Baker, Seattle, WA (US); Geoffrey Y. Berguig, Seattle, WA (US); Patrick S. Stayton, Seattle, WA (US); Yifan Song, Seattle, WA (US); Stephanie Ann Berger, Seattle, WA (US); Daniel-Adriano Silva, Seattle, WA (US)

(73) Assignee: University of Washington, Seattle, WA (US)

(*) Notice: Subject to any disclaimer, the term of this patent is extended or adjusted under 35 U.S.C. 154(b) by 0 days.

(21) Appl. No.: 15/262,716

(22) Filed: Sep. 12, 2016

(65) Prior Publication Data

US 2016/0376333 A1 Dec. 29, 2016

Related U.S. Application Data

(63) Continuation-in-part of application No. PCT/US2015/020155, filed on Mar. 12, 2015.

(60) Provisional application No. 61/951,988, filed on Mar. 12, 2014, provisional application No. 62/232,936, filed on Sep. 25, 2015.

(51) Int. Cl.

| | |
|---|---|
| *A61K 47/32* | (2006.01) |
| *C07K 14/47* | (2006.01) |
| *A61K 38/17* | (2006.01) |
| *A61K 39/395* | (2006.01) |
| *C07K 14/00* | (2006.01) |
| *G01N 33/569* | (2006.01) |
| *C07K 16/08* | (2006.01) |
| *C07K 14/005* | (2006.01) |
| *C12N 5/0781* | (2010.01) |
| *A61K 39/12* | (2006.01) |

(52) U.S. Cl.
CPC .......... *A61K 47/32* (2013.01); *A61K 38/1709* (2013.01); *A61K 39/395* (2013.01); *C07K 14/4747* (2013.01)

(58) Field of Classification Search
CPC ...... A61K 35/17; A61K 39/12; A61K 39/245; C12N 7/00; C12N 2710/16234; C12N 5/0636; C12N 2710/16211; C12N 5/0635; C07K 2317/76; C07K 14/005; C07K 16/085; C07K 14/4748; G01N 2333/05; G01N 33/56994; G01N 2317/76; G01N 2317/34; G01N 14/001
See application file for complete search history.

(56) References Cited

FOREIGN PATENT DOCUMENTS

| | | |
|---|---|---|
| WO | 02/097094 A1 | 12/2002 |
| WO | 2015/138711 A1 | 9/2015 |

OTHER PUBLICATIONS

International Search Report and Written Opinion for PCT/US2015/020155, mailed May 28, 2015.
Kelly et al: "An Epstein-Barr Virus Anti-Apoptotic Protein Constitutively Expressed in Transformed Cells and Implicated in Burkitt Lymphomagenesi s: The WP/BHRFI Link", PLOS Pathogens, vol. 5, No. 3, Mar. 13, 2009 (Mar. 13, 2009).
Kvansakul et al: "Structural Basis for Apoptosis Inhibition by Epstein-Barr Virus BHRFI", PLOS Pathogens, 6(12), Dec. 23, 2010 (Oct. 23, 2010), p. e1001236.
Li et al: "Human cellular protein VRK2 interacts specifically with Epstein-Barr virus BHRF1, a homologue of Bcl-2, and enhances cell survival", Journal of General Virology, vol. 87, No. 10, Oct. 1, 2006 (Oct. 1, 2006), pp. 2869-2878.
Labelle et al: "A stapled BIM peptide overcomes apoptotic resistance in hematologic cancers," Journal of Clinical Investigation, vol. 122, No. 6, Jun. 1, 2012 (Jun. 1, 2012), pp. 2018-2031.
Oltersdorf et al: "An inhibitor of BCL-2 family proteins induces regression of solid tumours," Nature, vol. 435, Jun. 2, 2005 (Jun. 2, 2005), pp. 677-681.
Procko et al: "A Computationally Designed Inhibitor of an Epstein-Barr Viral Bcl-2 Protein Induces Apoptosis in Infected Cells", Cell, vol. 157, No. 7, Jun. 19, 2014 (Jun. 19, 2014), pp. 1644-1656.
Shangaryet Al: "Peptides derived from BH3 domains of Bcl-2 family members: A comparative analysis of inhibition of Bcl-2, Bcl-xL and Bax oligomerization, induction of cytochrome c release, and activation of cell death," Biochemistry, vol. 41, No. 30, Jul. 30, 2002 (Jul. 30, 2002), pp. 9485-9495.
Tse et al: "ABT-263: a potent and orally bioavailable Bcl-2 family inhibitor", Cancer Research, vol. 68, No. 9, May 1, 2008 (May 1, 2008), pp. 3421-3428.
Altmann, M., and Hammerschmidt, W. (Dec. 2005) "Epstein-Barr virus provides a new paradigm: a requirement for the immediate inhibition of apoptosis," PLoS Biology, 3(12):e404.
Altschul, S.F., et al. (Sep. 1997) "Gapped Blast and PSI-BLAST: a new generation of protein database search programs," Nucleic Acids Research, 25(17):3389-3402.
Andersson, M., and Lindahl, T. (Aug. 1976) "Epstein-Barr virus DNA in human lymphoid cell lines: in vitro conversion," Virology, 73(1):96-105.
Azzarito, V., et al. (Mar. 2013) "Inhibition of α-helix-mediated protein-protein interactions using designed molecules," Nature Chemistry, 5(3):161-173.
Bae (May 2006) "Bcl-w Promotes Gastric Cancer Cell Invasion by Inducing Matrix Metalloproteinase-2 Expression via Phosphoinositide 3-Kinase, Akt, and Sp1," Cancer Research, 66(10):4991-4995.

(Continued)

*Primary Examiner* — Rachel B Gill
(74) *Attorney, Agent, or Firm* — McDonnell Boehnen Hulbert & Berghoff LLP

(57) ABSTRACT

The present invention provides designed polypeptides that selectively bind to and inhibit Epstein Barr protein BHFR1, and B cell lymphoma family proteins, and are thus useful for treating Epstein Barr-related diseases and cancer.

23 Claims, 25 Drawing Sheets

(56) References Cited

OTHER PUBLICATIONS

Baker, N.A., et al. (Aug. 2001) "Electrostatics of nanosystems: application to microtubules and the ribosome," Proceedings of the National Academy of Sciences USA, 98(18):10037-10041.

Berguig, G.Y., et al. (Dec. 2012) "Intracellular delivery and trafficking dynamics of a lymphoma-targeting antibody-polymer conjugate," Molecular Pharmaceutics, 9(12):3506-3514.

Boersma et al. (Jan. 2012) "Evaluation of Diverse α/β-Backbone Patterns for Functional α-Helix Mimicry: Analogues of the Bim BH3 domain," Journal of the American Chemical Society, 134(1):315-323.

Caria, S., et al. (Dec. 2012) "Crystallization and preliminary X-ray characterization of Epstein-Barr virus BHRF1 in complex with a benzoylurea peptidomimetic," Acta Crystallography, Section F: Structural Biology & Crystal Communications, 68(Pt 12):1521-1524.

Certo et al. (May 2006) "Mitochondria primed by death signals determine cellular addiction to antiapoptotic BCL-2 family members," Cancer Cell, 9(5):351-365.

Chao et al. (Jun. 2006) "Isolating and engineering human antibodies using yeast surface display," Nature Protocols, 1 (2):755-768.

Chen et al. (Feb. 2005) "Differential Targeting of Prosurvival Bcl-2 Proteins by Their BH3-Only Ligands Allows Complementary Apoptotic Function," Molecular Cell, 17(3)393-403.

Chin, J.W., and Schepartz, A. (Oct. 2001) "Design and evolution of a miniature Bcl-2 binding protein," Angewandte Chemie International Edition, 40(20):3806-3809.

Convertine, A.J., et al. (Nov. 2010). pH-Responsive Polymeric Micelle Carriers for siRNA Drugs, Biomacromolecules, 11(11):2904-2911.

Cooper et al. (Aug. 2010) Predicting protein structures with a multiplayer online game, Nature, 466(7307)156-760.

Correia, B.E., et al. (Mar. 2014) "Proof of principle for epitope-focused vaccine design," Nature, 507(7491):201-206.

Correia, B.E., et al. (Sep. 2010) "Computational design of epitope-scaffolds allows induction of antibodies specific for a poorly immunogenic HIV vaccine epitope," Structure, 18(9)1116-1126.

Czabotar et al. (Apr. 2007) "Structural insights into the degradation of Mcl-1 induced by BH3 domains," Proceedings of the National Academy of Sciences USA, 104(15):6217-6222.

DeBartolo et al. (Sep. 2012) "Predictive Bcl-2 Family Binding Models Rooted in Experiment or Structure," Journal of Molecular Biology, 422(1):124-144.

Desagher et al. (Sep. 2001) "Phosphorylation of bid by casein kinases I and II regulates its cleavage by caspase 8," Molecular Cell, 8(3):601-611.

Desbien, A.L., et al. (Apr. 2009) "The Epstein-Barr virus Bcl-2 homolog, BHRF1, blocks apoptosis by binding to a limited amount of Bim," Proceedings of the National Academy of Sciences USA, 106(14):5663-5668.

Du et al. (epub Nov. 2010) "BH3 Domains other than Bim and Bid Can Directly Activate Bax/Bak," Journal of Biological Chemistry, 286(1):491-501.

Dutta, S., et al. (Apr. 2013) "Peptide ligands for pro-survival protein Bfl-1 from computationally guided library screening," ACS Chemical Biology, 8(4):778-788.

Dutta, S., et al. (May 2010) "Determinants of BH3 binding specificity for Mcl-1 versus Bcl-xL," Journal of Molecular Biology, 398(5):747-762.

Duvall, C.L., et al. (Apr. 2010) "Intracellular delivery of a proapoptotic peptide via conjugation to a RAFT synthesized ?endosomolytic polymer," Molecular Pharmaceutics, 7(2):468-476.

Essafi et al. (Mar. 2005) "Direct transcriptional regulation of Bim by FoxO3a mediates STI571-induced apoptosis in Bcr-Abl-expressing cells," Oncogene, 24(14):2317-2329.

Fire, E., et al. (Mar. 2010) "Mcl-1-Bim complexes accommodate surprising point mutations via minor structural changes," Protein Science, 19(3):507-519.

Flanagan and A. Letai (Mar. 2008) "BH3 domains define selective inhibitory interactions with BHRF-1 and KSHV BCL-2," Cell Death and Differentiation, 15(3):580-588.

Fleishman et al. (2011; retrieved May 2017) "RosettaScripts: a scripting language interface to the Rosetta macromolecular modeling suite," PLoS One, 6(6):e20161.

Fleishman, S.J., et al. (May 2011) "Computational design of proteins targeting the conserved stem region of influenza hemagglutinin," Science, 332(6031):816-821.

Follis et al (Mar. 2013) "PUMA binding induces partial unfolding within BCL-xL to disrupt p53 binding and promote apoptosis," Nature Chemical Biology, 9(3):163-168.

Fowler et al. (Dec. 2011) "Enrich: software for analysis of protein function by enrichment and depletion of variants," Bioinformatics, 27(24):3430-3431.

Fowler et al. (Sep. 2010) "High-resolution mapping of protein sequence function relationships," Nature Methods, 7(9):741-746.

Fricker et al. (Jul. 2010) "Phosphorylation of Puma modulates its apoptotic function by regulating protein stability," Cell Death and Disease, 1:e59.

Gemperli, A.G., et al. (Feb. 2005) "Paralogselective ligands for bcl-2 proteins," Journal of the American Chemical Society, 127(6):1596-1597.

Goulet, A., et al. (Dec. 2009) "Acidianus filamentous virus 1 coat proteins display a helical fold spanning the flamentous archaeal viruses lineage," Proceedings of the National Academy of Sciences USA, 106(50):21155-21160.

Grant et al. (Aug. 2011) "Generalized fragment picking in Rosetta: design, protocols and applications," PLaS One, 6(8): e23294.

Henderson, S., et al. (Sep. 1993) "Epstein-Barr virus-coded BHRF1 protein, a viral homologue of Bcl-2, protects human B cells from programmed cell death," Proceedings of the National Academy of Sciences USA, 90(18):8479-8483.

Högbom, M., et al. (Mar. 2003) "Structural basis for recognition by an in vitro evolved affibody," Proceedings of the National Academy of Sciences USA, 100(6):3191-3196.

Hoover and J. Lubkowski (May 2002) "DNAWorks: an automated method for designing oligonucleotides for PCR-based gene synthesis," Nucleic Acids Research, 30(10):e43.

Ishii, H.H., et al. (Oct. 1995) "Cycloheximide-induced apoptosis in Burkitt lymphoma (BJA-B) cells with and without Epstein-Barr virus infection," Immunology and Cell Biology, 73(5):463-468.

Jones (Sep. 1999) "Protein secondary structure prediction based on position-specific scoring matrices," Journal of Molecular Biology, 292(2):195-202.

Kelly and A. Strasser (Sep .2011) "The role of Bcl-2 and its pro-survival relatives in tumourigenesis and cancer therapy," Cell Death and Differentiation, 18(9):1414-1424.

Kelly, G.L. et al. (Mar. 2013) "Different patterns of Epstein-Barr virus latency in endemic Burkitt lymphoma (BL) lead to distinct variants within the BL-associated gene expression signature," Journal of Virology, 87(5):2882-2894.

Kim et al (Nov. 2009) "Stepwise Activation of BAX and BAK by tBID, BIM, and PUMA Initiates Mitochondrial Apoptosis," Molecular Cell, 36(3):487-499.

Koga, N., et al. (Nov. 2012) "Principles for designing ideal protein structures," Nature, 491(7423):222-227.

Ku et al (epub Nov. 2010) "Evidence that inhibition of BAX activation by BCL-2 involves its tight and preferential Interaction with the BH3 domain of BAX," Cell Research, 21(4):627-641.

Ku et al. (Feb. 2008) "Structural and Biochemical Bases for the Inhibition of Autophagy and Apoptosis by Viral BCL-2 of Murine γ-Herpesvirus 68," PLoS Pathogenesis, 4(2):e25.

Kuhlman, B., et al. (Nov. 2003) "Design of a novel globular protein fold with atomic-level accuracy," Science, 302 (5649):1364-1368.

Kuwana et al. (Feb. 2005) "BH3 Domains of BH3-Only Proteins Differentially Regulate Bax-Mediated Mitochondrial Membrane Permeabilization Both Directly and Indirectly," Molecular Cell, 17(4):525-535.

Lanci, C.J., et al. (May 2012) "Computational design of a protein crystal," Proceedings of the National Academy of Sciences USA, 109(19):7304-7309.

(56) References Cited

OTHER PUBLICATIONS

Leao, M., et al. (Jan. 2007) "Epstein-barr virus-induced resistance to drugs that activate the mitotic spindle assembly checkpoint in Burkitt's lymphoma cells," Journal of Virology, 81(1):248-260.
Leaver-Fay, A., et al. (2011; retrieved May 2017) "ROSETTA3: an object-oriented software suite for the simulation and design of macromolecules," Methods in Enzymology, 487:545-574.
Lee et al. (Jun. 2009) "High-Resolution Structural Characterization of a Helical α/β-Peptide Foldamer Bound to the Anti-Apoptotic Protein Bcl-x L," Angewandte Chemie International Edition, 48(24):4318-4322.
Lee et al. (Jun. 2013) "Bcl-w Enhances Mesenchymal Changes and Invasiveness of Glioblastoma Cells by Inducing Nuclear Accumulation of β-Catenin," PLoS One, 8(6):e68030.
Lee et al. (Sep. 2011) "Structural Basis of Bcl-xL Recognition by a BH3-Mimetic α/β-Peptide Generated by Sequence-Based Design," ChemBioChem, 12(13):2025-2032.
Lee, E.F., et al. (Oct. 2009) "Conformational changes in Bcl-2 pro-survival proteins determine their capacity to bind igands," Journal of Biological Chemistry, 284(44):30508-30517.
Lessene, G., et al. (Jun. 2013) "Structure-guided design of a selective Bcl-X(L) inhibitor," Nature Chemical Biology, 9(6):390-397.
Letai et al (Sep. 2002) "Distinct BH3 domains either sensitize or activate mitochondrial apoptosis, serving as a prototype cancer therapeutics," Cancer Cell, 2(3):183-192.
Liu et al. (Sep. 2003) "The structure of a Bcl-xL/Bim fragment complex: implications for Bim function," Immunity, 19 (3):341-352.
London et al. (Jul. 2012) "In Silico and in Vitro Elucidation of BH3 Binding Specificity toward Bcl-2," Biochemistry, 51 (29):5841-5850.
Manganiello, M.J., et al. (Mar. 2012) "Diblock copolymers with tunable pH transitions for gene delivery," Biomaterials, 33(7):2301-2309.
Martinou, J.C., and Youle, R.J. (Jul. 2011) "Mitochondria in apoptosis: Bcl-2 family members and mitochondrial dynamics," Developmental Cell, 21(1):92-101.
Mathai et al (Apr. 2002) "Induction and endoplasmic reticulum location of BIK/NBK in response to apoptotic signaling by E1A and p53," Oncogene, 21(16):2534-2544.
McLaughlin, Jr. et al. (Nov. 2012) "The spatial architecture of protein function and adaptation," Nature, 491(7422):138-142.
Nakano and KH Vousden (Mar. 2001) "PUMA, a novel proapoptotic gene, is induced by p53," Molecular Cell, 7 (3):683-694.
O'Connor, O.A., et al. (May 2006) "The combination of the proteasome inhibitor bortezomib and the bcl-2 antisense molecule oblimersen sensitizes human B-cell lymphomas to cyclophosphamide," Clinical Cancer Research, 12 (9):2902-2911.

Ofek, G., et al. (Oct. 2010) "Elicitation of structure-specific antibodies by epitope scaffolds," Proceedings of the National Academy of Sciences USA, 107(42):17880-17887.
Okamoto et al. (Feb. 2013) "Stabilizing the Pro-Apoptotic BimBH3 Helix (BimSAHB) Does Not Necessarily Enhance Affinity or Biological Activity," ACS Chemical Biology, 8(2):297-302.
Placzek et al. (May 2010) "A survey of the anti-apoptotic Bcl-2 subfamily expression in cancer types provides a platform to poredict the efficacy of Bcl-2 antagonists in cancer therapy," Cell Death and Disease, 1:e40.
Procko, E., et al. (Sep. 2013) "Computational design of a protein-based enzyme inhibitor," Journal of Molecular Biology, 425(18):3563-3575.
Roberts et al. (Feb. 2012) "Substantial Susceptibility of Chronic Lymphocytic Leukemia to BCL2 Inhibition: Results of Phase I Study of Navitoclax in Patients With Relapsed or Refractory Disease," Journal of Clinical Oncology, 30 (5):488-496.
Rohl et al. (2004; retrieved May 2017) "Protein structure prediction using Rosetta," Methods in Enzymology, 383:66-93.
Sheffler and D. Baker (Jan. 2009) "RosettaHoles :rapid assessment of protein core packing for structure prediction, refinement, design, and validation," Protein Science, 18(1):229-239.
Smith et al. (Sep. 2013) "Structure-Guided Rational Design of α/β-Peptide Foldamers with High Affinity for BCL-2 Family Prosurvival Proteins," ChemBioChem, 14(13):1564-1572.
Thi et al. (Jun. 2013) "Transcriptional and post-translational regulation of Bim is essential for TGF-β and TNF-αinduced apoptosis of gastric cancer cell," Biochimica et Biophysica Acta (BBA)—General Subjects, 1830(6):3584-3592.
Walensky et al (Oct. 2006) "A Stapled BID BH3 Helix Directly Binds and Activates BAX," Molecular Cell, 24(2):199-210.
Watanabe, A., et al. (Mar. 2010) "Epstein-Barr virus-encoded Bcl-2 homologue functions as a survival factor in Wp-restricted Burkitt lymphoma cell line P3HR-1," Journal of Virology, 84(6):2893-2901.
Westphal et al. (Apr. 2011) "Molecular biology of Bax and Bak activation and action," Biochimica et Biophysica (BBA)—Molecualr Cell Research, 1813(4):521-531.
Whitehead et al. (May 2012) "Optimization of affinity, specificity and function of designed influenza inhibitors using deep sequencing," Nature Biotechnology, 30(6):543-548.
Willis (Jun. 2005) "Proapoptotic Bak is sequestered by Mc1-1 and Bcl-xL, but not Bcl-2, until displaced by BH3-only proteins," Genes & Development, 19(11)1294-1305.
Willis et al. (Feb. 2007) "Apoptosis Initiated When BH3 Ligands Engage Multiple Bcl-2 Homologs, Not Bax or Bak," Science, 315(5813):856-859.
Wilson et al. (Jan. 2000) "Bcl-w expression in colorectal adenocarcinoma," British Journal of Cancer, 82(1):178-185.
Young and PG Murray (Aug. 2003) "Epstein-Barr virus and oncogenesis: from latent genes to tumours," Oncogene, 22 (33):5108-5121.
Zhang et al. (May 2007) "Bcl-2 family proteins are essential for platelet survival," Cell Death and Differentiation, 14 (5):943-951.

SEQUENCE LISTING

<160> NUMBER OF SEQ ID NOS: 277

<210> SEQ ID NO 1
<211> LENGTH: 116
<212> TYPE: PRT
<213> ORGANISM: Artificial Sequence
<220> FEATURE:
<223> OTHER INFORMATION: synthetic

<400> SEQUENCE: 1

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
                20                  25                  30

Arg Lys Leu Asp Leu Thr Gln Glu Met Arg Arg Lys Leu Glu Leu Arg
            35                  40                  45

Tyr Ile Ala Ala Met Leu Met Ala Ile Gly Asp Ile Tyr Asn Ala Ile
        50                  55                  60

Arg Gln Ala Lys Gln Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Lys
                85                  90                  95

Glu Glu Ala Ser Arg Lys Ala Arg Asp Tyr Gly Arg Glu Phe Gln Leu
                100                 105                 110

Lys Leu Glu Tyr
        115

<210> SEQ ID NO 2
<211> LENGTH: 116
<212> TYPE: PRT
<213> ORGANISM: Artificial Sequence
<220> FEATURE:
<223> OTHER INFORMATION: synthetic

<400> SEQUENCE: 2

Ala Asp Pro Lys Lys Val Leu Asp Lys Ala Lys Asp Gln Ala Glu Asn
1               5                   10                  15

Arg Val Arg Glu Leu Lys Gln Val Leu Glu Glu Leu Tyr Lys Glu Ala
                20                  25                  30

Arg Lys Leu Asp Leu Thr Gln Glu Met Arg Lys Lys Leu Ile Glu Arg
            35                  40                  45

Tyr Ala Ala Ala Ile Ile Arg Ala Ile Gly Asp Ile Asn Asn Ala Ile
        50                  55                  60

Tyr Gln Ala Lys Gln Glu Ala Glu Lys Leu Lys Lys Ala Gly Leu Val
65                  70                  75                  80

Asn Ser Gln Gln Leu Asp Glu Leu Leu Arg Arg Leu Asp Glu Leu Gln
                85                  90                  95

Lys Glu Ala Ser Arg Lys Ala Asn Glu Tyr Gly Arg Glu Phe Glu Leu
                100                 105                 110

Lys Leu Glu Tyr
        115

<210> SEQ ID NO 3
<211> LENGTH: 116
<212> TYPE: PRT
<213> ORGANISM: Artificial Sequence
<220> FEATURE:
<223> OTHER INFORMATION: synthetic

<400> SEQUENCE: 3

Ala Asp Pro Lys Lys Val Leu Asp Lys Ala Lys Asp Glu Ala Glu Asn
1               5                   10                  15

Arg Val Arg Glu Leu Lys Gln Arg Leu Glu Glu Leu Tyr Lys Glu Ala
                20                  25                  30

Arg Lys Leu Asp Leu Thr Gln Glu Met Arg Gln Glu Leu Val Asp Lys
            35                  40                  45

Ala Arg Ala Ala Ser Leu Gln Ala Asn Gly Asp Ile Phe Tyr Ala Ile
        50                  55                  60

```
Leu Arg Ala Leu Ala Glu Ala Glu Lys Leu Lys Lys Ala Gly Leu Val
 65                  70                  75                  80

Asn Ser Gln Gln Leu Asp Glu Leu Lys Arg Arg Leu Glu Glu Leu Ala
                 85                  90                  95

Glu Glu Ala Arg Arg Lys Ala Glu Lys Leu Arg Asp Glu Phe Arg Leu
            100                 105                 110

Lys Leu Glu Tyr
        115

<210> SEQ ID NO 4
<211> LENGTH: 116
<212> TYPE: PRT
<213> ORGANISM: Artificial Sequence
<220> FEATURE:
<223> OTHER INFORMATION: synthetic

<400> SEQUENCE: 4

Ala Asp Pro Lys Lys Val Leu Asp Lys Ala Lys Asp Arg Ala Glu Asn
 1               5                  10                  15

Val Val Arg Lys Leu Lys Lys Glu Leu Glu Glu Leu Tyr Lys Glu Ala
                 20                  25                  30

Arg Lys Leu Asp Leu Thr Gln Glu Met Arg Asp Arg Ile Arg Arg Thr
            35                  40                  45

Ala Ile Ala Ala Arg Phe Gln Ala His Gly Asp Ile Phe His Ala Ile
        50                  55                  60

Lys His Ala Lys Glu Glu Ala Arg Lys Leu Lys Lys Ala Gly Leu Val
 65                  70                  75                  80

Asn Ser Gln Gln Leu Asp Glu Leu Lys Arg Arg Leu Arg Glu Leu Asp
                 85                  90                  95

Glu Glu Ala Glu Gln Arg Ala Glu Lys Leu Gly Lys Glu Phe Arg Leu
            100                 105                 110

Lys Leu Glu Tyr
        115

<210> SEQ ID NO 5
<211> LENGTH: 116
<212> TYPE: PRT
<213> ORGANISM: Artificial Sequence
<220> FEATURE:
<223> OTHER INFORMATION: synthetic

<400> SEQUENCE: 5

Ala Asp Pro Lys Lys Ile Leu Asp Lys Ala Lys Asp Gln Val Glu Asn
 1               5                  10                  15

Arg Val Arg Glu Leu Lys Gln Glu Leu Glu Arg Leu Tyr Lys Glu Ala
                 20                  25                  30

Arg Lys Leu Asp Leu Thr Gln Glu Met Arg Arg Lys Leu His Val Arg
            35                  40                  45

Tyr Ile Glu Ala Met Leu Lys Ala Ile Ala Ala Ile Met Asn Ala Ile
        50                  55                  60

Ala Gln Ala Glu Asn Glu Ala Asp Lys Leu Lys Lys Ala Gly Leu Val
 65                  70                  75                  80

Asn Ser Gln Gln Leu Asp Glu Leu Arg Arg Arg Leu Glu Glu Leu Thr
                 85                  90                  95

Glu Glu Ala Ala Gln Lys Ala His Asp Tyr Gly Arg Glu Leu Gln Leu
            100                 105                 110

Lys Leu Glu Tyr
```

<210> SEQ ID NO 6
<211> LENGTH: 116
<212> TYPE: PRT
<213> ORGANISM: Artificial Sequence
<220> FEATURE:
<223> OTHER INFORMATION: synthetic

<400> SEQUENCE: 6

```
Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Lys Arg Lys Lys Leu Glu Val Ala
        35                  40                  45

Thr Leu Gly Ala Val Leu Ala Ala His Gly Asp Ile Leu Asn Ala Ile
    50                  55                  60

Met Gln Ala Lys Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Lys
                85                  90                  95

Glu Glu Ala Leu Arg Lys Ala Ser Asp Tyr Gly Asn Glu Phe His Leu
            100                 105                 110

Lys Arg Arg Tyr
            115
```

<210> SEQ ID NO 7
<211> LENGTH: 116
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X is A/E/G/H/I/K/M/P/R/S/T/V/W/Y
<220> FEATURE:
<221> NAME/KEY: MISC_FEATURE
<222> LOCATION: (2)..(2)
<223> OTHER INFORMATION: X is A/C/D/E/F/G/H/I/K/L/M/N/P/Q/R/S/T/V/W/Y
<220> FEATURE:
<221> NAME/KEY: MISC_FEATURE
<222> LOCATION: (3)..(3)
<223> OTHER INFORMATION: X is A/C/D/E/F/G/H/K/L/M/N/P/Q/R/S/T/V/W/Y
<220> FEATURE:
<221> NAME/KEY: MISC_FEATURE
<222> LOCATION: (4)..(4)
<223> OTHER INFORMATION: X is A/E/G/H/I/K/M/N/P/Q/R/T/V/W
<220> FEATURE:
<221> NAME/KEY: MISC_FEATURE
<222> LOCATION: (5)..(5)
<223> OTHER INFORMATION: X is F/G/I/K/L/Q/R/T/V/W
<220> FEATURE:
<221> NAME/KEY: MISC_FEATURE
<222> LOCATION: (6)..(6)
<223> OTHER INFORMATION: X is A/F/G/I/L/P/S/V/W
<220> FEATURE:
<221> NAME/KEY: MISC_FEATURE
<222> LOCATION: (7)..(7)
<223> OTHER INFORMATION: X is A/D/E/G/I/L/M/Q/R/S/T/V/W/
<220> FEATURE:
<221> NAME/KEY: MISC_FEATURE
<222> LOCATION: (8)..(8)
<223> OTHER INFORMATION: X is A/C/D/F/G/I/K/L/N/P/Q/R/S/V/W/Y
<220> FEATURE:
<221> NAME/KEY: MISC_FEATURE
<222> LOCATION: (9)..(9)
<223> OTHER INFORMATION: X is H/K/L/N/Q/R/W -continued

```
<220> FEATURE:
<221> NAME/KEY: MISC_FEATURE
<222> LOCATION: (10)..(10)
<223> OTHER INFORMATION: X is A/H/S/T
<220> FEATURE:
<221> NAME/KEY: MISC_FEATURE
<222> LOCATION: (11)..(11)
<223> OTHER INFORMATION: X is A/D/E/G/H/K/N/Q/R/S/T/Y
<220> FEATURE:
<221> NAME/KEY: MISC_FEATURE
<222> LOCATION: (12)..(12)
<223> OTHER INFORMATION: X is A/D/E/F/G/H/K/L/M/N/Q/R/S/T/V/W/Y
<220> FEATURE:
<221> NAME/KEY: MISC_FEATURE
<222> LOCATION: (13)..(13)
<223> OTHER INFORMATION: X is D/E/G/I/K/L/M/N/Q/R/S/T/V/W/Y
<220> FEATURE:
<221> NAME/KEY: MISC_FEATURE
<222> LOCATION: (14)..(14)
<223> OTHER INFORMATION: X is A/C/I/L/M/N/Q/S/T/V
<220> FEATURE:
<221> NAME/KEY: MISC_FEATURE
<222> LOCATION: (15)..(15)
<223> OTHER INFORMATION: X is A/D/E/M/N/R/V/W/Y
<220> FEATURE:
<221> NAME/KEY: MISC_FEATURE
<222> LOCATION: (16)..(16)
<223> OTHER INFORMATION: X is A/D/F/G/H/I/K/L/M/N/P/Q/R/S/T/V/W/Y
<220> FEATURE:
<221> NAME/KEY: MISC_FEATURE
<222> LOCATION: (17)..(17)
<223> OTHER INFORMATION: X is A/C/E/G/H/I/K/L/M/P/R/S/T/V
<220> FEATURE:
<221> NAME/KEY: MISC_FEATURE
<222> LOCATION: (18)..(18)
<223> OTHER INFORMATION: X is A/I/K/M/T/V
<220> FEATURE:
<221> NAME/KEY: MISC_FEATURE
<222> LOCATION: (19)..(19)
<223> OTHER INFORMATION: X is A/C/D/E/F/G/K/L/M/N/Q/R/T/V/W/Y
<220> FEATURE:
<221> NAME/KEY: MISC_FEATURE
<222> LOCATION: (20)..(20)
<223> OTHER INFORMATION: X is A/D/E/F/G/I/K/L/M/N/Q/R/S/T/V/W/Y
<220> FEATURE:
<221> NAME/KEY: MISC_FEATURE
<222> LOCATION: (21)..(21)
<223> OTHER INFORMATION: X is F/H/I/L/M/Q/T/Y
<220> FEATURE:
<221> NAME/KEY: MISC_FEATURE
<222> LOCATION: (22)..(22)
<223> OTHER INFORMATION: X is A/C/H/I/K/Q/R
<220> FEATURE:
<221> NAME/KEY: MISC_FEATURE
<222> LOCATION: (23)..(23)
<223> OTHER INFORMATION: X is A/C/E/F/G/H/I/M/N/Q/R/S/T/W/Y
<220> FEATURE:
<221> NAME/KEY: MISC_FEATURE
<222> LOCATION: (24)..(24)
<223> OTHER INFORMATION: X is A/D/G/H/I/K/N/Q/R/T/Y
<220> FEATURE:
<221> NAME/KEY: MISC_FEATURE
<222> LOCATION: (25)..(25)
<223> OTHER INFORMATION: X is I/L/M/Q
<220> FEATURE:
<221> NAME/KEY: MISC_FEATURE
<222> LOCATION: (26)..(26)
<223> OTHER INFORMATION: X is A/C/D/E/G/I/K/N/Q/R/S/T/V/W
<220> FEATURE:
<221> NAME/KEY: MISC_FEATURE
<222> LOCATION: (27)..(27)
<223> OTHER INFORMATION: X is A/C/D/E/F/G/H/I/K/L/M/N/Q/R/S/T/V/W/Y
<220> FEATURE:
<221> NAME/KEY: MISC_FEATURE
<222> LOCATION: (28)..(28)
<223> OTHER INFORMATION: X is C/F/H/I/K/L/M/N/P/R/T/V/Y
<220> FEATURE:
<221> NAME/KEY: MISC_FEATURE
<222> LOCATION: (29)..(29)
```

```
<223> OTHER INFORMATION: X is A/D/E/H/I/L/P/Q/R/W/Y
<220> FEATURE:
<221> NAME/KEY: MISC_FEATURE
<222> LOCATION: (30)..(30)
<223> OTHER INFORMATION: X is A/E/F/G/H/K/L/M/N/Q/R/S/T/W/Y
<220> FEATURE:
<221> NAME/KEY: MISC_FEATURE
<222> LOCATION: (31)..(31)
<223> OTHER INFORMATION: X is A/D/E/F/G/H/I/K/L/M/N/Q/R/S/T/V/W/Y
<220> FEATURE:
<221> NAME/KEY: MISC_FEATURE
<222> LOCATION: (32)..(32)
<223> OTHER INFORMATION: X is A/F/G/H/K/L/N/P/R/S/T/Y
<220> FEATURE:
<221> NAME/KEY: MISC_FEATURE
<222> LOCATION: (33)..(33)
<223> OTHER INFORMATION: X is F/H/I/K/L/M/P/Q/R/T/V/Y
<220> FEATURE:
<221> NAME/KEY: MISC_FEATURE
<222> LOCATION: (34)..(34)
<223> OTHER INFORMATION: X is C/H/I/K/L/M/Q/R/S/T/V/Y
<220> FEATURE:
<221> NAME/KEY: MISC_FEATURE
<222> LOCATION: (35)..(35)
<223> OTHER INFORMATION: X is A/D/E/F/G/H/I/K/L/M/N/P/Q/R/S/T/V/W
<220> FEATURE:
<221> NAME/KEY: MISC_FEATURE
<222> LOCATION: (36)..(36)
<223> OTHER INFORMATION: X is A/C/D/E/G/H/K/L/M/N/Q/R/S/T/V/W/Y
<220> FEATURE:
<221> NAME/KEY: MISC_FEATURE
<222> LOCATION: (37)..(37)
<223> OTHER INFORMATION: X is A/D/E/F/H/I/K/L/M/N/P/Q/R/S/T/V/W/Y
<220> FEATURE:
<221> NAME/KEY: MISC_FEATURE
<222> LOCATION: (38)..(38)
<223> OTHER INFORMATION: X is A/D/E/G/K/N/P/Q/R/S/T
<220> FEATURE:
<221> NAME/KEY: MISC_FEATURE
<222> LOCATION: (39)..(39)
<223> OTHER INFORMATION: X is A/D/E/G/K/N/P/Q/R/S/T/V
<220> FEATURE:
<221> NAME/KEY: MISC_FEATURE
<222> LOCATION: (40)..(40)
<223> OTHER INFORMATION: X is A/D/E/F/G/H/I/K/L/M/N/P/Q/R/S/T/V
<220> FEATURE:
<221> NAME/KEY: MISC_FEATURE
<222> LOCATION: (41)..(41)
<223> OTHER INFORMATION: X is F/G/H/K/L/M/N/Q/R/T/V/W/Y
<220> FEATURE:
<221> NAME/KEY: MISC_FEATURE
<222> LOCATION: (42)..(42)
<223> OTHER INFORMATION: X is K/R
<220> FEATURE:
<221> NAME/KEY: MISC_FEATURE
<222> LOCATION: (44)..(44)
<223> OTHER INFORMATION: X is K/R
<220> FEATURE:
<221> NAME/KEY: MISC_FEATURE
<222> LOCATION: (45)..(45)
<223> OTHER INFORMATION: X is F/G/I/L/Q/V/W/Y
<220> FEATURE:
<221> NAME/KEY: MISC_FEATURE
<222> LOCATION: (46)..(46)
<223> OTHER INFORMATION: X is D/E/M/N/Q/T
<220> FEATURE:
<221> NAME/KEY: MISC_FEATURE
<222> LOCATION: (47)..(47)
<223> OTHER INFORMATION: X is F/L/M/W
<220> FEATURE:
<221> NAME/KEY: MISC_FEATURE
<222> LOCATION: (49)..(49)
<223> OTHER INFORMATION: X is E/F/W/Y
<220> FEATURE:
<221> NAME/KEY: MISC_FEATURE
<222> LOCATION: (51)..(51)
<223> OTHER INFORMATION: X is A/G
<220> FEATURE:
<221> NAME/KEY: MISC_FEATURE
```

```
<222> LOCATION: (52)..(52)
<223> OTHER INFORMATION: X is A/F/I/Q
<220> FEATURE:
<221> NAME/KEY: MISC_FEATURE
<222> LOCATION: (53)..(53)
<223> OTHER INFORMATION: X is D/H/L/M/N/W
<220> FEATURE:
<221> NAME/KEY: MISC_FEATURE
<222> LOCATION: (54)..(54)
<223> OTHER INFORMATION: X is I/L
<220> FEATURE:
<221> NAME/KEY: MISC_FEATURE
<222> LOCATION: (55)..(55)
<223> OTHER INFORMATION: X is G/I/M/S/V
<220> FEATURE:
<221> NAME/KEY: MISC_FEATURE
<222> LOCATION: (56)..(56)
<223> OTHER INFORMATION: X is A/C/F/G/I/L/M/P/S/T/V
<220> FEATURE:
<221> NAME/KEY: MISC_FEATURE
<222> LOCATION: (57)..(57)
<223> OTHER INFORMATION: X is A/I/M/S/T/V
<220> FEATURE:
<221> NAME/KEY: MISC_FEATURE
<222> LOCATION: (60)..(60)
<223> OTHER INFORMATION: X is I/L/M
<220> FEATURE:
<221> NAME/KEY: MISC_FEATURE
<222> LOCATION: (61)..(61)
<223> OTHER INFORMATION: X is F/M/W/Y
<220> FEATURE:
<221> NAME/KEY: MISC_FEATURE
<222> LOCATION: (62)..(62)
<223> OTHER INFORMATION: X is A/D/F/G/I/L/M/N/Q/S/T/V/W
<220> FEATURE:
<221> NAME/KEY: MISC_FEATURE
<222> LOCATION: (63)..(63)
<223> OTHER INFORMATION: X is A/F/I/L/M/T/V/Y
<220> FEATURE:
<221> NAME/KEY: MISC_FEATURE
<222> LOCATION: (64)..(64)
<223> OTHER INFORMATION: X is A/H/I/M/Y
<220> FEATURE:
<221> NAME/KEY: MISC_FEATURE
<222> LOCATION: (65)..(65)
<223> OTHER INFORMATION: X is R/Y
<220> FEATURE:
<221> NAME/KEY: MISC_FEATURE
<222> LOCATION: (66)..(66)
<223> OTHER INFORMATION: X is A/F/I/K/L/M/Q/R/V/W/Y
<220> FEATURE:
<221> NAME/KEY: MISC_FEATURE
<222> LOCATION: (67)..(67)
<223> OTHER INFORMATION: X is A/G
<220> FEATURE:
<221> NAME/KEY: MISC_FEATURE
<222> LOCATION: (68)..(68)
<223> OTHER INFORMATION: X is K/Q/R
<220> FEATURE:
<221> NAME/KEY: MISC_FEATURE
<222> LOCATION: (69)..(69)
<223> OTHER INFORMATION: X is A/F/G/I/K/L/N/Q/R/S/T/V/W/Y
<220> FEATURE:
<221> NAME/KEY: MISC_FEATURE
<222> LOCATION: (70)..(70)
<223> OTHER INFORMATION: X is A/D/E/F/G/H/I/K/L/M/N/Q/R/S/T/V/W/Y
<220> FEATURE:
<221> NAME/KEY: MISC_FEATURE
<222> LOCATION: (71)..(71)
<223> OTHER INFORMATION: X is A/G/I/M/S
<220> FEATURE:
<221> NAME/KEY: MISC_FEATURE
<222> LOCATION: (72)..(72)
<223> OTHER INFORMATION: X is A/D/E/F/G/H/I/L/M/Q/S/T/V/W/Y
<220> FEATURE:
<221> NAME/KEY: MISC_FEATURE
<222> LOCATION: (73)..(73)
<223> OTHER INFORMATION: X is F/K/R/Y
<220> FEATURE:
```

```
<221> NAME/KEY: MISC_FEATURE
<222> LOCATION: (74)..(74)
<223> OTHER INFORMATION: X is A/F/L/M/R/W/Y
<220> FEATURE:
<221> NAME/KEY: MISC_FEATURE
<222> LOCATION: (75)..(75)
<223> OTHER INFORMATION: X is A/F/H/K/N/R/S/T/Y
<220> FEATURE:
<221> NAME/KEY: MISC_FEATURE
<222> LOCATION: (76)..(76)
<223> OTHER INFORMATION: X is I/K/N/R/W
<220> FEATURE:
<221> NAME/KEY: MISC_FEATURE
<222> LOCATION: (77)..(77)
<223> OTHER INFORMATION: X is A/F/G/H/I/K/L/M/N/Q/R/S/T/V/W/Y
<220> FEATURE:
<221> NAME/KEY: MISC_FEATURE
<222> LOCATION: (78)..(78)
<223> OTHER INFORMATION: X is A/D/G/H/Q/R/S/T
<220> FEATURE:
<221> NAME/KEY: MISC_FEATURE
<222> LOCATION: (79)..(79)
<223> OTHER INFORMATION: X is A/K/L/R/T/V/W/Y
<220> FEATURE:
<221> NAME/KEY: MISC_FEATURE
<222> LOCATION: (80)..(80)
<223> OTHER INFORMATION: X is I/L/M/V
<220> FEATURE:
<221> NAME/KEY: MISC_FEATURE
<222> LOCATION: (81)..(81)
<223> OTHER INFORMATION: X is A/D/E/K/N/Q/R/S/T
<220> FEATURE:
<221> NAME/KEY: MISC_FEATURE
<222> LOCATION: (82)..(82)
<223> OTHER INFORMATION: X is D/E/G/K/M/P/Q/R/S/T/V
<220> FEATURE:
<221> NAME/KEY: MISC_FEATURE
<222> LOCATION: (83)..(83)
<223> OTHER INFORMATION: X is A/D/E/F/H/I/L/N/Q/R/S/T/V
<220> FEATURE:
<221> NAME/KEY: MISC_FEATURE
<222> LOCATION: (84)..(84)
<223> OTHER INFORMATION: X is D/E/H/M/N/Q/T/Y
<220> FEATURE:
<221> NAME/KEY: MISC_FEATURE
<222> LOCATION: (85)..(85)
<223> OTHER INFORMATION: X is A/F/G/H/L/M/R/T/V/W/Y
<220> FEATURE:
<221> NAME/KEY: MISC_FEATURE
<222> LOCATION: (86)..(86)
<223> OTHER INFORMATION: X is D/E/F/G/I/K/L/N/Q/S/T/V/W/Y
<220> FEATURE:
<221> NAME/KEY: MISC_FEATURE
<222> LOCATION: (87)..(87)
<223> OTHER INFORMATION: X is A/E/F/I/K/L/M/Q/T/W
<220> FEATURE:
<221> NAME/KEY: MISC_FEATURE
<222> LOCATION: (88)..(88)
<223> OTHER INFORMATION: X is A/F/I/L/M/T/V
<220> FEATURE:
<221> NAME/KEY: MISC_FEATURE
<222> LOCATION: (89)..(89)
<223> OTHER INFORMATION: X is A/I/K/Q/R/V
<220> FEATURE:
<221> NAME/KEY: MISC_FEATURE
<222> LOCATION: (90)..(90)
<223> OTHER INFORMATION: X is A/G/I/K/L/M/N/Q/R/S/T/V/W/Y
<220> FEATURE:
<221> NAME/KEY: MISC_FEATURE
<222> LOCATION: (91)..(91)
<223> OTHER INFORMATION: X is A/C/D/E/G/H/K/L/N/Q/R/S/T/V/Y
<220> FEATURE:
<221> NAME/KEY: MISC_FEATURE
<222> LOCATION: (92)..(92)
<223> OTHER INFORMATION: X is I/L
<220> FEATURE:
<221> NAME/KEY: MISC_FEATURE
<222> LOCATION: (93)..(93)
<223> OTHER INFORMATION: X is A/D/E/H/I/M/N/Q/T
```

```
-continued

<220> FEATURE:
<221> NAME/KEY: MISC_FEATURE
<222> LOCATION: (94)..(94)
<223> OTHER INFORMATION: X is A/C/D/E/F/G/H/I/K/L/M/N/Q/R/S/T/V/Y
<220> FEATURE:
<221> NAME/KEY: MISC_FEATURE
<222> LOCATION: (95)..(95)
<223> OTHER INFORMATION: X is A/L/T/V
<220> FEATURE:
<221> NAME/KEY: MISC_FEATURE
<222> LOCATION: (96)..(96)
<223> OTHER INFORMATION: X is K/Q/R
<220> FEATURE:
<221> NAME/KEY: MISC_FEATURE
<222> LOCATION: (97)..(97)
<223> OTHER INFORMATION: X is A/D/E/G/H/Q/S/T/V
<220> FEATURE:
<221> NAME/KEY: MISC_FEATURE
<222> LOCATION: (98)..(98)
<223> OTHER INFORMATION: X is A/D/E/F/H/K/M/N/P/Q/R/S/W/Y
<220> FEATURE:
<221> NAME/KEY: MISC_FEATURE
<222> LOCATION: (99)..(99)
<223> OTHER INFORMATION: X is A/S/V
<220> FEATURE:
<221> NAME/KEY: MISC_FEATURE
<222> LOCATION: (100)..(100)
<223> OTHER INFORMATION: X is A/G/N/Q/S/T
<220> FEATURE:
<221> NAME/KEY: MISC_FEATURE
<222> LOCATION: (101)..(101)
<223> OTHER INFORMATION: X is K/R
<220> FEATURE:
<221> NAME/KEY: MISC_FEATURE
<222> LOCATION: (102)..(102)
<223> OTHER INFORMATION: X is K/R
<220> FEATURE:
<221> NAME/KEY: MISC_FEATURE
<222> LOCATION: (103)..(103)
<223> OTHER INFORMATION: X is A/I/M/N/S/T/V
<220> FEATURE:
<221> NAME/KEY: MISC_FEATURE
<222> LOCATION: (104)..(104)
<223> OTHER INFORMATION: X is D/K/N/R
<220> FEATURE:
<221> NAME/KEY: MISC_FEATURE
<222> LOCATION: (105)..(105)
<223> OTHER INFORMATION: X is A/D/E/F/G/H/K/L/M/N/R/T/V/W/Y
<220> FEATURE:
<221> NAME/KEY: MISC_FEATURE
<222> LOCATION: (106)..(106)
<223> OTHER INFORMATION: X is A/E/G/H/I/T/Y
<220> FEATURE:
<221> NAME/KEY: MISC_FEATURE
<222> LOCATION: (107)..(107)
<223> OTHER INFORMATION: X is D/G/S
<220> FEATURE:
<221> NAME/KEY: MISC_FEATURE
<222> LOCATION: (108)..(108)
<223> OTHER INFORMATION: X is K/Q/R
<220> FEATURE:
<221> NAME/KEY: MISC_FEATURE
<222> LOCATION: (109)..(109)
<223> OTHER INFORMATION: X is A/D/E/F/G/H/K/L/R/S/V/W
<220> FEATURE:
<221> NAME/KEY: MISC_FEATURE
<222> LOCATION: (111)..(111)
<223> OTHER INFORMATION: X is D/E/H/M/Q
<220> FEATURE:
<221> NAME/KEY: MISC_FEATURE
<222> LOCATION: (112)..(112)
<223> OTHER INFORMATION: X is A/D/F/I/L/P/Q/R
<220> FEATURE:
<221> NAME/KEY: MISC_FEATURE
<222> LOCATION: (113)..(113)
<223> OTHER INFORMATION: X is K/Q
<220> FEATURE:
<221> NAME/KEY: MISC_FEATURE
<222> LOCATION: (114)..(114)
```

<223> OTHER INFORMATION: X is A/H/K/L/M/P/R/S/T/V/Y
<220> FEATURE:
<221> NAME/KEY: MISC_FEATURE
<222> LOCATION: (115)..(115)
<223> OTHER INFORMATION: X is D/E/P/R/T
<220> FEATURE:
<221> NAME/KEY: MISC_FEATURE
<222> LOCATION: (116)..(116)
<223> OTHER INFORMATION: X is D/E/G/H/K/Q/R/T/Y

<400> SEQUENCE: 7

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Arg Xaa Xaa Xaa Xaa Arg
        35                  40                  45

Xaa Ile Xaa Xaa Xaa Xaa Xaa Xaa Gly Asp Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Phe Xaa Xaa
            100                 105                 110

Xaa Xaa Xaa Xaa
        115
```

<210> SEQ ID NO 8
<211> LENGTH: 116
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X is A/E/G/P/S/T/V
<220> FEATURE:
<221> NAME/KEY: MISC_FEATURE
<222> LOCATION: (2)..(2)
<223> OTHER INFORMATION: X is A/D/E/G/H/K/N/S/T/V/Y
<220> FEATURE:
<221> NAME/KEY: MISC_FEATURE
<222> LOCATION: (3)..(3)
<223> OTHER INFORMATION: X is A/E/F/I/K/L/P/Q/R/S/T/V
<220> FEATURE:
<221> NAME/KEY: MISC_FEATURE
<222> LOCATION: (4)..(4)
<223> OTHER INFORMATION: X is E/H/K/N
<220> FEATURE:
<221> NAME/KEY: MISC_FEATURE
<222> LOCATION: (5)..(5)
<223> OTHER INFORMATION: X is D/E/K/M/Q
<220> FEATURE:
<221> NAME/KEY: MISC_FEATURE
<222> LOCATION: (6)..(6)
<223> OTHER INFORMATION: X is D/V
<220> FEATURE:
<221> NAME/KEY: MISC_FEATURE
<222> LOCATION: (7)..(7)
<223> OTHER INFORMATION: X is C/D/L/Y
<220> FEATURE:
<221> NAME/KEY: MISC_FEATURE
<222> LOCATION: (8)..(8)
<223> OTHER INFORMATION: X is D/L/N/W/Y
<220> FEATURE:
<221> NAME/KEY: MISC_FEATURE
<222> LOCATION: (9)..(9)
<223> OTHER INFORMATION: X is E/K/Q/T/V -continued

```
<220> FEATURE:
<221> NAME/KEY: MISC_FEATURE
<222> LOCATION: (10)..(10)
<223> OTHER INFORMATION: X is A/C/F/I/L/M/P/S/T/V/W
<220> FEATURE:
<221> NAME/KEY: MISC_FEATURE
<222> LOCATION: (11)..(11)
<223> OTHER INFORMATION: X is F/G/K/M/N/Q/S
<220> FEATURE:
<221> NAME/KEY: MISC_FEATURE
<222> LOCATION: (12)..(12)
<223> OTHER INFORMATION: X is D/E/H/N/P
<220> FEATURE:
<221> NAME/KEY: MISC_FEATURE
<222> LOCATION: (13)..(13)
<223> OTHER INFORMATION: X is E/F/H/K/R/V
<220> FEATURE:
<221> NAME/KEY: MISC_FEATURE
<222> LOCATION: (14)..(14)
<223> OTHER INFORMATION: X is A/C/D/F/H/I/L/M/P/W
<220> FEATURE:
<221> NAME/KEY: MISC_FEATURE
<222> LOCATION: (15)..(15)
<223> OTHER INFORMATION: X is E/F/S
<220> FEATURE:
<221> NAME/KEY: MISC_FEATURE
<222> LOCATION: (16)..(16)
<223> OTHER INFORMATION: X is K/N/R/W/Y
<220> FEATURE:
<221> NAME/KEY: MISC_FEATURE
<222> LOCATION: (17)..(17)
<223> OTHER INFORMATION: X is C/K/N/R
<220> FEATURE:
<221> NAME/KEY: MISC_FEATURE
<222> LOCATION: (18)..(18)
<223> OTHER INFORMATION: X is M/P/V
<220> FEATURE:
<221> NAME/KEY: MISC_FEATURE
<222> LOCATION: (19)..(19)
<223> OTHER INFORMATION: X is P/R
<220> FEATURE:
<221> NAME/KEY: MISC_FEATURE
<222> LOCATION: (20)..(20)
<223> OTHER INFORMATION: X is A/C/E/F/G/H/I/K/L/M/N/R/S/T/V/Y
<220> FEATURE:
<221> NAME/KEY: MISC_FEATURE
<222> LOCATION: (21)..(21)
<223> OTHER INFORMATION: X is F/K/L/M/R/V/Y
<220> FEATURE:
<221> NAME/KEY: MISC_FEATURE
<222> LOCATION: (22)..(22)
<223> OTHER INFORMATION: X is K/N
<220> FEATURE:
<221> NAME/KEY: MISC_FEATURE
<222> LOCATION: (23)..(23)
<223> OTHER INFORMATION: X is K/P/Q/R/W
<220> FEATURE:
<221> NAME/KEY: MISC_FEATURE
<222> LOCATION: (24)..(24)
<223> OTHER INFORMATION: X is K/R
<220> FEATURE:
<221> NAME/KEY: MISC_FEATURE
<222> LOCATION: (25)..(25)
<223> OTHER INFORMATION: X is F/I/K/L/R/W/Y
<220> FEATURE:
<221> NAME/KEY: MISC_FEATURE
<222> LOCATION: (26)..(26)
<223> OTHER INFORMATION: X is E/M/T
<220> FEATURE:
<221> NAME/KEY: MISC_FEATURE
<222> LOCATION: (27)..(27)
<223> OTHER INFORMATION: X is E/H/I/R/W
<220> FEATURE:
<221> NAME/KEY: MISC_FEATURE
<222> LOCATION: (28)..(28)
<223> OTHER INFORMATION: X is I/L/N
<220> FEATURE:
<221> NAME/KEY: MISC_FEATURE
<222> LOCATION: (29)..(29)
```

-continued

```
<223> OTHER INFORMATION: X is C/G/H/Y
<220> FEATURE:
<221> NAME/KEY: MISC_FEATURE
<222> LOCATION: (30)..(30)
<223> OTHER INFORMATION: X is E/K/N
<220> FEATURE:
<221> NAME/KEY: MISC_FEATURE
<222> LOCATION: (31)..(31)
<223> OTHER INFORMATION: X is E/M/R/T/W
<220> FEATURE:
<221> NAME/KEY: MISC_FEATURE
<222> LOCATION: (32)..(32)
<223> OTHER INFORMATION: X is A/F/I/L/M/R/T/V/W/Y
<220> FEATURE:
<221> NAME/KEY: MISC_FEATURE
<222> LOCATION: (35)..(35)
<223> OTHER INFORMATION: X is E/H/I/L/P/T/Y
<220> FEATURE:
<221> NAME/KEY: MISC_FEATURE
<222> LOCATION: (36)..(36)
<223> OTHER INFORMATION: X is D/E/N/V/Y
<220> FEATURE:
<221> NAME/KEY: MISC_FEATURE
<222> LOCATION: (37)..(37)
<223> OTHER INFORMATION: X is A/E/L/M/V
<220> FEATURE:
<221> NAME/KEY: MISC_FEATURE
<222> LOCATION: (38)..(38)
<223> OTHER INFORMATION: X is A/I/N/R/T
<220> FEATURE:
<221> NAME/KEY: MISC_FEATURE
<222> LOCATION: (39)..(39)
<223> OTHER INFORMATION: X is H/P/Q
<220> FEATURE:
<221> NAME/KEY: MISC_FEATURE
<222> LOCATION: (40)..(40)
<223> OTHER INFORMATION: X is D/E/V
<220> FEATURE:
<221> NAME/KEY: MISC_FEATURE
<222> LOCATION: (41)..(41)
<223> OTHER INFORMATION: X is M/R
<220> FEATURE:
<221> NAME/KEY: MISC_FEATURE
<222> LOCATION: (42)..(42)
<223> OTHER INFORMATION: X is D/H/P/Q/R/Y
<220> FEATURE:
<221> NAME/KEY: MISC_FEATURE
<222> LOCATION: (43)..(43)
<223> OTHER INFORMATION: X is H/K/Q/V
<220> FEATURE:
<221> NAME/KEY: MISC_FEATURE
<222> LOCATION: (44)..(44)
<223> OTHER INFORMATION: X is E/L/W
<220> FEATURE:
<221> NAME/KEY: MISC_FEATURE
<222> LOCATION: (45)..(45)
<223> OTHER INFORMATION: X is K/L/M/V
<220> FEATURE:
<221> NAME/KEY: MISC_FEATURE
<222> LOCATION: (46)..(46)
<223> OTHER INFORMATION: X is A/C/D/E/F/G/H/K/L/M/N/R/T/V/W
<220> FEATURE:
<221> NAME/KEY: MISC_FEATURE
<222> LOCATION: (47)..(47)
<223> OTHER INFORMATION: X is C/D/F/H/I/L/M/V/W/Y
<220> FEATURE:
<221> NAME/KEY: MISC_FEATURE
<222> LOCATION: (49)..(49)
<223> OTHER INFORMATION: X is A/G/H/K/N/Q/R/T/W/Y
<220> FEATURE:
<221> NAME/KEY: MISC_FEATURE
<222> LOCATION: (50)..(50)
<223> OTHER INFORMATION: X is A/D/E/G/L/M/R/V/W
<220> FEATURE:
<221> NAME/KEY: MISC_FEATURE
<222> LOCATION: (51)..(51)
<223> OTHER INFORMATION: X is A/G
<220> FEATURE:
<221> NAME/KEY: MISC_FEATURE
```

```
<222> LOCATION: (52)..(52)
<223> OTHER INFORMATION: X is A/N/R
<220> FEATURE:
<221> NAME/KEY: MISC_FEATURE
<222> LOCATION: (53)..(53)
<223> OTHER INFORMATION: X is D/H/I/K/M/N/R/S/W
<220> FEATURE:
<221> NAME/KEY: MISC_FEATURE
<222> LOCATION: (54)..(54)
<223> OTHER INFORMATION: X is L/N
<220> FEATURE:
<221> NAME/KEY: MISC_FEATURE
<222> LOCATION: (55)..(55)
<223> OTHER INFORMATION: X is A/K/Q
<220> FEATURE:
<221> NAME/KEY: MISC_FEATURE
<222> LOCATION: (56)..(56)
<223> OTHER INFORMATION: X is A/C/F/H/K/L/M/N/Q/S/V/W/Y
<220> FEATURE:
<221> NAME/KEY: MISC_FEATURE
<222> LOCATION: (57)..(57)
<223> OTHER INFORMATION: X is A/G/H/N/S/Y
<220> FEATURE:
<221> NAME/KEY: MISC_FEATURE
<222> LOCATION: (59)..(59)
<223> OTHER INFORMATION: X is D/N
<220> FEATURE:
<221> NAME/KEY: MISC_FEATURE
<222> LOCATION: (60)..(60)
<223> OTHER INFORMATION: X is C/E/F/G/I/L/M/N/Q/T
<220> FEATURE:
<221> NAME/KEY: MISC_FEATURE
<222> LOCATION: (63)..(63)
<223> OTHER INFORMATION: X is A/F/T
<220> FEATURE:
<221> NAME/KEY: MISC_FEATURE
<222> LOCATION: (64)..(64)
<223> OTHER INFORMATION: X is D/I/R
<220> FEATURE:
<221> NAME/KEY: MISC_FEATURE
<222> LOCATION: (65)..(65)
<223> OTHER INFORMATION: X is L/M
<220> FEATURE:
<221> NAME/KEY: MISC_FEATURE
<222> LOCATION: (66)..(66)
<223> OTHER INFORMATION: X is C/I/K/L/R/V
<220> FEATURE:
<221> NAME/KEY: MISC_FEATURE
<222> LOCATION: (68)..(68)
<223> OTHER INFORMATION: X is G/I/L/M/N/R/W/Y
<220> FEATURE:
<221> NAME/KEY: MISC_FEATURE
<222> LOCATION: (69)..(69)
<223> OTHER INFORMATION: X is A/F/M/W/Y
<220> FEATURE:
<221> NAME/KEY: MISC_FEATURE
<222> LOCATION: (70)..(70)
<223> OTHER INFORMATION: X is E/S
<220> FEATURE:
<221> NAME/KEY: MISC_FEATURE
<222> LOCATION: (71)..(71)
<223> OTHER INFORMATION: X is A/C/F/L/M/W
<220> FEATURE:
<221> NAME/KEY: MISC_FEATURE
<222> LOCATION: (72)..(72)
<223> OTHER INFORMATION: X is E/F/S/T/W
<220> FEATURE:
<221> NAME/KEY: MISC_FEATURE
<222> LOCATION: (73)..(73)
<223> OTHER INFORMATION: X is K/M
<220> FEATURE:
<221> NAME/KEY: MISC_FEATURE
<222> LOCATION: (75)..(75)
<223> OTHER INFORMATION: X is K/V/W
<220> FEATURE:
<221> NAME/KEY: MISC_FEATURE
<222> LOCATION: (76)..(76)
<223> OTHER INFORMATION: X is I/K
<220> FEATURE:
```

-continued

```
<221> NAME/KEY: MISC_FEATURE
<222> LOCATION: (77)..(77)
<223> OTHER INFORMATION: X is A/K
<220> FEATURE:
<221> NAME/KEY: MISC_FEATURE
<222> LOCATION: (79)..(79)
<223> OTHER INFORMATION: X is L/M/S
<220> FEATURE:
<221> NAME/KEY: MISC_FEATURE
<222> LOCATION: (80)..(80)
<223> OTHER INFORMATION: X is A/M/V
<220> FEATURE:
<221> NAME/KEY: MISC_FEATURE
<222> LOCATION: (81)..(81)
<223> OTHER INFORMATION: X is A/K/N/R
<220> FEATURE:
<221> NAME/KEY: MISC_FEATURE
<222> LOCATION: (82)..(82)
<223> OTHER INFORMATION: X is Q/S
<220> FEATURE:
<221> NAME/KEY: MISC_FEATURE
<222> LOCATION: (83)..(83)
<223> OTHER INFORMATION: X is L/Q/R
<220> FEATURE:
<221> NAME/KEY: MISC_FEATURE
<222> LOCATION: (84)..(84)
<223> OTHER INFORMATION: X is C/F/Q/W
<220> FEATURE:
<221> NAME/KEY: MISC_FEATURE
<222> LOCATION: (85)..(85)
<223> OTHER INFORMATION: X is I/L/T
<220> FEATURE:
<221> NAME/KEY: MISC_FEATURE
<222> LOCATION: (86)..(86)
<223> OTHER INFORMATION: X is A/D/I/L/M/Q/R/V/W/Y
<220> FEATURE:
<221> NAME/KEY: MISC_FEATURE
<222> LOCATION: (88)..(88)
<223> OTHER INFORMATION: X is F/L/Q/V
<220> FEATURE:
<221> NAME/KEY: MISC_FEATURE
<222> LOCATION: (89)..(89)
<223> OTHER INFORMATION: X is K/L
<220> FEATURE:
<221> NAME/KEY: MISC_FEATURE
<222> LOCATION: (90)..(90)
<223> OTHER INFORMATION: X is L/R
<220> FEATURE:
<221> NAME/KEY: MISC_FEATURE
<222> LOCATION: (91)..(91)
<223> OTHER INFORMATION: X is H/K/L/Q/R
<220> FEATURE:
<221> NAME/KEY: MISC_FEATURE
<222> LOCATION: (92)..(92)
<223> OTHER INFORMATION: X is D/I/K/L/N/R/T/V
<220> FEATURE:
<221> NAME/KEY: MISC_FEATURE
<222> LOCATION: (93)..(93)
<223> OTHER INFORMATION: X is D/E/Q
<220> FEATURE:
<221> NAME/KEY: MISC_FEATURE
<222> LOCATION: (94)..(94)
<223> OTHER INFORMATION: X is E/W
<220> FEATURE:
<221> NAME/KEY: MISC_FEATURE
<222> LOCATION: (95)..(95)
<223> OTHER INFORMATION: X is D/L/N/P/S
<220> FEATURE:
<221> NAME/KEY: MISC_FEATURE
<222> LOCATION: (96)..(96)
<223> OTHER INFORMATION: X is A/H/I/Q/V
<220> FEATURE:
<221> NAME/KEY: MISC_FEATURE
<222> LOCATION: (98)..(98)
<223> OTHER INFORMATION: X is D/E/F
<220> FEATURE:
<221> NAME/KEY: MISC_FEATURE
<222> LOCATION: (99)..(99)
<223> OTHER INFORMATION: X is A/P/V
```

```
<220> FEATURE:
<221> NAME/KEY: MISC_FEATURE
<222> LOCATION: (100)..(100)
<223> OTHER INFORMATION: X is A/C/F/G/K/R/V/Y
<220> FEATURE:
<221> NAME/KEY: MISC_FEATURE
<222> LOCATION: (101)..(101)
<223> OTHER INFORMATION: X is L/Q/R/V
<220> FEATURE:
<221> NAME/KEY: MISC_FEATURE
<222> LOCATION: (103)..(103)
<223> OTHER INFORMATION: X is A/D/E/F/G/H/I/K/L/M/N/Q/R/S/T/V/W/Y
<220> FEATURE:
<221> NAME/KEY: MISC_FEATURE
<222> LOCATION: (104)..(104)
<223> OTHER INFORMATION: X is A/D/E/G/P/S
<220> FEATURE:
<221> NAME/KEY: MISC_FEATURE
<222> LOCATION: (105)..(105)
<223> OTHER INFORMATION: X is K/P/Q/S
<220> FEATURE:
<221> NAME/KEY: MISC_FEATURE
<222> LOCATION: (106)..(106)
<223> OTHER INFORMATION: X is A/F/I/L/V/W
<220> FEATURE:
<221> NAME/KEY: MISC_FEATURE
<222> LOCATION: (107)..(107)
<223> OTHER INFORMATION: X is D/G/I/K/M/Q/R/T/W
<220> FEATURE:
<221> NAME/KEY: MISC_FEATURE
<222> LOCATION: (108)..(108)
<223> OTHER INFORMATION: X is A/D/E/H/K/N/R/V/Y
<220> FEATURE:
<221> NAME/KEY: MISC_FEATURE
<222> LOCATION: (109)..(109)
<223> OTHER INFORMATION: X is C/E/H/K/P/R/W
<220> FEATURE:
<221> NAME/KEY: MISC_FEATURE
<222> LOCATION: (110)..(110)
<223> OTHER INFORMATION: X is C/F/H/Q/R/W
<220> FEATURE:
<221> NAME/KEY: MISC_FEATURE
<222> LOCATION: (111)..(111)
<223> OTHER INFORMATION: X is H/R
<220> FEATURE:
<221> NAME/KEY: MISC_FEATURE
<222> LOCATION: (112)..(112)
<223> OTHER INFORMATION: X is G/L/N/P/Q/R/S
<220> FEATURE:
<221> NAME/KEY: MISC_FEATURE
<222> LOCATION: (113)..(113)
<223> OTHER INFORMATION: X is H/K/N/P
<220> FEATURE:
<221> NAME/KEY: MISC_FEATURE
<222> LOCATION: (114)..(114)
<223> OTHER INFORMATION: X is A/C/F/I/L/M/P/Q/R/S/W
<220> FEATURE:
<221> NAME/KEY: MISC_FEATURE
<222> LOCATION: (115)..(115)
<223> OTHER INFORMATION: X is A/C/E/G/H/K/N/Q/R/S/V/Y
<220> FEATURE:
<221> NAME/KEY: MISC_FEATURE
<222> LOCATION: (116)..(116)
<223> OTHER INFORMATION: X is D/F/H/N/S/Y

<400> SEQUENCE: 8

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Arg Lys Xaa Xaa Xaa Xaa Xaa Xaa Xaa Xaa Xaa Xaa Xaa Xaa Lys
            35                  40                  45

Xaa Xaa Xaa Xaa Xaa Xaa Xaa Xaa Xaa Gly Xaa Xaa Phe Tyr Xaa Xaa
        50                  55                  60
```

Xaa Xaa Ala Xaa Xaa Xaa Xaa Xaa Leu Xaa Xaa Xaa Gly Xaa Xaa
 65                  70                  75                  80

Xaa Xaa Xaa Xaa Xaa Xaa Glu Xaa Xaa Xaa Xaa Xaa Xaa Xaa Xaa
                 85                  90                  95

Glu Xaa Xaa Xaa Xaa Lys Xaa Xaa Xaa Xaa Xaa Xaa Xaa Xaa Xaa
            100                 105                 110

Xaa Xaa Xaa Xaa
        115

```
<210> SEQ ID NO 9
<211> LENGTH: 116
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X is A/E/G/P/R/S/T/V
<220> FEATURE:
<221> NAME/KEY: MISC_FEATURE
<222> LOCATION: (2)..(2)
<223> OTHER INFORMATION: X is A/D/E/G/H/N/S/V/Y
<220> FEATURE:
<221> NAME/KEY: MISC_FEATURE
<222> LOCATION: (3)..(3)
<223> OTHER INFORMATION: X is A/L/P/Q/R/S/T
<220> FEATURE:
<221> NAME/KEY: MISC_FEATURE
<222> LOCATION: (4)..(4)
<223> OTHER INFORMATION: X is A/E/I/K/N/Q/R/T
<220> FEATURE:
<221> NAME/KEY: MISC_FEATURE
<222> LOCATION: (5)..(5)
<223> OTHER INFORMATION: X is C/K/N/Q/R
<220> FEATURE:
<221> NAME/KEY: MISC_FEATURE
<222> LOCATION: (6)..(6)
<223> OTHER INFORMATION: X is G/I/M/S/V/W/Y
<220> FEATURE:
<221> NAME/KEY: MISC_FEATURE
<222> LOCATION: (7)..(7)
<223> OTHER INFORMATION: X is C/G/I/L
<220> FEATURE:
<221> NAME/KEY: MISC_FEATURE
<222> LOCATION: (8)..(8)
<223> OTHER INFORMATION: X is D/F/H/M/N/S/T/V/Y
<220> FEATURE:
<221> NAME/KEY: MISC_FEATURE
<222> LOCATION: (10)..(10)
<223> OTHER INFORMATION: X is A/E/H/Q/V/W/Y
<220> FEATURE:
<221> NAME/KEY: MISC_FEATURE
<222> LOCATION: (11)..(11)
<223> OTHER INFORMATION: X is C/G/K/Q/R
<220> FEATURE:
<221> NAME/KEY: MISC_FEATURE
<222> LOCATION: (12)..(12)
<223> OTHER INFORMATION: X is D/E/L/M/P/R/S/W/Y
<220> FEATURE:
<221> NAME/KEY: MISC_FEATURE
<222> LOCATION: (13)..(13)
<223> OTHER INFORMATION: X is R/S
<220> FEATURE:
<221> NAME/KEY: MISC_FEATURE
<222> LOCATION: (14)..(14)
<223> OTHER INFORMATION: X is A/D/F/G/H/L/M/N/R/V/Y
<220> FEATURE:
<221> NAME/KEY: MISC_FEATURE
<222> LOCATION: (15)..(15)
<223> OTHER INFORMATION: X is E/R
<220> FEATURE:
<221> NAME/KEY: MISC_FEATURE
<222> LOCATION: (16)..(16)
<223> OTHER INFORMATION: X is C/H/K/N
```

```
<220> FEATURE:
<221> NAME/KEY: MISC_FEATURE
<222> LOCATION: (17)..(17)
<223> OTHER INFORMATION: X is A/G/T/V
<220> FEATURE:
<221> NAME/KEY: MISC_FEATURE
<222> LOCATION: (18)..(18)
<223> OTHER INFORMATION: X is K/P/R/V
<220> FEATURE:
<221> NAME/KEY: MISC_FEATURE
<222> LOCATION: (19)..(19)
<223> OTHER INFORMATION: X is H/P/R/Y
<220> FEATURE:
<221> NAME/KEY: MISC_FEATURE
<222> LOCATION: (20)..(20)
<223> OTHER INFORMATION: X is E/K/N/Q/T/W
<220> FEATURE:
<221> NAME/KEY: MISC_FEATURE
<222> LOCATION: (21)..(21)
<223> OTHER INFORMATION: X is F/H/L/R/Y
<220> FEATURE:
<221> NAME/KEY: MISC_FEATURE
<222> LOCATION: (23)..(23)
<223> OTHER INFORMATION: X is G/H/K/M/N/Q/V
<220> FEATURE:
<221> NAME/KEY: MISC_FEATURE
<222> LOCATION: (24)..(24)
<223> OTHER INFORMATION: X is A/C/E/F/G/H/I/K/L/M/N/P/Q/R/S/V/W/Y
<220> FEATURE:
<221> NAME/KEY: MISC_FEATURE
<222> LOCATION: (25)..(25)
<223> OTHER INFORMATION: X is L/P
<220> FEATURE:
<221> NAME/KEY: MISC_FEATURE
<222> LOCATION: (26)..(26)
<223> OTHER INFORMATION: X is A/D/E/G/K/N/P/V/Y
<220> FEATURE:
<221> NAME/KEY: MISC_FEATURE
<222> LOCATION: (27)..(27)
<223> OTHER INFORMATION: X is E/G/I/K/L/M/R/S/V/W
<220> FEATURE:
<221> NAME/KEY: MISC_FEATURE
<222> LOCATION: (28)..(28)
<223> OTHER INFORMATION: X is E/F/G/I/K/L/M/Q/R/S/T/V/Y
<220> FEATURE:
<221> NAME/KEY: MISC_FEATURE
<222> LOCATION: (29)..(29)
<223> OTHER INFORMATION: X is F/H/N/Y
<220> FEATURE:
<221> NAME/KEY: MISC_FEATURE
<222> LOCATION: (30)..(30)
<223> OTHER INFORMATION: X is C/K/N/R
<220> FEATURE:
<221> NAME/KEY: MISC_FEATURE
<222> LOCATION: (31)..(31)
<223> OTHER INFORMATION: X is A/C/D/E/F/G/H/I/K/L/M/N/P/Q/R/S/T/V/W/Y
<220> FEATURE:
<221> NAME/KEY: MISC_FEATURE
<222> LOCATION: (32)..(32)
<223> OTHER INFORMATION: X is A/G/S/T/V
<220> FEATURE:
<221> NAME/KEY: MISC_FEATURE
<222> LOCATION: (34)..(34)
<223> OTHER INFORMATION: X is F/K/N
<220> FEATURE:
<221> NAME/KEY: MISC_FEATURE
<222> LOCATION: (35)..(35)
<223> OTHER INFORMATION: X is L/R/W/Y
<220> FEATURE:
<221> NAME/KEY: MISC_FEATURE
<222> LOCATION: (36)..(36)
<223> OTHER INFORMATION: X is A/C/D/E/H/I/K/L/M/P/Q/R/T/V/W
<220> FEATURE:
<221> NAME/KEY: MISC_FEATURE
<222> LOCATION: (37)..(37)
<223> OTHER INFORMATION: X is A/L/M/N
<220> FEATURE:
<221> NAME/KEY: MISC_FEATURE
<222> LOCATION: (38)..(38)
```

```
<223> OTHER INFORMATION: X is K/N/T
<220> FEATURE:
<221> NAME/KEY: MISC_FEATURE
<222> LOCATION: (39)..(39)
<223> OTHER INFORMATION: X is H/I/K/Q/R/S
<220> FEATURE:
<221> NAME/KEY: MISC_FEATURE
<222> LOCATION: (40)..(40)
<223> OTHER INFORMATION: X is E/F/G/H/I/K/M/N/P/R/T/V/W/Y
<220> FEATURE:
<221> NAME/KEY: MISC_FEATURE
<222> LOCATION: (41)..(41)
<223> OTHER INFORMATION: X is F/I/M
<220> FEATURE:
<221> NAME/KEY: MISC_FEATURE
<222> LOCATION: (42)..(42)
<223> OTHER INFORMATION: X is E/R
<220> FEATURE:
<221> NAME/KEY: MISC_FEATURE
<222> LOCATION: (43)..(43)
<223> OTHER INFORMATION: X is A/D/F/G/N/P/R/W
<220> FEATURE:
<221> NAME/KEY: MISC_FEATURE
<222> LOCATION: (44)..(44)
<223> OTHER INFORMATION: X is Q/R/Y
<220> FEATURE:
<221> NAME/KEY: MISC_FEATURE
<222> LOCATION: (45)..(45)
<223> OTHER INFORMATION: X is F/I/K/L/M/N/R/V/W/Y
<220> FEATURE:
<221> NAME/KEY: MISC_FEATURE
<222> LOCATION: (47)..(47)
<223> OTHER INFORMATION: X is L/M/P/R/T
<220> FEATURE:
<221> NAME/KEY: MISC_FEATURE
<222> LOCATION: (48)..(48)
<223> OTHER INFORMATION: X is A/I/K/L/Q/R/S/T/V/Y
<220> FEATURE:
<221> NAME/KEY: MISC_FEATURE
<222> LOCATION: (50)..(50)
<223> OTHER INFORMATION: X is F/I/L/W/Y
<220> FEATURE:
<221> NAME/KEY: MISC_FEATURE
<222> LOCATION: (51)..(51)
<223> OTHER INFORMATION: X is A/E/G/I/L/M/T/V
<220> FEATURE:
<221> NAME/KEY: MISC_FEATURE
<222> LOCATION: (52)..(52)
<223> OTHER INFORMATION: X is A/H/I/K/L/M/N/Q/R/W
<220> FEATURE:
<221> NAME/KEY: MISC_FEATURE
<222> LOCATION: (54)..(54)
<223> OTHER INFORMATION: X is F/I/W/Y
<220> FEATURE:
<221> NAME/KEY: MISC_FEATURE
<222> LOCATION: (55)..(55)
<223> OTHER INFORMATION: X is A/G/K/P/Q/R/W
<220> FEATURE:
<221> NAME/KEY: MISC_FEATURE
<222> LOCATION: (56)..(56)
<223> OTHER INFORMATION: X is A/F/H/I/K/L/M/P/S/T/V/W
<220> FEATURE:
<221> NAME/KEY: MISC_FEATURE
<222> LOCATION: (57)..(57)
<223> OTHER INFORMATION: X is F/H
<220> FEATURE:
<221> NAME/KEY: MISC_FEATURE
<222> LOCATION: (58)..(58)
<223> OTHER INFORMATION: X is A/G
<220> FEATURE:
<221> NAME/KEY: MISC_FEATURE
<222> LOCATION: (60)..(60)
<223> OTHER INFORMATION: X is D/E/F/I/L/Y
<220> FEATURE:
<221> NAME/KEY: MISC_FEATURE
<222> LOCATION: (62)..(62)
<223> OTHER INFORMATION: X is A/C/D/F/G/H/L/R/S/V/W/Y
<220> FEATURE:
<221> NAME/KEY: MISC_FEATURE
```

```
<222> LOCATION: (63)..(63)
<223> OTHER INFORMATION: X is A/F/L/S/T/V/W
<220> FEATURE:
<221> NAME/KEY: MISC_FEATURE
<222> LOCATION: (64)..(64)
<223> OTHER INFORMATION: X is A/D/E/G/I/K/L/R/S/W/Y
<220> FEATURE:
<221> NAME/KEY: MISC_FEATURE
<222> LOCATION: (65)..(65)
<223> OTHER INFORMATION: X is H/I/K/L/M/R/T
<220> FEATURE:
<221> NAME/KEY: MISC_FEATURE
<222> LOCATION: (66)..(66)
<223> OTHER INFORMATION: X is A/D/E/G/H/I/K/L/P/Q/R/S/T/V/W/Y
<220> FEATURE:
<221> NAME/KEY: MISC_FEATURE
<222> LOCATION: (67)..(67)
<223> OTHER INFORMATION: X is A/F/N/R/W
<220> FEATURE:
<221> NAME/KEY: MISC_FEATURE
<222> LOCATION: (68)..(68)
<223> OTHER INFORMATION: X is A/D/G/H/I/K/L/M/N/P/R/S/T
<220> FEATURE:
<221> NAME/KEY: MISC_FEATURE
<222> LOCATION: (69)..(69)
<223> OTHER INFORMATION: X is A/D/E/F/G/K/L/M/R/S/T/W/Y
<220> FEATURE:
<221> NAME/KEY: MISC_FEATURE
<222> LOCATION: (70)..(70)
<223> OTHER INFORMATION: X is A/C/E/F/G/I/P/Q/R/S/T/V/W
<220> FEATURE:
<221> NAME/KEY: MISC_FEATURE
<222> LOCATION: (71)..(71)
<223> OTHER INFORMATION: X is A/G/P/R/T
<220> FEATURE:
<221> NAME/KEY: MISC_FEATURE
<222> LOCATION: (74)..(74)
<223> OTHER INFORMATION: X is K/L/M/P/Q/R/V
<220> FEATURE:
<221> NAME/KEY: MISC_FEATURE
<222> LOCATION: (75)..(75)
<223> OTHER INFORMATION: X is K/R
<220> FEATURE:
<221> NAME/KEY: MISC_FEATURE
<222> LOCATION: (77)..(77)
<223> OTHER INFORMATION: X is A/K/T/W
<220> FEATURE:
<221> NAME/KEY: MISC_FEATURE
<222> LOCATION: (78)..(78)
<223> OTHER INFORMATION: X is G/I/K/L/R/S
<220> FEATURE:
<221> NAME/KEY: MISC_FEATURE
<222> LOCATION: (79)..(79)
<223> OTHER INFORMATION: X is E/G/I/K/L/M/R/S
<220> FEATURE:
<221> NAME/KEY: MISC_FEATURE
<222> LOCATION: (80)..(80)
<223> OTHER INFORMATION: X is K/N/V/W
<220> FEATURE:
<221> NAME/KEY: MISC_FEATURE
<222> LOCATION: (81)..(81)
<223> OTHER INFORMATION: X is G/N/W
<220> FEATURE:
<221> NAME/KEY: MISC_FEATURE
<222> LOCATION: (82)..(82)
<223> OTHER INFORMATION: X is K/Q/R/S/Y
<220> FEATURE:
<221> NAME/KEY: MISC_FEATURE
<222> LOCATION: (83)..(83)
<223> OTHER INFORMATION: X is K/Q
<220> FEATURE:
<221> NAME/KEY: MISC_FEATURE
<222> LOCATION: (84)..(84)
<223> OTHER INFORMATION: X is F/K/L/Q/R/W/Y
<220> FEATURE:
<221> NAME/KEY: MISC_FEATURE
<222> LOCATION: (85)..(85)
<223> OTHER INFORMATION: X is C/L/S/Y
<220> FEATURE:
```

```
<221> NAME/KEY: MISC_FEATURE
<222> LOCATION: (86)..(86)
<223> OTHER INFORMATION: X is D/E/G/K/R/T
<220> FEATURE:
<221> NAME/KEY: MISC_FEATURE
<222> LOCATION: (87)..(87)
<223> OTHER INFORMATION: X is E/K/R/W/Y
<220> FEATURE:
<221> NAME/KEY: MISC_FEATURE
<222> LOCATION: (88)..(88)
<223> OTHER INFORMATION: X is I/L/M/R
<220> FEATURE:
<221> NAME/KEY: MISC_FEATURE
<222> LOCATION: (89)..(89)
<223> OTHER INFORMATION: X is K/L/N
<220> FEATURE:
<221> NAME/KEY: MISC_FEATURE
<222> LOCATION: (91)..(91)
<223> OTHER INFORMATION: X is L/R
<220> FEATURE:
<221> NAME/KEY: MISC_FEATURE
<222> LOCATION: (92)..(92)
<223> OTHER INFORMATION: X is G/H/L/R/T/V/Y
<220> FEATURE:
<221> NAME/KEY: MISC_FEATURE
<222> LOCATION: (93)..(93)
<223> OTHER INFORMATION: X is A/E/F/G/H/I/K/L/M/Q/R/S/T/V/W/Y
<220> FEATURE:
<221> NAME/KEY: MISC_FEATURE
<222> LOCATION: (95)..(95)
<223> OTHER INFORMATION: X is E/K/L/M/S/Y
<220> FEATURE:
<221> NAME/KEY: MISC_FEATURE
<222> LOCATION: (96)..(96)
<223> OTHER INFORMATION: X is D/F/I/P/S/T/V/Y
<220> FEATURE:
<221> NAME/KEY: MISC_FEATURE
<222> LOCATION: (97)..(97)
<223> OTHER INFORMATION: X is E/L/S
<220> FEATURE:
<221> NAME/KEY: MISC_FEATURE
<222> LOCATION: (98)..(98)
<223> OTHER INFORMATION: X is C/E/H/M/Q/R
<220> FEATURE:
<221> NAME/KEY: MISC_FEATURE
<222> LOCATION: (99)..(99)
<223> OTHER INFORMATION: X is A/G/K/M/Q/T
<220> FEATURE:
<221> NAME/KEY: MISC_FEATURE
<222> LOCATION: (100)..(100)
<223> OTHER INFORMATION: X is A/E/F/H/I/K/L/Q/T/V/Y
<220> FEATURE:
<221> NAME/KEY: MISC_FEATURE
<222> LOCATION: (101)..(101)
<223> OTHER INFORMATION: X is A/D/L/Q/T/W
<220> FEATURE:
<221> NAME/KEY: MISC_FEATURE
<222> LOCATION: (103)..(103)
<223> OTHER INFORMATION: X is A/C/I/K/L/V
<220> FEATURE:
<221> NAME/KEY: MISC_FEATURE
<222> LOCATION: (104)..(104)
<223> OTHER INFORMATION: X is A/E/G/K/Q/V
<220> FEATURE:
<221> NAME/KEY: MISC_FEATURE
<222> LOCATION: (105)..(105)
<223> OTHER INFORMATION: X is A/C/K/L/M/S
<220> FEATURE:
<221> NAME/KEY: MISC_FEATURE
<222> LOCATION: (106)..(106)
<223> OTHER INFORMATION: X is L/Y
<220> FEATURE:
<221> NAME/KEY: MISC_FEATURE
<222> LOCATION: (107)..(107)
<223> OTHER INFORMATION: X is G/W
<220> FEATURE:
<221> NAME/KEY: MISC_FEATURE
<222> LOCATION: (108)..(108)
<223> OTHER INFORMATION: X is K/R/W
```

```
<220> FEATURE:
<221> NAME/KEY: MISC_FEATURE
<222> LOCATION: (109)..(109)
<223> OTHER INFORMATION: X is E/N/R/W
<220> FEATURE:
<221> NAME/KEY: MISC_FEATURE
<222> LOCATION: (110)..(110)
<223> OTHER INFORMATION: X is C/F/I/Y
<220> FEATURE:
<221> NAME/KEY: MISC_FEATURE
<222> LOCATION: (111)..(111)
<223> OTHER INFORMATION: X is A/D/E/F/G/H/I/K/L/M/N/Q/R/S/T/V/W/Y
<220> FEATURE:
<221> NAME/KEY: MISC_FEATURE
<222> LOCATION: (112)..(112)
<223> OTHER INFORMATION: X is F/L/M/R/T
<220> FEATURE:
<221> NAME/KEY: MISC_FEATURE
<222> LOCATION: (114)..(114)
<223> OTHER INFORMATION: X is K/L/M/P
<220> FEATURE:
<221> NAME/KEY: MISC_FEATURE
<222> LOCATION: (115)..(115)
<223> OTHER INFORMATION: X is A/D/E/G/K/Q/V
<220> FEATURE:
<221> NAME/KEY: MISC_FEATURE
<222> LOCATION: (116)..(116)
<223> OTHER INFORMATION: X is C/D/F/H/L/N/S/Y

<400> SEQUENCE: 9

Xaa Xaa Xaa Xaa Xaa Xaa Xaa Xaa Lys Xaa Xaa Xaa Xaa Xaa Xaa
1               5                   10                  15

Xaa Xaa Xaa Xaa Xaa Lys Xaa Xaa Xaa Xaa Xaa Xaa Xaa Xaa Xaa
            20                  25                  30

Arg Xaa Xaa Xaa Xaa Xaa Xaa Xaa Xaa Xaa Xaa Xaa Arg Xaa Xaa
        35                  40                  45

Ala Xaa Xaa Xaa Arg Xaa Xaa Xaa Xaa Xaa Asp Xaa Phe Xaa Xaa
    50                  55                  60

Xaa Xaa Xaa Xaa Xaa Xaa Xaa Arg Lys Xaa Xaa Lys Xaa Xaa Xaa
65                  70                  75                  80

Xaa Xaa Xaa Xaa Xaa Xaa Xaa Xaa Arg Xaa Xaa Xaa Glu Xaa Xaa
                85                  90                  95

Xaa Xaa Xaa Xaa Xaa Arg Xaa Xaa Xaa Xaa Xaa Xaa Xaa Xaa Xaa
                100                 105                 110

Lys Xaa Xaa Xaa
        115

<210> SEQ ID NO 10
<211> LENGTH: 116
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X is A/D/E/F/M/S/T/V
<220> FEATURE:
<221> NAME/KEY: MISC_FEATURE
<222> LOCATION: (2)..(2)
<223> OTHER INFORMATION: X is A/D/E/G/H/L/M/N/R/S/Y
<220> FEATURE:
<221> NAME/KEY: MISC_FEATURE
<222> LOCATION: (3)..(3)
<223> OTHER INFORMATION: X is C/F/G/L/P/Q/R/S/T/V
<220> FEATURE:
<221> NAME/KEY: MISC_FEATURE
<222> LOCATION: (4)..(4)
<223> OTHER INFORMATION: X is E/G/I/K/N/Q/R/S/T/W
<220> FEATURE:
```

-continued

```
<221> NAME/KEY: MISC_FEATURE
<222> LOCATION: (5)..(5)
<223> OTHER INFORMATION: X is A/E/F/K/L/N/P/Q/T/W
<220> FEATURE:
<221> NAME/KEY: MISC_FEATURE
<222> LOCATION: (6)..(6)
<223> OTHER INFORMATION: X is A/D/F/I/S/V
<220> FEATURE:
<221> NAME/KEY: MISC_FEATURE
<222> LOCATION: (7)..(7)
<223> OTHER INFORMATION: X is G/L/M/P/Q/T/V
<220> FEATURE:
<221> NAME/KEY: MISC_FEATURE
<222> LOCATION: (8)..(8)
<223> OTHER INFORMATION: X is A/D/E/G/H/N/R/S/T/W/Y
<220> FEATURE:
<221> NAME/KEY: MISC_FEATURE
<222> LOCATION: (9)..(9)
<223> OTHER INFORMATION: X is A/E/F/I/K/L/N/Q/R/T/Y
<220> FEATURE:
<221> NAME/KEY: MISC_FEATURE
<222> LOCATION: (10)..(10)
<223> OTHER INFORMATION: X is A/E
<220> FEATURE:
<221> NAME/KEY: MISC_FEATURE
<222> LOCATION: (11)..(11)
<223> OTHER INFORMATION: X is E/G/K/L/M/N/Q/R/S/T
<220> FEATURE:
<221> NAME/KEY: MISC_FEATURE
<222> LOCATION: (12)..(12)
<223> OTHER INFORMATION: X is A/C/D/E/F/G/H/N/V/Y
<220> FEATURE:
<221> NAME/KEY: MISC_FEATURE
<222> LOCATION: (13)..(13)
<223> OTHER INFORMATION: X is F/G/H/K/P/Q/R/V
<220> FEATURE:
<221> NAME/KEY: MISC_FEATURE
<222> LOCATION: (14)..(14)
<223> OTHER INFORMATION: X is A/C/E/G/L/S/T/V
<220> FEATURE:
<221> NAME/KEY: MISC_FEATURE
<222> LOCATION: (15)..(15)
<223> OTHER INFORMATION: X is A/C/D/E/K/S/W/Y
<220> FEATURE:
<221> NAME/KEY: MISC_FEATURE
<222> LOCATION: (16)..(16)
<223> OTHER INFORMATION: X is D/I/K/N/T
<220> FEATURE:
<221> NAME/KEY: MISC_FEATURE
<222> LOCATION: (17)..(17)
<223> OTHER INFORMATION: X is A/C/F/H/L/M/N/R/S/T/V/Y
<220> FEATURE:
<221> NAME/KEY: MISC_FEATURE
<222> LOCATION: (19)..(19)
<223> OTHER INFORMATION: X is A/C/G/H/K/R/S/T
<220> FEATURE:
<221> NAME/KEY: MISC_FEATURE
<222> LOCATION: (20)..(20)
<223> OTHER INFORMATION: X is A/D/E/G/K/Q/V/W/Y
<220> FEATURE:
<221> NAME/KEY: MISC_FEATURE
<222> LOCATION: (21)..(21)
<223> OTHER INFORMATION: X is L/M/P/T
<220> FEATURE:
<221> NAME/KEY: MISC_FEATURE
<222> LOCATION: (22)..(22)
<223> OTHER INFORMATION: X is A/E/F/I/K/N/Q/T/Y
<220> FEATURE:
<221> NAME/KEY: MISC_FEATURE
<222> LOCATION: (23)..(23)
<223> OTHER INFORMATION: X is A/H/K/N/P/Q/R/V
<220> FEATURE:
<221> NAME/KEY: MISC_FEATURE
<222> LOCATION: (24)..(24)
<223> OTHER INFORMATION: X is A/C/D/E/F/G/H/I/K/L/M/Q/R/T/V/Y
<220> FEATURE:
<221> NAME/KEY: MISC_FEATURE
<222> LOCATION: (25)..(25)
<223> OTHER INFORMATION: X is L/M/P/R
```

```
<220> FEATURE:
<221> NAME/KEY: MISC_FEATURE
<222> LOCATION: (26)..(26)
<223> OTHER INFORMATION: X is D/E/F/G/I/K/M/N/R
<220> FEATURE:
<221> NAME/KEY: MISC_FEATURE
<222> LOCATION: (27)..(27)
<223> OTHER INFORMATION: X is C/H/L/R/S
<220> FEATURE:
<221> NAME/KEY: MISC_FEATURE
<222> LOCATION: (28)..(28)
<223> OTHER INFORMATION: X is L/M/N/R
<220> FEATURE:
<221> NAME/KEY: MISC_FEATURE
<222> LOCATION: (29)..(29)
<223> OTHER INFORMATION: X is C/D/H/N/S/Y
<220> FEATURE:
<221> NAME/KEY: MISC_FEATURE
<222> LOCATION: (30)..(30)
<223> OTHER INFORMATION: X is K/M/N/Q/T/W
<220> FEATURE:
<221> NAME/KEY: MISC_FEATURE
<222> LOCATION: (31)..(31)
<223> OTHER INFORMATION: X is A/D/E/F/G/K/L/M/P/Q/T/W
<220> FEATURE:
<221> NAME/KEY: MISC_FEATURE
<222> LOCATION: (32)..(32)
<223> OTHER INFORMATION: X is A/E/G/M/P/S/T
<220> FEATURE:
<221> NAME/KEY: MISC_FEATURE
<222> LOCATION: (33)..(33)
<223> OTHER INFORMATION: X is C/H/I/L/N/R
<220> FEATURE:
<221> NAME/KEY: MISC_FEATURE
<222> LOCATION: (34)..(34)
<223> OTHER INFORMATION: X is D/G/H/K/N/Q/T
<220> FEATURE:
<221> NAME/KEY: MISC_FEATURE
<222> LOCATION: (35)..(35)
<223> OTHER INFORMATION: X is L/M/Q/R
<220> FEATURE:
<221> NAME/KEY: MISC_FEATURE
<222> LOCATION: (36)..(36)
<223> OTHER INFORMATION: X is A/D/H/K/N/Q/R/T/V/Y
<220> FEATURE:
<221> NAME/KEY: MISC_FEATURE
<222> LOCATION: (37)..(37)
<223> OTHER INFORMATION: X is L/M/P/Q/R
<220> FEATURE:
<221> NAME/KEY: MISC_FEATURE
<222> LOCATION: (38)..(38)
<223> OTHER INFORMATION: X is A/G/N/P/T
<220> FEATURE:
<221> NAME/KEY: MISC_FEATURE
<222> LOCATION: (39)..(39)
<223> OTHER INFORMATION: X is F/G/H/K/L/M/P/Q/R/T/W/Y
<220> FEATURE:
<221> NAME/KEY: MISC_FEATURE
<222> LOCATION: (40)..(40)
<223> OTHER INFORMATION: X is A/D/E/G/K/Q
<220> FEATURE:
<221> NAME/KEY: MISC_FEATURE
<222> LOCATION: (41)..(41)
<223> OTHER INFORMATION: X is C/F/I/K/L/M/R/S/V/W
<220> FEATURE:
<221> NAME/KEY: MISC_FEATURE
<222> LOCATION: (42)..(42)
<223> OTHER INFORMATION: X is C/G/H/L/P/R/S
<220> FEATURE:
<221> NAME/KEY: MISC_FEATURE
<222> LOCATION: (43)..(43)
<223> OTHER INFORMATION: X is A/C/D/F/G/H/I/L/N/P/Q/R/V/W/Y
<220> FEATURE:
<221> NAME/KEY: MISC_FEATURE
<222> LOCATION: (46)..(46)
<223> OTHER INFORMATION: X is A/C/D/E/F/G/H/I/L/M/N/P/Q/S/T/V/W/Y
<220> FEATURE:
<221> NAME/KEY: MISC_FEATURE
<222> LOCATION: (47)..(47)
```

```
<223> OTHER INFORMATION: X is F/H/I/K/L/M/P/R/T/V/W
<220> FEATURE:
<221> NAME/KEY: MISC_FEATURE
<222> LOCATION: (48)..(48)
<223> OTHER INFORMATION: X is D/E/G/Q/R
<220> FEATURE:
<221> NAME/KEY: MISC_FEATURE
<222> LOCATION: (49)..(49)
<223> OTHER INFORMATION: X is F/Y
<220> FEATURE:
<221> NAME/KEY: MISC_FEATURE
<222> LOCATION: (50)..(50)
<223> OTHER INFORMATION: X is I/L
<220> FEATURE:
<221> NAME/KEY: MISC_FEATURE
<222> LOCATION: (51)..(51)
<223> OTHER INFORMATION: X is A/D/E/G/H/I/K/L/M/N/P/Q/R/S/T/V/Y
<220> FEATURE:
<221> NAME/KEY: MISC_FEATURE
<222> LOCATION: (52)..(52)
<223> OTHER INFORMATION: X is A/G/I/T
<220> FEATURE:
<221> NAME/KEY: MISC_FEATURE
<222> LOCATION: (53)..(53)
<223> OTHER INFORMATION: X is M/N
<220> FEATURE:
<221> NAME/KEY: MISC_FEATURE
<222> LOCATION: (54)..(54)
<223> OTHER INFORMATION: X is I/L
<220> FEATURE:
<221> NAME/KEY: MISC_FEATURE
<222> LOCATION: (55)..(55)
<223> OTHER INFORMATION: X is F/G/K/M/P/S
<220> FEATURE:
<221> NAME/KEY: MISC_FEATURE
<222> LOCATION: (58)..(58)
<223> OTHER INFORMATION: X is A/C/F/G/P/R/S/W
<220> FEATURE:
<221> NAME/KEY: MISC_FEATURE
<222> LOCATION: (59)..(59)
<223> OTHER INFORMATION: X is A/C/D/E/F/G/H/I/K/L/M/N/P/Q/R/S/T/V/W/Y
<220> FEATURE:
<221> NAME/KEY: MISC_FEATURE
<222> LOCATION: (60)..(60)
<223> OTHER INFORMATION: X is I/W
<220> FEATURE:
<221> NAME/KEY: MISC_FEATURE
<222> LOCATION: (61)..(61)
<223> OTHER INFORMATION: X is A/L/M/P/S/T/V/W
<220> FEATURE:
<221> NAME/KEY: MISC_FEATURE
<222> LOCATION: (62)..(62)
<223> OTHER INFORMATION: X is A/G/M/N/P/Q/S
<220> FEATURE:
<221> NAME/KEY: MISC_FEATURE
<222> LOCATION: (63)..(63)
<223> OTHER INFORMATION: X is A/F/I/L/P
<220> FEATURE:
<221> NAME/KEY: MISC_FEATURE
<222> LOCATION: (64)..(64)
<223> OTHER INFORMATION: X is I/R
<220> FEATURE:
<221> NAME/KEY: MISC_FEATURE
<222> LOCATION: (65)..(65)
<223> OTHER INFORMATION: X is A/E/F/L/W/Y
<220> FEATURE:
<221> NAME/KEY: MISC_FEATURE
<222> LOCATION: (66)..(66)
<223> OTHER INFORMATION: X is F/N/Q/Y
<220> FEATURE:
<221> NAME/KEY: MISC_FEATURE
<222> LOCATION: (68)..(68)
<223> OTHER INFORMATION: X is C/E/G/H/N/R/S/T/V/W/Y
<220> FEATURE:
<221> NAME/KEY: MISC_FEATURE
<222> LOCATION: (69)..(69)
<223> OTHER INFORMATION: X is I/N
<220> FEATURE:
<221> NAME/KEY: MISC_FEATURE
```

```
<222> LOCATION: (71)..(71)
<223> OTHER INFORMATION: X is A/K/R/V
<220> FEATURE:
<221> NAME/KEY: MISC_FEATURE
<222> LOCATION: (72)..(72)
<223> OTHER INFORMATION: X is D/F/G/H/K/M/N/Q/R/S/T/V/W/Y
<220> FEATURE:
<221> NAME/KEY: MISC_FEATURE
<222> LOCATION: (73)..(73)
<223> OTHER INFORMATION: X is E/K
<220> FEATURE:
<221> NAME/KEY: MISC_FEATURE
<222> LOCATION: (74)..(74)
<223> OTHER INFORMATION: X is K/L
<220> FEATURE:
<221> NAME/KEY: MISC_FEATURE
<222> LOCATION: (76)..(76)
<223> OTHER INFORMATION: X is E/H/K
<220> FEATURE:
<221> NAME/KEY: MISC_FEATURE
<222> LOCATION: (78)..(78)
<223> OTHER INFORMATION: X is D/G
<220> FEATURE:
<221> NAME/KEY: MISC_FEATURE
<222> LOCATION: (79)..(79)
<223> OTHER INFORMATION: X is C/F/G/L/M/P/Q/R/S/V/W
<220> FEATURE:
<221> NAME/KEY: MISC_FEATURE
<222> LOCATION: (80)..(80)
<223> OTHER INFORMATION: X is A/C/D/F/G/I/V/Y
<220> FEATURE:
<221> NAME/KEY: MISC_FEATURE
<222> LOCATION: (81)..(81)
<223> OTHER INFORMATION: X is D/H/I/K/N/S/T/Y
<220> FEATURE:
<221> NAME/KEY: MISC_FEATURE
<222> LOCATION: (82)..(82)
<223> OTHER INFORMATION: X is A/C/F/I/L/N/P/S/T/Y
<220> FEATURE:
<221> NAME/KEY: MISC_FEATURE
<222> LOCATION: (83)..(83)
<223> OTHER INFORMATION: X is E/F/H/K/L/P/Q/R
<220> FEATURE:
<221> NAME/KEY: MISC_FEATURE
<222> LOCATION: (84)..(84)
<223> OTHER INFORMATION: X is A/E/H/K/P/Q/R
<220> FEATURE:
<221> NAME/KEY: MISC_FEATURE
<222> LOCATION: (85)..(85)
<223> OTHER INFORMATION: X is A/K/L/M/P/Q/R/V
<220> FEATURE:
<221> NAME/KEY: MISC_FEATURE
<222> LOCATION: (86)..(86)
<223> OTHER INFORMATION: X is A/D/E/G/L/N/R/V/Y
<220> FEATURE:
<221> NAME/KEY: MISC_FEATURE
<222> LOCATION: (87)..(87)
<223> OTHER INFORMATION: X is E/G/K/Q
<220> FEATURE:
<221> NAME/KEY: MISC_FEATURE
<222> LOCATION: (88)..(88)
<223> OTHER INFORMATION: X is L/M/P/R/T
<220> FEATURE:
<221> NAME/KEY: MISC_FEATURE
<222> LOCATION: (89)..(89)
<223> OTHER INFORMATION: X is A/C/G/H/P/Q/R
<220> FEATURE:
<221> NAME/KEY: MISC_FEATURE
<222> LOCATION: (90)..(90)
<223> OTHER INFORMATION: X is C/G/I/L/P/R/V
<220> FEATURE:
<221> NAME/KEY: MISC_FEATURE
<222> LOCATION: (91)..(91)
<223> OTHER INFORMATION: X is C/F/H/P/R/S/V/Y
<220> FEATURE:
<221> NAME/KEY: MISC_FEATURE
<222> LOCATION: (92)..(92)
<223> OTHER INFORMATION: X is F/L/M/P/Q/R
<220> FEATURE:
```

```
<221> NAME/KEY: MISC_FEATURE
<222> LOCATION: (93)..(93)
<223> OTHER INFORMATION: X is A/D/E/G/H/I/K/L/M/N/P/Q/R/S/T/V/Y
<220> FEATURE:
<221> NAME/KEY: MISC_FEATURE
<222> LOCATION: (94)..(94)
<223> OTHER INFORMATION: X is D/E/G/I/K/L/P/R/V
<220> FEATURE:
<221> NAME/KEY: MISC_FEATURE
<222> LOCATION: (95)..(95)
<223> OTHER INFORMATION: X is A/E/G/K/L/M/P/R/T/V
<220> FEATURE:
<221> NAME/KEY: MISC_FEATURE
<222> LOCATION: (96)..(96)
<223> OTHER INFORMATION: X is A/C/E/G/M/P/Q/S/T/V
<220> FEATURE:
<221> NAME/KEY: MISC_FEATURE
<222> LOCATION: (97)..(97)
<223> OTHER INFORMATION: X is A/D/E/G/H/K/N/Q/R/S/T/Y
<220> FEATURE:
<221> NAME/KEY: MISC_FEATURE
<222> LOCATION: (98)..(98)
<223> OTHER INFORMATION: X is C/D/E/F/G/M/Q/S/V/W
<220> FEATURE:
<221> NAME/KEY: MISC_FEATURE
<222> LOCATION: (99)..(99)
<223> OTHER INFORMATION: X is A/D/F/H/M/P/Q/S/T/V
<220> FEATURE:
<221> NAME/KEY: MISC_FEATURE
<222> LOCATION: (100)..(100)
<223> OTHER INFORMATION: X is A/D/G/S/T/V
<220> FEATURE:
<221> NAME/KEY: MISC_FEATURE
<222> LOCATION: (101)..(101)
<223> OTHER INFORMATION: X is A/C/D/E/G/H/I/L/M/N/Q/R/S/T/V/Y
<220> FEATURE:
<221> NAME/KEY: MISC_FEATURE
<222> LOCATION: (102)..(102)
<223> OTHER INFORMATION: X is A/E/G/I/K/M/R/S/T
<220> FEATURE:
<221> NAME/KEY: MISC_FEATURE
<222> LOCATION: (103)..(103)
<223> OTHER INFORMATION: X is A/E/F/G/S/T
<220> FEATURE:
<221> NAME/KEY: MISC_FEATURE
<222> LOCATION: (104)..(104)
<223> OTHER INFORMATION: X is D/H/K/M/N/P/Q/R
<220> FEATURE:
<221> NAME/KEY: MISC_FEATURE
<222> LOCATION: (105)..(105)
<223> OTHER INFORMATION: X is A/C/D/E/G/L/N/Q/S/V/Y
<220> FEATURE:
<221> NAME/KEY: MISC_FEATURE
<222> LOCATION: (106)..(106)
<223> OTHER INFORMATION: X is C/D/F/H/T/Y
<220> FEATURE:
<221> NAME/KEY: MISC_FEATURE
<222> LOCATION: (107)..(107)
<223> OTHER INFORMATION: X is C/D/G/L
<220> FEATURE:
<221> NAME/KEY: MISC_FEATURE
<222> LOCATION: (108)..(108)
<223> OTHER INFORMATION: X is C/E/H/L/R/S/T/Y
<220> FEATURE:
<221> NAME/KEY: MISC_FEATURE
<222> LOCATION: (109)..(109)
<223> OTHER INFORMATION: X is D/E/K/P/T
<220> FEATURE:
<221> NAME/KEY: MISC_FEATURE
<222> LOCATION: (110)..(110)
<223> OTHER INFORMATION: X is C/F/I/L/S/V/Y
<220> FEATURE:
<221> NAME/KEY: MISC_FEATURE
<222> LOCATION: (111)..(111)
<223> OTHER INFORMATION: X is E/F/H/K/Q/R/S/Y
<220> FEATURE:
<221> NAME/KEY: MISC_FEATURE
<222> LOCATION: (112)..(112)
<223> OTHER INFORMATION: X is H/I/L/N/P/Q/R/S/T
```

```
<220> FEATURE:
<221> NAME/KEY: MISC_FEATURE
<222> LOCATION: (113)..(113)
<223> OTHER INFORMATION: X is A/E/H/I/K/N/Q/Y
<220> FEATURE:
<221> NAME/KEY: MISC_FEATURE
<222> LOCATION: (114)..(114)
<223> OTHER INFORMATION: X is E/L/M/P/Q/V
<220> FEATURE:
<221> NAME/KEY: MISC_FEATURE
<222> LOCATION: (115)..(115)
<223> OTHER INFORMATION: X is D/E/G/H/K/L/N/S/V/W
<220> FEATURE:
<221> NAME/KEY: MISC_FEATURE
<222> LOCATION: (116)..(116)
<223> OTHER INFORMATION: X is C/D/G/H/L/R/Y

<400> SEQUENCE: 10

Xaa Xaa Xaa Xaa Xaa Xaa Xaa Xaa Xaa Xaa Xaa Xaa Xaa Xaa Xaa
1               5                   10                  15

Xaa Val Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Lys Leu Xaa Xaa Xaa
            35                  40                  45

Xaa Xaa Xaa Xaa Xaa Xaa Xaa Ala Ile Xaa Xaa Xaa Xaa Xaa Xaa Xaa
        50                  55                  60

Xaa Xaa Ala Xaa Xaa Glu Xaa Xaa Xaa Lys Xaa Ala Xaa Xaa Xaa
65              70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
                100                 105                 110

Xaa Xaa Xaa Xaa
        115

<210> SEQ ID NO 11
<211> LENGTH: 116
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X is A, D, F, G, H, K, L, M, P, R, S, T, V,
      W or Y
<220> FEATURE:
<221> NAME/KEY: MISC_FEATURE
<222> LOCATION: (2)..(2)
<223> OTHER INFORMATION: X is A, C, D, E, F, G, H, I, L, M, N, P, Q, S,
      T, V, W or Y
<220> FEATURE:
<221> NAME/KEY: MISC_FEATURE
<222> LOCATION: (3)..(3)
<223> OTHER INFORMATION: X is A, C, D, F, G, I, K, L, P, Q, R, S, T, V,
      W or Y
<220> FEATURE:
<221> NAME/KEY: MISC_FEATURE
<222> LOCATION: (4)..(4)
<223> OTHER INFORMATION: X is C, D, E, F, I, K, L, M, N, Q, R, T, V, W
      or Y
<220> FEATURE:
<221> NAME/KEY: MISC_FEATURE
<222> LOCATION: (5)..(5)
<223> OTHER INFORMATION: X is E, H, I, K, M, N, P, Q, R or T
<220> FEATURE:
<221> NAME/KEY: MISC_FEATURE
<222> LOCATION: (6)..(6)
<223> OTHER INFORMATION: X is A, D, E, F, G, I or V
<220> FEATURE:
```

-continued

```
<221> NAME/KEY: MISC_FEATURE
<222> LOCATION: (7)..(7)
<223> OTHER INFORMATION: X is A, E, F, H, L, M, P, Q, R, T, V, W or Y
<220> FEATURE:
<221> NAME/KEY: MISC_FEATURE
<222> LOCATION: (8)..(8)
<223> OTHER INFORMATION: X is A, C, D, E, G, H, I, K, L, M, N, P, R, S,
      V, W or Y
<220> FEATURE:
<221> NAME/KEY: MISC_FEATURE
<222> LOCATION: (9)..(9)
<223> OTHER INFORMATION: X is A, C, D, E, F, G, H, I, K, L, M, N, P, Q,
      R, S, T, V, W or Y
<220> FEATURE:
<221> NAME/KEY: MISC_FEATURE
<222> LOCATION: (10)..(10)
<223> OTHER INFORMATION: X is A, E, F, G, H, I, L, M, N, P, S, T, V, W
      or Y
<220> FEATURE:
<221> NAME/KEY: MISC_FEATURE
<222> LOCATION: (11)..(11)
<223> OTHER INFORMATION: X is E, F, I, K, L, M, N, Q, T, V, W or Y
<220> FEATURE:
<221> NAME/KEY: MISC_FEATURE
<222> LOCATION: (12)..(12)
<223> OTHER INFORMATION: X is A, D, E, G, H, I, K, L, M, N, R, V, W or Y
<220> FEATURE:
<221> NAME/KEY: MISC_FEATURE
<222> LOCATION: (13)..(13)
<223> OTHER INFORMATION: X is A, D, E, G, H, I, K, L, M, N, R, V, W or Y
<220> FEATURE:
<221> NAME/KEY: MISC_FEATURE
<222> LOCATION: (14)..(14)
<223> OTHER INFORMATION: X is C, D, E, H, I, K, L, M, P, Q, W or Y
<220> FEATURE:
<221> NAME/KEY: MISC_FEATURE
<222> LOCATION: (15)..(15)
<223> OTHER INFORMATION: X is A, C, E, F, G, I, L, M, N, Q, S, T, V, W
      or Y
<220> FEATURE:
<221> NAME/KEY: MISC_FEATURE
<222> LOCATION: (16)..(16)
<223> OTHER INFORMATION: X is A, C, D, E, F, G, K, L, M, N, S, V or Y
<220> FEATURE:
<221> NAME/KEY: MISC_FEATURE
<222> LOCATION: (17)..(17)
<223> OTHER INFORMATION: X is A, D, E, G, H, I, K, N, Q, S, T, V or W
<220> FEATURE:
<221> NAME/KEY: MISC_FEATURE
<222> LOCATION: (18)..(18)
<223> OTHER INFORMATION: X is A, H, I, L, P, R, S, T or V
<220> FEATURE:
<221> NAME/KEY: MISC_FEATURE
<222> LOCATION: (19)..(19)
<223> OTHER INFORMATION: X is A, D, G, H, M, S, T or V
<220> FEATURE:
<221> NAME/KEY: MISC_FEATURE
<222> LOCATION: (20)..(20)
<223> OTHER INFORMATION: X is A, C, E, G, H, L, M, R, T or W
<220> FEATURE:
<221> NAME/KEY: MISC_FEATURE
<222> LOCATION: (21)..(21)
<223> OTHER INFORMATION: X is A, D, E, F, G, H, I, K, L, M, N, P, Q, R,
      S, T, V, W or Y
<220> FEATURE:
<221> NAME/KEY: MISC_FEATURE
<222> LOCATION: (22)..(22)
<223> OTHER INFORMATION: X is A, F, G, H, I, K, L, M, N, P, Q, R, S, T,
      V, W or Y
<220> FEATURE:
<221> NAME/KEY: MISC_FEATURE
<222> LOCATION: (23)..(23)
<223> OTHER INFORMATION: X is E, G, H, I, K, L, M, N, Q, R, T, W or Y
<220> FEATURE:
<221> NAME/KEY: MISC_FEATURE
<222> LOCATION: (24)..(24)
<223> OTHER INFORMATION: X is A, D, E, H, K, M, N, Q, R, S, T or W
<220> FEATURE:
<221> NAME/KEY: MISC_FEATURE
```

```
<222> LOCATION: (26)..(26)
<223> OTHER INFORMATION: X is A, C, E, F, G, H, I, K, L, M, P, Q, R, S,
      T, V, W or Y
<220> FEATURE:
<221> NAME/KEY: MISC_FEATURE
<222> LOCATION: (27)..(27)
<223> OTHER INFORMATION: X is A, C, D, E, F, G, H, K, L, M, Q, R, S, V,
      W or Y
<220> FEATURE:
<221> NAME/KEY: MISC_FEATURE
<222> LOCATION: (28)..(28)
<223> OTHER INFORMATION: X is A, D, E, F, G, H, I, K, L, M, N, Q, R, S,
      T, V, W or Y
<220> FEATURE:
<221> NAME/KEY: MISC_FEATURE
<222> LOCATION: (29)..(29)
<223> OTHER INFORMATION: X is I, L, S, T or V
<220> FEATURE:
<221> NAME/KEY: MISC_FEATURE
<222> LOCATION: (30)..(30)
<223> OTHER INFORMATION: X is A, C, D, F, G, H, I, L, M, P, R, S, T, V,
      W or Y
<220> FEATURE:
<221> NAME/KEY: MISC_FEATURE
<222> LOCATION: (31)..(31)
<223> OTHER INFORMATION: X is H, I, K, N, Q, T or Y
<220> FEATURE:
<221> NAME/KEY: MISC_FEATURE
<222> LOCATION: (32)..(32)
<223> OTHER INFORMATION: X is A, C, D, E, F, G, H, I, K, L, M, N, P, Q,
      R, S, T, V, W or Y
<220> FEATURE:
<221> NAME/KEY: MISC_FEATURE
<222> LOCATION: (33)..(33)
<223> OTHER INFORMATION: X is A, C, D, F, G, H, I, L, M, P, R, S, V, W
      or Y
<220> FEATURE:
<221> NAME/KEY: MISC_FEATURE
<222> LOCATION: (34)..(34)
<223> OTHER INFORMATION: X is C, H, K, M, N, R, S, T or Y
<220> FEATURE:
<221> NAME/KEY: MISC_FEATURE
<222> LOCATION: (34)..(34)
<223> OTHER INFORMATION: X is K, L, N or R
<220> FEATURE:
<221> NAME/KEY: MISC_FEATURE
<222> LOCATION: (35)..(35)
<223> OTHER INFORMATION: X is F, H, I, L, P or R
<220> FEATURE:
<221> NAME/KEY: MISC_FEATURE
<222> LOCATION: (36)..(36)
<223> OTHER INFORMATION: X is A, D, E, F, G, H, I, K, L, M, N, P, Q, R,
      S, T, V, W or Y
<220> FEATURE:
<221> NAME/KEY: MISC_FEATURE
<222> LOCATION: (37)..(37)
<223> OTHER INFORMATION: X is A, D, E, F, H, I, K, L, M, N, P, Q, R, S,
      T, V or W
<220> FEATURE:
<221> NAME/KEY: MISC_FEATURE
<222> LOCATION: (38)..(38)
<223> OTHER INFORMATION: X is A, D, E, G, H, I, K, M, N, P, Q, R, S, T,
      V or Y
<220> FEATURE:
<221> NAME/KEY: MISC_FEATURE
<222> LOCATION: (39)..(39)
<223> OTHER INFORMATION: X is A, E, G, H, I, K, L, M, N, P, Q, S, T or V
<220> FEATURE:
<221> NAME/KEY: MISC_FEATURE
<222> LOCATION: (40)..(40)
<223> OTHER INFORMATION: X is A, D, E, F, G, K, N or Y
<220> FEATURE:
<221> NAME/KEY: MISC_FEATURE
<222> LOCATION: (41)..(41)
<223> OTHER INFORMATION: X is A, F, G, H, I, K, L, M, P, S, T, W or Y
<220> FEATURE:
<221> NAME/KEY: MISC_FEATURE
<222> LOCATION: (42)..(42)
<223> OTHER INFORMATION: X is A, C, D, E, F, G, H, I, L, M, N, P, Q, R,
```

```
        S, V, W or Y
<220> FEATURE:
<221> NAME/KEY: MISC_FEATURE
<222> LOCATION: (43)..(43)
<223> OTHER INFORMATION: X is A, E, G, H, I, K, L, M, N, P, Q, R, S, T
      or V
<220> FEATURE:
<221> NAME/KEY: MISC_FEATURE
<222> LOCATION: (44)..(44)
<223> OTHER INFORMATION: X is K, N, Q, R or T
<220> FEATURE:
<221> NAME/KEY: MISC_FEATURE
<222> LOCATION: (45)..(45)
<223> OTHER INFORMATION: X is I, L, P or V
<220> FEATURE:
<221> NAME/KEY: MISC_FEATURE
<222> LOCATION: (46)..(46)
<223> OTHER INFORMATION: X is A, D, E, F, G, H, K, L, N, P, Q, R, S or W
<220> FEATURE:
<221> NAME/KEY: MISC_FEATURE
<222> LOCATION: (47)..(47)
<223> OTHER INFORMATION: X is A, D, E, F, H, I, L, M, N, P, T, V or Y
<220> FEATURE:
<221> NAME/KEY: MISC_FEATURE
<222> LOCATION: (48)..(48)
<223> OTHER INFORMATION: X is A, E or G
<220> FEATURE:
<221> NAME/KEY: MISC_FEATURE
<222> LOCATION: (49)..(49)
<223> OTHER INFORMATION: X is A, C, D, E, F, G, H, I, K, L, M, N, P, Q,
        S, T, V, W or Y
<220> FEATURE:
<221> NAME/KEY: MISC_FEATURE
<222> LOCATION: (50)..(50)
<223> OTHER INFORMATION: X is F, I, L, M, N, S or T
<220> FEATURE:
<221> NAME/KEY: MISC_FEATURE
<222> LOCATION: (52)..(52)
<223> OTHER INFORMATION: X is A, E, F, G, I, L, S, T, V, W or Y
<220> FEATURE:
<221> NAME/KEY: MISC_FEATURE
<222> LOCATION: (53)..(53)
<223> OTHER INFORMATION: X is C, F, G, I, L, M, N, P, V, W or Y
<220> FEATURE:
<221> NAME/KEY: MISC_FEATURE
<222> LOCATION: (54)..(54)
<223> OTHER INFORMATION: X is L or M
<220> FEATURE:
<221> NAME/KEY: MISC_FEATURE
<222> LOCATION: (55)..(55)
<223> OTHER INFORMATION: X is A or G
<220> FEATURE:
<221> NAME/KEY: MISC_FEATURE
<222> LOCATION: (56)..(56)
<223> OTHER INFORMATION: X is A, C, F, G, L, M, N, T, V, W or Y
<220> FEATURE:
<221> NAME/KEY: MISC_FEATURE
<222> LOCATION: (57)..(57)
<223> OTHER INFORMATION: X is H, I, N, T or V
<220> FEATURE:
<221> NAME/KEY: MISC_FEATURE
<222> LOCATION: (59)..(59)
<223> OTHER INFORMATION: X is A, D, E, N, V or Y
<220> FEATURE:
<221> NAME/KEY: MISC_FEATURE
<222> LOCATION: (60)..(60)
<223> OTHER INFORMATION: X is F, I, L or W
<220> FEATURE:
<221> NAME/KEY: MISC_FEATURE
<222> LOCATION: (61)..(61)
<223> OTHER INFORMATION: X is I, L or V
<220> FEATURE:
<221> NAME/KEY: MISC_FEATURE
<222> LOCATION: (62)..(62)
<223> OTHER INFORMATION: X is D, H, K, N, S or T
<220> FEATURE:
<221> NAME/KEY: MISC_FEATURE
<222> LOCATION: (63)..(63)
<223> OTHER INFORMATION: X is A, C, D, E, F, G, I, L, M, N, Q, S, T or V
```

```
<220> FEATURE:
<221> NAME/KEY: MISC_FEATURE
<222> LOCATION: (64)..(64)
<223> OTHER INFORMATION: X is C, E, I, M, T, V or W
<220> FEATURE:
<221> NAME/KEY: MISC_FEATURE
<222> LOCATION: (65)..(65)
<223> OTHER INFORMATION: X is M or W
<220> FEATURE:
<221> NAME/KEY: MISC_FEATURE
<222> LOCATION: (66)..(66)
<223> OTHER INFORMATION: X is C, D, E, G, H, K, L, M, N, P, Q, R, S or T
<220> FEATURE:
<221> NAME/KEY: MISC_FEATURE
<222> LOCATION: (67)..(67)
<223> OTHER INFORMATION: X is A, D, E, G, H, N, R, S, W or Y
<220> FEATURE:
<221> NAME/KEY: MISC_FEATURE
<222> LOCATION: (68)..(68)
<223> OTHER INFORMATION: X is K, M, N, P, R, T, W or Y
<220> FEATURE:
<221> NAME/KEY: MISC_FEATURE
<222> LOCATION: (69)..(69)
<223> OTHER INFORMATION: X is A, C, D, E, F, G, H, I, K, L, N, P, Q, R,
     S, T, V, W or Y
<220> FEATURE:
<221> NAME/KEY: MISC_FEATURE
<222> LOCATION: (70)..(70)
<223> OTHER INFORMATION: X is A, D, E, I, K, M, N or W
<220> FEATURE:
<221> NAME/KEY: MISC_FEATURE
<222> LOCATION: (71)..(71)
<223> OTHER INFORMATION: X is A, P or T
<220> FEATURE:
<221> NAME/KEY: MISC_FEATURE
<222> LOCATION: (72)..(72)
<223> OTHER INFORMATION: X is A, D, E, F, G, H, I, N, P, V, W or Y
<220> FEATURE:
<221> NAME/KEY: MISC_FEATURE
<222> LOCATION: (73)..(73)
<223> OTHER INFORMATION: X is A, D, E, F, G, H, I, K, L, M, N, P, Q, R,
     S, T, V, W or Y
<220> FEATURE:
<221> NAME/KEY: MISC_FEATURE
<222> LOCATION: (74)..(74)
<223> OTHER INFORMATION: X is A, C, D, E, F, H, I, L, M, P, Q, R, T or V
<220> FEATURE:
<221> NAME/KEY: MISC_FEATURE
<222> LOCATION: (75)..(75)
<223> OTHER INFORMATION: X is A, E, H, I, K, N, P, R, S or W
<220> FEATURE:
<221> NAME/KEY: MISC_FEATURE
<222> LOCATION: (76)..(76)
<223> OTHER INFORMATION: X is A, D, E, F, G, H, I, K, L, M, N, P, Q, R,
     S, T, V, W or Y
<220> FEATURE:
<221> NAME/KEY: MISC_FEATURE
<222> LOCATION: (77)..(77)
<223> OTHER INFORMATION: X is A, D, E, F, G, H, K, L, N, P, Q, R, S, T,
     V, W or Y
<220> FEATURE:
<221> NAME/KEY: MISC_FEATURE
<222> LOCATION: (78)..(78)
<223> OTHER INFORMATION: X is G, K, N, P, Q or R
<220> FEATURE:
<221> NAME/KEY: MISC_FEATURE
<222> LOCATION: (79)..(79)
<223> OTHER INFORMATION: X is F, G, I, L, M, P, Q, R, S, T, V, W or Y
<220> FEATURE:
<221> NAME/KEY: MISC_FEATURE
<222> LOCATION: (80)..(80)
<223> OTHER INFORMATION: X is A, D, G, I, P, R or V
<220> FEATURE:
<221> NAME/KEY: MISC_FEATURE
<222> LOCATION: (81)..(81)
<223> OTHER INFORMATION: X is I, K, N, R or S
<220> FEATURE:
<221> NAME/KEY: MISC_FEATURE
<222> LOCATION: (82)..(82)
```

```
<223> OTHER INFORMATION: X is A, C, E, F, G, H, I, K, L, M, N, P, R, S,
      T, V, W or Y
<220> FEATURE:
<221> NAME/KEY: MISC_FEATURE
<222> LOCATION: (83)..(83)
<223> OTHER INFORMATION: X is A, F, H, I, K, L, N, P, Q, R, T, V or Y
<220> FEATURE:
<221> NAME/KEY: MISC_FEATURE
<222> LOCATION: (84)..(84)
<223> OTHER INFORMATION: X is G, H, I, K, L, M, Q, R, S or T
<220> FEATURE:
<221> NAME/KEY: MISC_FEATURE
<222> LOCATION: (85)..(85)
<223> OTHER INFORMATION: X is A, C, E, H, K, L, M, P, Q, R or V
<220> FEATURE:
<221> NAME/KEY: MISC_FEATURE
<222> LOCATION: (86)..(86)
<223> OTHER INFORMATION: X is A, C, D, E, F, G, H, I, K, L, M, N, Q, R,
      S, T, V, W or Y
<220> FEATURE:
<221> NAME/KEY: MISC_FEATURE
<222> LOCATION: (87)..(87)
<223> OTHER INFORMATION: X is A, D, E, F, G, H, I, K, M, N, P, Q, R, S,
      T or V
<220> FEATURE:
<221> NAME/KEY: MISC_FEATURE
<222> LOCATION: (88)..(88)
<223> OTHER INFORMATION: X is A, C, E, L, M, N, R, S, T or Y
<220> FEATURE:
<221> NAME/KEY: MISC_FEATURE
<222> LOCATION: (89)..(89)
<223> OTHER INFORMATION: X is A, C, D, E, F, G, H, I, K, L, M, N, P, Q,
      R, S, T, V, W or Y
<220> FEATURE:
<221> NAME/KEY: MISC_FEATURE
<222> LOCATION: (90)..(90)
<223> OTHER INFORMATION: X is D, H, K, R or T
<220> FEATURE:
<221> NAME/KEY: MISC_FEATURE
<222> LOCATION: (91)..(91)
<223> OTHER INFORMATION: X is K, R, W or Y
<220> FEATURE:
<221> NAME/KEY: MISC_FEATURE
<222> LOCATION: (92)..(92)
<223> OTHER INFORMATION: X is A, C, I, L, M, N, P, Q, S or T
<220> FEATURE:
<221> NAME/KEY: MISC_FEATURE
<222> LOCATION: (93)..(93)
<223> OTHER INFORMATION: X is A, E, I, K, L, P, Q, R, T or V
<220> FEATURE:
<221> NAME/KEY: MISC_FEATURE
<222> LOCATION: (94)..(94)
<223> OTHER INFORMATION: X is D, E, F, G, I, K, L, M, N, Q, R, S, T, V,
      W or Y
<220> FEATURE:
<221> NAME/KEY: MISC_FEATURE
<222> LOCATION: (95)..(95)
<223> OTHER INFORMATION: X is A, E, F, G, H, I, K, L, M, N, P, Q, R, S,
      T, V, W or Y
<220> FEATURE:
<221> NAME/KEY: MISC_FEATURE
<222> LOCATION: (96)..(96)
<223> OTHER INFORMATION: X is K or Y
<220> FEATURE:
<221> NAME/KEY: MISC_FEATURE
<222> LOCATION: (97)..(97)
<223> OTHER INFORMATION: X is A, D, E, N or S
<220> FEATURE:
<221> NAME/KEY: MISC_FEATURE
<222> LOCATION: (98)..(98)
<223> OTHER INFORMATION: X is A, E, F, G, M, Q, R, T, V, W or Y
<220> FEATURE:
<221> NAME/KEY: MISC_FEATURE
<222> LOCATION: (99)..(99)
<223> OTHER INFORMATION: X is A, E, F, I or T
<220> FEATURE:
<221> NAME/KEY: MISC_FEATURE
<222> LOCATION: (100)..(100)
<223> OTHER INFORMATION: X is F, L, N or Y
```

```
<220> FEATURE:
<221> NAME/KEY: MISC_FEATURE
<222> LOCATION: (101)..(101)
<223> OTHER INFORMATION: X is H, Q, R or S
<220> FEATURE:
<221> NAME/KEY: MISC_FEATURE
<222> LOCATION: (102)..(102)
<223> OTHER INFORMATION: X is A, E, G, H, I, K, N, Q, R, S, V or W
<220> FEATURE:
<221> NAME/KEY: MISC_FEATURE
<222> LOCATION: (103)..(103)
<223> OTHER INFORMATION: X is A, C, E, F, G, H, I, K, L, M, N, P, Q, S,
      T, V or Y
<220> FEATURE:
<221> NAME/KEY: MISC_FEATURE
<222> LOCATION: (104)..(104)
<223> OTHER INFORMATION: X is A, C, D, E, G, H, K, N, P, Q, R, S, T or Y
<220> FEATURE:
<221> NAME/KEY: MISC_FEATURE
<222> LOCATION: (105)..(105)
<223> OTHER INFORMATION: X is A, D, E, F, G, I, L, P, Q or V
<220> FEATURE:
<221> NAME/KEY: MISC_FEATURE
<222> LOCATION: (106)..(106)
<223> OTHER INFORMATION: X is A, C, D, E, F, G, H, I, K, L, N, P, Q, R,
      S, T, V, W or Y
<220> FEATURE:
<221> NAME/KEY: MISC_FEATURE
<222> LOCATION: (107)..(107)
<223> OTHER INFORMATION: X is A, C, D, F, G, I, L, M, N, P, Q, R, S, T,
      V or W
<220> FEATURE:
<221> NAME/KEY: MISC_FEATURE
<222> LOCATION: (108)..(108)
<223> OTHER INFORMATION: X is A, D, E, G, H, K, N, P, Q, R or S
<220> FEATURE:
<221> NAME/KEY: MISC_FEATURE
<222> LOCATION: (109)..(109)
<223> OTHER INFORMATION: X is D, E, F, M, P, V or Y
<220> FEATURE:
<221> NAME/KEY: MISC_FEATURE
<222> LOCATION: (110)..(110)
<223> OTHER INFORMATION: X is A, C, D, E, F, G, H, I, K, L, M, N, P, Q,
      R, S, T, V, W or Y
<220> FEATURE:
<221> NAME/KEY: MISC_FEATURE
<222> LOCATION: (111)..(111)
<223> OTHER INFORMATION: X is A, C, D, E, F, G, H, I, K, L, M, N, P, Q,
      R, S, T, V, W or Y
<220> FEATURE:
<221> NAME/KEY: MISC_FEATURE
<222> LOCATION: (112)..(112)
<223> OTHER INFORMATION: X is A, C, D, E, G, H, K, L, M, N, P, Q, R, S,
      T, V, W or Y
<220> FEATURE:
<221> NAME/KEY: MISC_FEATURE
<222> LOCATION: (113)..(113)
<223> OTHER INFORMATION: X is A, E, I, K, P, Q or R
<220> FEATURE:
<221> NAME/KEY: MISC_FEATURE
<222> LOCATION: (114)..(114)
<223> OTHER INFORMATION: X is A, C, D, E, F, G, H, I, K, L, M, N, P, Q,
      R, S, V, W or Y
<220> FEATURE:
<221> NAME/KEY: MISC_FEATURE
<222> LOCATION: (115)..(115)
<223> OTHER INFORMATION: X is A, D, E, G, H, K, L, M, N, P, Q, R, S, T,
      V or W
<220> FEATURE:
<221> NAME/KEY: MISC_FEATURE
<222> LOCATION: (116)..(116)
<223> OTHER INFORMATION: X is A, C, D, E, F, G, H, K, L, M, N, P, Q, R,
      S, T, W or Y

<400> SEQUENCE: 11

Xaa Xaa Xaa Xaa Xaa Xaa Xaa Xaa Xaa Xaa Xaa Xaa Xaa Xaa Xaa Xaa
1               5                   10                  15
```

Xaa Xaa Xaa Xaa Xaa Xaa Xaa Lys Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

Xaa Xaa Gly Xaa Xaa Xaa Xaa Xaa Gly Xaa Xaa Xaa Xaa Xaa
        50                  55                  60

Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa
        115

<210> SEQ ID NO 12
<211> LENGTH: 116
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X is A/E/G/H/I/K/M/P/R/S/T/V/W/Y
<220> FEATURE:
<221> NAME/KEY: MISC_FEATURE
<222> LOCATION: (2)..(2)
<223> OTHER INFORMATION: X is A/C/D/E/F/G/H/I/K/L/M/N/P/Q/R/S/T/V/W/Y
<220> FEATURE:
<221> NAME/KEY: MISC_FEATURE
<222> LOCATION: (3)..(3)
<223> OTHER INFORMATION: X is A/C/D/E/F/G/H/K/L/M/N/P/Q/R/S/T/V/W/Y
<220> FEATURE:
<221> NAME/KEY: MISC_FEATURE
<222> LOCATION: (4)..(4)
<223> OTHER INFORMATION: X is A/E/G/H/I/K/M/N/P/Q/R/T/V/W
<220> FEATURE:
<221> NAME/KEY: MISC_FEATURE
<222> LOCATION: (5)..(5)
<223> OTHER INFORMATION: X is F/G/I/K/L/Q/R/T/V/W
<220> FEATURE:
<221> NAME/KEY: MISC_FEATURE
<222> LOCATION: (6)..(6)
<223> OTHER INFORMATION: X is A/F/G/I/L/P/S/V/W
<220> FEATURE:
<221> NAME/KEY: MISC_FEATURE
<222> LOCATION: (7)..(7)
<223> OTHER INFORMATION: X is A/D/E/G/I/L/M/Q/R/S/T/V/W/Y
<220> FEATURE:
<221> NAME/KEY: MISC_FEATURE
<222> LOCATION: (8)..(8)
<223> OTHER INFORMATION: X is A/C/D/F/G/I/K/L/N/P/Q/R/S/V/W/Y
<220> FEATURE:
<221> NAME/KEY: MISC_FEATURE
<222> LOCATION: (9)..(9)
<223> OTHER INFORMATION: X is H/K/L/N/Q/R/W
<220> FEATURE:
<221> NAME/KEY: MISC_FEATURE
<222> LOCATION: (10)..(10)
<223> OTHER INFORMATION: X is A/H/S/T
<220> FEATURE:
<221> NAME/KEY: MISC_FEATURE
<222> LOCATION: (11)..(11)
<223> OTHER INFORMATION: X is A/D/E/G/H/K/N/Q/R/S/T/Y
<220> FEATURE:
<221> NAME/KEY: MISC_FEATURE
<222> LOCATION: (12)..(12)
<223> OTHER INFORMATION: X is A/D/E/F/G/H/K/L/M/N/Q/R/S/T/V/W/Y
<220> FEATURE:
<221> NAME/KEY: MISC_FEATURE
<222> LOCATION: (13)..(13)

```
<223> OTHER INFORMATION: X is D/E/G/I/K/L/M/N/Q/R/S/T/V/W/Y
<220> FEATURE:
<221> NAME/KEY: MISC_FEATURE
<222> LOCATION: (14)..(14)
<223> OTHER INFORMATION: X is A/C/I/L/M/N/Q/S/T/V
<220> FEATURE:
<221> NAME/KEY: MISC_FEATURE
<222> LOCATION: (15)..(15)
<223> OTHER INFORMATION: X is A/D/E/M/N/R/V/W/Y
<220> FEATURE:
<221> NAME/KEY: MISC_FEATURE
<222> LOCATION: (16)..(16)
<223> OTHER INFORMATION: X is A/D/F/G/H/I/K/L/M/N/P/Q/R/S/T/V/W/Y
<220> FEATURE:
<221> NAME/KEY: MISC_FEATURE
<222> LOCATION: (17)..(17)
<223> OTHER INFORMATION: X is A/C/E/G/H/I/K/L/M/P/R/S/T/V
<220> FEATURE:
<221> NAME/KEY: MISC_FEATURE
<222> LOCATION: (18)..(18)
<223> OTHER INFORMATION: X is A/I/K/M/T/V
<220> FEATURE:
<221> NAME/KEY: MISC_FEATURE
<222> LOCATION: (19)..(19)
<223> OTHER INFORMATION: X is A/C/D/E/F/G/K/L/M/N/Q/R/T/V/W/Y
<220> FEATURE:
<221> NAME/KEY: MISC_FEATURE
<222> LOCATION: (20)..(20)
<223> OTHER INFORMATION: X is A/D/E/F/G/I/K/L/M/N/Q/R/S/T/V/W/Y
<220> FEATURE:
<221> NAME/KEY: MISC_FEATURE
<222> LOCATION: (21)..(21)
<223> OTHER INFORMATION: X is F/H/I/L/M/Q/T/Y
<220> FEATURE:
<221> NAME/KEY: MISC_FEATURE
<222> LOCATION: (22)..(22)
<223> OTHER INFORMATION: X is A/C/H/I/K/Q/R
<220> FEATURE:
<221> NAME/KEY: MISC_FEATURE
<222> LOCATION: (23)..(23)
<223> OTHER INFORMATION: X is A/C/E/F/G/H/I/M/N/Q/R/S/T/W/Y
<220> FEATURE:
<221> NAME/KEY: MISC_FEATURE
<222> LOCATION: (24)..(24)
<223> OTHER INFORMATION: X is A/D/G/H/I/K/N/Q/R/T/Y/V
<220> FEATURE:
<221> NAME/KEY: MISC_FEATURE
<222> LOCATION: (25)..(25)
<223> OTHER INFORMATION: X is I/L/M/Q
<220> FEATURE:
<221> NAME/KEY: MISC_FEATURE
<222> LOCATION: (26)..(26)
<223> OTHER INFORMATION: X is A/C/D/E/G/I/K/N/Q/R/S/T/V/W
<220> FEATURE:
<221> NAME/KEY: MISC_FEATURE
<222> LOCATION: (27)..(27)
<223> OTHER INFORMATION: X is A/C/D/E/F/G/H/I/K/L/M/N/Q/R/S/T/V/W/Y
<220> FEATURE:
<221> NAME/KEY: MISC_FEATURE
<222> LOCATION: (28)..(28)
<223> OTHER INFORMATION: X is C/F/H/I/K/L/M/N/P/R/T/V/Y
<220> FEATURE:
<221> NAME/KEY: MISC_FEATURE
<222> LOCATION: (29)..(29)
<223> OTHER INFORMATION: X is A/D/E/H/I/L/P/Q/R/W/Y
<220> FEATURE:
<221> NAME/KEY: MISC_FEATURE
<222> LOCATION: (30)..(30)
<223> OTHER INFORMATION: X is A/E/F/G/H/K/L/M/N/Q/R/S/T/W/Y
<220> FEATURE:
<221> NAME/KEY: MISC_FEATURE
<222> LOCATION: (31)..(31)
<223> OTHER INFORMATION: X is A/D/E/F/G/H/I/K/L/M/N/Q/R/S/T/V/W/Y
<220> FEATURE:
<221> NAME/KEY: MISC_FEATURE
<222> LOCATION: (32)..(32)
<223> OTHER INFORMATION: X is A/F/G/H/K/L/N/P/R/S/T/Y
<220> FEATURE:
<221> NAME/KEY: MISC_FEATURE
```

```
<222> LOCATION: (33)..(33)
<223> OTHER INFORMATION: X is F/H/I/K/L/M/P/Q/R/T/V/Y
<220> FEATURE:
<221> NAME/KEY: MISC_FEATURE
<222> LOCATION: (34)..(34)
<223> OTHER INFORMATION: X is C/H/I/K/L/M/Q/R/S/T/V/Y
<220> FEATURE:
<221> NAME/KEY: MISC_FEATURE
<222> LOCATION: (35)..(35)
<223> OTHER INFORMATION: X is A/D/E/F/G/H/I/K/L/M/N/P/Q/R/S/T/V/W
<220> FEATURE:
<221> NAME/KEY: MISC_FEATURE
<222> LOCATION: (36)..(36)
<223> OTHER INFORMATION: X is A/C/D/E/G/H/K/L/M/N/Q/R/S/T/V/W/Y
<220> FEATURE:
<221> NAME/KEY: MISC_FEATURE
<222> LOCATION: (37)..(37)
<223> OTHER INFORMATION: X is A/D/E/F/H/I/K/L/M/N/P/Q/R/S/T/V/W/Y
<220> FEATURE:
<221> NAME/KEY: MISC_FEATURE
<222> LOCATION: (38)..(38)
<223> OTHER INFORMATION: X is A/D/E/G/K/N/P/Q/R/S/T
<220> FEATURE:
<221> NAME/KEY: MISC_FEATURE
<222> LOCATION: (39)..(39)
<223> OTHER INFORMATION: X is A/D/E/G/K/N/P/Q/R/S/T/V
<220> FEATURE:
<221> NAME/KEY: MISC_FEATURE
<222> LOCATION: (40)..(40)
<223> OTHER INFORMATION: X is A/D/E/F/G/H/I/K/L/M/N/P/Q/R/S/T/V
<220> FEATURE:
<221> NAME/KEY: MISC_FEATURE
<222> LOCATION: (41)..(41)
<223> OTHER INFORMATION: X is F/G/H/K/L/M/N/Q/R/T/V/W/Y
<220> FEATURE:
<221> NAME/KEY: MISC_FEATURE
<222> LOCATION: (42)..(42)
<223> OTHER INFORMATION: X is K/R
<220> FEATURE:
<221> NAME/KEY: MISC_FEATURE
<222> LOCATION: (44)..(44)
<223> OTHER INFORMATION: X is K/R
<220> FEATURE:
<221> NAME/KEY: MISC_FEATURE
<222> LOCATION: (45)..(45)
<223> OTHER INFORMATION: X is F/G/I/L/Q/V/W/Y
<220> FEATURE:
<221> NAME/KEY: MISC_FEATURE
<222> LOCATION: (46)..(46)
<223> OTHER INFORMATION: X is D/E/M/N/Q/T/I
<220> FEATURE:
<221> NAME/KEY: MISC_FEATURE
<222> LOCATION: (47)..(47)
<223> OTHER INFORMATION: X is F/L/M/W/E
<220> FEATURE:
<221> NAME/KEY: MISC_FEATURE
<222> LOCATION: (49)..(49)
<223> OTHER INFORMATION: X is E/F/W/Y
<220> FEATURE:
<221> NAME/KEY: MISC_FEATURE
<222> LOCATION: (51)..(51)
<223> OTHER INFORMATION: X is A/G
<220> FEATURE:
<221> NAME/KEY: MISC_FEATURE
<222> LOCATION: (52)..(52)
<223> OTHER INFORMATION: X is A/F/I/Q
<220> FEATURE:
<221> NAME/KEY: MISC_FEATURE
<222> LOCATION: (53)..(53)
<223> OTHER INFORMATION: X is D/H/L/M/N/W/I
<220> FEATURE:
<221> NAME/KEY: MISC_FEATURE
<222> LOCATION: (54)..(54)
<223> OTHER INFORMATION: X is I/L
<220> FEATURE:
<221> NAME/KEY: MISC_FEATURE
<222> LOCATION: (55)..(55)
<223> OTHER INFORMATION: X is G/I/M/S/V/R
<220> FEATURE:
```

```
<221> NAME/KEY: MISC_FEATURE
<222> LOCATION: (56)..(56)
<223> OTHER INFORMATION: X is A/C/F/G/I/L/M/P/S/T/V
<220> FEATURE:
<221> NAME/KEY: MISC_FEATURE
<222> LOCATION: (57)..(57)
<223> OTHER INFORMATION: X is A/I/M/S/T/V
<220> FEATURE:
<221> NAME/KEY: MISC_FEATURE
<222> LOCATION: (60)..(60)
<223> OTHER INFORMATION: X is I/L/M
<220> FEATURE:
<221> NAME/KEY: MISC_FEATURE
<222> LOCATION: (61)..(61)
<223> OTHER INFORMATION: X is F/M/W/Y/N
<220> FEATURE:
<221> NAME/KEY: MISC_FEATURE
<222> LOCATION: (62)..(62)
<223> OTHER INFORMATION: X is A/D/F/G/I/L/M/N/Q/S/T/V/W
<220> FEATURE:
<221> NAME/KEY: MISC_FEATURE
<222> LOCATION: (63)..(63)
<223> OTHER INFORMATION: X is A/F/I/L/M/T/V/Y
<220> FEATURE:
<221> NAME/KEY: MISC_FEATURE
<222> LOCATION: (64)..(64)
<223> OTHER INFORMATION: X is A/H/I/M/Y
<220> FEATURE:
<221> NAME/KEY: MISC_FEATURE
<222> LOCATION: (65)..(65)
<223> OTHER INFORMATION: X is R/Y
<220> FEATURE:
<221> NAME/KEY: MISC_FEATURE
<222> LOCATION: (66)..(66)
<223> OTHER INFORMATION: X is A/F/I/K/L/M/Q/R/V/W/Y
<220> FEATURE:
<221> NAME/KEY: MISC_FEATURE
<222> LOCATION: (67)..(67)
<223> OTHER INFORMATION: X is A/G
<220> FEATURE:
<221> NAME/KEY: MISC_FEATURE
<222> LOCATION: (68)..(68)
<223> OTHER INFORMATION: X is K/Q/R
<220> FEATURE:
<221> NAME/KEY: MISC_FEATURE
<222> LOCATION: (69)..(69)
<223> OTHER INFORMATION: X is A/F/G/I/K/L/N/Q/R/S/T/V/W/Y
<220> FEATURE:
<221> NAME/KEY: MISC_FEATURE
<222> LOCATION: (70)..(70)
<223> OTHER INFORMATION: X is A/D/E/F/G/H/I/K/L/M/N/Q/R/S/T/V/W/Y
<220> FEATURE:
<221> NAME/KEY: MISC_FEATURE
<222> LOCATION: (71)..(71)
<223> OTHER INFORMATION: X is A/G/I/M/S
<220> FEATURE:
<221> NAME/KEY: MISC_FEATURE
<222> LOCATION: (72)..(72)
<223> OTHER INFORMATION: X is A/D/E/F/G/H/I/L/M/Q/S/T/V/W/Y
<220> FEATURE:
<221> NAME/KEY: MISC_FEATURE
<222> LOCATION: (73)..(73)
<223> OTHER INFORMATION: X is F/K/R/Y
<220> FEATURE:
<221> NAME/KEY: MISC_FEATURE
<222> LOCATION: (74)..(74)
<223> OTHER INFORMATION: X is A/F/L/M/R/W/Y
<220> FEATURE:
<221> NAME/KEY: MISC_FEATURE
<222> LOCATION: (75)..(75)
<223> OTHER INFORMATION: X is A/F/H/K/N/R/S/T/Y
<220> FEATURE:
<221> NAME/KEY: MISC_FEATURE
<222> LOCATION: (76)..(76)
<223> OTHER INFORMATION: X is I/K/N/R/W
<220> FEATURE:
<221> NAME/KEY: MISC_FEATURE
<222> LOCATION: (77)..(77)
<223> OTHER INFORMATION: X is A/F/G/H/I/K/L/M/N/Q/R/S/T/V/W/Y
```

```
<220> FEATURE:
<221> NAME/KEY: MISC_FEATURE
<222> LOCATION: (78)..(78)
<223> OTHER INFORMATION: X is A/D/G/H/Q/R/S/T
<220> FEATURE:
<221> NAME/KEY: MISC_FEATURE
<222> LOCATION: (79)..(79)
<223> OTHER INFORMATION: X is A/K/L/R/T/V/W/Y
<220> FEATURE:
<221> NAME/KEY: MISC_FEATURE
<222> LOCATION: (80)..(80)
<223> OTHER INFORMATION: X is I/L/M/V
<220> FEATURE:
<221> NAME/KEY: MISC_FEATURE
<222> LOCATION: (81)..(81)
<223> OTHER INFORMATION: X is A/D/E/K/N/Q/R/S/T
<220> FEATURE:
<221> NAME/KEY: MISC_FEATURE
<222> LOCATION: (82)..(82)
<223> OTHER INFORMATION: X is D/E/G/K/M/P/Q/R/S/T/V
<220> FEATURE:
<221> NAME/KEY: MISC_FEATURE
<222> LOCATION: (83)..(83)
<223> OTHER INFORMATION: X is A/D/E/F/H/I/L/N/Q/R/S/T/V
<220> FEATURE:
<221> NAME/KEY: MISC_FEATURE
<222> LOCATION: (84)..(84)
<223> OTHER INFORMATION: X is D/E/H/M/N/Q/T/Y
<220> FEATURE:
<221> NAME/KEY: MISC_FEATURE
<222> LOCATION: (85)..(85)
<223> OTHER INFORMATION: X is A/F/G/H/L/M/R/T/V/W/Y
<220> FEATURE:
<221> NAME/KEY: MISC_FEATURE
<222> LOCATION: (86)..(86)
<223> OTHER INFORMATION: X is D/E/F/G/I/K/L/N/Q/S/T/V/W/Y
<220> FEATURE:
<221> NAME/KEY: MISC_FEATURE
<222> LOCATION: (87)..(87)
<223> OTHER INFORMATION: X is A/E/F/I/K/L/M/Q/T/W
<220> FEATURE:
<221> NAME/KEY: MISC_FEATURE
<222> LOCATION: (88)..(88)
<223> OTHER INFORMATION: X is A/F/I/L/M/T/V
<220> FEATURE:
<221> NAME/KEY: MISC_FEATURE
<222> LOCATION: (89)..(89)
<223> OTHER INFORMATION: X is A/I/K/Q/R/V/L
<220> FEATURE:
<221> NAME/KEY: MISC_FEATURE
<222> LOCATION: (90)..(90)
<223> OTHER INFORMATION: X is A/G/I/K/L/M/N/Q/R/S/T/V/W/Y
<220> FEATURE:
<221> NAME/KEY: MISC_FEATURE
<222> LOCATION: (91)..(91)
<223> OTHER INFORMATION: X is A/C/D/E/G/H/K/L/N/Q/R/S/T/V/Y
<220> FEATURE:
<221> NAME/KEY: MISC_FEATURE
<222> LOCATION: (92)..(92)
<223> OTHER INFORMATION: X is I/L
<220> FEATURE:
<221> NAME/KEY: MISC_FEATURE
<222> LOCATION: (93)..(93)
<223> OTHER INFORMATION: X is A/D/E/H/I/M/N/Q/T
<220> FEATURE:
<221> NAME/KEY: MISC_FEATURE
<222> LOCATION: (94)..(94)
<223> OTHER INFORMATION: X is A/C/D/E/F/G/H/I/K/L/M/N/Q/R/S/T/V/Y
<220> FEATURE:
<221> NAME/KEY: MISC_FEATURE
<222> LOCATION: (95)..(95)
<223> OTHER INFORMATION: X is A/L/T/V
<220> FEATURE:
<221> NAME/KEY: MISC_FEATURE
<222> LOCATION: (96)..(96)
<223> OTHER INFORMATION: X is K/Q/R
<220> FEATURE:
<221> NAME/KEY: MISC_FEATURE
<222> LOCATION: (97)..(97)
```

```
<223> OTHER INFORMATION: X is A/D/E/G/H/Q/S/T/V
<220> FEATURE:
<221> NAME/KEY: MISC_FEATURE
<222> LOCATION: (98)..(98)
<223> OTHER INFORMATION: X is A/D/E/F/H/K/M/N/P/Q/R/S/W/Y
<220> FEATURE:
<221> NAME/KEY: MISC_FEATURE
<222> LOCATION: (99)..(99)
<223> OTHER INFORMATION: X is A/S/V
<220> FEATURE:
<221> NAME/KEY: MISC_FEATURE
<222> LOCATION: (100)..(100)
<223> OTHER INFORMATION: X is A/G/N/Q/S/T
<220> FEATURE:
<221> NAME/KEY: MISC_FEATURE
<222> LOCATION: (101)..(102)
<223> OTHER INFORMATION: X is K/R
<220> FEATURE:
<221> NAME/KEY: MISC_FEATURE
<222> LOCATION: (103)..(103)
<223> OTHER INFORMATION: X is A/I/M/N/S/T/V
<220> FEATURE:
<221> NAME/KEY: MISC_FEATURE
<222> LOCATION: (104)..(104)
<223> OTHER INFORMATION: X is D/K/N/R
<220> FEATURE:
<221> NAME/KEY: MISC_FEATURE
<222> LOCATION: (105)..(105)
<223> OTHER INFORMATION: X is A/D/E/F/G/H/K/L/M/N/R/T/V/W/Y
<220> FEATURE:
<221> NAME/KEY: MISC_FEATURE
<222> LOCATION: (106)..(106)
<223> OTHER INFORMATION: X is A/E/G/H/I/T/Y
<220> FEATURE:
<221> NAME/KEY: MISC_FEATURE
<222> LOCATION: (107)..(107)
<223> OTHER INFORMATION: X is D/G/S
<220> FEATURE:
<221> NAME/KEY: MISC_FEATURE
<222> LOCATION: (108)..(108)
<223> OTHER INFORMATION: X is K/Q/R
<220> FEATURE:
<221> NAME/KEY: MISC_FEATURE
<222> LOCATION: (109)..(109)
<223> OTHER INFORMATION: X is A/D/E/F/G/H/K/L/R/S/V/W
<220> FEATURE:
<221> NAME/KEY: MISC_FEATURE
<222> LOCATION: (111)..(111)
<223> OTHER INFORMATION: X is D/E/H/M/Q
<220> FEATURE:
<221> NAME/KEY: MISC_FEATURE
<222> LOCATION: (112)..(112)
<223> OTHER INFORMATION: X is A/D/F/I/L/P/Q/R
<220> FEATURE:
<221> NAME/KEY: MISC_FEATURE
<222> LOCATION: (113)..(113)
<223> OTHER INFORMATION: X is K/Q
<220> FEATURE:
<221> NAME/KEY: MISC_FEATURE
<222> LOCATION: (114)..(114)
<223> OTHER INFORMATION: X is A/H/K/L/M/P/R/S/T/V/Y
<220> FEATURE:
<221> NAME/KEY: MISC_FEATURE
<222> LOCATION: (115)..(115)
<223> OTHER INFORMATION: X is D/E/P/R/T
<220> FEATURE:
<221> NAME/KEY: MISC_FEATURE
<222> LOCATION: (116)..(116)
<223> OTHER INFORMATION: X is D/E/G/H/K/Q/R/T/Y

<400> SEQUENCE: 12

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Lys Xaa Xaa Xaa Xaa Arg
```

```
                35                  40                  45
Xaa Ala Xaa Xaa Xaa Xaa Xaa Xaa Gly Asp Xaa Xaa Xaa Xaa
    50                  55                  60
Xaa Xaa Xaa Xaa Xaa Xaa Xaa Xaa Xaa Xaa Xaa Xaa Xaa Xaa
65                  70                  75                  80
Xaa Xaa Xaa Xaa Xaa Xaa Xaa Xaa Xaa Xaa Xaa Xaa Xaa Xaa
                85                  90                  95
Xaa Xaa Xaa Xaa Xaa Xaa Xaa Xaa Xaa Xaa Xaa Phe Xaa Xaa
            100                 105                 110
Xaa Xaa Xaa Xaa
        115

<210> SEQ ID NO 13
<211> LENGTH: 116
<212> TYPE: PRT
<213> ORGANISM: Artificial Sequence
<220> FEATURE:
<223> OTHER INFORMATION: synthetic

<400> SEQUENCE: 13

Ala Asp Trp Lys Lys Val Leu Asp Lys Ala Lys Asp Ile Ala Glu Asn
1               5                   10                  15
Arg Val Arg Glu Ile Lys Gln Lys Leu Glu Glu Phe Tyr Lys Lys Ala
            20                  25                  30
Met Lys Leu Asp Leu Thr Gln Glu Met Arg Arg Lys Leu Met Leu Glu
        35                  40                  45
Trp Ile Ala Ala Met Leu Met Ala Ile Gly Asp Ile Phe Asn Ala Ile
    50                  55                  60
Glu Gln Ala Lys Gln Glu Ala Asp Lys Leu Lys Lys Ala Gly Gln Val
65                  70                  75                  80
Asn Ser Gln Leu Leu Asp Glu Leu Lys Arg Arg Leu Glu Glu Leu Lys
                85                  90                  95
Glu Glu Ala Ser Arg Lys Cys His Asp Tyr Gly Arg Glu Phe Gln Leu
            100                 105                 110
Lys Leu Glu Tyr
        115

<210> SEQ ID NO 14
<211> LENGTH: 13
<212> TYPE: PRT
<213> ORGANISM: Artificial Sequence
<220> FEATURE:
<223> OTHER INFORMATION: synthetic

<400> SEQUENCE: 14

Gly Arg Lys Lys Arg Arg Gln Arg Arg Arg Pro Pro Gln
1               5                   10

<210> SEQ ID NO 15
<211> LENGTH: 16
<212> TYPE: PRT
<213> ORGANISM: Artificial Sequence
<220> FEATURE:
<223> OTHER INFORMATION: synthetic

<400> SEQUENCE: 15

Arg Gln Ile Lys Ile Trp Phe Gln Asn Arg Arg Met Lys Trp Lys Lys
1               5                   10                  15

<210> SEQ ID NO 16
```

```
<211> LENGTH: 18
<212> TYPE: PRT
<213> ORGANISM: Artificial Sequence
<220> FEATURE:
<223> OTHER INFORMATION: synthetic

<400> SEQUENCE: 16

Lys Leu Ala Leu Lys Leu Ala Leu Lys Ala Leu Lys Ala Ala Leu Lys
1               5                   10                  15

Leu Ala

<210> SEQ ID NO 17
<211> LENGTH: 27
<212> TYPE: PRT
<213> ORGANISM: Artificial Sequence
<220> FEATURE:
<223> OTHER INFORMATION: synthetic

<400> SEQUENCE: 17

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 18
<211> LENGTH: 17
<212> TYPE: PRT
<213> ORGANISM: Artificial Sequence
<220> FEATURE:
<223> OTHER INFORMATION: synthetic

<400> SEQUENCE: 18

Asn Ala Lys Thr Arg Arg His Glu Arg Arg Arg Lys Leu Ala Ile Glu
1               5                   10                  15

Arg

<210> SEQ ID NO 19
<211> LENGTH: 8
<212> TYPE: PRT
<213> ORGANISM: Artificial Sequence
<220> FEATURE:
<223> OTHER INFORMATION: synthetic

<400> SEQUENCE: 19

Arg Arg Arg Arg Arg Arg Arg Arg
1               5

<210> SEQ ID NO 20
<211> LENGTH: 17
<212> TYPE: PRT
<213> ORGANISM: Artificial Sequence
<220> FEATURE:
<223> OTHER INFORMATION: synthetic

<400> SEQUENCE: 20

Gly Ala Leu Phe Leu Gly Phe Leu Gly Ala Ala Gly Ser Thr Met Gly
1               5                   10                  15

Ala

<210> SEQ ID NO 21
<211> LENGTH: 21
<212> TYPE: PRT
<213> ORGANISM: Artificial Sequence
<220> FEATURE:
<223> OTHER INFORMATION: synthetic
```

-continued

```
<400> SEQUENCE: 21

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 22
<211> LENGTH: 18
<212> TYPE: PRT
<213> ORGANISM: Artificial Sequence
<220> FEATURE:
<223> OTHER INFORMATION: synthetic

<400> SEQUENCE: 22

Leu Leu Ile Ile Leu Arg Arg Arg Ile Arg Lys Gln Ala His Ala His
1               5                   10                  15

Ser Lys

<210> SEQ ID NO 23
<211> LENGTH: 16
<212> TYPE: PRT
<213> ORGANISM: Artificial Sequence
<220> FEATURE:
<223> OTHER INFORMATION: synthetic

<400> SEQUENCE: 23

Tyr Thr Ala Ile Ala Trp Val Lys Ala Phe Ile Arg Lys Leu Arg Lys
1               5                   10                  15

<210> SEQ ID NO 24
<211> LENGTH: 17
<212> TYPE: PRT
<213> ORGANISM: Artificial Sequence
<220> FEATURE:
<223> OTHER INFORMATION: synthetic

<400> SEQUENCE: 24

Ile Ala Trp Val Lys Ala Phe Ile Arg Lys Leu Arg Lys Gly Pro Leu
1               5                   10                  15

Gly

<210> SEQ ID NO 25
<211> LENGTH: 22
<212> TYPE: PRT
<213> ORGANISM: Artificial Sequence
<220> FEATURE:
<223> OTHER INFORMATION: synthetic

<400> SEQUENCE: 25

Met Val Thr Val Leu Phe Arg Arg Leu Arg Ile Arg Arg Ala Cys Gly
1               5                   10                  15

Pro Pro Arg Val Arg Val
            20

<210> SEQ ID NO 26
<211> LENGTH: 20
<212> TYPE: PRT
<213> ORGANISM: Artificial Sequence
<220> FEATURE:
<223> OTHER INFORMATION: synthetic

<400> SEQUENCE: 26

Gly Leu Trp Arg Ala Leu Trp Arg Leu Leu Arg Ser Leu Trp Arg Leu
```

<210> SEQ ID NO 27

<400> SEQUENCE: 27

000

<210> SEQ ID NO 28
<211> LENGTH: 116
<212> TYPE: PRT
<213> ORGANISM: Artificial Sequence
<220> FEATURE:
<223> OTHER INFORMATION: synthetic

<400> SEQUENCE: 28

```
Ala Asp Pro Lys Lys Val Leu Asp Lys Ala Lys Asp Gln Ala Glu Asn
1               5                   10                  15

Arg Val Arg Glu Leu Lys Gln Glu Leu Glu Glu Leu Tyr Lys Lys Ala
            20                  25                  30

Arg Lys Leu Asp Leu Thr Gln Glu Glu Arg Arg Lys Leu Glu Glu Glu
        35                  40                  45

Ala Ile Ala Ala Leu Leu Arg Ala Ile Gly Asp Ile Tyr Asn Ala Ile
    50                  55                  60

Gln Gln Ala Leu Asn Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Lys
                85                  90                  95

Lys Glu Ala Ser Lys Lys Ala Arg Asp Tyr Gly Leu Gly Phe Phe Glu
            100                 105                 110

Lys Leu Asp Tyr
        115
```

<210> SEQ ID NO 29
<211> LENGTH: 116
<212> TYPE: PRT
<213> ORGANISM: Artificial Sequence
<220> FEATURE:
<223> OTHER INFORMATION: synthetic

<400> SEQUENCE: 29

```
Ala Asp Pro Lys Lys Val Leu Asp Lys Ala Lys Asp Gln Ala Glu Asn
1               5                   10                  15

Arg Val Arg Glu Leu Lys Gln Glu Leu Glu Glu Leu Tyr Lys Glu Ala
            20                  25                  30

Arg Lys Leu Asp Leu Thr Gln Glu Glu Arg Arg Lys Leu Glu Glu Ser
        35                  40                  45

Tyr Ile Ala Ala Met Leu Arg Ala Ile Gly Asp Ile Phe Asn Ala Ile
    50                  55                  60

Met Gln Ala Lys Asn Glu Ala Asp Lys Leu Lys Lys Ala Gly Leu Val
65                  70                  75                  80

Asn Ser Gln Gln Leu Asp Glu Leu Arg Arg Arg Leu Glu Glu Leu Arg
                85                  90                  95

Lys Glu Ala Ser Leu Lys Ala Glu Asp Tyr Gly Arg Glu Phe Gln Glu
            100                 105                 110

Lys Leu Glu Tyr
        115
```

```
<210> SEQ ID NO 30
<211> LENGTH: 116
<212> TYPE: PRT
<213> ORGANISM: Artificial Sequence
<220> FEATURE:
<223> OTHER INFORMATION: synthetic

<400> SEQUENCE: 30

Ala Asp Pro Lys Lys Val Leu Asp Lys Ala Lys Asp Gln Ala Glu Asn
1               5                   10                  15

Arg Val Arg Glu Leu Lys Gln Asp Leu Glu Arg Leu Tyr Lys Glu Ala
            20                  25                  30

Arg Lys Leu Asp Leu Thr Gln Glu Met Arg Arg Lys Leu Gln Glu Lys
        35                  40                  45

Ala Ala Ala Ala Met Ile Arg Ala Ile Gly Asp Ile Asn Asn Ala Ile
    50                  55                  60

Tyr Gln Ala Leu Gln Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Gln
                85                  90                  95

Lys Glu Ala Ser Arg Lys Ala Gln Ala Tyr Gly Glu Glu Phe Met Leu
            100                 105                 110

Lys Leu Glu Tyr
        115

<210> SEQ ID NO 31
<211> LENGTH: 117
<212> TYPE: PRT
<213> ORGANISM: Artificial Sequence
<220> FEATURE:
<223> OTHER INFORMATION: synthetic

<400> SEQUENCE: 31

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Met Arg Lys Lys Leu Gln Ile Ala
        35                  40                  45

Ala Leu Gly Ala Met Leu Ala Ala Ile Gly Asp Ile Leu Asn Ala Ile
    50                  55                  60

Met Gln Ala Lys Glu Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Lys
                85                  90                  95

Glu Glu Ala Leu Arg Lys Ala Ser Asp Tyr Gly Ser Glu Phe His Leu
            100                 105                 110

Lys Arg Glu Tyr Gly
        115

<210> SEQ ID NO 32
<211> LENGTH: 116
<212> TYPE: PRT
<213> ORGANISM: Artificial Sequence
<220> FEATURE:
<223> OTHER INFORMATION: synthetic

<400> SEQUENCE: 32
```

-continued

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Glu Arg His Arg Leu Glu Thr Lys
        35                  40                  45

Ala Leu Ser Ala Leu Leu Ala Ala Ile Gly Asp Ile Leu Asp Ala Ile
    50                  55                  60

Met Gln Ala Leu Gln Glu Ala Ala Lys Leu Lys Lys Ala Gly Leu Val
65                  70                  75                  80

Asn Ser Gln Gln Leu Asp Glu Leu Lys Arg Arg Leu Glu Glu Leu Arg
                85                  90                  95

Lys Glu Ala Ser Arg Lys Ala Arg Asp Tyr Gly Arg Glu Phe Trp Leu
            100                 105                 110

Lys Leu Asp Tyr
        115

<210> SEQ ID NO 33
<211> LENGTH: 116
<212> TYPE: PRT
<213> ORGANISM: Artificial Sequence
<220> FEATURE:
<223> OTHER INFORMATION: synthetic

<400> SEQUENCE: 33

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Glu Arg Glu Lys Leu Lys Thr Lys
        35                  40                  45

Tyr Leu Ser Ala Met Leu Ala Ala Ile Gly Asp Ile Leu Asp Ala Ile
    50                  55                  60

Met Gln Ala Leu Asn Glu Ala Gln Lys Leu Lys Lys Ala Gly Leu Val
65                  70                  75                  80

Asn Ser Gln Gln Leu Asp Glu Leu Lys Arg Arg Leu Glu Glu Leu Arg
                85                  90                  95

Lys Glu Ala Ser Arg Lys Ala Arg Asp Tyr Gly Arg Glu Phe Glu Leu
            100                 105                 110

Lys Leu Asp Tyr
        115

<210> SEQ ID NO 34
<211> LENGTH: 117
<212> TYPE: PRT
<213> ORGANISM: Artificial Sequence
<220> FEATURE:
<223> OTHER INFORMATION: synthetic

<400> SEQUENCE: 34

Ala Asp Pro Lys Lys Val Leu Asp Lys Ala Lys Asp Gln Ala Glu Asn
1               5                   10                  15

Val Val Arg Lys Leu Lys Gln Glu Leu Glu Glu Leu Tyr Lys Glu Ala
            20                  25                  30

Arg Lys Leu Asp Leu Thr Gln Asp Met Arg Glu Lys Ile Lys Leu Arg
        35                  40                  45

Ala Glu Ala Ala Glu Leu Gln Ala Ile Gly Asp Ile Phe Gln Ala Ile
    50                  55                  60

```
Leu Gln Ala Lys Met Glu Ala Lys Leu Tyr Asp Ala Gly Leu Val
 65                  70                  75                  80

Asn Ser Gln Gln Leu Asp Glu Leu Lys Arg Arg Leu Glu Glu Leu Ala
                 85                  90                  95

Lys Glu Ala Glu Asp Arg Ala Ala Lys Leu Gly Lys Gly Phe Leu Gln
                100                 105                 110

Lys Leu Glu Tyr Gly
            115
```

<210> SEQ ID NO 35
<211> LENGTH: 117
<212> TYPE: PRT
<213> ORGANISM: Artificial Sequence
<220> FEATURE:
<223> OTHER INFORMATION: synthetic

<400> SEQUENCE: 35

```
Ala Asp Pro Lys Lys Val Leu Asp Lys Ala Lys Asp Arg Ala Glu Asn
  1               5                  10                  15

Ala Val Arg Glu Leu Lys Gln Lys Leu Glu Glu Leu Tyr Lys Glu Ala
                 20                  25                  30

Arg Lys Leu Asp Leu Thr Gln Asp Met Arg Asn Lys Leu Ile Met Lys
             35                  40                  45

Ala Ile Ala Ala Glu Leu Arg Ala Ile Gly Asp Ile Phe Gln Ala Ile
 50                  55                  60

Leu Glu Ala Lys Ala Glu Ala Lys Lys Leu Asp Ala Gly Leu Val
 65                  70                  75                  80

Asn Ser Gln Gln Phe Asp Leu Lys Arg Arg Leu Glu Glu Leu Glu
                 85                  90                  95

Glu Glu Ala Ala Glu Arg Ala Arg Lys Leu Gly Asp Glu Phe Arg Gln
                100                 105                 110

Lys Leu Glu Tyr Gly
            115
```

<210> SEQ ID NO 36
<211> LENGTH: 116
<212> TYPE: PRT
<213> ORGANISM: Artificial Sequence
<220> FEATURE:
<223> OTHER INFORMATION: synthetic

<400> SEQUENCE: 36

```
Ala Asp Pro Lys Lys Val Leu Asp Lys Ala Lys Asp Gln Ala Glu Asn
  1               5                  10                  15

Arg Val Arg Glu Leu Lys Gln Lys Leu Glu Glu Leu Tyr Lys Glu Ala
                 20                  25                  30

Arg Lys Leu Asp Leu Thr Gln Glu Met Arg Arg Glu Leu Lys Glu Arg
             35                  40                  45

Ala Leu Ala Ala Arg Leu Gln Ala Val Gly Asp Ile Phe Tyr Ala Ile
 50                  55                  60

Leu Gln Ala Lys Ser Glu Ala Asp Lys Leu Lys Ala Gly Leu Val
 65                  70                  75                  80

Asn Ser Gln Gln Leu Asp Glu Leu Lys Arg Arg Leu Glu Glu Leu Ala
                 85                  90                  95

Glu Glu Ala Gln Arg Lys Ala Arg Asp Tyr Gly Ile Glu Phe Ala Leu
                100                 105                 110

Lys Leu Glu Tyr
```

-continued

```
            115

<210> SEQ ID NO 37
<211> LENGTH: 116
<212> TYPE: PRT
<213> ORGANISM: Artificial Sequence
<220> FEATURE:
<223> OTHER INFORMATION: synthetic

<400> SEQUENCE: 37

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Met Arg Glu Lys Leu Gln Glu Gln
        35                  40                  45

Ala Leu Ala Ala Trp Leu Asn Ala Ala Gly Asp Ile Ile Glu Ala Ile
    50                  55                  60

Ser Arg Ala Leu Gln Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Ala
                85                  90                  95

Glu Glu Ala Ala Arg Lys Ala Glu Lys Tyr Gly Glu Glu Phe Lys Lys
            100                 105                 110

Lys Leu Glu Tyr
        115

<210> SEQ ID NO 38
<211> LENGTH: 116
<212> TYPE: PRT
<213> ORGANISM: Artificial Sequence
<220> FEATURE:
<223> OTHER INFORMATION: synthetic

<400> SEQUENCE: 38

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Met Arg Ala Glu Leu Asn Ala Arg
        35                  40                  45

Phe Ala Ala Ala Thr Leu Ala Ala Ala Gly Asp Ile Ile Asn Ala Ile
    50                  55                  60

Ser Glu Ala Leu Ala Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Ala
                85                  90                  95

Gln Glu Ala Glu Arg Lys Ala Glu Glu Tyr Gly Gln Glu Phe Leu Leu
            100                 105                 110

Lys Leu Glu Tyr
        115

<210> SEQ ID NO 39
<211> LENGTH: 116
<212> TYPE: PRT
<213> ORGANISM: Artificial Sequence
<220> FEATURE:
<223> OTHER INFORMATION: synthetic

<400> SEQUENCE: 39
```

-continued

Ala Asp Pro Lys Lys Val Leu Asp Lys Ala Lys Asp Glu Ala Glu Asn
1               5                   10                  15

Arg Val Arg Glu Leu Lys Gln Lys Leu Glu Glu Leu Tyr Lys Glu Ala
                20                  25                  30

Arg Lys Leu Asp Leu Thr Gln Glu Met Arg Gln Glu Leu Val Asp Lys
            35                  40                  45

Ala Arg Ala Ala Ser Leu Gln Ala Ser Gly Asp Ile Phe Tyr Ala Ile
        50                  55                  60

Leu Arg Ala Leu Ala Glu Ala Glu Lys Leu Lys Lys Ala Gly Leu Val
65                  70                  75                  80

Asn Ser Gln Gln Leu Asp Glu Leu Lys Arg Arg Leu Glu Glu Leu Ala
                85                  90                  95

Glu Glu Ala Arg Arg Lys Ala Glu Lys Leu Gly Asp Glu Phe Arg Leu
                100                 105                 110

Lys Leu Glu Tyr
            115

<210> SEQ ID NO 40
<211> LENGTH: 116
<212> TYPE: PRT
<213> ORGANISM: Artificial Sequence
<220> FEATURE:
<223> OTHER INFORMATION: synthetic

<400> SEQUENCE: 40

Ala Asp Pro Lys Lys Val Leu Asp Lys Ala Lys Asp Asp Ala Glu Asn
1               5                   10                  15

Arg Val Arg Glu Leu Lys Gln Lys Leu Glu Glu Leu Tyr Lys Glu Ala
                20                  25                  30

Arg Lys Leu Asp Leu Thr Gln Glu Glu Arg Asp Glu Lys Leu Lys
            35                  40                  45

Ala Ile Ala Ala Ser Leu Gln Ala Ser Gly Asp Ile Tyr Asn Ala Ile
        50                  55                  60

Leu Arg Ala Leu Glu Glu Ala Arg Lys Leu Lys Lys Ala Gly Leu Val
65                  70                  75                  80

Asn Ser Gln Gln Leu Asp Glu Leu Lys Arg Arg Leu Glu Glu Leu Ala
                85                  90                  95

Glu Glu Ala Gln Arg Lys Ala Asn Lys Leu Gly Asp Glu Phe Arg Leu
                100                 105                 110

Lys Leu Glu Tyr
            115

<210> SEQ ID NO 41
<211> LENGTH: 116
<212> TYPE: PRT
<213> ORGANISM: Artificial Sequence
<220> FEATURE:
<223> OTHER INFORMATION: synthetic

<400> SEQUENCE: 41

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
                20                  25                  30

Arg Lys Leu Asp Leu Thr Gln Glu Met Arg Arg Glu Leu Gln Ala Arg
            35                  40                  45

Tyr Ile Ala Ala Met Leu Ala Ala Ala Gly Asp Ile Met Glu Ala Ile

```
                50                  55                  60
Gln Gln Ala Lys Asn Glu Ala Asp Lys Leu Lys Lys Ala Gly Leu Val
 65                  70                  75                  80

Asn Ser Gln Gln Leu Asp Glu Leu Lys Arg Arg Leu Glu Glu Leu Ala
                 85                  90                  95

Lys Glu Ala Ala Arg Lys Ala Glu Asp Tyr Gly Arg Glu Phe Gln Leu
                100                 105                 110

Lys Leu Glu Tyr
            115

<210> SEQ ID NO 42
<211> LENGTH: 116
<212> TYPE: PRT
<213> ORGANISM: Artificial Sequence
<220> FEATURE:
<223> OTHER INFORMATION: synthetic

<400> SEQUENCE: 42

Ala Asp Pro Lys Lys Val Leu Asp Lys Ala Lys Asp Gln Ala Glu Asn
 1               5                  10                  15

Arg Val Arg Glu Leu Lys Gln Lys Leu Glu Glu Leu Tyr Lys Glu Ala
                 20                  25                  30

Arg Lys Leu Asp Leu Thr Gln Glu Met Arg Lys Glu Leu Val Ala Arg
             35                  40                  45

Tyr Ile Ala Ala Met Leu Ala Ala Ala Gly Asp Ile Val Gln Ala Ile
         50                  55                  60

Gln Asp Ala Lys Asn Glu Ala Asp Lys Leu Lys Lys Ala Gly Leu Val
 65                  70                  75                  80

Asn Ser Gln Gln Leu Asp Glu Leu Lys Arg Arg Leu Glu Glu Leu Ala
                 85                  90                  95

Lys Glu Ala Ala Arg Lys Ala Thr Asp Tyr Gly Arg Glu Phe Gln Leu
                100                 105                 110

Lys Leu Glu Tyr
            115

<210> SEQ ID NO 43
<211> LENGTH: 116
<212> TYPE: PRT
<213> ORGANISM: Artificial Sequence
<220> FEATURE:
<223> OTHER INFORMATION: synthetic

<400> SEQUENCE: 43

Ala Asp Pro Lys Lys Val Leu Asp Lys Ala Lys Asp Gln Ala Glu Asn
 1               5                  10                  15

Arg Val Arg Glu Leu Lys Gln Lys Leu Glu Glu Leu Tyr Lys Glu Ala
                 20                  25                  30

Arg Lys Leu Asp Leu Thr Gln Glu Met Arg Arg Glu Leu Arg Asn Arg
             35                  40                  45

Ala Ile Ala Ala Ile Leu Gln Ala Ile Gly Asp Leu Leu Asn Ala Ile
         50                  55                  60

Gln Gln Ala Lys Asp Glu Ala Asp Lys Leu Lys Lys Ala Gly Leu Val
 65                  70                  75                  80

Asn Ser Gln Gln Leu Asp Glu Leu Lys Arg Arg Leu Glu Glu Leu Gln
                 85                  90                  95

Asn Glu Ala Ala Glu Lys Ala Ala Asp Tyr Gly Glu Glu Phe Trp Leu
                100                 105                 110
```

```
Lys Leu Glu Tyr
        115

<210> SEQ ID NO 44
<211> LENGTH: 116
<212> TYPE: PRT
<213> ORGANISM: Artificial Sequence
<220> FEATURE:
<223> OTHER INFORMATION: synthetic

<400> SEQUENCE: 44

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Asp Arg Lys Arg Leu Leu Leu Gln
        35                  40                  45

Tyr Ile Ala Ala Met Leu Ala Ala Ile Gly Asp Leu Glu Asn Ala Ile
    50                  55                  60

Arg Trp Ala Lys Arg Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Ala
                85                  90                  95

Lys Glu Ala Ala Glu Lys Ala Ala Asp Tyr Gly Glu Glu Phe Asn Leu
            100                 105                 110

Lys Leu Glu Tyr
        115

<210> SEQ ID NO 45
<211> LENGTH: 116
<212> TYPE: PRT
<213> ORGANISM: Artificial Sequence
<220> FEATURE:
<223> OTHER INFORMATION: synthetic

<400> SEQUENCE: 45

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Met Arg Arg Gln Leu Arg Asp Gln
        35                  40                  45

Tyr Ile Ala Ala Met Leu Ala Ala Ile Gly Asp Leu Leu Asn Ala Ile
    50                  55                  60

Met Gln Ala Lys Arg Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Glu
                85                  90                  95

Glu Glu Ala Ala Gln Lys Ala Ala Asp Tyr Gly Gln Glu Phe Leu Leu
            100                 105                 110

Lys Leu Glu Tyr
        115

<210> SEQ ID NO 46
<211> LENGTH: 116
<212> TYPE: PRT
<213> ORGANISM: Artificial Sequence
<220> FEATURE:
<223> OTHER INFORMATION: synthetic
```

<400> SEQUENCE: 46

Ala Asp Pro Lys Lys Val Leu Asp Lys Ala Lys Asp Arg Ala Glu Asn
1               5                   10                  15

Arg Val Arg Glu Leu Lys Lys Leu Glu Lys Leu Tyr Lys Glu Ala
            20                  25                  30

Arg Lys Leu Asp Leu Thr Gln Glu Gln Arg Asn Lys Ile Ile Asn Ala
        35                  40                  45

Ala Met Ala Ala Met Ile Ala Ala Phe Gly Asp Ile Phe His Ala Ile
    50                  55                  60

Gln Glu Ala Lys Glu Glu Ala Lys Lys Leu Lys Lys Ala Gly Leu Val
65                  70                  75                  80

Asn Ser Gln Gln Leu Asp Glu Leu Lys Arg Arg Leu Asp Glu Leu Asp
            85                  90                  95

Glu Glu Ala Ala Gln Arg Ala Glu Lys Leu Gly Lys Glu Phe Asn Leu
            100                 105                 110

Lys Phe Glu Tyr
        115

<210> SEQ ID NO 47
<211> LENGTH: 116
<212> TYPE: PRT
<213> ORGANISM: Artificial Sequence
<220> FEATURE:
<223> OTHER INFORMATION: synthetic

<400> SEQUENCE: 47

Ala Asp Pro Lys Lys Val Leu Asp Lys Ala Lys Asp Arg Ala Glu Asn
1               5                   10                  15

Val Val Arg Lys Leu Lys Lys Glu Leu Glu Glu Leu Tyr Lys Glu Ala
            20                  25                  30

Arg Lys Leu Asp Leu Thr Gln Glu Met Arg Asp Arg Ile Arg Leu Ala
        35                  40                  45

Ala Ile Ala Ala Arg Ile Ala Ala Phe Gly Asp Ile Phe His Ala Ile
    50                  55                  60

Met Glu Ala Leu Glu Glu Ala Arg Lys Leu Lys Lys Ala Gly Leu Val
65                  70                  75                  80

Asn Ser Gln Gln Leu Asp Glu Leu Lys Arg Arg Leu Glu Glu Leu Asp
            85                  90                  95

Glu Glu Ala Ala Gln Arg Ala Glu Lys Leu Gly Lys Glu Phe Glu Leu
            100                 105                 110

Lys Leu Glu Tyr
        115

<210> SEQ ID NO 48
<211> LENGTH: 116
<212> TYPE: PRT
<213> ORGANISM: Artificial Sequence
<220> FEATURE:
<223> OTHER INFORMATION: synthetic

<400> SEQUENCE: 48

Ala Asp Pro Lys Lys Val Leu Asp Lys Ala Lys Asp Arg Ala Glu Asn
1               5                   10                  15

Arg Val Arg Lys Leu Lys Lys Glu Leu Glu Lys Leu Tyr Lys Glu Ala
            20                  25                  30

Arg Lys Leu Asp Leu Thr Gln Glu Gln Arg Asp Arg Ile Ile Asn Ala
        35                  40                  45

```
Ala Ile Ala Ala Met Ile Ala Ala Phe Gly Asp Ile Phe His Ala Ile
        50                  55                  60

Met Glu Ala Lys Glu Glu Ala Arg Lys Leu Lys Lys Ala Gly Leu Val
 65                  70                  75                  80

Asn Ser Gln Gln Leu Asp Glu Leu Lys Arg Arg Leu Asp Glu Leu Asp
                 85                  90                  95

Glu Glu Ala Ala Gln Arg Ala Glu Lys Leu Gly Lys Glu Phe Arg Leu
                100                 105                 110

Lys Phe Glu Tyr
            115

<210> SEQ ID NO 49
<211> LENGTH: 116
<212> TYPE: PRT
<213> ORGANISM: Artificial Sequence
<220> FEATURE:
<223> OTHER INFORMATION: synthetic

<400> SEQUENCE: 49

Ala Asp Pro Lys Lys Val Leu Asp Lys Ala Lys Asp Gln Ala Glu Asn
 1               5                  10                  15

Arg Val Arg Glu Leu Lys Gln Lys Leu Glu Glu Leu Tyr Lys Glu Ala
                20                  25                  30

Arg Lys Leu Asp Leu Thr Gln Glu Met Arg Lys Leu Ile Gln Lys
            35                  40                  45

Ala Leu Ser Ala Leu Leu Lys Ala Ile Gly Asp Ile Leu Asp Ala Ile
        50                  55                  60

Ala Arg Ala Lys Ala Glu Asp Lys Leu Lys Lys Ala Gly Leu Val
 65                  70                  75                  80

Asn Ser Gln Gln Leu Asp Glu Leu Lys Arg Arg Leu Glu Glu Leu Leu
                 85                  90                  95

Lys Glu Ala Ala Arg Lys Ala Leu Asp Tyr Gly Arg Glu Phe Trp Leu
                100                 105                 110

Lys Leu Glu Tyr
            115

<210> SEQ ID NO 50
<211> LENGTH: 116
<212> TYPE: PRT
<213> ORGANISM: Artificial Sequence
<220> FEATURE:
<223> OTHER INFORMATION: synthetic

<400> SEQUENCE: 50

Ala Asp Pro Lys Lys Val Leu Asp Lys Ala Lys Asp Gln Ala Glu Asn
 1               5                  10                  15

Arg Val Arg Glu Leu Lys Gln Lys Leu Glu Glu Leu Tyr Lys Glu Ala
                20                  25                  30

Arg Lys Leu Asp Leu Thr Gln Glu Met Arg Arg Glu Leu Arg Glu Arg
            35                  40                  45

Tyr Ile Ala Ala Met Leu Ala Ala Ala Gly Asp Leu Trp Tyr Ala Ile
        50                  55                  60

Thr Gln Ala Lys Arg Glu Ala Asp Lys Leu Lys Lys Ala Gly Leu Val
 65                  70                  75                  80

Asn Ser Gln Gln Leu Asp Glu Leu Lys Arg Arg Leu Glu Glu Leu Leu
                 85                  90                  95

Glu Glu Ala Ala Arg Lys Ala Glu Asp Tyr Gly Glu Glu Phe Arg Leu
                100                 105                 110
```

```
Lys Leu Glu Tyr
        115

<210> SEQ ID NO 51
<211> LENGTH: 116
<212> TYPE: PRT
<213> ORGANISM: Artificial Sequence
<220> FEATURE:
<223> OTHER INFORMATION: synthetic

<400> SEQUENCE: 51

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Met Arg Arg Glu Leu Arg Asp Arg
        35                  40                  45

Tyr Ile Ala Ala Met Leu Ala Ala Ile Gly Asp Leu Phe Asn Ala Ile
    50                  55                  60

Gln Trp Ala Lys Gln Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Ala
                85                  90                  95

Glu Glu Ala Ala Arg Lys Ala Asp Tyr Gly Glu Glu Phe Lys Leu
            100                 105                 110

Lys Leu Glu Tyr
        115

<210> SEQ ID NO 52
<211> LENGTH: 116
<212> TYPE: PRT
<213> ORGANISM: Artificial Sequence
<220> FEATURE:
<223> OTHER INFORMATION: synthetic

<400> SEQUENCE: 52

Ala Asp Pro Lys Lys Val Leu Asp Lys Ala Lys Asp Gln Ala Glu Asn
1               5                   10                  15

Arg Val Arg Glu Leu Lys Gln Glu Leu Glu Arg Leu Tyr Lys Glu Ala
            20                  25                  30

Arg Lys Leu Asp Leu Thr Gln Glu Met Arg Arg Lys Leu Glu Trp Arg
        35                  40                  45

Tyr Ile Ala Ala Met Leu Lys Ala Ile Gly Asp Ile Leu Asn Ala Ile
    50                  55                  60

Ala Gln Ala Glu Asn Glu Ala Asp Lys Leu Lys Lys Ala Gly Leu Val
65                  70                  75                  80

Asn Ser Gln Gln Leu Asp Glu Leu Arg Arg Arg Leu Glu Glu Leu Ala
                85                  90                  95

Lys Glu Ala Ala Arg Lys Ala His Asp Tyr Gly Arg Glu Phe Gln Leu
            100                 105                 110

Lys Leu Glu Tyr
        115

<210> SEQ ID NO 53
<211> LENGTH: 116
<212> TYPE: PRT
<213> ORGANISM: Artificial Sequence
<220> FEATURE:
<223> OTHER INFORMATION: synthetic
```

<400> SEQUENCE: 53

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Met Arg Lys Lys Leu Gln Tyr Ala
        35                  40                  45

Ala Ile Gly Ala Met Leu Ala Ala Ile Gly Asp Ile Leu Asn Ala Ile
    50                  55                  60

Met Gln Ala Lys Gln Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Lys
                85                  90                  95

Glu Glu Ala Leu Arg Lys Ala His Asp Tyr Gly Ser Glu Phe Tyr Leu
            100                 105                 110

Lys Leu Glu Tyr
            115

<210> SEQ ID NO 54
<211> LENGTH: 117
<212> TYPE: PRT
<213> ORGANISM: Artificial Sequence
<220> FEATURE:
<223> OTHER INFORMATION: synthetic

<400> SEQUENCE: 54

Ala Asp Pro Lys Lys Val Leu Asp Lys Ala Lys Asp Arg Ala Glu Asn
1               5                   10                  15

Val Val Arg Lys Leu Lys Lys Glu Leu Glu Glu Leu Tyr Lys Glu Ala
            20                  25                  30

Arg Lys Leu Asp Leu Thr Gln Glu Met Arg Asp Arg Ile Arg Arg Ala
        35                  40                  45

Ala Ile Ala Ala Arg Ile Gln Ala His Gly Asp Ile Phe His Ala Ile
    50                  55                  60

Lys His Ala Leu Arg Glu Ala Arg Lys Leu Lys Lys Ala Gly Leu Val
65                  70                  75                  80

Asn Ser Gln Gln Leu Asp Glu Leu Lys Arg Arg Leu Glu Glu Leu Asp
                85                  90                  95

Glu Glu Ala Glu Gln Arg Ala Glu Leu Gly Lys Glu Phe Glu Leu
            100                 105                 110

Lys Leu Glu Tyr Gly
            115

<210> SEQ ID NO 55
<211> LENGTH: 117
<212> TYPE: PRT
<213> ORGANISM: Artificial Sequence
<220> FEATURE:
<223> OTHER INFORMATION: synthetic

<400> SEQUENCE: 55

Ala Asp Pro Lys Lys Val Leu Asp Lys Ala Lys Asp Arg Ala Glu Asn
1               5                   10                  15

Val Val Arg Lys Leu Lys Lys Glu Leu Glu Glu Leu Tyr Lys Glu Ala
            20                  25                  30

Arg Lys Leu Asp Leu Thr Gln Glu Met Arg Asp Arg Ile Arg Arg Thr
        35                  40                  45

Ala Ile Ala Ala Arg Phe Gln Ala His Gly Asp Ile Phe His Ala Ile
        50                  55                  60

Lys Glu Ala Lys Arg Glu Ala Arg Lys Leu Lys Lys Ala Gly Leu Val
65                  70                  75                  80

Asn Ser Gln Gln Leu Asp Glu Leu Lys Arg Arg Leu Glu Glu Leu Asp
                85                  90                  95

Glu Glu Ala Glu Gln Arg Ala Glu Lys Leu Gly Lys Glu Phe Glu Leu
                100                 105                 110

Lys Leu Glu Tyr Gly
                115

<210> SEQ ID NO 56
<211> LENGTH: 117
<212> TYPE: PRT
<213> ORGANISM: Artificial Sequence
<220> FEATURE:
<223> OTHER INFORMATION: synthetic

<400> SEQUENCE: 56

Ala Asp Pro Lys Lys Val Leu Asp Lys Ala Lys Asp Arg Ala Glu Asn
1               5                   10                  15

Val Val Arg Lys Leu Lys Lys Glu Leu Glu Leu Tyr Lys Glu Ala
                20                  25                  30

Arg Lys Leu Asp Leu Thr Gln Glu Met Arg Asp Arg Ile Arg Arg Ala
                35                  40                  45

Ala Ile Ala Ala Arg Phe Ala Ala His Gly Asp Ile Phe His Ala Ile
        50                  55                  60

Lys Glu Ala Lys Glu Glu Ala Arg Lys Leu Lys Lys Ala Gly Leu Val
65                  70                  75                  80

Asn Ser Gln Gln Leu Asp Glu Leu Lys Arg Arg Leu Arg Glu Leu Asp
                85                  90                  95

Glu Glu Ala Glu Gln Arg Ala Glu Lys Leu Gly Lys Glu Phe Arg Leu
                100                 105                 110

Lys Leu Glu Tyr Gly
                115

<210> SEQ ID NO 57
<211> LENGTH: 117
<212> TYPE: PRT
<213> ORGANISM: Artificial Sequence
<220> FEATURE:
<223> OTHER INFORMATION: synthetic

<400> SEQUENCE: 57

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
                20                  25                  30

Arg Lys Leu Asp Leu Thr Gln Glu Met Arg Lys Lys Leu Gln Ile Ala
                35                  40                  45

Ala Leu Gly Ala Met Leu Ala Ala Ile Gly Asp Ile Leu Asn Ala Ile
        50                  55                  60

Met Gln Ala Lys Glu Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Lys
                85                  90                  95

Glu Glu Ala Leu Arg Lys Ala Ser Asp Tyr Gly Ser Glu Phe His Leu

<210> SEQ ID NO 58
<211> LENGTH: 117
<212> TYPE: PRT
<213> ORGANISM: Artificial Sequence
<220> FEATURE:
<223> OTHER INFORMATION: synthetic

<400> SEQUENCE: 58

Ala Asp Pro Lys Lys Ile Leu Asp Lys Ala Lys Asp Gln Val Glu Asn
1               5                   10                  15

Arg Val Arg Glu Leu Lys Gln Glu Leu Glu Arg Leu Tyr Lys Glu Ala
            20                  25                  30

Arg Lys Leu Asp Leu Thr Gln Glu Met Arg Arg Lys Leu His Val Arg
        35                  40                  45

Tyr Ile Ala Ala Met Leu Lys Ala Ile Ala Ile Leu Asn Ala Ile
    50                  55                  60

Ala Gln Ala Glu Asn Glu Ala Asp Lys Leu Lys Lys Ala Gly Leu Val
65                  70                  75                  80

Asn Ser Gln Gln Leu Asp Glu Leu Arg Arg Arg Leu Glu Glu Leu Thr
                85                  90                  95

Glu Glu Ala Ala Gln Lys Ala His Asp Tyr Gly Arg Glu Phe Gln Leu
            100                 105                 110

Lys Leu Glu Tyr Gly
        115

<210> SEQ ID NO 59
<211> LENGTH: 117
<212> TYPE: PRT
<213> ORGANISM: Artificial Sequence
<220> FEATURE:
<223> OTHER INFORMATION: synthetic

<400> SEQUENCE: 59

Ala Asp Pro Lys Lys Ile Leu Asp Lys Ala Lys Asp Gln Val Glu Asn
1               5                   10                  15

Arg Val Arg Glu Leu Lys Gln Glu Leu Glu Arg Leu Tyr Lys Glu Ala
            20                  25                  30

Arg Lys Leu Asp Leu Thr Gln Glu Met Arg Arg Lys Leu His Val Arg
        35                  40                  45

Tyr Ile Ala Ala Met Leu Lys Ala Ile Ala Ser Ile Leu Asn Ala Ile
    50                  55                  60

Ala Gln Ala Glu Asn Glu Ala Asp Lys Leu Lys Lys Ala Gly Leu Val
65                  70                  75                  80

Asn Ser Gln Gln Leu Asp Glu Leu Arg Arg Arg Leu Glu Glu Leu Thr
                85                  90                  95

Glu Glu Ala Ala Gln Lys Ala His Asp Tyr Gly Arg Glu Phe Gln Leu
            100                 105                 110

Lys Leu Glu Tyr Gly
        115

<210> SEQ ID NO 60
<211> LENGTH: 117
<212> TYPE: PRT
<213> ORGANISM: Artificial Sequence
<220> FEATURE:

<223> OTHER INFORMATION: synthetic

<400> SEQUENCE: 60

Ala Asp Pro Lys Lys Ile Leu Asp Lys Ala Lys Asp Gln Val Glu Asn
1               5                   10                  15

Arg Val Arg Glu Leu Lys Gln Glu Leu Glu Arg Leu Tyr Lys Glu Ala
            20                  25                  30

Arg Lys Leu Asp Leu Thr Gln Glu Met Arg Arg Lys Leu His Val Arg
        35                  40                  45

Tyr Ile Ala Ala Met Leu Lys Ala Ile Ala Asp Ile Leu Asn Ala Ile
    50                  55                  60

Ala Gln Ala Glu Asn Glu Ala Asp Lys Leu Lys Lys Ala Gly Leu Val
65                  70                  75                  80

Asn Ser Gln Gln Leu Asp Glu Leu Arg Arg Arg Leu Glu Glu Leu Thr
                85                  90                  95

Glu Glu Ala Ala Arg Lys Ala His Asp Tyr Gly Arg Glu Phe Gln Leu
            100                 105                 110

Lys Leu Glu Tyr Gly
        115

<210> SEQ ID NO 61
<211> LENGTH: 117
<212> TYPE: PRT
<213> ORGANISM: Artificial Sequence
<220> FEATURE:
<223> OTHER INFORMATION: synthetic

<400> SEQUENCE: 61

Ala Asp Pro Lys Lys Ile Leu Asp Lys Ala Lys Asp Gln Val Glu Asn
1               5                   10                  15

Arg Val Arg Glu Leu Lys Gln Glu Leu Glu Arg Leu Tyr Lys Glu Ala
            20                  25                  30

Arg Lys Leu Asp Leu Thr Gln Glu Met Arg Arg Lys Leu His Trp Arg
        35                  40                  45

Tyr Ile Ala Ala Met Leu Lys Ala Ile Ala Asp Ile Leu Asn Ala Ile
    50                  55                  60

Ala Gln Ala Glu Asn Glu Ala Asp Lys Leu Lys Lys Ala Gly Leu Val
65                  70                  75                  80

Asn Ser Gln Gln Leu Asp Glu Leu Arg Arg Arg Leu Glu Glu Leu Thr
                85                  90                  95

Glu Glu Ala Ala Arg Lys Ala His Asp Tyr Gly Arg Glu Phe Gln Leu
            100                 105                 110

Lys Leu Glu Tyr Gly
        115

<210> SEQ ID NO 62
<211> LENGTH: 117
<212> TYPE: PRT
<213> ORGANISM: Artificial Sequence
<220> FEATURE:
<223> OTHER INFORMATION: synthetic

<400> SEQUENCE: 62

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Met Arg Lys Lys Leu Glu Ile Ala

```
                35                  40                  45

Ala Leu Gly Ala Val Leu Ala Ala His Gly Asp Ile Leu Asn Ala Ile
         50                  55                  60

Met Gln Ala Lys Glu Glu Ala Asp Lys Leu Lys Lys Ala Gly Leu Val
 65                  70                  75                  80

Asn Ser Gln Gln Leu Asp Glu Leu Lys Arg Arg Leu Glu Glu Leu Lys
                 85                  90                  95

Glu Glu Ala Leu Arg Lys Ala Ser Asp Tyr Gly Lys Glu Phe His Leu
            100                 105                 110

Lys Arg Gln Tyr Gly
        115

<210> SEQ ID NO 63
<211> LENGTH: 117
<212> TYPE: PRT
<213> ORGANISM: Artificial Sequence
<220> FEATURE:
<223> OTHER INFORMATION: synthetic

<400> SEQUENCE: 63

Ala Asp Pro Lys Lys Val Leu Asp Lys Ala Lys Asp Gln Ala Glu Asn
 1               5                  10                  15

Arg Val Arg Glu Leu Lys Gln Lys Leu Glu Glu Leu Tyr Lys Glu Ala
             20                  25                  30

Arg Lys Leu Asp Leu Thr Gln Glu Met Arg Lys Lys Leu Glu Ile Ala
         35                  40                  45

Ala Leu Gly Ala Val Leu Ala Ala His Gly Asp Ile Leu Asn Ala Ile
         50                  55                  60

Met Gln Ala Lys Glu Glu Ala Asp Lys Leu Lys Lys Ala Gly Leu Val
 65                  70                  75                  80

Asn Ser Gln Gln Leu Asp Glu Leu Lys Arg Arg Leu Glu Glu Leu Lys
                 85                  90                  95

Glu Glu Ala Leu Arg Lys Ala Ser Asp Tyr Gly Lys Glu Phe His Leu
            100                 105                 110

Lys Arg Arg Tyr Gly
        115

<210> SEQ ID NO 64
<211> LENGTH: 117
<212> TYPE: PRT
<213> ORGANISM: Artificial Sequence
<220> FEATURE:
<223> OTHER INFORMATION: synthetic

<400> SEQUENCE: 64

Ala Asp Pro Lys Lys Val Leu Asp Lys Ala Lys Asp Gln Ala Glu Asn
 1               5                  10                  15

Arg Val Arg Glu Leu Lys Gln Lys Leu Glu Glu Leu Tyr Lys Glu Ala
             20                  25                  30

Arg Lys Leu Asp Leu Thr Gln Glu Met Arg Lys Lys Leu Glu Val Ala
         35                  40                  45

Ala Leu Gly Ala Val Leu Ala Ala His Gly Asp Ile Leu Asn Ala Ile
         50                  55                  60

Met Gln Ala Lys Glu Glu Ala Asp Lys Leu Lys Lys Ala Gly Leu Val
 65                  70                  75                  80

Asn Ser Gln Gln Leu Asp Glu Leu Lys Arg Arg Leu Glu Glu Leu Lys
                 85                  90                  95
```

Glu Glu Ala Leu Arg Lys Ala Ser Asp Tyr Gly Lys Glu Phe His Leu
                100                 105                 110

Lys Arg Gln Tyr Gly
        115

<210> SEQ ID NO 65
<211> LENGTH: 117
<212> TYPE: PRT
<213> ORGANISM: Artificial Sequence
<220> FEATURE:
<223> OTHER INFORMATION: synthetic

<400> SEQUENCE: 65

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Met Arg Lys Lys Leu Glu Val Ala
        35                  40                  45

Ala Leu Gly Ala Val Leu Ala Ala His Gly Asp Ile Leu Asn Ala Ile
    50                  55                  60

Met Gln Ala Lys Glu Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Lys
                85                  90                  95

Glu Glu Ala Leu Arg Lys Ala Ser Asp Tyr Gly Lys Glu Phe His Leu
                100                 105                 110

Lys Arg Arg Tyr Gly
        115

<210> SEQ ID NO 66
<211> LENGTH: 117
<212> TYPE: PRT
<213> ORGANISM: Artificial Sequence
<220> FEATURE:
<223> OTHER INFORMATION: synthetic

<400> SEQUENCE: 66

Ala Asp Pro Lys Lys Val Leu Asp Lys Ala Lys Asp Gln Ala Glu Asn
1               5                   10                  15

Arg Val Arg Glu Leu Lys Gln Lys Leu Glu Glu Leu Tyr Lys Glu Ala
            20                  25                  30

Arg Lys Leu Asp Leu Thr Gln Glu Met Arg Lys Lys Leu Gln Ile Ala
        35                  40                  45

Ala Leu Gly Ala Met Leu Ala Ala Ile Gly Asp Ile Leu Asn Ala Ile
    50                  55                  60

Met Gln Ala Lys Glu Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Lys
                85                  90                  95

Glu Glu Ala Leu Arg Lys Ala Ser Asp Tyr Gly Lys Glu Phe His Leu
                100                 105                 110

Lys Arg Gln Tyr Gly
        115

<210> SEQ ID NO 67
<211> LENGTH: 160
<212> TYPE: PRT
<213> ORGANISM: Artificial Sequence

```
<220> FEATURE:
<223> OTHER INFORMATION: synthetic

<400> SEQUENCE: 67

Ala Tyr Ser Thr Arg Glu Ile Leu Leu Ala Leu Cys Ile Arg Asp Ser
1               5                   10                  15

Arg Val His Gly Asn Gly Thr Leu His Pro Val Leu Glu Leu Ala Ala
            20                  25                  30

Arg Glu Thr Pro Leu Arg Leu Ser Pro Glu Asp Thr Val Val Leu Arg
        35                  40                  45

Tyr His Val Leu Leu Glu Glu Ile Ile Glu Arg Asn Ser Glu Thr Phe
    50                  55                  60

Thr Glu Thr Trp Asn Arg Phe Ile Thr His Thr Glu His Val Asp Leu
65                  70                  75                  80

Asp Phe Asn Ser Val Phe Leu Glu Ile Phe His Arg Gly Asp Pro Ser
                85                  90                  95

Leu Gly Arg Ala Leu Ala Trp Met Ala Trp Cys Met His Ala Cys Arg
            100                 105                 110

Thr Leu Cys Cys Asn Gln Ser Thr Pro Tyr Tyr Val Val Asp Leu Ser
        115                 120                 125

Val Arg Gly Met Leu Glu Ala Ser Glu Gly Leu Asp Gly Trp Ile His
    130                 135                 140

Gln Gln Gly Gly Trp Ser Thr Leu Ile Glu Asp Asn Ile Pro Gly Ser
145                 150                 155                 160

<210> SEQ ID NO 68
<211> LENGTH: 158
<212> TYPE: PRT
<213> ORGANISM: Artificial Sequence
<220> FEATURE:
<223> OTHER INFORMATION: synthetic

<400> SEQUENCE: 68

Gly Ser Asp Glu Leu Tyr Arg Gln Ser Leu Glu Ile Ile Ser Arg Tyr
1               5                   10                  15

Leu Arg Glu Gln Ala Thr Gly Ala Lys Asp Thr Lys Pro Met Gly Arg
            20                  25                  30

Ser Gly Ala Thr Ser Arg Lys Ala Leu Glu Thr Leu Arg Arg Val Gly
        35                  40                  45

Asp Gly Val Gln Arg Asn His Glu Thr Ala Phe Gln Gly Met Leu Arg
    50                  55                  60

Lys Leu Asp Ile Lys Asn Glu Asp Asp Val Lys Ser Leu Ser Arg Val
65                  70                  75                  80

Met Ile His Val Phe Ser Asp Gly Val Thr Asn Trp Gly Arg Ile Val
                85                  90                  95

Thr Leu Ile Ser Phe Gly Ala Phe Val Ala Lys His Leu Lys Thr Ile
            100                 105                 110

Asn Gln Glu Ser Cys Ile Glu Pro Leu Ala Glu Ser Ile Thr Asp Val
        115                 120                 125

Leu Val Arg Thr Lys Arg Asp Trp Leu Val Lys Gln Arg Gly Trp Asp
    130                 135                 140

Gly Phe Val Glu Phe Phe His Val Glu Asp Leu Glu Gly Gly
145                 150                 155

<210> SEQ ID NO 69
<211> LENGTH: 206
<212> TYPE: PRT
```

<213> ORGANISM: Artificial Sequence
<220> FEATURE:
<223> OTHER INFORMATION: synthetic

<400> SEQUENCE: 69

```
Ala His Ala Gly Arg Thr Gly Tyr Asp Asn Arg Glu Ile Val Met Lys
1               5                   10                  15
Tyr Ile His Tyr Lys Leu Ser Gln Arg Gly Tyr Glu Trp Asp Ala Gly
            20                  25                  30
Asp Val Gly Ala Ala Pro Pro Gly Ala Ala Pro Ala Pro Gly Ile Phe
        35                  40                  45
Ser Ser Gln Pro Gly His Thr Pro His Pro Ala Ala Ser Arg Asp Pro
    50                  55                  60
Val Ala Arg Thr Ser Pro Leu Gln Thr Pro Ala Ala Pro Gly Ala Ala
65                  70                  75                  80
Ala Gly Pro Ala Leu Ser Pro Val Pro Pro Val Val His Leu Thr Leu
                85                  90                  95
Arg Gln Ala Gly Asp Asp Phe Ser Arg Arg Tyr Arg Arg Asp Phe Ala
            100                 105                 110
Glu Met Ser Ser Gln Leu His Leu Thr Pro Phe Thr Ala Arg Gly Arg
        115                 120                 125
Phe Ala Thr Val Val Glu Glu Leu Phe Arg Asp Gly Val Asn Trp Gly
    130                 135                 140
Arg Ile Val Ala Phe Phe Glu Phe Gly Gly Val Met Cys Val Glu Ser
145                 150                 155                 160
Val Asn Arg Glu Met Ser Pro Leu Val Asp Asn Ile Ala Leu Trp Met
                165                 170                 175
Thr Glu Tyr Leu Asn Arg His Leu His Thr Trp Ile Gln Asp Asn Gly
            180                 185                 190
Gly Trp Asp Ala Phe Val Glu Leu Tyr Gly Pro Ser Met Arg
        195                 200                 205
```

<210> SEQ ID NO 70
<211> LENGTH: 204
<212> TYPE: PRT
<213> ORGANISM: Artificial Sequence
<220> FEATURE:
<223> OTHER INFORMATION: synthetic

<400> SEQUENCE: 70

```
Ser Gln Ser Asn Arg Glu Leu Val Val Asp Phe Leu Ser Tyr Lys Leu
1               5                   10                  15
Ser Gln Lys Gly Tyr Ser Trp Ser Gln Phe Ser Asp Val Glu Glu Asn
            20                  25                  30
Arg Thr Glu Ala Pro Glu Gly Thr Glu Ser Glu Met Glu Thr Pro Ser
        35                  40                  45
Ala Ile Asn Gly Asn Pro Ser Trp His Leu Ala Asp Ser Pro Ala Val
    50                  55                  60
Asn Gly Ala Thr Gly His Ser Ser Ser Leu Asp Ala Arg Glu Val Ile
65                  70                  75                  80
Pro Met Ala Ala Val Lys Gln Ala Leu Arg Glu Ala Gly Asp Glu Phe
                85                  90                  95
Glu Leu Arg Tyr Arg Arg Ala Phe Ser Asp Leu Thr Ser Gln Leu His
            100                 105                 110
Ile Thr Pro Gly Thr Ala Tyr Gln Ser Phe Glu Gln Val Val Asn Glu
        115                 120                 125
```

```
Leu Phe Arg Asp Gly Val Asn Trp Gly Arg Ile Val Ala Phe Phe Ser
            130                 135                 140

Phe Gly Gly Ala Leu Cys Val Glu Ser Val Asp Lys Glu Met Gln Val
145                 150                 155                 160

Leu Val Ser Arg Ile Ala Ala Trp Met Ala Thr Tyr Leu Asn Asp His
                165                 170                 175

Leu Glu Pro Trp Ile Gln Glu Asn Gly Gly Trp Asp Thr Phe Val Glu
            180                 185                 190

Leu Tyr Gly Asn Asn Ala Ala Ala Glu Ser Arg Lys
        195                 200
```

<210> SEQ ID NO 71
<211> LENGTH: 164
<212> TYPE: PRT
<213> ORGANISM: Artificial Sequence
<220> FEATURE:
<223> OTHER INFORMATION: synthetic

<400> SEQUENCE: 71

```
Ala Asp Pro Leu Arg Glu Arg Thr Glu Leu Leu Ala Asp Tyr Leu
1               5                   10                  15

Gly Tyr Cys Ala Arg Glu Pro Gly Thr Pro Glu Pro Ala Pro Ser Thr
                20                  25                  30

Pro Glu Ala Ala Val Leu Arg Ser Ala Ala Arg Leu Arg Gln Ile
            35                  40                  45

His Arg Ser Phe Phe Ser Ala Tyr Leu Gly Tyr Pro Gly Asn Arg Phe
        50                  55                  60

Glu Leu Val Ala Leu Met Ala Asp Ser Val Leu Ser Asp Ser Pro Gly
65                  70                  75                  80

Pro Thr Trp Gly Arg Val Val Thr Leu Val Thr Phe Ala Gly Thr Leu
                85                  90                  95

Leu Glu Arg Gly Pro Leu Val Thr Ala Arg Trp Lys Lys Trp Gly Phe
            100                 105                 110

Gln Pro Arg Leu Lys Glu Gln Glu Gly Asp Val Ala Arg Asp Cys Gln
        115                 120                 125

Arg Leu Val Ala Leu Leu Ser Ser Arg Leu Met Gly Gln His Arg Ala
    130                 135                 140

Trp Leu Gln Ala Gln Gly Gly Trp Asp Gly Phe Cys His Phe Phe Arg
145                 150                 155                 160

Thr Pro Phe Pro
```

<210> SEQ ID NO 72
<211> LENGTH: 152
<212> TYPE: PRT
<213> ORGANISM: Artificial Sequence
<220> FEATURE:
<223> OTHER INFORMATION: synthetic

<400> SEQUENCE: 72

```
Thr Asp Ser Glu Phe Gly Tyr Ile Tyr Arg Leu Ala Gln Asp Tyr Leu
1               5                   10                  15

Gln Cys Val Leu Gln Ile Pro Gln Pro Gly Ser Gly Pro Ser Lys Thr
                20                  25                  30

Ser Arg Val Leu Gln Asn Val Ala Phe Ser Val Gln Lys Glu Val Glu
            35                  40                  45

Lys Asn Leu Lys Ser Cys Leu Asp Asn Val Asn Val Val Ser Val Asp
        50                  55                  60
```

-continued

Thr Ala Arg Thr Leu Phe Asn Gln Val Met Glu Lys Glu Phe Glu Asp
65                  70                  75                  80

Gly Ile Ile Asn Trp Gly Arg Ile Val Thr Ile Phe Ala Phe Glu Gly
                85                  90                  95

Ile Leu Ile Lys Lys Leu Leu Arg Gln Gln Ile Ala Pro Asp Val Asp
            100                 105                 110

Thr Tyr Lys Glu Ile Ser Tyr Phe Val Ala Glu Phe Ile Met Asn Asn
        115                 120                 125

Thr Gly Glu Trp Ile Arg Gln Asn Gly Gly Trp Glu Asn Gly Phe Val
    130                 135                 140

Lys Lys Phe Glu Pro Lys Ser Gly
145                 150

<210> SEQ ID NO 73
<211> LENGTH: 116
<212> TYPE: PRT
<213> ORGANISM: Artificial Sequence
<220> FEATURE:
<223> OTHER INFORMATION: synthetic

<400> SEQUENCE: 73

Ala Asp Trp Lys Lys Val Leu Asp Lys Ala Lys Asp Ile Ala Glu Asn
1               5                   10                  15

Arg Val Arg Glu Leu Lys Gln Lys Leu Glu Glu Phe Tyr Lys Glu Ala
            20                  25                  30

Met Lys Leu Asp Leu Thr Gln Glu Met Arg Arg Lys Leu Met Leu Arg
        35                  40                  45

Trp Ile Ala Ala Met Leu Met Ala Ile Gly Asp Ile Phe Asn Ala Ile
    50                  55                  60

Arg Gln Ala Lys Gln Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Lys
                85                  90                  95

Glu Glu Ala Ser Arg Lys Ala Arg Asp Tyr Gly Arg Glu Phe Gln Leu
            100                 105                 110

Lys Leu Glu Tyr
        115

<210> SEQ ID NO 74

<400> SEQUENCE: 74

000

<210> SEQ ID NO 75
<211> LENGTH: 23
<212> TYPE: PRT
<213> ORGANISM: Artificial Sequence
<220> FEATURE:
<223> OTHER INFORMATION: synthetic

<400> SEQUENCE: 75

Gly Leu Asn Asp Ile Phe Glu Ala Gln Lys Ile Glu Trp His Glu Gly
1               5                   10                  15

Ser His His His His His His
            20

<210> SEQ ID NO 76
<211> LENGTH: 8
<212> TYPE: PRT

```
<213> ORGANISM: Artificial Sequence
<220> FEATURE:
<223> OTHER INFORMATION: synthetic

<400> SEQUENCE: 76

Leu Glu His His His His His His
1               5

<210> SEQ ID NO 77
<211> LENGTH: 5
<212> TYPE: PRT
<213> ORGANISM: Artificial Sequence
<220> FEATURE:
<223> OTHER INFORMATION: synthetic

<400> SEQUENCE: 77

Met Gly Ser Cys Ala
1               5

<210> SEQ ID NO 78
<211> LENGTH: 11
<212> TYPE: PRT
<213> ORGANISM: Artificial Sequence
<220> FEATURE:
<223> OTHER INFORMATION: synthetic

<400> SEQUENCE: 78

Met Ser Gly His His His His His His Gly Ser
1               5                   10

<210> SEQ ID NO 79
<211> LENGTH: 5
<212> TYPE: PRT
<213> ORGANISM: Artificial Sequence
<220> FEATURE:
<223> OTHER INFORMATION: synthetic

<400> SEQUENCE: 79

Ser Gly Cys Ala Glu
1               5

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Ser Ser Gly Asp Ser Gly Cys Ala Glu
1               5

<210> SEQ ID NO 81
<211> LENGTH: 12
<212> TYPE: PRT
<213> ORGANISM: Artificial Sequence
<220> FEATURE:
<223> OTHER INFORMATION: synthetic

<400> SEQUENCE: 81

Ser Glu His His His His His His Gly Ser Cys Glu
1               5                   10

<210> SEQ ID NO 82
<211> LENGTH: 116
<212> TYPE: PRT
<213> ORGANISM: Artificial Sequence
```

<220> FEATURE:
<223> OTHER INFORMATION: Synthetic

<400> SEQUENCE: 82

Ala Asp Trp Lys Lys Val Leu Asp Lys Ala Lys Asp Ile Ala Glu Asn
1               5                   10                  15

Arg Val Arg Glu Ile Lys Gln Lys Leu Glu Glu Phe Tyr Lys Lys Ala
            20                  25                  30

Met Lys Leu Asp Leu Thr Gln Glu Met Arg Arg Lys Leu Met Leu Glu
        35                  40                  45

Trp Ile Ala Ala Met Leu Met Ala Ile Gly Asp Ile Phe Asn Ala Ile
    50                  55                  60

Glu Gln Ala Lys Gln Glu Ala Asp Lys Leu Lys Lys Ala Gly Gln Val
65                  70                  75                  80

Asn Ser Gln Leu Leu Asp Glu Leu Lys Arg Arg Leu Glu Glu Leu Lys
                85                  90                  95

Glu Glu Ala Ser Arg Lys Cys His Asp Tyr Gly Arg Glu Phe Gln Leu
            100                 105                 110

Lys Leu Glu Tyr
        115

<210> SEQ ID NO 83
<211> LENGTH: 116
<212> TYPE: PRT
<213> ORGANISM: Artificial Sequence
<220> FEATURE:
<223> OTHER INFORMATION: Synthetic

<400> SEQUENCE: 83

Lys Arg Leu Glu Glu Thr Val Glu Glu Thr Glu Arg Arg Leu Arg Glu
1               5                   10                  15

Ala Leu Arg Glu Val Tyr Leu Leu Ile Leu Leu Ala Glu Glu Ala
            20                  25                  30

Lys Lys Lys Asp Leu Lys Glu Gln Asn Arg His Glu Tyr Val Phe Lys
        35                  40                  45

Trp Ile Ala Phe Met Leu Met Ala Ile Gly Asp Ile Phe Asn Ile Ala
    50                  55                  60

Glu Glu Ser Lys Arg Arg Leu Asp Leu Phe Ala Lys Trp Gly Leu His
65                  70                  75                  80

Asp Arg Asn Lys Ile Asp Glu Ala Lys Lys Ile Asp Lys Leu Ala
                85                  90                  95

Leu Glu Ala Ile Glu Arg Ala Lys Lys Tyr Gly Asp Trp Phe Leu Asn
            100                 105                 110

Glu Leu Asp Lys
        115

<210> SEQ ID NO 84
<211> LENGTH: 116
<212> TYPE: PRT
<213> ORGANISM: Artificial Sequence
<220> FEATURE:
<223> OTHER INFORMATION: Synthetic

<400> SEQUENCE: 84

Lys Ser Leu Leu Gly Ile Ala Leu Glu Ala Leu Glu Glu Ala Lys Arg
1               5                   10                  15

Asp Leu Glu Lys Ala Lys Lys Gln Met Glu Glu Met Leu Lys Lys Lys
            20                  25                  30

```
Trp Lys Phe Asp Thr Thr Arg Asp Leu Lys Ala Arg Ala Ser Ala Glu
         35                  40                  45

Trp Ile Ala Ala Ala Leu Lys Ala Ile Gly Asp Arg Phe Asn Ala Lys
 50                  55                  60

Leu Leu Ile Glu Leu Gly Leu Asp Glu Leu Phe Asn Lys Gly Leu Ile
 65                  70                  75                  80

Thr Gln Asp Ile Lys Glu Asp Ile Lys Arg Arg Ala Glu Glu Ile Phe
                 85                  90                  95

Glu Lys Ile Glu Arg Leu Ile Lys Gln Ala Ile Lys Asp Lys Asp Arg
            100                 105                 110

Phe Glu Lys Leu
        115
```

```
<210> SEQ ID NO 85
<211> LENGTH: 116
<212> TYPE: PRT
<213> ORGANISM: Artificial Sequence
<220> FEATURE:
<223> OTHER INFORMATION: Synthetic

<400> SEQUENCE: 85

Leu Asp His Asp Lys Ile Val Asp Glu Ala Arg Lys Lys Met Glu Lys
 1               5                  10                  15

Lys Ile Arg Glu Ala Lys Asp Lys Ala Lys Glu Phe Val Leu Lys Ala
            20                  25                  30

Leu Asp Asn Asn His Asp Leu Lys Gln Phe Arg Glu Leu Ala His Lys
         35                  40                  45

Trp Ile Ala Leu Met Leu Met Ala Ile Gly Asp Ala Phe Asn Ile Met
 50                  55                  60

Met Glu Ala Lys Arg Lys Ala Glu Trp Leu Arg Glu Gln Gly Gln Gln
 65                  70                  75                  80

Asp Glu Asp Lys Ala Glu Glu Ala Lys Glu Lys Leu Asp Lys Ala Phe
                 85                  90                  95

Lys Glu Ala Ala Glu Arg Phe Glu Glu Ile Ala Lys Ile Tyr Gly Lys
            100                 105                 110

Gln Ala Lys Asn
        115
```

```
<210> SEQ ID NO 86
<211> LENGTH: 116
<212> TYPE: PRT
<213> ORGANISM: Artificial Sequence
<220> FEATURE:
<223> OTHER INFORMATION: Synthetic

<400> SEQUENCE: 86

Leu Leu Ala Glu Glu Gly Arg Glu Gln Ala Glu Glu Arg Leu Arg Glu
 1               5                  10                  15

Ala Arg Lys Lys Ala Gly Lys Ala Gly Asp Lys Ile Lys Asp Leu Ala
            20                  25                  30

Lys Tyr Gly Gln Asp Ser Asp Asp Glu Lys Lys Lys Phe Met Leu Lys
         35                  40                  45

Trp Ile Ala Ala Gln Leu Met Val Ile Gly Asp Met Phe Asn His Ala
 50                  55                  60

Met Glu Ala Leu Trp Glu Leu Leu Arg Arg Leu Lys Asn Asn Lys Ile
 65                  70                  75                  80

Ser Trp Asp Ala Phe Leu Lys Ala Lys Glu Glu Ile Glu Arg Glu Glu
                 85                  90                  95
```

```
Lys Glu Ala Ala Arg Asp Ser Arg Glu Lys Gly Arg Glu Ala Ala Lys
            100                 105                 110

Met Ile Asp Gln
        115
```

<210> SEQ ID NO 87
<211> LENGTH: 26
<212> TYPE: PRT
<213> ORGANISM: Artificial Sequence
<220> FEATURE:
<223> OTHER INFORMATION: Synthetic

<400> SEQUENCE: 87

```
Asp Met Arg Pro Glu Ile Trp Ile Ala Gln Glu Leu Arg Arg Ile Gly
1               5                   10                  15

Asp Glu Phe Asn Ala Tyr Tyr Ala Arg Arg
            20                  25
```

<210> SEQ ID NO 88
<211> LENGTH: 26
<212> TYPE: PRT
<213> ORGANISM: Artificial Sequence
<220> FEATURE:
<223> OTHER INFORMATION: Synthetic

<400> SEQUENCE: 88

```
Arg Lys Leu Met Leu Glu Trp Ile Ala Ala Met Leu Met Ala Ile Gly
1               5                   10                  15

Asp Ile Phe Asn Ala Ile Glu Gln Ala Lys
            20                  25
```

<210> SEQ ID NO 89
<211> LENGTH: 26
<212> TYPE: PRT
<213> ORGANISM: Artificial Sequence
<220> FEATURE:
<223> OTHER INFORMATION: Synthetic

<400> SEQUENCE: 89

```
Arg Lys Leu Glu Leu Arg Tyr Ile Ala Ala Met Leu Met Ala Ile Gly
1               5                   10                  15

Asp Ile Tyr Asn Ala Ile Arg Gln Ala Lys
            20                  25
```

<210> SEQ ID NO 90
<211> LENGTH: 26
<212> TYPE: PRT
<213> ORGANISM: Artificial Sequence
<220> FEATURE:
<223> OTHER INFORMATION: Synthetic

<400> SEQUENCE: 90

```
Asp Met Arg Pro Glu Ile Tyr Ile Ala Gln Glu Leu Arg Arg Ile Gly
1               5                   10                  15

Asp Glu Tyr Asn Ala Tyr Tyr Ala Arg Arg
            20                  25
```

<210> SEQ ID NO 91
<211> LENGTH: 26
<212> TYPE: PRT
<213> ORGANISM: Artificial Sequence
<220> FEATURE:
<223> OTHER INFORMATION: Synthetic -continued

```
<400> SEQUENCE: 91

Asp Met Arg Glu Glu Arg Tyr Ile Ala Gln Glu Leu Arg Arg Ile Gly
1               5                   10                  15

Asp Glu Tyr Asn Ala Tyr Arg Ala Arg Arg
            20                  25

<210> SEQ ID NO 92
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 92

Gly Ala Asp Trp Lys Lys Val Leu Asp Lys Ala Lys Asp Ile Ala Glu
1               5                   10                  15

Asn Arg Val Arg Glu Ile Lys Gln Lys Leu Glu Glu Phe Tyr Lys Lys
            20                  25                  30

Ala Met Lys Leu Asp Leu Thr Gln Glu Met Arg Arg Lys Leu Met Leu
        35                  40                  45

Glu Trp Ile Ala Ala Met Leu Met Ala Ile Gly Asp Ile Phe Asn Ala
    50                  55                  60

Ile Glu Gln Ala Lys Gln Glu Ala Asp Lys Leu Lys Lys Ala Gly Gln
65                  70                  75                  80

Val Asn Ser Gln Leu Leu Asp Glu Leu Lys Arg Arg Leu Glu Glu Leu
                85                  90                  95

Lys Glu Glu Ala Ser Arg Lys Cys His Asp Tyr Gly Arg Glu Phe Gln
            100                 105                 110

Leu Lys Leu Glu Tyr Gly
        115

<210> SEQ ID NO 93
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 93

Gly Lys Arg Leu Glu Glu Thr Val Glu Glu Thr Glu Arg Arg Leu Arg
1               5                   10                  15

Glu Ala Leu Arg Glu Val Tyr Leu Leu Ile Leu Leu Leu Ala Glu Glu
            20                  25                  30

Ala Lys Lys Lys Asp Leu Lys Glu Gln Asn Arg His Glu Tyr Val Phe
        35                  40                  45

Lys Trp Ile Ala Phe Met Leu Met Ala Ile Gly Asp Ile Phe Asn Ile
    50                  55                  60
```

Ala Glu Glu Ser Lys Arg Arg Leu Asp Leu Phe Ala Lys Trp Gly Leu
65                  70                  75                  80

His Asp Arg Asn Lys Ile Asp Glu Ala Lys Lys Ile Asp Lys Leu
            85                  90                  95

Ala Leu Glu Ala Ile Glu Arg Ala Lys Lys Tyr Gly Asp Trp Phe Leu
            100                 105                 110

Asn Glu Leu Asp Lys Gly
        115

<210> SEQ ID NO 94
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 94

Gly Lys Ser Leu Leu Gly Ile Ala Leu Glu Ala Leu Glu Ala Lys
1               5                   10                  15

Arg Asp Leu Glu Lys Ala Lys Lys Gln Met Glu Glu Met Leu Lys Lys
            20                  25                  30

Lys Trp Lys Phe Asp Thr Thr Arg Asp Leu Lys Ala Arg Ala Ser Ala
        35                  40                  45

Glu Trp Ile Ala Ala Leu Lys Ala Ile Gly Asp Arg Phe Asn Ala
    50                  55                  60

Lys Leu Leu Ile Glu Leu Gly Leu Asp Glu Leu Phe Asn Lys Gly Leu
65                  70                  75                  80

Ile Thr Gln Asp Ile Lys Glu Asp Ile Lys Arg Arg Ala Glu Glu Ile
            85                  90                  95

Phe Glu Lys Ile Glu Arg Leu Ile Lys Gln Ala Ile Lys Asp Lys Asp
            100                 105                 110

Arg Phe Glu Lys Leu Gly
        115

<210> SEQ ID NO 95
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 95

Gly Leu Asp His Asp Lys Ile Val Asp Glu Ala Arg Lys Lys Met Glu
1               5                   10                  15

Lys Lys Ile Arg Glu Ala Lys Asp Lys Ala Lys Glu Phe Val Leu Lys
            20                  25                  30

Ala Leu Asp Asn Asn His Asp Leu Lys Gln Phe Arg Glu Leu Ala His
         35                  40                  45

Lys Trp Ile Ala Leu Met Leu Met Ala Ile Gly Asp Ala Phe Asn Ile
 50                  55                  60

Met Met Glu Ala Lys Arg Lys Ala Glu Trp Leu Arg Glu Gln Gly Gln
 65                  70                  75                  80

Gln Asp Glu Asp Lys Ala Glu Ala Lys Glu Lys Leu Asp Lys Ala
                 85                  90                  95

Phe Lys Glu Ala Ala Glu Arg Phe Glu Ile Ala Lys Ile Tyr Gly
            100                 105                 110

Lys Gln Ala Lys Asn Gly
        115

<210> SEQ ID NO 96
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 96

Gly Leu Leu Ala Glu Glu Gly Arg Glu Gln Ala Glu Glu Arg Leu Arg
 1               5                  10                  15

Glu Ala Arg Lys Lys Ala Glu Lys Ala Gly Asp Lys Ile Lys Asp Leu
                 20                  25                  30

Ala Lys Tyr Gly Gln Asp Ser Asp Asp Glu Lys Lys Phe Met Leu
         35                  40                  45

Lys Trp Ile Ala Ala Gln Leu Met Val Ile Gly Asp Met Phe Asn His
 50                  55                  60

Ala Met Glu Ala Leu Trp Glu Leu Leu Arg Arg Leu Lys Asn Asn Lys
 65                  70                  75                  80

Ile Ser Trp Asp Ala Phe Leu Lys Ala Lys Glu Glu Ile Glu Arg Glu
                 85                  90                  95

Glu Lys Glu Ala Ala Arg Asp Ser Arg Glu Lys Gly Arg Glu Ala Ala
            100                 105                 110

Lys Met Ile Asp Gln Gly
        115

<210> SEQ ID NO 97
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 97

Gly Lys Asp Ala Asp Lys Lys Asp Glu Ala Lys Lys Lys Ala Glu

```
                1               5                  10                 15
Trp Lys Glu Arg Glu Val Phe Glu Arg Leu Glu Lys Met Glu Trp Lys
                20                 25                 30

Lys Arg Lys Asp Ser Val Ser Lys Asp Asp Ala Arg Lys Phe Thr Leu
        35                 40                 45

Lys Trp Ile Ala Asp Asp Leu Glu Leu Ile Gly Asp Leu Phe Asn Leu
    50                 55                 60

Lys Glu Glu Ala Arg Glu Val Ala Glu Asp Ala Ala Arg Asn Asn Gln
65                 70                 75                 80

Ile Thr Glu Glu Gln Arg Glu Glu Asp Glu Lys Asp Leu Glu Lys Leu
                85                 90                 95

Ala Lys Glu His Ser Trp Arg Ala Ala Tyr Arg Gly Lys Leu Lys Ala
            100                105                110

Lys Glu Phe Trp Glu Gly
            115
```

<210> SEQ ID NO 98
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 98

```
Gly Arg Ser Ala Asn Asp Ile Leu Lys Gln Phe Leu Glu Met Leu Gln
1               5                  10                 15

Glu Ala Leu Arg Lys Phe Asp Gly Lys Lys Asn Lys Ile Glu Asp Glu
                20                 25                 30

Trp Lys Gln Phe Asp Leu Ser Thr Gln Arg Arg Glu Glu Ala Thr His
            35                 40                 45

Lys Trp Ile Ala Ala Ala Leu Met Ala Ile Gly Asp Met Phe Asn Ala
    50                 55                 60

Leu Arg Trp Ala Leu Glu Glu Ala Leu Lys Ala Lys Leu Lys Asn Leu
65                 70                 75                 80

Gln Ser Ser Asp Asp Leu Lys Glu Ala Ile Glu Arg Met Met Lys Leu
                85                 90                 95

Met Leu Glu Lys Ala Gln Glu Ile Gln Glu Lys Gly Arg Glu Leu Ala
            100                105                110

Asp Lys Ile Glu Gln Gly
            115
```

<210> SEQ ID NO 99
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)

<223> OTHER INFORMATION: optionally absent

<400> SEQUENCE: 99

```
Gly Glu Glu Phe Lys Lys Leu Lys Lys Trp Glu Trp Leu Leu
1               5                   10                  15

Lys Ala Thr Asn Glu Ala Glu Asn Gln Ala Arg Asn Met Trp Gln Lys
            20                  25                  30

Ala Glu Gln Thr Asp Leu Glu Asp Gln Arg Ile Arg Ala Val Asp
        35                  40                  45

Phe Trp Ile Ala Ile Ala Leu Met Ala Ile Gly Asp Lys Phe Asn Ala
50                  55                  60

Asp Gln Glu Gly Asp Glu Phe Glu Lys Tyr Lys Lys Gly Arg
65                  70                  75                  80

Ala Ser Glu Asp Lys Ile Lys Glu Ala Lys Asp Glu Arg Asp Arg Ala
            85                  90                  95

Lys Lys Arg Trp Glu Gln Phe Val Lys Glu Ala Gly Glu Arg Ala Phe
                100                 105                 110

Arg Gly Glu Gln Leu Gly
        115
```

<210> SEQ ID NO 100
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 100

```
Gly Trp Asp Ala Arg Arg Ala Leu Lys Tyr Val Tyr Glu Arg Met Arg
1               5                   10                  15

Glu Asp Leu Glu Tyr Ala Arg Asn Gln Ile Asp Asn Met Glu Asp Arg
            20                  25                  30

Ala Asp Gln Tyr Asp Ala Arg Thr Glu Glu Arg Lys Glu Phe Thr Lys
        35                  40                  45

Arg Trp Ile Ala Leu Ala Leu Met Leu Ile Gly Asp Gly Phe Asn Ala
50                  55                  60

Phe Glu Arg Ala Lys Glu Trp Ile Asp Asp Gly Lys Asn Asn Asn Gln
65                  70                  75                  80

Arg Ser Ser Asp Glu Ala Asp Tyr Ala Lys Glu Ala Leu Lys Phe
            85                  90                  95

Ile Phe Tyr Ala Ala Phe Glu Ala Arg Arg Lys Gly Asp Glu Leu Asp
                100                 105                 110

Lys Lys Ala Glu Gly Gly
        115
```

<210> SEQ ID NO 101
<211> LENGTH: 118
<212> TYPE: PRT
<213> ORGANISM: Artificial Sequence
<220> FEATURE:
<223> OTHER INFORMATION: Synthetic

<400> SEQUENCE: 101

```
Gly Lys Glu Ala Lys Lys Arg Ile Gln Glu Ala Leu Glu Glu Ala Lys
1               5                   10                  15

Arg Lys Ala Glu Lys Leu Leu Arg Glu His Glu Lys Lys Lys Lys Glu
            20                  25                  30

His Leu Leu Gly Asp Lys Arg Asp Arg Glu Lys Thr Glu Glu Thr Asp
        35                  40                  45

Lys Trp Ile Ala Glu Ala Leu Met Leu Ile Gly Asp Ile Phe Asn Leu
    50                  55                  60

Tyr Met Lys Phe Glu Trp Glu Lys Glu Arg Glu Lys Lys Leu Gly Leu
65                  70                  75                  80

Leu Arg Glu Glu Glu Lys Glu Val Glu Asp Glu Ala Lys Asp Ala
                85                  90                  95

Tyr Leu Lys Ala Leu Lys Leu Ala Tyr Leu Val Ser Lys Lys Gly His
            100                 105                 110

Glu Val Ala Glu Leu Gly
        115
```

<210> SEQ ID NO 102
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 102

```
Gly Asp Ser Asp Asp Asp Leu Lys Asp Ala Leu Leu Arg Met Leu
1               5                   10                  15

Trp Ala Ala Ala Gln Ala Ile Tyr His Ser Leu Glu Asn Met Glu Arg
            20                  25                  30

Lys Glu Lys Phe Asp Met His Phe Glu Glu Arg Arg Asp Thr Leu
        35                  40                  45

Gln Trp Ile Ala Asp Ala Leu Arg Ala Ile Gly Asp Ala Phe Asn Glu
    50                  55                  60

Met Met Arg Arg Arg Glu Leu Gly Lys Lys Arg Glu Asn Asn Ile
65                  70                  75                  80

Ile Ser Glu Gln Arg Ala Arg Leu Tyr Glu Glu Phe Leu Lys Arg Phe
                85                  90                  95

Ala Glu Trp Ala Ser Arg Glu Leu Ala Lys Ala Gly Lys Lys Glu Ala
            100                 105                 110

Asn Lys Leu Asn Glu Gly
        115
```

<210> SEQ ID NO 103
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:

```
<221> NAME/KEY: MISC_FEATURE
<222> LOCATION: (118)..(118)
<223> OTHER INFORMATION: optionally absent

<400> SEQUENCE: 103

Gly Asn Ile Leu Asp Glu Ala Lys Asp Glu Met Arg Glu Met Glu
1               5                   10                  15

Lys Leu Trp Lys Lys Phe Lys Asp Glu Val Glu Glu Arg Lys Glu
            20                  25                  30

Ala Glu Arg Glu Glu Lys His Phe Gln Glu Arg Ala Glu Leu Thr Lys
        35                  40                  45

Arg Trp Ile Ala Arg Ala Leu Met Ala Ile Gly Asp Met Phe Asn Arg
50                  55                  60

Phe Arg Glu Ala Lys Glu Lys Leu Glu Lys Arg Glu Leu Gly Leu
65                  70                  75                  80

Ile Ser Glu Glu Asp Ala Arg Lys Ala Leu Leu Leu Glu Glu Phe
                85                  90                  95

Met Arg Arg Met Ala Glu Phe Ala Lys Lys Leu Gly Asp Asp Leu Met
            100                 105                 110

Arg Asp Ala Glu Lys Gly
        115

<210> SEQ ID NO 104
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 104

Gly Glu Asp Asp Asp Lys Val Leu Lys Trp Ala Leu Glu Ala Leu Arg
1               5                   10                  15

Lys Val Leu Asp Glu Ala Lys Glu Lys Leu Glu Lys Leu Lys Lys Tyr
            20                  25                  30

Thr Asp Gly Asp Gly Phe Gly Glu Asp Tyr Arg Arg Glu Phe Phe Arg
        35                  40                  45

Lys Trp Ile Ala Ile Ala Leu Glu Ala Ile Gly Asp Ile Phe Asn Ile
50                  55                  60

Met Met Glu Ala Leu Gln Lys Ala Asp Lys His Lys Lys Leu Asn Thr
65                  70                  75                  80

His Asp Ser Gln Lys Ala Asp Glu Ala Lys Glu Lys Ile Lys Lys Phe
                85                  90                  95

Ala Asp Glu Ala Glu Glu Arg Ala Lys Glu Leu Ala Lys Lys Gly Glu
            100                 105                 110

Ala Trp Leu Leu Lys Gly
        115

<210> SEQ ID NO 105
<211> LENGTH: 118
<212> TYPE: PRT
<213> ORGANISM: Artificial Sequence
<220> FEATURE:
<223> OTHER INFORMATION: Synthetic
```

<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 105

Gly Ser Lys Trp Glu Glu Asp Arg Glu Lys Ala Lys Arg Ala Glu
1               5                   10                  15

Lys Lys Leu Asp Glu Ala Lys Asp Lys Leu Asp Leu Tyr Lys Asp Phe
            20                  25                  30

Ala Leu Arg Phe Asp Ala Ser Asp Glu Leu Lys Thr Lys Trp Thr Leu
        35                  40                  45

Glu Trp Ile Ala Leu Ala Leu Glu Met Ile Gly Asp Val Phe Asn Tyr
    50                  55                  60

Ala Leu Glu Ala Lys Glu Phe Ala Glu Lys Lys Ala Arg Asn Asn Leu
65                  70                  75                  80

Leu Leu Asp Asp Leu Lys Asp Leu Tyr Lys Leu Tyr Leu Ala Leu Leu
                85                  90                  95

Ala Lys Glu Glu Ser Lys Lys Ala Ile Glu Glu Gly Asp Lys Leu Arg
            100                 105                 110

Glu Ala Ile Glu Lys Gly
        115

<210> SEQ ID NO 106
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 106

Gly Leu Ser Ala Asp Asp Leu Phe Asp Tyr Ala Glu Asp Arg Met Arg
1               5                   10                  15

Glu Gly Trp Lys Asp Phe Glu Glu Leu Ala Gly Glu Ala Lys Lys
            20                  25                  30

Ala Lys Glu His Thr Leu Ser Asp Gln Glu Arg Arg Glu Ala Thr Glu
        35                  40                  45

Lys Trp Ile Ala Ala Ala Leu Glu Leu Ile Gly Asp Ala Phe Asn Ala
    50                  55                  60

Ile Arg Trp Ala Glu Glu Leu Gly Lys Leu Tyr Val Lys Leu Asn Leu
65                  70                  75                  80

Asp Asp Lys Gln Lys Val Glu Glu Leu Lys Lys Lys Leu Glu Glu Arg
                85                  90                  95

Ala Lys Glu Glu Ala Gln Lys Ala Arg Lys Arg Gly Asp Lys Leu Glu
            100                 105                 110

Asp Leu Ala Asp Ser Gly
        115

<210> SEQ ID NO 107

```
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 107

Gly Asn Asp Arg Asp Gln Ile Glu Glu Tyr His Arg Glu Arg Met Asp
1               5                   10                  15

Glu Glu Leu Asp Arg Ala Lys Lys Arg Leu Glu Glu Leu Lys Lys Leu
            20                  25                  30

Trp Glu Lys Leu Asp Gly Asp Asp Leu Met Lys Phe Phe Trp Thr Phe
        35                  40                  45

Lys Trp Ile Ala Glu Ser Leu Lys Ile Ile Gly Asp Leu Phe Asn Arg
    50                  55                  60

Leu Leu Arg Thr Trp Glu Phe Ala Glu Ala Leu Lys Lys Gly Ile Gly
65                  70                  75                  80

Phe Asp Glu Lys Lys Ala Glu Glu Ala Lys Glu Arg Ala Tyr Glu Arg
                85                  90                  95

Ala Ala Glu Ala Ala Trp Lys Ala Ala Lys Leu Ser Arg Glu Met Arg
            100                 105                 110

Glu Phe Leu Leu Lys Gly
        115

<210> SEQ ID NO 108
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 108

Gly Asn Ser Ala Asp Asp Ile Leu Asp Glu Ala Arg Asp Arg His Glu
1               5                   10                  15

Arg Thr Ala Leu Trp Ala Lys Asp Gln Glu Asp Asn Leu Lys Asp Glu
            20                  25                  30

Ala Glu Lys Gly Asp Ile Gly Thr Glu Gln Leu Ile Arg Leu Thr Met
        35                  40                  45

Lys Trp Ile Ala Ile Gln Leu Met Ala Ile Gly Asp Ala Phe Asn Phe
    50                  55                  60

Ala Met Glu Ala Lys Lys Lys Leu Asp Leu Leu Lys Lys Leu Asn Leu
65                  70                  75                  80

Val Gln Ala Gln Lys Leu Glu Glu Ala Lys Glu Arg Ala Asp Lys Phe
                85                  90                  95

Glu Lys Lys Ala Asp Gln Leu Ser Ser Lys Phe Gly Arg Glu Met Ala
            100                 105                 110
```

Arg Asp Leu Ala Gln Gly
        115

<210> SEQ ID NO 109
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 109

Gly Arg Ser Ala Glu Ile Met Arg Glu Ile Leu Glu Lys Gln Ala Glu
1               5                   10                  15

Asp Asp Ala Lys Lys Ile Arg Asp Ile Ala Gln Lys Trp Lys Glu Arg
            20                  25                  30

Arg Lys Arg Tyr Asp Pro Arg Asp Glu Glu Arg Glu Glu Glu Val Glu
        35                  40                  45

Lys Trp Ile Ala Phe Ala Leu Met Ala Ile Gly Asp Ile Phe Asn Leu
    50                  55                  60

Ala Arg Trp Ala Leu Leu Gln Ala Arg Trp Glu Arg Trp Asn Leu
65                  70                  75                  80

Ser His Glu Asp Glu Gly Lys Asn His Glu Glu Asn Val Lys Asp Ala
                85                  90                  95

Glu Asp Arg Ala His Trp Lys Ala Arg Glu Ala Ala Arg Glu Gly Ala
            100                 105                 110

Lys Met Ser Trp Glu Gly
        115

<210> SEQ ID NO 110
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 110

Gly Gly Thr Glu Asp Asp Ile Lys Asp Leu Ala Glu Lys Trp Arg Asp
1               5                   10                  15

Asp Met Lys Lys Glu Phe Leu Arg Glu Phe Leu Arg Ile Lys Glu Trp
            20                  25                  30

Thr Lys Tyr Trp Gly Trp Arg Glu Glu Gly Arg Lys Leu Ala Thr Leu
        35                  40                  45

Arg Trp Ile Ala Leu Ser Leu Met His Ile Gly Asp Leu Phe Asn Leu
    50                  55                  60

Lys Glu Leu Ala Lys Lys Leu Val Asp Asp Ile Lys Lys Gly Leu
65                  70                  75                  80

Glu His Glu Glu Arg Ala Glu Arg Ala Arg Glu Glu Ala Glu Lys Ile

```
                85                  90                  95
Met Glu Lys Ala Ala Lys Leu Asp Ser Ile Leu Ser Lys Leu Ala Ala
            100                 105                 110

Lys Leu Ile Glu Glu Gly
        115

<210> SEQ ID NO 111
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 111

Gly Glu Arg Val Glu Glu Ile Leu Arg Lys Met Leu Asp Asp Ala Leu
1               5                   10                  15

Leu His Phe Leu Glu His Arg Asp Asp Ala Arg Glu Arg Lys Glu Arg
            20                  25                  30

Gly Glu Arg His Gln Pro Arg Asp Glu Arg Glu Glu Leu Ser His
        35                  40                  45

Asp Trp Ile Ala Ala Ala Leu Met Ala Ile Gly Asp Ile Phe Asn Ala
    50                  55                  60

Lys Leu Arg Ala Glu Glu Arg Ala Glu Phe Leu Lys Trp Gly Leu
65                  70                  75                  80

Arg Ser Gln Asp Asp Lys Lys Glu Leu Glu Arg Ala Lys Glu Ala
                85                  90                  95

Ala Lys Ile Ala Leu Lys Trp Ala Glu Glu Ala Gly Lys Glu Ala Asp
            100                 105                 110

Glu Ala Glu Lys Ala Gly
        115

<210> SEQ ID NO 112
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 112

Gly Leu Arg Phe Glu Glu Ile Glu Arg Tyr Ala Arg Glu Glu Ala Asp
1               5                   10                  15

Lys Ile Ala Asp Glu Ala Lys Glu Arg Phe Glu Lys Leu Lys Lys Leu
            20                  25                  30

Phe Leu Trp Leu Thr Asp Lys Asp Glu Glu Arg Leu Lys Met Thr His
        35                  40                  45

Leu Trp Ile Ala Gly Ala Leu Glu Ala Ile Gly Asp Leu Phe Asn Ala
    50                  55                  60
```

Ala Glu Leu Ala Lys Glu Leu Ala Glu Lys Ala Arg Leu Thr Ser
65                  70                  75                  80

Gln Asp Ala Asn Arg Arg Asp Glu Ala Arg Lys Lys Ile Asp Glu Ala
                85                  90                  95

Glu Lys Glu Ala Ala Asp Lys Val Ser Lys Ala Ala Lys Glu Ala Ala
            100                 105                 110

Lys Phe Phe Glu Gln Gly
        115

<210> SEQ ID NO 113
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 113

Gly Phe Asp Trp Lys Lys Val Leu Asp Lys Ala Lys Asp Leu Ala Glu
1               5                   10                  15

Asn Asp Val Arg Glu Ala Lys Gln Lys Leu Glu Glu Phe Tyr Lys Lys
                20                  25                  30

Ala Met Lys Leu Asp Leu Thr Gln Glu Met Arg Arg Lys Leu Met Leu
            35                  40                  45

Glu Trp Ile Ala Ala Met Leu Met Ala Ile Gly Asp Ile Phe Asn Ala
    50                  55                  60

Ile Glu Gln Gly Lys Gln Glu Ala Asp Lys Leu Lys Lys Leu Gly Lys
65                  70                  75                  80

Val Leu Ser Gln Leu Leu Asp Glu Leu Lys Arg Arg Leu Glu Glu Leu
                85                  90                  95

Lys Glu Glu Ala Ala Leu Lys Ala His Asp Phe Gly Arg Glu Phe Glu
            100                 105                 110

Leu Lys Leu Leu Phe Gly
        115

<210> SEQ ID NO 114
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 114

Gly Ser Ser Ala Glu Asp Leu Arg Asp Trp Ala Arg Asp Gln His Glu
1               5                   10                  15

Lys Asp Val Asp Lys Met Glu Lys Arg Leu Arg Leu Leu Tyr Phe Glu
                20                  25                  30

```
Leu Ala Arg Lys Asp Phe Asn Glu Glu Leu Lys Lys Ala Thr Glu
        35                  40                  45

Lys Trp Ile Ala Ala Leu Asp Ala Ile Gly Asp His Phe Asn Ala
 50                  55                  60

Ala Leu Lys Ala Arg Leu Leu Ala Arg Asp Ala Lys Lys Gly Leu
 65                  70                  75                  80

Ile Asp Arg Asn Lys Leu Asp Glu Val Glu Lys Met Ala Glu Leu Phe
                 85                  90                  95

Glu Glu Leu Gly Glu Arg Lys Ala Ala Leu Lys Gly Arg Glu Phe Leu
            100                 105                 110

Arg Trp Val Leu Leu Gly
        115
```

```
<210> SEQ ID NO 115
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 115

Gly Glu Asp Glu Glu Lys Asp His Lys Asp Thr Glu Glu Lys Ala Arg
 1               5                  10                  15

Arg Leu His Glu Arg Ala Arg Asp Met Leu Asp Lys Val Lys Asp Leu
                20                  25                  30

Glu Glu Lys Thr Asp Ala Gln Asp Asn Glu Arg Arg Arg Ala Thr His
            35                  40                  45

Asp Trp Ile Ala Ala Ala Leu Met Met Ile Gly Asp Ala Phe Asn Ser
 50                  55                  60

Phe Glu Asp Thr Lys Arg Arg Ala Glu Lys Lys Arg Glu Leu Asn Leu
 65                  70                  75                  80

Ile Ser Glu Asp Glu Ala Lys Glu Lys Ile Lys Arg Ala Glu Glu Leu
                 85                  90                  95

Arg Lys Arg Ile Tyr Glu Leu Leu Lys Lys Ala Ala Glu Phe Ala Arg
            100                 105                 110

Glu Ala Glu Lys Gly Gly
        115
```

```
<210> SEQ ID NO 116
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 116

Gly Glu Leu Ala Arg Glu Ala Ala Glu Glu Ala His Arg Arg Val Glu
```

```
   1               5                  10                 15
Glu Asp Ala Arg Asp Ala Lys Asn Arg Leu Asp Glu Phe Lys Lys Arg
              20                  25                 30
Tyr Lys Ile Thr Gln Leu Ser Lys Ser Asp Ile Ser Arg Ala Thr Ala
              35                  40                 45
Leu Trp Ile Ala Ala Ala Leu Asp Ala Ile Gly Asp Ile Phe Asn Ala
 50                  55                  60
Lys Gln Lys Ala Glu Lys Ile Leu Gly Leu Trp Tyr Lys Leu Gly Leu
 65                  70                  75                 80
Val Gln Leu Gln Glu Phe Leu Glu Lys Glu Asp Lys Ala Arg Tyr His
              85                  90                 95
Trp Gln Ala Ala Leu Glu Arg Ala Phe Glu Ala Gly Arg Asp Met Leu
             100                 105                110
Glu Val Ala Ala Tyr Gly
             115
```

<210> SEQ ID NO 117
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 117

```
Gly Ala Asn His Glu Asp Ala Ile Trp Glu Ala Leu Tyr Lys Ala Glu
 1               5                  10                 15
Asp Ala Phe Lys Asp His Leu Lys Glu Ile Glu Ile Tyr Arg Glu Phe
              20                  25                 30
Ser Glu Lys Phe Trp Pro Leu Asp Asp Tyr Lys Asp Asn Leu Arg Ala
              35                  40                 45
His Trp Ile Ala Ala Ala Leu Ala Ala Ile Gly Asp Trp Phe Asn Val
 50                  55                  60
Phe Phe Glu Ala Glu Leu Lys Phe Arg Glu Ala Lys Arg Lys Asn Leu
 65                  70                  75                 80
Arg Ser Glu Asp Asp Ile Lys Lys Tyr Arg Trp Arg Leu Phe Lys Ala
              85                  90                 95
Leu Asp Ile Ala Ile Asp Leu Ala Asp Arg Val Gly Asp Glu Ala Glu
             100                 105                110
Lys Ala Glu Arg Leu Gly
             115
```

<210> SEQ ID NO 118
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)

<223> OTHER INFORMATION: optionally absent

<400> SEQUENCE: 118

Gly Arg Phe Ala Glu Arg Leu Phe Lys Lys Met Leu Ile Lys Gln Leu
1               5                   10                  15

Leu Asn Thr Gln Tyr Phe Arg Asp Gln Leu Lys Gln Leu Lys Asp Arg
            20                  25                  30

Ser Lys Lys Tyr Asp Ala Ser Asp Asp Lys Asp Glu Ala Thr His
        35                  40                  45

Arg Trp Ile Ala Phe Ala Leu Met Ala Ile Gly Asp Val Phe Asn Asp
    50                  55                  60

Lys Leu Glu Ile Glu Leu Leu Ile Glu Leu Phe Ala Lys Tyr Gly Leu
65                  70                  75                  80

Val His Glu Glu Glu Arg Lys Glu Phe Arg Lys Arg Leu Asp Glu Phe
                85                  90                  95

Glu Lys Ile Phe Arg Lys Trp Leu Asp Glu Leu Lys Lys Leu Ala Leu
                100                 105                 110

Glu Ala Leu Asn Gln Gly
        115

<210> SEQ ID NO 119
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 119

Gly Leu Asp Gly Asp Tyr Leu Met Asp Glu Ala Phe Lys Phe Ile Glu
1               5                   10                  15

Arg Glu Arg Glu Arg Ala Glu Glu Ala Lys Lys Met Tyr Glu Leu
            20                  25                  30

Ala Glu Lys Gly Lys Tyr Tyr Glu Glu Arg Lys Thr Lys Ala Thr Lys
        35                  40                  45

Phe Trp Ile Ala Leu Ala Leu Glu Met Ile Gly Asp Phe Phe Asn Phe
    50                  55                  60

Glu Met Trp Phe Arg Lys Tyr Ala Glu Lys Asn Arg Glu Asn Asn Gln
65                  70                  75                  80

Arg Arg Glu Asp Leu Leu Arg Arg Trp Glu Leu Leu Leu Arg Phe Gln
                85                  90                  95

Ala Trp Asp Ala Ala Glu Arg Ala Arg Glu Leu Gly Lys Arg Leu Glu
                100                 105                 110

Leu Trp Phe Lys Lys Gly
        115

<210> SEQ ID NO 120
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 120

Gly Lys Glu Gly Ser Arg Leu Arg Glu Ala Glu Arg Arg Gly Leu
1               5                   10                  15

Arg Lys Leu Leu Glu Val Ile Leu Arg Trp Leu Glu Asp Ala Leu Arg
            20                  25                  30

Met Ile Tyr Gly Gln Asp Lys Asp Glu Asp Arg Lys Glu Ala Thr His
        35                  40                  45

Arg Trp Ile Ala Asp Ala Leu Glu Leu Ile Gly Asp Ile Phe Asn Ala
    50                  55                  60

Leu Leu Glu Ala Phe Ile Lys Met Glu Leu Ala Arg Arg Phe Gly Leu
65                  70                  75                  80

Leu Glu Glu Gln Arg Ala Arg Asp Glu Lys Lys Ala Leu Glu Arg
                85                  90                  95

Ala Glu Glu Phe Ser Lys Arg Ala Arg Glu Leu Gly Glu Lys Leu Thr
            100                 105                 110

Gln Ile Leu Glu Gly Gly
        115

<210> SEQ ID NO 121
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 121

Gly Glu Val Ala Lys Asp Leu Ala Lys Leu Ala Ile Asp Leu Ala Lys
1               5                   10                  15

Lys Leu Met Leu Leu Phe Trp Trp Phe Glu Leu Phe Lys Leu Phe
            20                  25                  30

Ala Lys Phe Thr Asp Glu Trp Gln Glu Trp Lys Ala Arg Gly Thr Ala
        35                  40                  45

Phe Trp Ile Ala Leu Ser Leu Ala Ala Ile Gly Asp Phe Phe Asn Ala
    50                  55                  60

Arg Arg Arg Ala Glu Leu Gln Ala Arg Glu Gly Lys Gln Lys Gly Leu
65                  70                  75                  80

Thr Thr Glu Glu Lys Glu Lys Arg Trp Arg His Leu Lys Glu Ala
                85                  90                  95

Trp Glu Lys Leu Glu Lys Ile Ser Arg Leu Ala Phe Leu Phe Ala Gln
            100                 105                 110

Glu Ala Glu Asn Gln Gly
        115

<210> SEQ ID NO 122
<211> LENGTH: 118
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 122
```

Gly Ser Arg Trp Phe Asp Ala Glu Asp Lys Met Arg Glu Arg Lys Asp
1               5                   10                  15

Arg Ala Ile Leu Gln Leu Leu Phe Met Leu Trp Ile Ile Phe Tyr Ile
            20                  25                  30

Leu Trp Tyr Gly Asp Asp Thr Glu Glu Ala Lys Arg Lys Ala Met Ala
        35                  40                  45

Ala Trp Ile Ala Leu Ala Leu Ile Gly Ile Gly Asp Ile Phe Asn Ala
    50                  55                  60

Glu Ala Glu Phe Leu Glu Glu Leu Glu Arg Ala Ile Lys Gln Gly Gln
65                  70                  75                  80

Val Ser Asp Gln Leu Lys Glu Glu Leu Leu Lys Arg Met Glu Asp Asp
                85                  90                  95

Lys Arg Asp Leu Glu Lys Arg Leu Tyr Glu Phe Leu Leu Lys Ala Leu
            100                 105                 110

Leu Gln Trp Met Gln Gly
        115

```
<210> SEQ ID NO 123
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 123
```

Gly Asp Gln Ala Asp Lys Ile Lys Asp Lys Ile Lys Asp Glu Ala Lys
1               5                   10                  15

Lys Lys Ala Asp Glu Phe Lys Lys Arg Leu Glu Gln Phe Arg Glu Tyr
            20                  25                  30

Leu Glu Lys Val Tyr Ser Asp Asp Leu Lys Glu Ile Tyr Leu Thr Ile
            35                  40                  45

Phe Trp Ile Ala Leu Ala Leu Met Leu Ile Gly Asp Ala Phe Asn Glu
        50                  55                  60

Lys Met Leu Leu Glu Trp Gly Phe Lys Glu Arg Lys Lys Arg Asn Leu
65                  70                  75                  80

Arg His Glu Glu Glu Leu Lys Glu Glu Lys Lys Lys Arg Glu Glu Ala
                85                  90                  95

Glu Lys Ala Leu Glu Trp Ala Ser Lys Tyr Ala Ser Gln Val Gly Lys
            100                 105                 110

Glu Ala Ala Glu Glu Gly
        115

<210> SEQ ID NO 124
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 124

Gly Gly Asp Glu Asn Lys Leu Lys Asp Tyr Val Lys Asp Ile Glu
1               5                   10                  15

Arg Gly Leu Asn Glu Ile Glu Asp Leu Ala Arg Lys Ile Glu Gln Leu
            20                  25                  30

Ala Arg Arg Phe Phe Pro Lys Asp Glu Glu Arg Met Lys Phe Thr Met
        35                  40                  45

Trp Trp Ile Ala Ala Ala Leu Met Ala Ile Gly Asp Ile Phe Asn Ala
    50                  55                  60

Lys Glu Tyr Ala Arg Glu Arg Ala Glu Ile Arg Arg Lys Gly Leu
65                  70                  75                  80

Arg Arg Glu Glu Glu Ala Arg Arg Ile Glu Lys Phe Ile Glu Glu Glu
                85                  90                  95

Ala Glu Lys Ala Ala Lys Lys Ala Ala Lys Leu Gly Asp His Leu Ala
            100                 105                 110

Glu Glu Leu Phe Arg Gly
        115

<210> SEQ ID NO 125
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 125

Gly Lys Gln Trp Gln Glu Ala Phe Glu Ala Arg Arg Arg Ile Glu
1               5                   10                  15

Glu Lys Ala Arg Glu Phe Glu Asp Arg Ala Lys Lys Glu Ala Leu Leu
            20                  25                  30

His Leu Phe Phe Ile Pro His Asp Lys Glu Ile Ala Asp Asn Ser Lys
        35                  40                  45

Lys Trp Ile Ala Trp Ala Leu Met Leu Ile Gly Asp Ile Phe Asn Leu
    50                  55                  60

Glu Glu Glu Ala Ala Glu Arg Ala Arg Arg His Val Lys Arg Gly Glu
65                  70                  75                  80

Ile Ser Glu Asp Asp Ala Lys Gln Ile Arg Lys Arg Leu Gln Glu Gln
                85                  90                  95

Ala Lys Arg Ala Ala Trp Trp Met Arg Tyr Trp Gly Glu Glu Ser Ala
            100                 105                 110

Lys Phe Ala Phe Ile Gly
        115

<210> SEQ ID NO 126
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 126

Gly Lys Phe Lys Lys Leu Phe Glu Asn Tyr Ala Glu Leu Phe Ala Arg
1               5                   10                  15

Trp Val Ala Asp Lys Gly Lys Lys Leu Ala Glu Glu Leu Arg Glu Lys
            20                  25                  30

Ala Glu Lys Gly Leu Lys Leu Gln Lys Leu Trp Leu Ile Phe Thr Met
        35                  40                  45

Ile Trp Ile Ala Ile Met Leu Met Ser Ile Gly Asp Ala Phe Asn Leu
    50                  55                  60

Ala Leu Leu Ala Glu Leu Trp Val Gln Ala Ala Lys Asn Tyr Gly Trp
65                  70                  75                  80

Leu Arg Asp Asn Glu Ala Asp Glu Ala Glu Asp Arg Val Arg Lys Phe
                85                  90                  95

Ala Asp Glu Ala Ser Arg Arg Ala Leu Glu Lys Gly Leu Glu Ala Leu
            100                 105                 110

Arg Lys Ile Leu Glu Gly
        115

<210> SEQ ID NO 127
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 127

Gly Gly Asp Gly Val Lys Glu Leu Glu Leu Glu Lys Arg Lys Asp
1               5                   10                  15

Glu Lys Lys Asn Lys Ala Glu Asp Arg Ile Lys Lys Phe Lys Asp Glu
            20                  25                  30

Ala Lys Tyr Ala Asp Asp Arg Thr Glu Asp Lys Glu Lys Leu Ala His
        35                  40                  45

Arg Trp Ile Ala Leu Ala Leu Asp Ile Ile Gly Asp Ala Phe Asn Leu
    50                  55                  60

Lys Glu Glu Ala Arg Arg Arg Phe Leu Arg His Lys Phe Arg Gly Glu

```
                65                  70                  75                  80
Leu Asp Asp Ser Lys Lys Glu Tyr Ala Glu Lys Glu Met Lys Arg Phe
                    85                  90                  95
Glu Asp Asp Val Glu Lys Asp Ala Glu Leu Ala Gln Lys Ala Lys
                100                 105                 110
Glu Ala Phe Lys Glu Gly
        115
```

<210> SEQ ID NO 128
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 128

```
Gly Tyr Thr Lys Glu Trp Ile Arg Asp Arg Ala Lys Glu Glu Leu Asp
1               5                   10                  15
Arg Phe Ala Asp Glu Ala Lys Asp Lys Ala Lys Ile Arg Asp Asp
            20                  25                  30
Phe Glu Lys Arg Asp Asp Lys Asn Gln Ile Ala Ala Glu Leu Thr Lys
                35                  40                  45
Lys Trp Ile Ala Ala Glu Leu Glu Ala Ile Gly Asp Ala Phe Asn Arg
        50                  55                  60
Ala Glu Glu Ala Lys Glu Arg Leu Lys Lys Leu Lys Leu Gly Leu
65                  70                  75                  80
Thr Arg Lys Glu Glu Ala Glu Glu Ala Ala Lys Leu Glu Lys Leu
                    85                  90                  95
Glu Lys Glu Ala Ser Glu Lys Leu Ser Lys Ile Ala His Glu Val Ser
                100                 105                 110
Lys His Asp Asp Gln Gly
        115
```

<210> SEQ ID NO 129
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 129

```
Gly Asp Phe Trp Leu Lys Ala Ile Glu Ile Ala Gly Gly Arg Met Leu
1               5                   10                  15
Glu Arg Ala Arg Glu Ser Trp Tyr Arg Ala Leu Tyr Phe Ile Leu Met
            20                  25                  30
Val Lys Leu Phe Tyr Pro Ser Asp Asp Leu Arg Arg Ile Phe Thr Leu
            35                  40                  45
```

```
Arg Trp Ile Ala Glu Ser Leu Lys Leu Ile Gly Asp Ala Phe Asn Leu
        50                  55                  60

Phe Glu Leu Ala Arg Glu Leu Glu Leu Tyr Tyr Lys Tyr Gly Trp
65                  70                  75                  80

Ile Thr Leu Glu Lys Ala Leu Lys Ala Leu Trp Ile Leu Leu Lys Leu
                85                  90                  95

Glu Glu Ile Phe Ser Lys Ala Ser Lys Asp Leu Gly Glu Arg Leu Ala
                100                 105                 110

Glu Glu Ile Glu Arg Gly
        115
```

```
<210> SEQ ID NO 130
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 130

Gly Glu Lys Leu Lys Lys Leu Ala Glu Glu Leu Glu Lys Lys Phe Arg
1               5                   10                  15

Lys Leu Phe Phe Ile Leu Lys Asp Glu Leu Asp Arg Ala Tyr Leu Ile
                20                  25                  30

Ala Leu Lys Thr Gln Val Gln Arg Gln Glu Leu Ala Arg Asp Thr Lys
                35                  40                  45

Leu Trp Ile Ala Val Ala Leu Met Ile Ile Gly Asp Leu Phe Asn Ala
        50                  55                  60

Glu Ile Gln Gly Lys Glu Leu Arg Asp Lys Leu Ile Lys Lys Asn Gln
65                  70                  75                  80

Val Glu Glu Gln Lys Ala Lys Glu Phe Trp Lys Trp Glu Glu Val
                85                  90                  95

Lys Gln Arg Ala Glu Glu Leu Ile Lys Lys Gly Gly Glu Met Val Glu
                100                 105                 110

Arg Leu Ala Asp Tyr Gly
        115
```

```
<210> SEQ ID NO 131
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 131

Gly Lys Lys Tyr Leu Lys Ala Ala Arg Leu Ala Leu Tyr Leu Leu Trp
1               5                   10                  15
```

-continued

Glu Ala Tyr Leu Arg Gly Tyr Leu Asn Leu Leu Asp Glu Leu Glu
            20                  25                  30

Ala Glu Phe Phe Asp Pro His Asp Glu Arg Lys Ile Arg Tyr Thr Ile
        35                  40                  45

Asn Trp Ile Ala Asp Ala Leu Met Leu Ile Gly Asp Leu Phe Asn Ala
 50                  55                  60

Arg Leu Lys Met Glu Lys Ala Leu Trp Glu Leu Lys Lys Glu Gly Lys
 65                  70                  75                  80

Leu Arg Glu Glu Asp Tyr Glu Lys Met Glu Arg Leu Phe Arg Lys Trp
                85                  90                  95

Met Glu Leu Ala Phe Lys Trp Leu Glu His Phe Arg Glu Met Ala Glu
            100                 105                 110

Lys Ala Lys Lys Lys Gly
        115

<210> SEQ ID NO 132
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 132

Gly Asn Glu Ala Glu Gln Arg Arg Glu Glu Phe Lys Glu Ile Met Glu
1               5                   10                  15

Lys Lys Lys Asp Glu Ala Glu Lys Lys Ser Glu Lys Ile Lys Arg Leu
            20                  25                  30

Ala Leu Ala Phe Asp Leu Ser Asp Asp Lys Thr Lys Ala Thr Asp
        35                  40                  45

Glu Trp Ile Ala Ile Ser Leu Glu Ile Ile Gly Asp Ala Phe Asn Phe
 50                  55                  60

Gly Glu Gly Leu Lys Asp Glu Ala Lys Arg Arg Lys Lys Arg Gly Leu
 65                  70                  75                  80

Lys Arg Asp Glu Glu Val Asp Lys Phe Glu Lys Ile Ala Glu Gln Ala
                85                  90                  95

Ile Glu Glu Leu Arg Lys Leu Ala Glu Glu Ala Asp Gly Arg Gly Ala
            100                 105                 110

Lys His Leu Arg Asp Gly
        115

<210> SEQ ID NO 133
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 133

Gly Glu Gln Glu Asp Lys Val Lys Glu Arg Ala Lys Arg Ala Leu
1               5                   10                  15

Glu Arg Ala Arg Glu Met Phe Glu Lys Met Arg Lys Ala Ile Tyr Leu
            20                  25                  30

Ala Glu Leu Tyr Ile Asn Asn Asp Glu Gly Lys Thr Lys Leu Thr Asp
        35                  40                  45

Arg Trp Ile Ala Phe Ala Leu Met Met Ile Gly Asp Ile Phe Asn Ile
    50                  55                  60

Ala Leu Glu Ala Arg Leu Glu Ala Leu Lys Leu Val Leu Lys Gly Leu
65                  70                  75                  80

Arg Ser Gln Glu Asp Ala Glu Lys Val Lys Leu Ala Glu Glu Ala
                85                  90                  95

Glu Arg Glu Ala Ala Lys Arg Ala Ala Lys Leu Gly Asp Lys Met Asp
                100                 105                 110

Glu Lys Glu His Glu Gly
            115

<210> SEQ ID NO 134
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 134

Gly Gln Gln Glu Glu Gln Phe Ile Glu Asp Phe Lys Lys Glu Val Leu
1               5                   10                  15

Arg Ala Ala Asp Asp Ala Lys Asp Asp Met Glu Lys Arg Ala Glu Glu
            20                  25                  30

Phe Leu Lys Lys Asp Gly Asp Asp Asn Glu Lys Lys Arg Lys Ile Leu
        35                  40                  45

Lys Trp Ile Ala Asp Ala Leu Glu Ala Ile Gly Asp Leu Phe Asn Ala
    50                  55                  60

Ala Gln Glu Ala Lys Arg Arg Ala Glu Leu Tyr Phe Lys Leu Gly Leu
65                  70                  75                  80

Leu Lys Lys Glu Arg Lys Glu Glu Ala Glu Glu Glu Ala Lys Ala
                85                  90                  95

Lys Glu Glu Ala Ser Lys Lys Leu His Lys Ala Ala Arg Glu Ala Arg
                100                 105                 110

Ile Lys Met Glu Lys Gly
            115

<210> SEQ ID NO 135
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 135

Gly Lys Lys Ala Glu Glu Val Leu Lys Glu Ala Arg Lys Leu His Glu
1               5                   10                  15

Ala Gln Leu Arg Tyr Ala Tyr Leu Met Met Lys Asp Trp Arg Glu Lys
            20                  25                  30

Lys Gln Gln Glu Glu Lys Gln Thr Gln Arg Glu Glu Lys Trp Thr Ala
        35                  40                  45

Trp Trp Ile Ala Leu Met Leu Met Ala Ile Gly Asp Ile Phe Asn Phe
    50                  55                  60

Ala Glu Trp Ala Lys Glu Glu Leu Asp Lys Leu Arg Glu Lys Gly Leu
65                  70                  75                  80

Val Glu Lys Lys Lys Ala Glu Glu Ala Lys Lys Ala Glu Lys Leu
                85                  90                  95

Ala Glu Glu Ala Ser Arg Arg Ala Ser Glu Phe Ala Gln Leu Phe Ala
            100                 105                 110

Lys Trp Asp Lys Glu Gly
        115

<210> SEQ ID NO 136
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 136

Gly Glu Ser Gly Glu Trp Ile Leu Glu Lys Thr Arg Glu Lys Ile Glu
1               5                   10                  15

Arg Ala Ile Arg Asp Ala Glu Lys Lys Leu Arg Leu Ile Ile Leu Leu
            20                  25                  30

Ile Arg Leu Phe His Pro Gly Asp Asp Leu Arg Ala Leu Phe Ala Ala
        35                  40                  45

Ile Trp Ile Ala Ala Glu Leu Glu Leu Ile Gly Asp Ile Phe Asn Glu
    50                  55                  60

Lys Gln Asp Ala Glu Glu Lys Phe Lys Glu Leu Leu Lys Lys Asn Gln
65                  70                  75                  80

Phe Arg Trp Glu Glu Leu Trp Arg Lys Trp Leu Ile Leu Glu Trp Ile
                85                  90                  95

Phe Gln Lys Ala Arg Arg Lys Ser Lys Glu Leu Ala Glu Arg Ala Lys
            100                 105                 110

Lys Ala Phe Asp Phe Gly
        115

<210> SEQ ID NO 137
<211> LENGTH: 118
<212> TYPE: PRT
<213> ORGANISM: Artificial Sequence
<220> FEATURE:

```
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 137

Gly Tyr Ser Leu Asp Asp Phe Leu Lys Leu Ala Lys Leu Leu Ala Glu
1               5                   10                  15

Leu Leu Lys Arg Phe Ile Arg Lys Glu Ala Glu Arg Leu Arg Glu Leu
            20                  25                  30

Lys Glu Trp Leu Leu Asp Thr Thr Leu Gly Arg Leu Ile Leu Thr Leu
        35                  40                  45

Glu Trp Ile Ala Ile Glu Leu Met Ile Ile Gly Asp Ile Phe Asn Ala
    50                  55                  60

Lys Met Leu Leu Asp Lys Phe Ala Lys Tyr Ala Glu Trp Leu Gly Leu
65                  70                  75                  80

Met Lys Glu Glu Ala Lys Gln Ala Lys Lys Leu Ala Lys Leu Leu
                85                  90                  95

Leu Asp Glu Val Lys Asp Glu Ala Arg Lys Lys Ala Asp Asp Gly Glu
            100                 105                 110

Lys Phe Ala Glu Glu Gly
            115

<210> SEQ ID NO 138
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 138

Gly Arg Asp Gly Glu Arg Val Val Lys Trp Ala Lys Asn Gln His Glu
1               5                   10                  15

Asn Thr Val Asp Glu Ala Lys Asp Lys Met Asp Asn Gln Glu Asp Glu
            20                  25                  30

Met Arg Lys Lys Asn Ala Asp Asp Glu Lys Leu Arg Lys Glu Thr His
        35                  40                  45

Lys Trp Ile Ala Phe Ala Leu Glu Ala Ile Gly Asp Val Phe Asn Asp
    50                  55                  60

Ala Met Gln Ala Phe Glu Leu Leu Glu Arg Phe Lys Lys Phe Gly Gln
65                  70                  75                  80

Gln Glu Gln Lys Lys Leu Asp Glu Phe Lys Glu Lys Val Glu Arg Leu
                85                  90                  95

Ala Arg Glu Ala Ser Arg Lys Leu Thr Tyr Leu Gly Lys Arg Phe Ala
            100                 105                 110

Leu Asp Ile Glu Ser Gly
            115
```

```
<210> SEQ ID NO 139
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 139

Gly Trp Ser Ala Asp Trp Ile Lys Asp Gln Ala Lys Glu Leu Met Leu
1               5                   10                  15

Arg Ala Ala Glu Glu Met Lys Lys Arg Ala Asp Glu Glu Glu Lys Lys
            20                  25                  30

Phe Lys Tyr Lys Gln Phe Thr Thr Glu Phe Leu Thr Lys Ala Thr Met
        35                  40                  45

Arg Trp Ile Ala Leu Ala Leu Met Ala Ile Gly Asp Val Phe Asn Val
    50                  55                  60

Leu Met Trp Ala Leu Glu Trp Ala Lys Arg Met Ala Lys Leu Asn Gln
65                  70                  75                  80

Tyr Arg Lys Glu Glu Leu Glu Lys Ala Lys Glu Ala Lys Lys Leu
                85                  90                  95

Ala Glu Lys Ala Ala Arg Arg Ile Thr Glu Ile Gly Arg Glu Ala Glu
            100                 105                 110

Gln Lys Ala Leu Lys Gly
        115

<210> SEQ ID NO 140
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 140

Gly Glu Lys Gly Lys Glu Lys Ala Gln Lys Phe Arg Asp Ile Ile Lys
1               5                   10                  15

Asp Ile Leu Glu Glu Ala Ile Arg Leu Ala Lys Asp Leu Ala Glu Asp
            20                  25                  30

Ala Lys Lys Phe Asp Leu Lys Leu Glu Lys Leu Leu Glu Ala Thr Leu
        35                  40                  45

Lys Trp Ile Ala Ala Ala Leu Met Ala Ile Gly Asp Leu Phe Asn Phe
    50                  55                  60

Lys Asp Leu Ala Glu Lys Glu Val Arg Glu Arg His Asp Arg Gly Glu
65                  70                  75                  80

Ile Ser Ser Asp Arg Arg Asp Lys Tyr Glu Lys Glu Ala Arg Glu Gly
                85                  90                  95

Ala Asp Glu Ala Ala Lys Glu Leu Ser Lys Leu Ala Lys Ile Ala Glu
            100                 105                 110
```

```
Lys Lys Ile Leu Glu Gly
        115

<210> SEQ ID NO 141
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 141

Gly Trp Ser Lys Asp Trp Val Leu Glu Trp Leu Arg Glu Lys Leu Glu
1               5                   10                  15

Glu Ile Asp Arg Glu Ala Leu Trp Lys Phe Ile Leu Ile Trp Ile Glu
            20                  25                  30

Lys Met Leu Gly Val Asp Asp Glu Gln Arg Arg Lys Asp Ala Ala
        35                  40                  45

Lys Trp Ile Ala Gly Ser Leu Glu Ala Ile Gly Asp Ile Phe Asn Ala
    50                  55                  60

Met Met Trp Ala Lys Arg Leu Leu Glu Trp Leu Glu Lys Ala Asn Leu
65                  70                  75                  80

Val Arg Arg Glu Glu Leu Glu Lys Ala Lys Gln Lys Ala Glu Glu Leu
                85                  90                  95

Ala Lys Lys Ala Ala Leu Arg Ala Ala Ile Tyr Ser Lys Ile Ala Glu
            100                 105                 110

Glu Trp Leu Trp Lys Gly
        115

<210> SEQ ID NO 142
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 142

Gly Lys Arg Ala Glu Glu Leu Arg Glu Glu Ala Glu Arg Ala Lys
1               5                   10                  15

Glu Ala Phe Lys Glu Thr Glu Gln Lys Leu Arg Glu Val Glu Glu Arg
            20                  25                  30

Ser Arg Gln Thr Leu Ala Arg Asp Glu Glu Leu Arg Lys Ala Ala Leu
        35                  40                  45

Leu Trp Ile Ala Ala Ala Leu Met Gly Ile Gly Asp Leu Phe Asn Lys
    50                  55                  60

Lys Glu Lys Gly Lys Glu Ala Leu Glu Lys Glu Lys Asn Gly Lys
65                  70                  75                  80
```

Arg Arg Thr Glu Arg Ala Glu Arg Glu Lys Glu Arg Leu Glu Lys Glu
            85                  90                  95

Val Ser Arg Glu Ala Gln Arg Phe Lys Lys Gly Glu Glu Glu
            100                 105                 110

Lys Lys His Lys Tyr Gly
        115

<210> SEQ ID NO 143
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 143

Gly Trp Thr Ala Leu Trp Leu Lys Asp Phe Thr Glu Gln Glu Ala Arg
1               5                   10                  15

Lys Lys Phe Arg Glu Ala Leu Tyr Tyr Gly Trp Met Met Ala Met Arg
            20                  25                  30

Ala Leu Glu His Gln Leu Gln Ala Asp Glu Leu Ala Met Trp Thr Ala
        35                  40                  45

Leu Trp Ile Ala Ala Met Leu Glu Ala Ile Gly Asp Met Phe Asn Asp
    50                  55                  60

Lys Leu Arg Ala Glu Lys Tyr Ala Leu Leu Ile Trp Leu Asn Leu
65                  70                  75                  80

Tyr His Lys Asp Ile Ala Glu Lys Trp Arg Glu His Glu Glu Lys
                85                  90                  95

Leu Lys Glu Ala Leu Gln Glu Met Phe Glu Ala Ala Glu Lys Phe Asp
            100                 105                 110

Lys Phe Ala Lys Phe Gly
        115

<210> SEQ ID NO 144
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 144

Gly Asn Asp Lys Glu Lys Phe Arg Glu Asp Val Lys Lys Ala Lys
1               5                   10                  15

Tyr Ala Leu Trp Lys Leu Lys Lys Leu Ala Asp Glu Ala Lys Glu Arg
            20                  25                  30

Ala Leu Lys Phe Asp Pro Ser Glu Glu Met Lys Arg Glu Phe Thr Leu
        35                  40                  45

Glu Trp Ile Ala Trp Ala Leu Glu Ala Ile Gly Asp Ile Phe Asn Ala

```
                  50                  55                  60
Trp Leu Asp Gly Lys Lys Tyr Ala Asp Glu Ala Lys Lys Gln Gly Lys
 65                  70                  75                  80

Ala Arg Lys Glu Glu Ala Glu Glu Thr Lys Lys Glu Ala Thr Arg Ile
                 85                  90                  95

Ala Lys Glu Ala His Glu Lys Ala Ser Glu Leu Ala Arg Lys Ile Leu
                100                 105                 110

Tyr His Met Leu Leu Gly
            115

<210> SEQ ID NO 145
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 145

Gly His Val Ala Glu Glu Ile Arg Arg Phe Leu Arg Lys Ala Glu
  1               5                  10                  15

Lys Val Leu Gln Glu Ala Arg Arg Lys Met Glu Lys Arg Arg Arg Glu
                 20                  25                  30

Ala Glu Glu His Asp Thr Thr Thr Trp Leu Leu Ala Arg Gly Thr Ile
                 35                  40                  45

Glu Trp Ile Ala Asp Ala Leu Met Leu Ile Gly Asp Ala Phe Asn Phe
 50                  55                  60

Arg Arg Glu Ala Tyr Ile Arg Gly Glu Leu Tyr Lys Lys Phe Gly Leu
 65                  70                  75                  80

Ile Arg Glu Asp Asp Leu Lys Asp Arg Leu Lys Glu Ala Asp Gln Arg
                 85                  90                  95

Leu Asp Glu Phe Ala Lys Lys Met Ala Leu Phe Gly Leu Glu Leu His
                100                 105                 110

Leu Arg Leu Arg Glu Gly
            115

<210> SEQ ID NO 146
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 146

Gly Asp Lys His Glu Glu Ala Lys Glu Glu Ala Glu Lys Lys Phe Glu
  1               5                  10                  15

Lys Leu Arg Ile Glu Ala Arg Leu Lys Ala Glu Trp Leu Lys Lys Ala
                 20                  25                  30
```

Gly Lys Tyr Gly Leu Gln Leu Gln Glu Leu Trp Ala Lys Leu Ser Asp
            35                  40                  45

Tyr Trp Ile Ala Phe Ala Leu Glu Ile Ile Gly Asp Leu Phe Asn Phe
     50                  55                  60

Leu Glu Glu His Lys Glu Lys Ile Glu Lys Asp Leu Lys Lys Gly Glu
 65                  70                  75                  80

Ala Leu Asp Asp Arg Ala Asp Asp Ile Leu Lys Asp Leu Glu Lys Lys
                 85                  90                  95

Ala Lys Glu Val Ser Lys His Ala Met Lys Leu Gly Arg Glu Ala Gln
            100                 105                 110

Gln Phe Ile Glu Leu Gly
        115

<210> SEQ ID NO 147
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 147

Gly Glu Glu Ala Glu Lys Leu Ile Lys Glu Ala Lys Asp Lys Phe Glu
  1               5                  10                  15

Asp Leu Arg Glu Lys Ala Glu Glu Leu Leu Tyr Lys Met Trp Leu Ile
             20                  25                  30

Arg Tyr Leu Ser Ser Lys Asp Thr Lys Arg Gly Glu Ile Tyr Thr Lys
            35                  40                  45

Lys Trp Ile Ala Ile Met Leu Met Met Ile Gly Asp Ala Phe Asn Met
     50                  55                  60

Ala Leu Arg Ala Arg Leu Tyr Leu Glu Glu Arg Arg Lys Arg Gly Glu
 65                  70                  75                  80

Lys His Glu Glu Glu Ala Glu Glu Lys Glu Arg Arg Ala Arg Trp Glu
                 85                  90                  95

Gln Glu Asp Ala Tyr Lys Lys Ala Lys Lys Gly Ala Lys Arg Ala Arg
            100                 105                 110

Leu Tyr Asp Lys Leu Gly
        115

<210> SEQ ID NO 148
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 148

Gly Glu Ser Ala Glu Lys Trp Arg Glu Arg Leu Arg Glu Lys Ala Gly
1               5                   10                  15

Tyr Trp Ala Glu Tyr Ala Phe Trp Leu Ala Asp Glu Ala Glu Lys Arg
            20                  25                  30

Ala Lys Ile Tyr Ser Ala Ser Ser Glu Arg Arg Ala Glu Trp Thr Met
            35                  40                  45

Arg Trp Ile Ala Ile Ala Leu Ala Ala Ile Gly Asp Val Phe Asn Glu
    50                  55                  60

Gly Gln Lys Ala Asp Glu Lys Phe Asp Glu Leu Lys Lys Gln Asn Lys
65                  70                  75                  80

Arg Ser Asp Asp Leu Asp Asp Tyr Lys Asp Lys Phe Lys Glu Glu
                85                  90                  95

Val Glu Lys Ala Leu Arg Lys Leu Leu Lys Ala Gly Asp Lys Ile Ala
            100                 105                 110

Asp Leu Ala Glu Gln Gly
            115

<210> SEQ ID NO 149
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 149

Gly Asp Leu Lys Glu Glu Leu Lys Glu Arg Ala Lys Lys Ile Ile Arg
1               5                   10                  15

Arg Ala Leu Asp Glu Ala Lys Asp Ala Glu Asp Leu Ile Lys Lys Glu
            20                  25                  30

Ala Glu Lys Arg Tyr Val Thr Thr Glu Met Ala Thr Lys Phe Val Ala
            35                  40                  45

Trp Trp Ile Ala Gly Ala Leu Met Ile Ile Gly Asp Ile Phe Asn Ala
    50                  55                  60

Ala Arg Glu Val Lys Glu Arg Ala Lys Ala Leu Lys Trp Gly Val
65                  70                  75                  80

Leu Ser Gln Asp Asp Ile Lys Glu Leu Leu Glu Leu Glu Asn Leu
                85                  90                  95

Glu Gln Glu Ala Lys Gly Arg Ala Lys Glu Phe Gly Glu Lys Ala Glu
            100                 105                 110

Lys Phe Lys Lys Met Gly
            115

<210> SEQ ID NO 150
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 150

```
Gly Glu Lys Ala Lys Leu Glu Glu Tyr Ala Arg Glu Glu Ile Glu
1               5                  10                  15

Arg Ala Leu Arg Glu Gly Gly Asp Leu Met Glu Glu Arg Glu Phe
            20                  25                  30

Gly Glu Lys Thr Glu Leu Thr Thr Glu Trp Lys His Arg Ala Met Ala
            35                  40                  45

Tyr Trp Ile Ala Ala Ala Leu Met Ile Ile Gly Asp Gly Phe Asn Ala
        50                  55                  60

Leu Gln Phe Ile Glu Glu Gly Arg Lys Phe Ile Arg Lys Gly Glu
65                  70                  75                  80

Phe Ala Arg Gln Lys Ile Glu Glu His Lys Glu Arg Ala Lys Glu Arg
                85                  90                  95

Leu Glu Lys Ala Leu Lys Gln Ala Lys Lys Arg Gly Asp Glu Leu Asp
                100                 105                 110

Arg Phe Ala Arg Leu Gly
        115
```

<210> SEQ ID NO 151
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 151

```
Gly Ile Thr Leu Glu Lys Leu Trp Lys Glu Ala Lys Glu Lys Ile Arg
1               5                  10                  15

Lys Arg Glu Asp Glu Ala Leu Leu Lys Ala Glu Trp Phe Lys Lys Lys
            20                  25                  30

Ala Asn Asn Val Leu Asp Leu Asn Asp Met Lys Ala Lys Met Thr Ala
            35                  40                  45

Lys Trp Ile Ala Leu Ala Leu Met Ala Ile Gly Asp Ile Phe Asn Tyr
        50                  55                  60

Leu Leu Glu Thr Glu Ile Lys Ala Arg Leu Leu Val Arg Leu Gly Leu
65                  70                  75                  80

Phe Arg Gln Glu Glu Ala Glu Lys Lys Lys Glu Ala Lys Glu Glu
                85                  90                  95

Ala Ile Lys Ser Ser Arg Asn Ile Ala Lys Arg Gly Glu Glu Ala Ala
                100                 105                 110

Lys Gln Met Glu Gln Gly
        115
```

<210> SEQ ID NO 152
<211> LENGTH: 118
<212> TYPE: PRT
<213> ORGANISM: Artificial Sequence
<220> FEATURE:
<223> OTHER INFORMATION: Synthetic
<220> FEATURE:

<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 152

```
Gly Arg Gln Glu Asp Glu Ile Lys Asp Glu Ala Thr Lys Arg Ala Leu
1               5                   10                  15

Glu Ile Leu Gln Lys Leu Glu Gln Lys Val Arg Lys Ala Lys Lys Phe
            20                  25                  30

Ala Lys Tyr Gly Leu Leu Leu Gln Arg Trp Trp Ala Trp Ile Thr Lys
        35                  40                  45

Val Trp Ile Ala Ala Ala Leu Asp Ala Ile Gly Asp Ala Phe Asn Leu
    50                  55                  60

Gly Glu Glu Leu Lys Arg Ile Leu Glu Leu Arg Arg Arg Gly Leu
65                  70                  75                  80

Ser Ser Glu Glu Lys Ala Gln Glu Ile Lys Asn Trp Ile Glu Trp Leu
                85                  90                  95

Glu Lys Trp Val Ala Ile Met Ala Lys Leu Phe Gly Glu Glu Leu Glu
            100                 105                 110

Lys Gln Phe Lys Gln Gly
            115
```

<210> SEQ ID NO 153
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 153

```
Gly Glu His Leu Asp Glu Leu Leu Lys Leu Leu Trp Leu Ala Ile
1               5                   10                  15

Gln Phe Ala Glu Arg Ala Lys Leu Thr Ile Glu Leu Trp Lys Leu Trp
            20                  25                  30

Gly Lys Ile Thr Gln Ser Tyr Asn Glu Trp Ala Glu Lys Ala Ala Arg
        35                  40                  45

Asp Trp Ile Ala Ala Ala Leu Met Ile Ile Gly Asp Met Phe Asn His
    50                  55                  60

Lys Gln Lys Ala Glu Glu Ala Lys Lys Phe Ala Lys Lys Gly Leu
65                  70                  75                  80

Lys Arg Lys Glu Glu Leu Glu Glu Leu Leu Lys Lys Leu Glu Glu Phe
                85                  90                  95

Ile Lys Arg Ala Lys Lys Leu Ile Lys Glu Thr Ala Gln Lys His Glu
            100                 105                 110

Glu Ala Ser Lys Met Gly
            115
```

<210> SEQ ID NO 154
<211> LENGTH: 118

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 154

Gly Lys Leu Gly Glu Glu Leu Arg Glu Asp Ala Glu Lys Lys Gly Glu
1               5                   10                  15

Glu Asp Met Arg Arg Phe Glu Arg Arg Ile Arg Glu Ile Lys Arg Lys
            20                  25                  30

Leu Lys Phe Gly Tyr Asp Phe Glu Gln Arg Lys Arg Glu Ala Thr His
        35                  40                  45

Lys Trp Ile Ala Phe Ala Leu Glu Met Ile Gly Asp Ala Phe Asn Phe
    50                  55                  60

Ala Gln Lys Leu Glu Arg Ala Leu Glu Leu Phe Lys Lys Trp Asn Ile
65                  70                  75                  80

Tyr Ser Glu Asp Asp Leu Arg Glu Leu Lys Lys Arg Phe Glu Glu Ala
                85                  90                  95

Lys Glu Lys Leu Lys Lys Phe Ala Asp Arg Ile Arg Asp Glu Gly Leu
            100                 105                 110

Lys Ala Val Leu Leu Gly
        115

<210> SEQ ID NO 155
<211> LENGTH: 118
<212> TYPE: PRT
<213> ORGANISM: Artificial Sequence
<220> FEATURE:
<223> OTHER INFORMATION: Synthetic

<400> SEQUENCE: 155

Gly Asp Asp Lys Glu Lys Val Lys Asp Tyr Ala Lys Lys Arg Ala Leu
1               5                   10                  15

Glu Asp Val Leu Arg Ala Lys Glu Leu Ala Glu Lys Phe Ile Asp Glu
            20                  25                  30

Ala Lys Lys Ser Asp His Ser Lys Gln Asn Glu Arg Gln Tyr Ile Ile
        35                  40                  45

Ala Trp Ile Ala Phe Met Leu Met Ala Ile Gly Asp Val Phe Asn Ala
    50                  55                  60

Met Met Glu Ala Lys Arg Leu Ala Glu Leu Leu Lys Arg Leu Gly Leu
65                  70                  75                  80

Arg Arg Trp Glu Glu Ala Glu Glu Val Lys Gln Lys Ala Glu Glu Leu
                85                  90                  95

Ala Glu Glu Ala Ser Arg Leu Leu Ala Asp Leu Gly Lys Asp Phe Ala
            100                 105                 110

Lys Lys Ile Glu Gln Gly
        115

<210> SEQ ID NO 156
<211> LENGTH: 118
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 156

Gly Leu Ser Gly Asp Asp Ala Glu Asp Phe Ala Arg Gln Glu Ile Glu
1               5                   10                  15

Lys Arg Ala Arg Glu Ala Glu Glu Lys Ala Arg Lys Leu Ile Trp Leu
            20                  25                  30

Ala Ser Lys Tyr Asp Ala Lys Arg Glu Glu Ala Leu Lys Phe His Leu
        35                  40                  45

Arg Trp Ile Ala Phe Ala Leu Met Met Ile Gly Asp Ala Phe Asn Ala
    50                  55                  60

Glu Glu Ile Ala Arg Glu Met Leu Glu Ile Ala Arg Glu Leu Gly Leu
65                  70                  75                  80

Thr Arg Glu Glu Glu Ala Lys Glu Lys Leu Glu Lys Ile Arg Lys Lys
                85                  90                  95

Glu Thr Glu Ala Ser Lys Lys Met Ala Glu Arg Gly Arg Arg Leu Asp
            100                 105                 110

Asn Gln Ala Asn Asn Gly
        115

<210> SEQ ID NO 157
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 157

Gly Asn Asp Leu Lys Asp Ile Ala Arg Gln Ile Glu Glu Gln Ala Lys
1               5                   10                  15

Lys Ala Leu Asp Asp Met Ala Lys Leu Ile Arg Glu Leu Ala Glu Lys
            20                  25                  30

Ala Glu Lys Phe Tyr Pro Ser Lys Asp Asp Ile Arg Arg Leu Thr His
        35                  40                  45

Tyr Trp Ile Ala Ala Ala Leu Met Ala Ile Gly Asp Ala Phe Asn Arg
    50                  55                  60

Leu Gln Glu Ala Arg Arg Arg Ala Glu Trp Leu Arg Lys Trp Gly Leu
65                  70                  75                  80

Arg Arg Glu Glu Glu Ala Glu Lys Ala Lys Lys Glu Ala Glu Arg
                85                  90                  95

His Glu Arg Ala Lys Glu Leu Ala His Lys Met Gly Asp Glu Met Glu
            100                 105                 110

Glu Lys Leu Lys Arg Gly
        115
```

```
<210> SEQ ID NO 158
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 158

Gly Arg Ser Lys Asp Asp Ala Thr Lys Glu Ala Trp Glu Arg Leu Glu
1               5                   10                  15

Arg Leu Leu Lys Glu Phe Lys Glu Lys Ala Glu Lys Leu Arg Asp Lys
            20                  25                  30

Ala Gln Ala His Tyr Val Tyr Lys Gln Phe Ala Leu Lys Val Thr Ile
        35                  40                  45

Leu Trp Ile Ala Trp Ala Leu Lys Leu Ile Gly Asp Ala Phe Asn Phe
    50                  55                  60

Ile Glu Glu Ala Glu Lys Lys Met Arg Glu Asn Glu Arg Asn Leu
65                  70                  75                  80

Ile Ser Glu Asp Asp Ala Arg Glu Glu Lys Arg Lys Leu Glu Glu Phe
                85                  90                  95

Ala Arg Arg Ala Ser Lys Lys Ala Asn Lys Ile Gly Asp Asp Leu Asp
            100                 105                 110

Arg Gln Leu Glu Leu Gly
        115

<210> SEQ ID NO 159
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 159

Gly Asn Arg Ser Glu Glu Val Lys Glu Leu Met Arg Glu Leu Ala Glu
1               5                   10                  15

Arg Val Leu Leu Lys Phe Arg Trp Arg Ala Asp Glu Met Asn Lys Glu
            20                  25                  30

Lys Asp Lys Lys Tyr Asp Lys Glu Leu Lys Arg Glu Leu Thr Glu
        35                  40                  45

Lys Trp Ile Ala Phe Ala Leu Asp Ala Ile Gly Asp Leu Phe Asn Ala
    50                  55                  60

Ala Glu Leu Ala Lys Lys Leu Ala Asp Leu Phe Lys Lys Gly Thr Gly
65                  70                  75                  80

Phe Leu Glu Glu Arg Leu Glu Arg Arg Lys Glu Glu Ile Glu Lys Leu
                85                  90                  95

Glu Glu Lys Gly Ser Arg Lys Val Ser Tyr Gly Arg Glu Ala
            100                 105                 110
```

Glu Lys Ile Glu Ser Gly
        115

<210> SEQ ID NO 160
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 160

Gly Val Ser Ile Glu Trp Ala Phe Asp Phe Leu Glu Asn Lys Ala Glu
1               5                   10                  15

Glu Asp Ala Arg Glu Ala Arg Arg Leu Ala Gln Lys Leu Ala Glu Glu
            20                  25                  30

Phe Phe Lys His Ser Ala Arg Glu Glu Asp Arg Ala Lys Leu Thr Lys
        35                  40                  45

Lys Trp Ile Ala Val Ala Leu Met Ile Ile Gly Asp Ile Phe Asn Val
    50                  55                  60

Glu Gln Phe Thr Lys Gln Gln Gly Glu Phe Val Lys Arg Gly Leu
65                  70                  75                  80

Arg Ser Glu Asp Asp Phe Lys Glu Tyr Leu Arg Lys Met Glu Glu Lys
                85                  90                  95

Lys Glu Glu Ala Glu Arg Ile Ala Lys Arg Ala Lys Asp Met Leu
            100                 105                 110

Lys Ala Arg Asp Leu Gly
        115

<210> SEQ ID NO 161
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 161

Gly Glu Gln Ala Glu Lys Ala Leu Arg Arg Ala Lys Arg Ala Lys
1               5                   10                  15

Trp Gly Leu Asp Asp Ala Lys Asp Ile Leu Asp Ile Glu Ala Glu
            20                  25                  30

Ile Arg Trp Tyr Tyr Pro Arg Asp Glu Glu Arg Phe Lys Phe Val Asp
        35                  40                  45

Arg Trp Ile Ala Ala Met Leu Met Val Ile Gly Asp Leu Phe Asn Ala
    50                  55                  60

Lys Arg Glu Ala Leu Glu Arg Ala Leu Arg Leu Met Arg Lys Gly Leu
65                  70                  75                  80

```
Ile Ser Gln Asp Gln Phe Lys Lys Phe Met Glu Lys Leu Glu Lys Ile
            85                  90                  95

Ile Leu Trp Gly Lys Phe Gln Ala Arg Lys Leu Gly Arg Glu Lys Glu
            100                 105                 110

Ser Glu Ile Thr Gln Gly
        115

<210> SEQ ID NO 162
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 162

Gly Leu Leu Trp Leu Ala Ile Ile Leu Lys Ala Glu Glu Leu Ala Arg
1               5                   10                  15

Lys Lys Asp Asp Glu Ala Glu Glu Arg Ile Arg Arg Leu Glu Asp Glu
            20                  25                  30

Lys Arg Lys Gly Asp Pro Gly Thr Leu Gly Glu Ala Glu Arg Thr Asp
            35                  40                  45

Arg Trp Ile Ala Ile Met Leu Met Ala Ile Gly Asp Ala Phe Asn Val
        50                  55                  60

Met Leu Glu Ala Lys Glu Ala Glu Lys Leu Glu Lys Leu Gly Leu
65                  70                  75                  80

Val His Lys Glu Leu Leu Glu Lys Val Lys Glu Glu Ala Glu Arg Leu
                85                  90                  95

Phe Glu Arg Ser Ser Asp Asn Phe Glu Glu Ala Ala Lys Arg Ala Asp
            100                 105                 110

Asp Met Glu Lys Glu Gly
        115

<210> SEQ ID NO 163
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 163

Gly Glu Arg Ala Glu Arg Ala Arg Asp Trp Ala Lys Asp Gln Met Asp
1               5                   10                  15

Asp Glu Leu Glu Lys Ala Arg Glu Lys Leu Trp Lys Leu Ala Phe Ile
            20                  25                  30

Ala Phe Lys Phe Tyr Leu Lys Leu Glu Leu Leu Phe Lys Leu Met Phe
            35                  40                  45

Arg Trp Ile Ala Ile Met Leu Glu Ala Ile Gly Asp Phe Phe Asn Val
```

```
                    50                  55                  60
Trp Ala Ile Ala Lys Arg Trp Leu Glu Arg Tyr Lys Leu Gln Asn Asn
 65                  70                  75                  80

Ile Arg Lys Glu Glu Ile Glu Lys Ala Lys Glu Arg Ala Lys Lys Leu
                 85                  90                  95

Tyr Glu Glu Ala Ala Asp Lys Ala Ala Lys Leu Gly Arg Phe Tyr Met
            100                 105                 110

Lys Leu Leu Thr Ser Gly
        115

<210> SEQ ID NO 164
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 164

Gly Gly Ser Tyr Asp Asp Ile Ala Asp Leu Ala Lys Lys Leu His Lys
  1               5                  10                  15

Lys Ile Ala Glu Glu Ala Lys Lys Ile Asp Glu Leu Leu Lys Glu
                 20                  25                  30

Ala Phe Glu Asp Lys Pro Tyr Glu Glu Glu Phe Ala Lys Lys Met Phe
             35                  40                  45

Lys Trp Ile Ala Ile Ala Leu Met Ala Ile Gly Asp Leu Phe Asn Ala
 50                  55                  60

Ala Glu Leu Ala Lys Arg Leu Ala Glu Asp Leu Lys Lys Asp Asn Asn
 65                  70                  75                  80

Arg Asp Glu Asn Lys Ala Glu Glu Ala Lys Gln Arg Ala Glu Gln Phe
                 85                  90                  95

Glu Lys Glu Gly Ala Glu Glu Leu Ala Lys Lys Gly Glu Glu Ala Ala
            100                 105                 110

Lys Lys Leu Ala Gly Gly
        115

<210> SEQ ID NO 165
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 165

Gly Lys Asp Leu Asp Glu Ile Ile Asp Glu Ala Arg Lys Glu Met Asp
  1               5                  10                  15

Asp Asp Ala Asp Asp Gly Lys Lys Lys Ala Glu Lys Leu Leu Lys Leu
                 20                  25                  30
```

His Ala Gly Thr Asn His Ser Gln Asp Asp Phe Asn Glu Ala His Arg
            35                  40                  45

Arg Trp Ile Ala Val Ala Leu Glu Glu Ile Gly Asp Leu Phe Asn Ala
 50                  55                  60

Ala Leu Arg Ala Trp Arg Lys Ile Glu Glu Ile Arg Lys Asn Gln
 65                  70                  75                  80

Arg Arg Lys Glu Glu Ala Glu Lys Ala Lys Glu Lys Val Ser Lys Glu
                85                  90                  95

Tyr Glu Arg Ala Ser Arg Lys Ala Ala Glu Leu Gly Lys Glu Phe Glu
            100                 105                 110

Glu Arg Val Glu Gln Gly
        115

<210> SEQ ID NO 166
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (118)..(118)
<223> OTHER INFORMATION: optionally absent

<400> SEQUENCE: 166

Gly Thr Asp His Gln Ala Phe Asp Glu Trp Ala Arg Arg Glu Leu Glu
 1               5                  10                  15

Arg Ile Val Glu Glu Ala Arg Glu Arg Ala Glu Arg Leu Arg Glu Trp
            20                  25                  30

Ile Glu Gln Lys Asp Ala Ser Arg Glu Leu Thr Lys Phe Phe Ala
            35                  40                  45

Ile Trp Ile Ala Ile Ser Leu Met Ala Ile Gly Asp Leu Phe Asn Val
 50                  55                  60

Lys Glu Gln Ala Lys Arg Leu Ala Glu Leu Leu Glu Phe Leu Gly Leu
 65                  70                  75                  80

Gln Arg Lys Glu Glu Ile Glu Lys Ser Lys Lys Asn Ala Glu Lys Leu
                85                  90                  95

Ala Asp Glu Ala Met Lys Lys Ala Ser Lys Leu Asp Ala Lys Val Glu
            100                 105                 110

Lys Glu Leu Met Gln Gly
        115

<210> SEQ ID NO 167
<211> LENGTH: 18
<212> TYPE: DNA
<213> ORGANISM: Artificial Sequence
<220> FEATURE:
<223> OTHER INFORMATION: Synthetic

<400> SEQUENCE: 167
agtcattgca gtcattgc                                                 18

<210> SEQ ID NO 168
<211> LENGTH: 18
<212> TYPE: DNA
<213> ORGANISM: Artificial Sequence
<220> FEATURE:

<223> OTHER INFORMATION: Synthetic

<400> SEQUENCE: 168
tcaactggtt caactggt                                                  18

<210> SEQ ID NO 169
<211> LENGTH: 18
<212> TYPE: DNA
<213> ORGANISM: Artificial Sequence
<220> FEATURE:
<223> OTHER INFORMATION: Synthetic

<400> SEQUENCE: 169
ttaagcctgt taagcctg                                                  18

<210> SEQ ID NO 170
<211> LENGTH: 18
<212> TYPE: DNA
<213> ORGANISM: Artificial Sequence
<220> FEATURE:
<223> OTHER INFORMATION: Synthetic

<400> SEQUENCE: 170
ttagaccact tagaccac                                                  18

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
gctatcatcg ctatcatc                                                  18

<210> SEQ ID NO 172
<211> LENGTH: 18
<212> TYPE: DNA
<213> ORGANISM: Artificial Sequence
<220> FEATURE:
<223> OTHER INFORMATION: Synthetic

<400> SEQUENCE: 172
acagcttcaa cagcttca                                                  18

<210> SEQ ID NO 173
<211> LENGTH: 18
<212> TYPE: DNA
<213> ORGANISM: Artificial Sequence
<220> FEATURE:
<223> OTHER INFORMATION: Synthetic

<400> SEQUENCE: 173
tccaacatgt ccaacatg                                                  18

<210> SEQ ID NO 174
<211> LENGTH: 18
<212> TYPE: DNA
<213> ORGANISM: Artificial Sequence
<220> FEATURE:
<223> OTHER INFORMATION: Synthetic

<400> SEQUENCE: 174
ctgaactgac tgaactga                                                  18

```
<210> SEQ ID NO 175
<211> LENGTH: 18
<212> TYPE: DNA
<213> ORGANISM: Artificial Sequence
<220> FEATURE:
<223> OTHER INFORMATION: Synthetic

<400> SEQUENCE: 175
tgacgcattt gacgcatt                                                18

<210> SEQ ID NO 176
<211> LENGTH: 18
<212> TYPE: DNA
<213> ORGANISM: Artificial Sequence
<220> FEATURE:
<223> OTHER INFORMATION: Synthetic

<400> SEQUENCE: 176
ggaatcgatg gaatcgat                                                18

<210> SEQ ID NO 177
<211> LENGTH: 18
<212> TYPE: DNA
<213> ORGANISM: Artificial Sequence
<220> FEATURE:
<223> OTHER INFORMATION: Synthetic

<400> SEQUENCE: 177
gaaggctatg aaggctat                                                18

<210> SEQ ID NO 178
<211> LENGTH: 18
<212> TYPE: DNA
<213> ORGANISM: Artificial Sequence
<220> FEATURE:
<223> OTHER INFORMATION: Synthetic

<400> SEQUENCE: 178
gacgttacag acgttaca                                                18

<210> SEQ ID NO 179
<211> LENGTH: 18
<212> TYPE: DNA
<213> ORGANISM: Artificial Sequence
<220> FEATURE:
<223> OTHER INFORMATION: Synthetic

<400> SEQUENCE: 179
agtggcataa gtggcata                                                18

<210> SEQ ID NO 180
<211> LENGTH: 18
<212> TYPE: DNA
<213> ORGANISM: Artificial Sequence
<220> FEATURE:
<223> OTHER INFORMATION: Synthetic

<400> SEQUENCE: 180
tagatcgagt agatcgag                                                18

<210> SEQ ID NO 181
<211> LENGTH: 18
<212> TYPE: DNA
<213> ORGANISM: Artificial Sequence
<220> FEATURE:
<223> OTHER INFORMATION: Synthetic
```

<400> SEQUENCE: 181
ccttgagaac cttgagaa                                                 18

<210> SEQ ID NO 182
<211> LENGTH: 18
<212> TYPE: DNA
<213> ORGANISM: Artificial Sequence
<220> FEATURE:
<223> OTHER INFORMATION: Synthetic

<400> SEQUENCE: 182
catgtctcac atgtctca                                                 18

<210> SEQ ID NO 183
<211> LENGTH: 17
<212> TYPE: DNA
<213> ORGANISM: Artificial Sequence
<220> FEATURE:
<223> OTHER INFORMATION: Synthetic

<400> SEQUENCE: 183
atctgctaca tctgcta                                                  17

<210> SEQ ID NO 184
<211> LENGTH: 18
<212> TYPE: DNA
<213> ORGANISM: Artificial Sequence
<220> FEATURE:
<223> OTHER INFORMATION: Synthetic

<400> SEQUENCE: 184
ccatcttagc catcttag                                                 18

<210> SEQ ID NO 185
<211> LENGTH: 18
<212> TYPE: DNA
<213> ORGANISM: Artificial Sequence
<220> FEATURE:
<223> OTHER INFORMATION: Synthetic

<400> SEQUENCE: 185
ttgccgattt tgccgatt                                                 18

<210> SEQ ID NO 186
<211> LENGTH: 18
<212> TYPE: DNA
<213> ORGANISM: Artificial Sequence
<220> FEATURE:
<223> OTHER INFORMATION: Synthetic

<400> SEQUENCE: 186
cacgattctc acgattct                                                 18

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
agaattgcca gaattgcc                                                 18

<210> SEQ ID NO 188
<211> LENGTH: 18

```
<212> TYPE: DNA
<213> ORGANISM: Artificial Sequence
<220> FEATURE:
<223> OTHER INFORMATION: Synthetic

<400> SEQUENCE: 188
attagtcgga ttagtcgg                                                   18

<210> SEQ ID NO 189
<211> LENGTH: 18
<212> TYPE: DNA
<213> ORGANISM: Artificial Sequence
<220> FEATURE:
<223> OTHER INFORMATION: Synthetic

<400> SEQUENCE: 189
gatgacttcg atgacttc                                                   18

<210> SEQ ID NO 190
<211> LENGTH: 17
<212> TYPE: DNA
<213> ORGANISM: Artificial Sequence
<220> FEATURE:
<223> OTHER INFORMATION: Synthetic

<400> SEQUENCE: 190
tcgatctcat cgatctc                                                    17

<210> SEQ ID NO 191
<211> LENGTH: 18
<212> TYPE: DNA
<213> ORGANISM: Artificial Sequence
<220> FEATURE:
<223> OTHER INFORMATION: Synthetic

<400> SEQUENCE: 191
tgtctagtgt gtctagtg                                                   18

<210> SEQ ID NO 192
<211> LENGTH: 18
<212> TYPE: DNA
<213> ORGANISM: Artificial Sequence
<220> FEATURE:
<223> OTHER INFORMATION: Synthetic

<400> SEQUENCE: 192
ggatgttctg gatgttct                                                   18

<210> SEQ ID NO 193
<211> LENGTH: 18
<212> TYPE: DNA
<213> ORGANISM: Artificial Sequence
<220> FEATURE:
<223> OTHER INFORMATION: Synthetic

<400> SEQUENCE: 193
atggtgtcta tggtgtct                                                   18

<210> SEQ ID NO 194
<211> LENGTH: 18
<212> TYPE: DNA
<213> ORGANISM: Artificial Sequence
<220> FEATURE:
<223> OTHER INFORMATION: Synthetic

<400> SEQUENCE: 194
```
ctcagatcac tcagatca                                                         18

<210> SEQ ID NO 195
<211> LENGTH: 18
<212> TYPE: DNA
<213> ORGANISM: Artificial Sequence
<220> FEATURE:
<223> OTHER INFORMATION: Synthetic

<400> SEQUENCE: 195
ctacgacatc tacgacat                                                         18

<210> SEQ ID NO 196
<211> LENGTH: 18
<212> TYPE: DNA
<213> ORGANISM: Artificial Sequence
<220> FEATURE:
<223> OTHER INFORMATION: Synthetic

<400> SEQUENCE: 196
ctaggtgtac taggtgta                                                         18

<210> SEQ ID NO 197
<211> LENGTH: 18
<212> TYPE: DNA
<213> ORGANISM: Artificial Sequence
<220> FEATURE:
<223> OTHER INFORMATION: Synthetic

<400> SEQUENCE: 197
aagttgacca agttgacc                                                         18

<210> SEQ ID NO 198
<211> LENGTH: 18
<212> TYPE: DNA
<213> ORGANISM: Artificial Sequence
<220> FEATURE:
<223> OTHER INFORMATION: Synthetic

<400> SEQUENCE: 198
aaggccatta aggccatt                                                         18

<210> SEQ ID NO 199
<211> LENGTH: 18
<212> TYPE: DNA
<213> ORGANISM: Artificial Sequence
<220> FEATURE:
<223> OTHER INFORMATION: Synthetic

<400> SEQUENCE: 199
tggcttctat ggcttcta                                                         18

<210> SEQ ID NO 200
<211> LENGTH: 18
<212> TYPE: DNA
<213> ORGANISM: Artificial Sequence
<220> FEATURE:
<223> OTHER INFORMATION: Synthetic

<400> SEQUENCE: 200
gtcttctgag tcttctga                                                         18

<210> SEQ ID NO 201
<211> LENGTH: 18
<212> TYPE: DNA
<213> ORGANISM: Artificial Sequence
<220> FEATURE:
<223> OTHER INFORMATION: Synthetic

<400> SEQUENCE: 201
tgctcacaat gctcacaa                                                 18

<210> SEQ ID NO 202
<211> LENGTH: 18
<212> TYPE: DNA
<213> ORGANISM: Artificial Sequence
<220> FEATURE:
<223> OTHER INFORMATION: Synthetic

<400> SEQUENCE: 202
atagctgaga tagctgag                                                 18

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
aagtcagaga agtcagag                                                 18

<210> SEQ ID NO 204
<211> LENGTH: 18
<212> TYPE: DNA
<213> ORGANISM: Artificial Sequence
<220> FEATURE:
<223> OTHER INFORMATION: Synthetic

<400> SEQUENCE: 204
tattgcctct attgcctc                                                 18

<210> SEQ ID NO 205
<211> LENGTH: 18
<212> TYPE: DNA
<213> ORGANISM: Artificial Sequence
<220> FEATURE:
<223> OTHER INFORMATION: Synthetic

<400> SEQUENCE: 205
gcttatggtg cttatggt                                                 18

<210> SEQ ID NO 206
<211> LENGTH: 18
<212> TYPE: DNA
<213> ORGANISM: Artificial Sequence
<220> FEATURE:
<223> OTHER INFORMATION: Synthetic

<400> SEQUENCE: 206
gctgtatacg ctgtatac                                                 18

<210> SEQ ID NO 207
<211> LENGTH: 18
<212> TYPE: DNA
<213> ORGANISM: Artificial Sequence
<220> FEATURE:
<223> OTHER INFORMATION: Synthetic

<400> SEQUENCE: 207
gaatcctcag aatcctca                                                 18

```
<210> SEQ ID NO 208
<211> LENGTH: 18
<212> TYPE: DNA
<213> ORGANISM: Artificial Sequence
<220> FEATURE:
<223> OTHER INFORMATION: Synthetic

<400> SEQUENCE: 208
catcagtgtc atcagtgt                                                 18

<210> SEQ ID NO 209
<211> LENGTH: 18
<212> TYPE: DNA
<213> ORGANISM: Artificial Sequence
<220> FEATURE:
<223> OTHER INFORMATION: Synthetic

<400> SEQUENCE: 209
acctgtaaca cctgtaac                                                 18

<210> SEQ ID NO 210
<211> LENGTH: 18
<212> TYPE: DNA
<213> ORGANISM: Artificial Sequence
<220> FEATURE:
<223> OTHER INFORMATION: Synthetic

<400> SEQUENCE: 210
ccgtaattgc cgtaattg                                                 18

<210> SEQ ID NO 211
<211> LENGTH: 18
<212> TYPE: DNA
<213> ORGANISM: Artificial Sequence
<220> FEATURE:
<223> OTHER INFORMATION: Synthetic

<400> SEQUENCE: 211
ccaagcaatc caagcaat                                                 18

<210> SEQ ID NO 212
<211> LENGTH: 18
<212> TYPE: DNA
<213> ORGANISM: Artificial Sequence
<220> FEATURE:
<223> OTHER INFORMATION: Synthetic

<400> SEQUENCE: 212
tagcgtactt agcgtact                                                 18

<210> SEQ ID NO 213
<211> LENGTH: 18
<212> TYPE: DNA
<213> ORGANISM: Artificial Sequence
<220> FEATURE:
<223> OTHER INFORMATION: Synthetic

<400> SEQUENCE: 213
gcaactatgg caactatg                                                 18

<210> SEQ ID NO 214
<211> LENGTH: 18
<212> TYPE: DNA
<213> ORGANISM: Artificial Sequence
<220> FEATURE:
<223> OTHER INFORMATION: Synthetic
```

```
<400> SEQUENCE: 214
ctgtcgtaac tgtcgtaa                                                 18

<210> SEQ ID NO 215
<211> LENGTH: 18
<212> TYPE: DNA
<213> ORGANISM: Artificial Sequence
<220> FEATURE:
<223> OTHER INFORMATION: Synthetic

<400> SEQUENCE: 215
ttactgacgt tactgacg                                                 18

<210> SEQ ID NO 216
<211> LENGTH: 18
<212> TYPE: DNA
<213> ORGANISM: Artificial Sequence
<220> FEATURE:
<223> OTHER INFORMATION: Synthetic

<400> SEQUENCE: 216
cgtatgatgc gtatgatg                                                 18

<210> SEQ ID NO 217
<211> LENGTH: 17
<212> TYPE: DNA
<213> ORGANISM: Artificial Sequence
<220> FEATURE:
<223> OTHER INFORMATION: Synthetic

<400> SEQUENCE: 217
tcggtagtat cggtagt                                                  17

<210> SEQ ID NO 218
<211> LENGTH: 18
<212> TYPE: DNA
<213> ORGANISM: Artificial Sequence
<220> FEATURE:
<223> OTHER INFORMATION: Synthetic

<400> SEQUENCE: 218
gatcaactgg atcaactg                                                 18

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219
agtctaccta gtctacct                                                 18

<210> SEQ ID NO 220
<211> LENGTH: 18
<212> TYPE: DNA
<213> ORGANISM: Artificial Sequence
<220> FEATURE:
<223> OTHER INFORMATION: Synthetic

<400> SEQUENCE: 220
atgatcggta tgatcggt                                                 18

<210> SEQ ID NO 221
```

```
<211> LENGTH: 18
<212> TYPE: DNA
<213> ORGANISM: Artificial Sequence
<220> FEATURE:
<223> OTHER INFORMATION: Synthetic

<400> SEQUENCE: 221
gtgcaatgtg tgcaatgt                                                 18

<210> SEQ ID NO 222
<211> LENGTH: 18
<212> TYPE: DNA
<213> ORGANISM: Artificial Sequence
<220> FEATURE:
<223> OTHER INFORMATION: Synthetic

<400> SEQUENCE: 222
tgaatgccat gaatgcca                                                 18

<210> SEQ ID NO 223
<211> LENGTH: 18
<212> TYPE: DNA
<213> ORGANISM: Artificial Sequence
<220> FEATURE:
<223> OTHER INFORMATION: Synthetic

<400> SEQUENCE: 223
aacagtccaa acagtcca                                                 18

<210> SEQ ID NO 224
<211> LENGTH: 18
<212> TYPE: DNA
<213> ORGANISM: Artificial Sequence
<220> FEATURE:
<223> OTHER INFORMATION: Synthetic

<400> SEQUENCE: 224
tcctaacgtt cctaacgt                                                 18

<210> SEQ ID NO 225
<211> LENGTH: 18
<212> TYPE: DNA
<213> ORGANISM: Artificial Sequence
<220> FEATURE:
<223> OTHER INFORMATION: Synthetic

<400> SEQUENCE: 225
agcagatgta gcagatgt                                                 18

<210> SEQ ID NO 226
<211> LENGTH: 18
<212> TYPE: DNA
<213> ORGANISM: Artificial Sequence
<220> FEATURE:
<223> OTHER INFORMATION: Synthetic

<400> SEQUENCE: 226
gtatcagtcg tatcagtc                                                 18

<210> SEQ ID NO 227
<211> LENGTH: 18
<212> TYPE: DNA
<213> ORGANISM: Artificial Sequence
<220> FEATURE:
<223> OTHER INFORMATION: Synthetic

<400> SEQUENCE: 227
```

```
aatcgtggaa atcgtgga                                                 18

<210> SEQ ID NO 228
<211> LENGTH: 18
<212> TYPE: DNA
<213> ORGANISM: Artificial Sequence
<220> FEATURE:
<223> OTHER INFORMATION: Synthetic

<400> SEQUENCE: 228
ctcgtaatgc tcgtaatg                                                 18

<210> SEQ ID NO 229
<211> LENGTH: 18
<212> TYPE: DNA
<213> ORGANISM: Artificial Sequence
<220> FEATURE:
<223> OTHER INFORMATION: Synthetic

<400> SEQUENCE: 229
ttcagtgagt tcagtgag                                                 18

<210> SEQ ID NO 230
<211> LENGTH: 18
<212> TYPE: DNA
<213> ORGANISM: Artificial Sequence
<220> FEATURE:
<223> OTHER INFORMATION: Synthetic

<400> SEQUENCE: 230
gtaagtcacg taagtcac                                                 18

<210> SEQ ID NO 231
<211> LENGTH: 18
<212> TYPE: DNA
<213> ORGANISM: Artificial Sequence
<220> FEATURE:
<223> OTHER INFORMATION: Synthetic

<400> SEQUENCE: 231
cttatccagc ttatccag                                                 18

<210> SEQ ID NO 232
<211> LENGTH: 18
<212> TYPE: DNA
<213> ORGANISM: Artificial Sequence
<220> FEATURE:
<223> OTHER INFORMATION: Synthetic

<400> SEQUENCE: 232
aggacagtta ggacagtt                                                 18

<210> SEQ ID NO 233
<211> LENGTH: 18
<212> TYPE: DNA
<213> ORGANISM: Artificial Sequence
<220> FEATURE:
<223> OTHER INFORMATION: Synthetic

<400> SEQUENCE: 233
gtcatgcatg tcatgcat                                                 18

<210> SEQ ID NO 234
<211> LENGTH: 18
<212> TYPE: DNA
```

```
<213> ORGANISM: Artificial Sequence
<220> FEATURE:
<223> OTHER INFORMATION: Synthetic

<400> SEQUENCE: 234
ttcaccgtat tcaccgta                                                 18

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235
tagtacgctt agtacgct                                                 18

<210> SEQ ID NO 236
<211> LENGTH: 18
<212> TYPE: DNA
<213> ORGANISM: Artificial Sequence
<220> FEATURE:
<223> OTHER INFORMATION: Synthetic

<400> SEQUENCE: 236
tcgttgaagt cgttgaag                                                 18

<210> SEQ ID NO 237
<211> LENGTH: 18
<212> TYPE: DNA
<213> ORGANISM: Artificial Sequence
<220> FEATURE:
<223> OTHER INFORMATION: Synthetic

<400> SEQUENCE: 237
cattaacgcc attaacgc                                                 18

<210> SEQ ID NO 238
<211> LENGTH: 18
<212> TYPE: DNA
<213> ORGANISM: Artificial Sequence
<220> FEATURE:
<223> OTHER INFORMATION: Synthetic

<400> SEQUENCE: 238
tagtggcaat agtggcaa                                                 18

<210> SEQ ID NO 239
<211> LENGTH: 18
<212> TYPE: DNA
<213> ORGANISM: Artificial Sequence
<220> FEATURE:
<223> OTHER INFORMATION: Synthetic

<400> SEQUENCE: 239
accgtaagaa ccgtaaga                                                 18

<210> SEQ ID NO 240
<211> LENGTH: 18
<212> TYPE: DNA
<213> ORGANISM: Artificial Sequence
<220> FEATURE:
<223> OTHER INFORMATION: Synthetic

<400> SEQUENCE: 240
gacgagattg acgagatt                                                 18
```

<210> SEQ ID NO 241
<211> LENGTH: 18
<212> TYPE: DNA
<213> ORGANISM: Artificial Sequence
<220> FEATURE:
<223> OTHER INFORMATION: Synthetic

<400> SEQUENCE: 241
tacgaagtct acgaagtc                                               18

<210> SEQ ID NO 242
<211> LENGTH: 50
<212> TYPE: DNA
<213> ORGANISM: Artificial Sequence
<220> FEATURE:
<223> OTHER INFORMATION: Synthetic

<400> SEQUENCE: 242
ccatacgacg ttccagacta cgctctgcag gctagtggtg gaggaggctc            50

<210> SEQ ID NO 243
<211> LENGTH: 57
<212> TYPE: DNA
<213> ORGANISM: Artificial Sequence
<220> FEATURE:
<223> OTHER INFORMATION: Synthetic

<400> SEQUENCE: 243
cactgttgtt atcagatctc tattacaagt cctcttcaga ataagctttt tgttcgg    57

<210> SEQ ID NO 244
<211> LENGTH: 49
<212> TYPE: DNA
<213> ORGANISM: Artificial Sequence
<220> FEATURE:
<223> OTHER INFORMATION: Synthetic

<400> SEQUENCE: 244
tctttcccta cacgacgctc ttccgatctt tccagactac gctctgcag             49

<210> SEQ ID NO 245
<211> LENGTH: 58
<212> TYPE: DNA
<213> ORGANISM: Artificial Sequence
<220> FEATURE:
<223> OTHER INFORMATION: Synthetic

<400> SEQUENCE: 245
gtgactggag ttcagacgtg tgctcttccg atctcatcta cactgttgtt atcagatc   58

<210> SEQ ID NO 246
<211> LENGTH: 48
<212> TYPE: DNA
<213> ORGANISM: Artificial Sequence
<220> FEATURE:
<223> OTHER INFORMATION: Synthetic

<400> SEQUENCE: 246
tctttcccta cacgacgctc ttccgatcta gggtcggcta gccatatg              48

<210> SEQ ID NO 247
<211> LENGTH: 54
<212> TYPE: DNA
<213> ORGANISM: Artificial Sequence
<220> FEATURE:

<223> OTHER INFORMATION: Synthetic

<400> SEQUENCE: 247
gtgactggag ttcagacgtg tgctcttccg atctgagctt tacgagacgc ttct        54

<210> SEQ ID NO 248
<211> LENGTH: 50
<212> TYPE: DNA
<213> ORGANISM: Artificial Sequence
<220> FEATURE:
<223> OTHER INFORMATION: Synthetic

<400> SEQUENCE: 248
tctttcccta cacgacgctc ttccgatctc tcaaacagaa actggaagag        50

<210> SEQ ID NO 249
<211> LENGTH: 55
<212> TYPE: DNA
<213> ORGANISM: Artificial Sequence
<220> FEATURE:
<223> OTHER INFORMATION: Synthetic

<400> SEQUENCE: 249
gtgactggag ttcagacgtg tgctcttccg atctataagc ttttgttcgg atccg        55

<210> SEQ ID NO 250
<211> LENGTH: 58
<212> TYPE: DNA
<213> ORGANISM: Artificial Sequence
<220> FEATURE:
<223> OTHER INFORMATION: Synthetic

<400> SEQUENCE: 250
aatgatacgg cgaccaccga gatctacact ctttccctac acgacgctct tccgatct        58

<210> SEQ ID NO 251
<211> LENGTH: 58
<212> TYPE: DNA
<213> ORGANISM: Artificial Sequence
<220> FEATURE:
<223> OTHER INFORMATION: Synthetic

<400> SEQUENCE: 251
caagcagaag acggcatacg agatcgtgat gtgactggag ttcagacgtg tgctcttc        58

<210> SEQ ID NO 252
<211> LENGTH: 58
<212> TYPE: DNA
<213> ORGANISM: Artificial Sequence
<220> FEATURE:
<223> OTHER INFORMATION: Synthetic

<400> SEQUENCE: 252
caagcagaag acggcatacg agatacatcg gtgactggag ttcagacgtg tgctcttc        58

<210> SEQ ID NO 253
<211> LENGTH: 58
<212> TYPE: DNA
<213> ORGANISM: Artificial Sequence
<220> FEATURE:
<223> OTHER INFORMATION: Synthetic

<400> SEQUENCE: 253
caagcagaag acggcatacg agatgcctaa gtgactggag ttcagacgtg tgctcttc        58

<210> SEQ ID NO 254
<211> LENGTH: 58
<212> TYPE: DNA
<213> ORGANISM: Artificial Sequence
<220> FEATURE:
<223> OTHER INFORMATION: Synthetic

<400> SEQUENCE: 254
caagcagaag acggcatacg agattggtca gtgactggag ttcagacgtg tgctcttc    58

<210> SEQ ID NO 255
<211> LENGTH: 58
<212> TYPE: DNA
<213> ORGANISM: Artificial Sequence
<220> FEATURE:
<223> OTHER INFORMATION: Synthetic

<400> SEQUENCE: 255
caagcagaag acggcatacg agatcactgt gtgactggag ttcagacgtg tgctcttc    58

<210> SEQ ID NO 256
<211> LENGTH: 58
<212> TYPE: DNA
<213> ORGANISM: Artificial Sequence
<220> FEATURE:
<223> OTHER INFORMATION: Synthetic

<400> SEQUENCE: 256
caagcagaag acggcatacg agatattggc gtgactggag ttcagacgtg tgctcttc    58

<210> SEQ ID NO 257
<211> LENGTH: 58
<212> TYPE: DNA
<213> ORGANISM: Artificial Sequence
<220> FEATURE:
<223> OTHER INFORMATION: Synthetic

<400> SEQUENCE: 257
caagcagaag acggcatacg agatgatctg gtgactggag ttcagacgtg tgctcttc    58

<210> SEQ ID NO 258
<211> LENGTH: 58
<212> TYPE: DNA
<213> ORGANISM: Artificial Sequence
<220> FEATURE:
<223> OTHER INFORMATION: Synthetic

<400> SEQUENCE: 258
caagcagaag acggcatacg agattcaagt gtgactggag ttcagacgtg tgctcttc    58

<210> SEQ ID NO 259
<211> LENGTH: 116
<212> TYPE: PRT
<213> ORGANISM: Artificial Sequence
<220> FEATURE:
<223> OTHER INFORMATION: Synthetic

<400> SEQUENCE: 259

Ala Asp Trp Lys Lys Val Leu Asp Lys Ala Lys Asp Ile Ala Glu Asn
1               5                   10                  15

Arg Val Arg Glu Ile Lys Gln Lys Leu Glu Glu Phe Tyr Lys Glu Ala
            20                  25                  30

Met Lys Leu Asp Leu Thr Gln Glu Met Arg Arg Lys Leu Met Leu Arg
        35                  40                  45

Trp Ile Ala Ala Met Leu Met Ala Ile Gly Asp Ile Phe Asn Ala Ile

Arg Gln Ala Lys Gln Glu Ala Asp Lys Leu Lys Lys Ala Gly Gln Val
65                  70                  75                  80

Asn Ser Gln Leu Leu Asp Glu Leu Lys Arg Arg Leu Glu Glu Leu Lys
                85                  90                  95

Glu Glu Ala Ser Arg Lys Cys His Asp Tyr Gly Arg Glu Phe Gln Leu
            100                 105                 110

Lys Leu Glu Tyr
        115

<210> SEQ ID NO 260
<211> LENGTH: 116
<212> TYPE: PRT
<213> ORGANISM: Artificial Sequence
<220> FEATURE:
<223> OTHER INFORMATION: Synthetic

<400> SEQUENCE: 260

Ala Asp Trp Lys Lys Val Leu Asp Lys Ala Lys Asp Ile Ala Glu Asn
1               5                   10                  15

Arg Val Arg Glu Leu Lys Gln Lys Leu Glu Glu Phe Tyr Lys Glu Ala
            20                  25                  30

Met Lys Leu Asp Leu Thr Gln Glu Met Arg Arg Lys Leu Met Leu Arg
        35                  40                  45

Trp Ile Ala Ala Met Leu Met Ala Ile Gly Asp Ile Phe Asn Ala Ile
    50                  55                  60

Arg Gln Ala Lys Gln Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Lys
                85                  90                  95

Glu Glu Ala Ser Arg Lys Cys Arg Asp Tyr Gly Arg Glu Phe Gln Leu
            100                 105                 110

Lys Leu Glu Tyr
        115

<210> SEQ ID NO 261
<211> LENGTH: 116
<212> TYPE: PRT
<213> ORGANISM: Artificial Sequence
<220> FEATURE:
<223> OTHER INFORMATION: Synthetic

<400> SEQUENCE: 261

Ala Asp Trp Lys Lys Val Leu Asp Lys Ala Lys Asp Ile Ala Glu Asn
1               5                   10                  15

Arg Val Arg Glu Leu Lys Gln Lys Leu Glu Glu Phe Tyr Lys Glu Ala
            20                  25                  30

Met Lys Leu Asp Leu Thr Gln Glu Met Arg Arg Lys Leu Met Leu Arg
        35                  40                  45

Trp Ile Ala Ala Met Leu Met Ala Ile Gly Asp Ile Phe Asn Ala Ile
    50                  55                  60

Arg Gln Ala Lys Gln Glu Ala Asp Lys Leu Lys Lys Ala Gly Leu Val
65                  70                  75                  80

Asn Ser Gln Gln Leu Asp Glu Leu Lys Arg Arg Leu Glu Glu Leu Lys
                85                  90                  95

Glu Glu Ala Ser Arg Lys Ala Arg Asp Tyr Gly Arg Glu Phe Gln Leu
            100                 105                 110

```
Lys Leu Glu Tyr
        115

<210> SEQ ID NO 262
<211> LENGTH: 115
<212> TYPE: PRT
<213> ORGANISM: Artificial Sequence
<220> FEATURE:
<223> OTHER INFORMATION: Synthetic

<400> SEQUENCE: 262

Asp Pro Lys Lys Val Phe Asp Lys Ala Lys Asp Lys Ala Glu Asn Gln
1               5                   10                  15

Val Arg Tyr Leu Lys Gln Arg Leu Glu Glu Leu Tyr Lys Glu Ala Arg
            20                  25                  30

Lys Lys Asp Leu Thr Gln Glu Gln Arg Arg Lys Leu Lys Glu Lys Tyr
        35                  40                  45

Leu Ala Ala Lys Leu Ala Ala Ile Leu Ala Ala Ile Gly Asp Ala Phe
    50                  55                  60

Asn Ala Leu Ala Glu Ala Arg Glu Leu His Lys Gln Gly Lys Val Asn
65                  70                  75                  80

Lys Gln Gln Leu Asp Glu Leu Ala Lys Arg Leu Asp Arg Leu Ala Glu
                85                  90                  95

Glu Ala Ile Gln Lys Ala Glu Asp Tyr Ala Arg Glu Phe Ala Tyr Lys
            100                 105                 110

Leu Glu Tyr
        115

<210> SEQ ID NO 263
<211> LENGTH: 115
<212> TYPE: PRT
<213> ORGANISM: Artificial Sequence
<220> FEATURE:
<223> OTHER INFORMATION: Synthetic

<400> SEQUENCE: 263

Asp Pro Lys Lys Val Leu Asp Lys Ala Arg Asp Gln Ala Leu Lys Arg
1               5                   10                  15

Leu Glu Glu Met Arg Lys Lys Leu Glu Glu Ser Tyr Lys Glu Ala Arg
            20                  25                  30

Lys Lys Asp Leu Thr Gln Glu Glu Arg Arg Lys Leu Glu Glu Lys Tyr
        35                  40                  45

Ala Glu Ala Met Lys Arg Ala Ala Glu Asp Ile Tyr Asn Met Ile Gln
    50                  55                  60

Gln Ala Leu Lys Glu Ala Glu Lys Glu Lys Lys Ala Gly Gln Val Asn
65                  70                  75                  80

Ser Gln Gln Leu Asp Lys Leu Arg Glu Asp Leu Asn Asn Lys Leu Ile
                85                  90                  95

Ala Ala Ala Leu Ala Ala Ile Gly Asp Ala Phe Asn Met Ala Ala Asn
            100                 105                 110

Leu Arg Thr
        115

<210> SEQ ID NO 264
<211> LENGTH: 115
<212> TYPE: PRT
<213> ORGANISM: Artificial Sequence
<220> FEATURE:
<223> OTHER INFORMATION: Synthetic
```

<400> SEQUENCE: 264

Asp Pro Lys Lys Val Phe Asp Glu Ala Lys Asp Arg Ala Glu Asn Asn
1               5                   10                  15

Val Arg Arg Leu Lys Gln Lys Leu Glu Glu Leu Tyr Lys Glu Ala Arg
            20                  25                  30

Lys Lys Asp Leu Thr Gln Glu Glu Arg Glu Lys Leu Lys Glu Lys Tyr
        35                  40                  45

Lys Thr Ala Met Ala Ala Ala Leu Ala Ala Ile Gly Asp Ala Phe
    50                  55                  60

Asn Ala Leu Leu Lys Ala Arg Lys Leu His Lys Asn Gly Gln Val Asn
65                  70                  75                  80

Glu Gln Gln Leu Glu Glu Leu Ala Arg Arg Leu Gln Glu Leu Ala Lys
                85                  90                  95

Glu Ala Phe Gln Lys Ala Lys Asp Tyr Ala Asn Glu Phe Glu Tyr Lys
            100                 105                 110

Leu Glu Tyr
        115

<210> SEQ ID NO 265
<211> LENGTH: 115
<212> TYPE: PRT
<213> ORGANISM: Artificial Sequence
<220> FEATURE:
<223> OTHER INFORMATION: Synthetic

<400> SEQUENCE: 265

Asp Pro Lys Lys Val Phe Asp Glu Leu Lys Asp Arg Ala Glu Asn Asn
1               5                   10                  15

Val Arg Arg Leu Lys Gln Lys Leu Glu Glu Leu Tyr Lys Glu Ala Arg
            20                  25                  30

Lys Lys Asp Leu Thr Gln Glu Glu Arg Glu Lys Leu Lys Thr Lys Tyr
        35                  40                  45

Lys Thr Ala Met Gln Leu Ala Ala Leu Ala Ala Glu Gly Asp Ile Met
    50                  55                  60

Asn Ala Leu Leu Lys Ala Arg Lys Leu His Lys Asn Gly Gln Val Asn
65                  70                  75                  80

Glu Gln Gln Leu Glu Glu Leu Ala Arg Arg Leu Met Glu Leu Ala Lys
                85                  90                  95

Glu Ala Phe Gln Lys Ala Lys Asp Tyr Ala Asn Glu Phe Lys Tyr Lys
            100                 105                 110

Leu Glu Tyr
        115

<210> SEQ ID NO 266
<211> LENGTH: 115
<212> TYPE: PRT
<213> ORGANISM: Artificial Sequence
<220> FEATURE:
<223> OTHER INFORMATION: Synthetic

<400> SEQUENCE: 266

Asp Pro Lys Lys Val Phe Asp Glu Leu Lys Asp Arg Ala Glu Asn Asn
1               5                   10                  15

Val Arg Gln Leu Lys Gln Lys Leu Glu Glu Leu Tyr Lys Glu Ala Arg
            20                  25                  30

Lys Lys Asp Leu Thr Gln Glu Glu Arg Glu Lys Leu Lys Asp Lys Tyr
        35                  40                  45

```
Lys Thr Ala Met His Ile Ala Ala Leu Ala Ala Glu Gly Asp Ile Met
 50                  55                  60

Asn Ala Leu Leu Lys Ala Arg Lys Leu His Lys Arg Gly Gln Val Asn
 65                  70                  75                  80

Glu Gln Gln Leu Arg Glu Leu Ala Arg Arg Leu Met Glu Leu Ala Lys
                 85                  90                  95

Glu Ala Phe Gln Lys Ala Lys Asp Tyr Ala Asn Glu Phe Lys Tyr Lys
            100                 105                 110

Leu Glu Tyr
        115

<210> SEQ ID NO 267
<211> LENGTH: 115
<212> TYPE: PRT
<213> ORGANISM: Artificial Sequence
<220> FEATURE:
<223> OTHER INFORMATION: Synthetic

<400> SEQUENCE: 267

Asp Pro Lys Lys Val Phe Asp Glu Leu Lys Asp Arg Ala Glu Asn Asn
 1               5                  10                  15

Val Arg Arg Leu Lys Gln Lys Leu Glu Glu Leu Tyr Lys Glu Ala Arg
                20                  25                  30

Lys Lys Asp Leu Thr Gln Glu Glu Arg Glu Lys Leu Lys Thr Lys Tyr
            35                  40                  45

Lys Thr Ala Met His Ile Ala Ala Leu Ala Ala Glu Gly Asp Ile Ile
 50                  55                  60

Asn Ala Leu Leu Lys Ala Arg Lys Leu His Lys Arg Gly Gln Val Asn
 65                  70                  75                  80

Glu Gln Gln Leu Arg Glu Leu Ala Arg Arg Leu Met Glu Leu Ala Lys
                 85                  90                  95

Glu Ala Phe Gln Lys Ala Lys Asp Tyr Ala Asn Glu Phe Glu Tyr Lys
            100                 105                 110

Leu Glu Tyr
        115

<210> SEQ ID NO 268
<211> LENGTH: 115
<212> TYPE: PRT
<213> ORGANISM: Artificial Sequence
<220> FEATURE:
<223> OTHER INFORMATION: Synthetic

<400> SEQUENCE: 268

Asp Pro Lys Lys Val Phe Asp Glu Leu Lys Asp Arg Ala Glu Asn Asn
 1               5                  10                  15

Val Arg Asn Leu Lys Gln Lys Leu Glu Glu Leu Tyr Lys Glu Ala Arg
                20                  25                  30

Lys Lys Asp Leu Thr Gln Glu Glu Arg Glu Lys Leu Lys Asp Lys Tyr
            35                  40                  45

Lys Thr Ala Met Gln Ile Ala Ala Leu Ala Ala Glu Gly Asp Ile Met
 50                  55                  60

Asn Ala Leu Leu Lys Ala Arg Lys Leu His Lys Asn Gly Gln Val Asn
 65                  70                  75                  80

Glu Gln Gln Leu Arg Glu Leu Ala Arg Arg Leu Met Glu Leu Ala Lys
                 85                  90                  95

Glu Ala Phe Gln Lys Ala Lys Asp Tyr Ala Asn Glu Phe Lys Tyr Lys
            100                 105                 110
```

-continued

Leu Glu Tyr
        115

<210> SEQ ID NO 269
<211> LENGTH: 115
<212> TYPE: PRT
<213> ORGANISM: Artificial Sequence
<220> FEATURE:
<223> OTHER INFORMATION: Synthetic

<400> SEQUENCE: 269

Asp Pro Lys Lys Val Phe Asp Glu Leu Lys Asp Arg Ala Glu Asn Asn
1               5                   10                  15

Val Arg Asn Leu Lys Gln Lys Leu Glu Glu Leu Tyr Lys Glu Ala Arg
            20                  25                  30

Lys Lys Asp Leu Thr Gln Glu Glu Arg Glu Lys Leu Lys Thr Lys Tyr
        35                  40                  45

Lys Thr Ala Met Ala Ile Ala Ala Leu Ala Ala Glu Gly Asp Leu Leu
    50                  55                  60

Asn Ala Leu Leu Lys Ala Arg Lys Leu His Lys Arg Gly Gln Val Asn
65                  70                  75                  80

Glu Gln Gln Leu Arg Glu Leu Ala Arg Arg Leu Met Glu Leu Ala Lys
                85                  90                  95

Glu Ala Phe Gln Lys Ala Lys Asp Tyr Ala Asn Glu Phe Lys Tyr Lys
            100                 105                 110

Leu Glu Tyr
        115

<210> SEQ ID NO 270
<211> LENGTH: 115
<212> TYPE: PRT
<213> ORGANISM: Artificial Sequence
<220> FEATURE:
<223> OTHER INFORMATION: Synthetic

<400> SEQUENCE: 270

Asp Pro Lys Lys Val Phe Asp Glu Leu Lys Asp Arg Ala Glu Asn Asn
1               5                   10                  15

Val Arg Arg Leu Lys Gln Lys Leu Glu Glu Leu Tyr Lys Glu Ala Arg
            20                  25                  30

Lys Lys Asp Leu Thr Gln Glu Glu Arg Glu Lys Leu Lys Thr Lys Tyr
        35                  40                  45

Lys Thr Ala Met Ala Ile Ala Ala Leu Ala Ala Glu Gly Asp Ile Met
    50                  55                  60

Asn Ala Leu Leu Lys Ala Arg Lys Leu His Lys Arg Gly Gln Val Asn
65                  70                  75                  80

Glu Gln Gln Leu Arg Glu Leu Ala Arg Arg Leu Met Glu Leu Ala Lys
                85                  90                  95

Glu Ala Phe Gln Lys Ala Lys Asp Tyr Ala Asn Glu Phe Lys Tyr Lys
            100                 105                 110

Leu Glu Tyr
        115

<210> SEQ ID NO 271
<211> LENGTH: 115
<212> TYPE: PRT
<213> ORGANISM: Artificial Sequence
<220> FEATURE:
<223> OTHER INFORMATION: Synthetic

<400> SEQUENCE: 271

Asp Pro Lys Lys Val Phe Asp Glu Leu Lys Asp Arg Ala Glu Asn Asn
1               5                   10                  15

Val Arg Arg Leu Lys Gln Lys Leu Glu Glu Leu Tyr Lys Glu Ala Arg
                20                  25                  30

Lys Lys Asp Leu Thr Gln Glu Glu Arg Glu Lys Leu Lys Thr Lys Tyr
            35                  40                  45

Lys Thr Ala Met Ala Ala Ala Leu Ala Ala Glu Gly Asp Ala Phe
        50                  55                  60

Asn Ala Leu Leu Lys Ala Arg Lys Leu His Lys Arg Gly Gln Val Asn
65                  70                  75                  80

Glu Gln Gln Leu Arg Glu Leu Ala Arg Arg Leu Met Glu Leu Ala Lys
                85                  90                  95

Glu Ala Phe Gln Lys Ala Lys Asp Tyr Ala Asn Glu Phe Lys Tyr Lys
                100                 105                 110

Leu Glu Tyr
        115

<210> SEQ ID NO 272
<211> LENGTH: 115
<212> TYPE: PRT
<213> ORGANISM: Artificial Sequence
<220> FEATURE:
<223> OTHER INFORMATION: Synthetic

<400> SEQUENCE: 272

Asp Pro Lys Lys Val Phe Asp Glu Leu Lys Asp Arg Ala Glu Asn Asn
1               5                   10                  15

Val Arg Arg Leu Lys Gln Lys Leu Glu Glu Leu Tyr Lys Glu Ala Arg
                20                  25                  30

Lys Lys Asp Leu Thr Gln Glu Glu Arg Glu Lys Leu Lys Glu Lys Tyr
            35                  40                  45

Lys Thr Ala Met Ala Ala Ala Leu Ala Ala Glu Gly Asp Ala Phe
        50                  55                  60

Asn Ala Leu Leu Lys Ala Arg Lys Leu His Lys Asn Gly Gln Val Asn
65                  70                  75                  80

Glu Gln Gln Leu Arg Glu Leu Ala Arg Arg Leu Met Glu Leu Ala Lys
                85                  90                  95

Glu Ala Phe Gln Lys Ala Lys Asp Tyr Ala Asn Glu Phe Lys Tyr Lys
                100                 105                 110

Leu Glu Tyr
        115

<210> SEQ ID NO 273
<211> LENGTH: 115
<212> TYPE: PRT
<213> ORGANISM: Artificial Sequence
<220> FEATURE:
<223> OTHER INFORMATION: Synthetic

<400> SEQUENCE: 273

Asp Pro Lys Lys Val Phe Asp Glu Leu Lys Asp Arg Ala Glu Asn Asn
1               5                   10                  15

Val Arg Arg Leu Lys Gln Lys Leu Glu Glu Leu Tyr Lys Glu Ala Arg
                20                  25                  30

Lys Lys Asp Leu Thr Gln Glu Glu Arg Glu Lys Leu Lys Glu Lys Tyr
            35                  40                  45

```
Lys Thr Ala Met Ala Ala Ala Leu Ala Ala Glu Gly Asp Ala Phe
    50                  55                  60

Asn Ala Leu Leu Lys Ala Arg Lys Leu His Lys Asn Gly Gln Val Asn
 65                  70                  75                  80

Glu Gln Gln Leu Arg Glu Leu Ala Arg Arg Leu Met Glu Leu Ala Lys
                 85                  90                  95

Glu Ala Phe Gln Lys Ala Lys Asp Tyr Ala Asn Glu Phe Glu Tyr Lys
                100                 105                 110

Leu Glu Tyr
        115

<210> SEQ ID NO 274
<211> LENGTH: 193
<212> TYPE: PRT
<213> ORGANISM: Artificial Sequence
<220> FEATURE:
<223> OTHER INFORMATION: Synthetic

<400> SEQUENCE: 274

Met Ala Thr Pro Ala Ser Ala Pro Asp Thr Arg Ala Leu Val Ala Asp
  1               5                  10                  15

Phe Val Gly Tyr Lys Leu Arg Gln Lys Gly Tyr Val Cys Gly Ala Gly
                 20                  25                  30

Pro Gly Glu Gly Pro Ala Ala Asp Pro Leu His Gln Ala Met Arg Ala
             35                  40                  45

Ala Gly Asp Glu Phe Glu Thr Arg Phe Arg Arg Thr Phe Ser Asp Leu
     50                  55                  60

Ala Ala Gln Leu His Val Thr Pro Gly Ser Ala Gln Gln Arg Phe Thr
 65                  70                  75                  80

Gln Val Ser Asp Glu Leu Phe Gln Gly Gly Pro Asn Trp Gly Arg Leu
                 85                  90                  95

Val Ala Phe Phe Val Phe Gly Ala Ala Leu Cys Ala Glu Ser Val Asn
                100                 105                 110

Lys Glu Met Glu Pro Leu Val Gly Gln Val Gln Glu Trp Met Val Ala
            115                 120                 125

Tyr Leu Glu Thr Gln Leu Ala Asp Trp Ile His Ser Ser Gly Gly Trp
130                 135                 140

Ala Glu Phe Thr Ala Leu Tyr Gly Asp Gly Ala Leu Glu Glu Ala Arg
145                 150                 155                 160

Arg Leu Arg Glu Gly Asn Trp Ala Ser Val Arg Thr Val Leu Thr Gly
                165                 170                 175

Ala Val Ala Leu Gly Ala Leu Val Thr Val Gly Ala Phe Phe Ala Ser
            180                 185                 190

Lys

<210> SEQ ID NO 275
<211> LENGTH: 333
<212> TYPE: PRT
<213> ORGANISM: Artificial Sequence
<220> FEATURE:
<223> OTHER INFORMATION: Synthetic

<400> SEQUENCE: 275

Met Ala Thr Pro Ala Ser Ala Pro Asp Thr Arg Ala Leu Val Ala Asp
  1               5                  10                  15

Phe Val Gly Tyr Lys Leu Arg Gln Lys Gly Tyr Val Cys Gly Ala Gly
                 20                  25                  30
```

```
Pro Gly Glu Gly Pro Ala Ala Asp Pro Leu His Gln Ala Met Arg Ala
        35                  40                  45

Ala Gly Asp Glu Phe Glu Thr Arg Phe Arg Arg Thr Phe Ser Asp Leu
 50                  55                  60

Ala Ala Gln Leu His Val Thr Pro Gly Ser Ala Gln Gln Arg Phe Thr
 65                  70                  75                  80

Gln Val Ser Asp Glu Leu Phe Gln Gly Pro Asn Trp Gly Arg Leu
                 85                  90                  95

Val Ala Phe Phe Val Phe Gly Ala Ala Leu Cys Ala Glu Ser Val Asn
                100                 105                 110

Lys Glu Met Glu Pro Leu Val Gly Gln Val Gln Glu Trp Met Val Ala
                115                 120                 125

Tyr Leu Glu Thr Gln Leu Ala Asp Trp Ile His Ser Ser Gly Gly Trp
        130                 135                 140

Glu Leu Glu Ala Ile Lys Ala Arg Val Arg Glu Met Glu Glu Glu Ala
145                 150                 155                 160

Glu Lys Leu Lys Glu Leu Gln Asn Glu Val Glu Lys Gln Met Asn Met
                165                 170                 175

Ser Pro Pro Gly Asn Ala Gly Pro Val Ile Met Ser Ile Glu Glu
                180                 185                 190

Lys Met Glu Ala Asp Ala Arg Ser Ile Tyr Val Gly Asn Val Asp Tyr
        195                 200                 205

Gly Ala Thr Ala Glu Glu Leu Glu Ala His Phe His Gly Cys Gly Ser
        210                 215                 220

Val Asn Arg Val Thr Ile Leu Cys Asp Lys Phe Ser Gly His Pro Lys
225                 230                 235                 240

Gly Phe Ala Tyr Ile Glu Phe Ser Asp Lys Glu Ser Val Arg Thr Ser
                245                 250                 255

Leu Ala Leu Asp Glu Ser Leu Phe Arg Gly Arg Gln Ile Lys Val Ile
                260                 265                 270

Pro Lys Arg Thr Asn Arg Pro Gly Ile Ser Thr Thr Asp Arg Gly Phe
        275                 280                 285

Pro Arg Ala Arg Tyr Arg Ala Arg Thr Thr Asn Tyr Asn Ser Ser Arg
        290                 295                 300

Ser Arg Phe Tyr Ser Gly Phe Asn Ser Arg Pro Arg Gly Arg Val Tyr
305                 310                 315                 320

Arg Gly Arg Ala Arg Ala Thr Ser Trp Tyr Ser Pro Tyr
                325                 330

<210> SEQ ID NO 276
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is C, D, E, K, L, M, N, R, S, V, W or Y
<220> FEATURE:
<221> NAME/KEY: MISC_FEATURE
<222> LOCATION: (2)..(2)
<223> OTHER INFORMATION: Xaa is A, D, E, G, H, L, N, P, Q, R, T, or W
<220> FEATURE:
<221> NAME/KEY: MISC_FEATURE
<222> LOCATION: (3)..(3)
<223> OTHER INFORMATION: Xaa is A, C, F, G, H, I, K, M, Q, R, T, V or Y
<220> FEATURE:
<221> NAME/KEY: MISC_FEATURE
```

```
<222> LOCATION: (4)..(4)
<223> OTHER INFORMATION: Xaa is D, F, G, I, K, M, N, R, S, T, V or W
<220> FEATURE:
<221> NAME/KEY: MISC_FEATURE
<222> LOCATION: (5)..(5)
<223> OTHER INFORMATION: Xaa is I, L, M, N, T, V, W or Y
<220> FEATURE:
<221> NAME/KEY: MISC_FEATURE
<222> LOCATION: (6)..(6)
<223> OTHER INFORMATION: Xaa is E, F, I, L, Q, T, V, W, or Y
<220> FEATURE:
<221> NAME/KEY: MISC_FEATURE
<222> LOCATION: (7)..(7)
<223> OTHER INFORMATION: Xaa is A, C, D, F, L, W or Y
<220> FEATURE:
<221> NAME/KEY: MISC_FEATURE
<222> LOCATION: (8)..(8)
<223> OTHER INFORMATION: Xaa is D, E, H, I or V
<220> FEATURE:
<221> NAME/KEY: MISC_FEATURE
<222> LOCATION: (9)..(9)
<223> OTHER INFORMATION: Xaa is A, E, H, L or Y
<220> FEATURE:
<221> NAME/KEY: MISC_FEATURE
<222> LOCATION: (10)..(10)
<223> OTHER INFORMATION: Xaa is A, H, I, K, M, N, Q, R, S, T or Y
<220> FEATURE:
<221> NAME/KEY: MISC_FEATURE
<222> LOCATION: (11)..(11)
<223> OTHER INFORMATION: Xaa is C, D, E, G, H, K, M, Q, R, S, T or W
<220> FEATURE:
<221> NAME/KEY: MISC_FEATURE
<222> LOCATION: (12)..(12)
<223> OTHER INFORMATION: Xaa is A, D, E, G, L, N, Q, R, S, V or W
<220> FEATURE:
<221> NAME/KEY: MISC_FEATURE
<222> LOCATION: (13)..(13)
<223> OTHER INFORMATION: Xaa is A, C, F, H, K, L, M, N, S, Tor V
<220> FEATURE:
<221> NAME/KEY: MISC_FEATURE
<222> LOCATION: (14)..(14)
<223> OTHER INFORMATION: Xaa is A, D, E, F, G, H, I, L, M, Q, S, V, W
      or Y
<220> FEATURE:
<221> NAME/KEY: MISC_FEATURE
<222> LOCATION: (15)..(15)
<223> OTHER INFORMATION: Xaa is A, E, G, H, M, N, Q, R, W or Y
<220> FEATURE:
<221> NAME/KEY: MISC_FEATURE
<222> LOCATION: (16)..(16)
<223> OTHER INFORMATION: Xaa is A, F, L, M, N, S, V, W or Y
<220> FEATURE:
<221> NAME/KEY: MISC_FEATURE
<222> LOCATION: (17)..(17)
<223> OTHER INFORMATION: Xaa is F, G, H, I, K, M, Q, R, T or V
<220> FEATURE:
<221> NAME/KEY: MISC_FEATURE
<222> LOCATION: (18)..(18)
<223> OTHER INFORMATION: Xaa is A, C, E, H, K, L, N, Q, R, S, V or W
<220> FEATURE:
<221> NAME/KEY: MISC_FEATURE
<222> LOCATION: (19)..(19)
<223> OTHER INFORMATION: Xaa is I, M, N, Q or R
<220> FEATURE:
<221> NAME/KEY: MISC_FEATURE
<222> LOCATION: (20)..(20)
<223> OTHER INFORMATION: Xaa is A, F, G, I, K, L, M, P, T, V, W or Y
<220> FEATURE:
<221> NAME/KEY: MISC_FEATURE
<222> LOCATION: (21)..(21)
<223> OTHER INFORMATION: Xaa is I, K, N, S, T or W
<220> FEATURE:
<221> NAME/KEY: MISC_FEATURE
<222> LOCATION: (22)..(22)
<223> OTHER INFORMATION: Xaa is A, F, G, H, I, K, L, M, N, P, Q, R, S,
      V, W or Y
<220> FEATURE:
<221> NAME/KEY: MISC_FEATURE
<222> LOCATION: (23)..(23)
```

-continued

```
<223> OTHER INFORMATION: Xaa is I, K, L, R or V
<220> FEATURE:
<221> NAME/KEY: MISC_FEATURE
<222> LOCATION: (24)..(24)
<223> OTHER INFORMATION: Xaa is A, D, F, H, K, L, M, R, S or V
<220> FEATURE:
<221> NAME/KEY: MISC_FEATURE
<222> LOCATION: (25)..(25)
<223> OTHER INFORMATION: Xaa is A, C, D, E, G, H, L, M, S, V or W
<220> FEATURE:
<221> NAME/KEY: MISC_FEATURE
<222> LOCATION: (26)..(26)
<223> OTHER INFORMATION: Xaa is A, D, E, F, G, H, I, L, M, Q, R, S, V,
      W or Y
<220> FEATURE:
<221> NAME/KEY: MISC_FEATURE
<222> LOCATION: (27)..(27)
<223> OTHER INFORMATION: Xaa is A, F, G, I, K, L, M or Y
<220> FEATURE:
<221> NAME/KEY: MISC_FEATURE
<222> LOCATION: (28)..(28)
<223> OTHER INFORMATION: Xaa is F, H, I, K, L, Q, S, V, W or Y
<220> FEATURE:
<221> NAME/KEY: MISC_FEATURE
<222> LOCATION: (29)..(29)
<223> OTHER INFORMATION: Xaa is A, F, G, H, I, K, M, N, P, Q, R, S, T,
      V, W or Y
<220> FEATURE:
<221> NAME/KEY: MISC_FEATURE
<222> LOCATION: (30)..(30)
<223> OTHER INFORMATION: Xaa is D, E, G, H, L, M, N, Q, S, V, W or Y
<220> FEATURE:
<221> NAME/KEY: MISC_FEATURE
<222> LOCATION: (31)..(31)
<223> OTHER INFORMATION: Xaa is A, F, G, M, P, S, V or Y
<220> FEATURE:
<221> NAME/KEY: MISC_FEATURE
<222> LOCATION: (32)..(32)
<223> OTHER INFORMATION: Xaa is A, E, G, H, I, M, N, P, Q, R or T
<220> FEATURE:
<221> NAME/KEY: MISC_FEATURE
<222> LOCATION: (33)..(33)
<223> OTHER INFORMATION: Xaa is A, H, I, K, M, P, R, T, V, W or Y
<220> FEATURE:
<221> NAME/KEY: MISC_FEATURE
<222> LOCATION: (34)..(34)
<223> OTHER INFORMATION: Xaa is A, E, G, H, I, K, N, P, R, S, T or W
<220> FEATURE:
<221> NAME/KEY: MISC_FEATURE
<222> LOCATION: (35)..(35)
<223> OTHER INFORMATION: Xaa is A, C, D, E, G, H, K, L, M, N, P, R, S,
      T, V, W or Y
<220> FEATURE:
<221> NAME/KEY: MISC_FEATURE
<222> LOCATION: (36)..(36)
<223> OTHER INFORMATION: Xaa is A, D, E, F, K, L, R or S
<220> FEATURE:
<221> NAME/KEY: MISC_FEATURE
<222> LOCATION: (37)..(37)
<223> OTHER INFORMATION: Xaa is G, R, S or T
<220> FEATURE:
<221> NAME/KEY: MISC_FEATURE
<222> LOCATION: (38)..(38)
<223> OTHER INFORMATION: Xaa is A, E, G, H, K, L, P, Q, S, V or W
<220> FEATURE:
<221> NAME/KEY: MISC_FEATURE
<222> LOCATION: (39)..(39)
<223> OTHER INFORMATION: Xaa is A, D, E, G, I, K, M, N, P, Q, R, S, T,
      V, W or Y
<220> FEATURE:
<221> NAME/KEY: MISC_FEATURE
<222> LOCATION: (40)..(40)
<223> OTHER INFORMATION: Xaa is A, D, E, G, I, R, W or Y
<220> FEATURE:
<221> NAME/KEY: MISC_FEATURE
<222> LOCATION: (41)..(41)
<223> OTHER INFORMATION: Xaa is H, K, L, Q, R or Y
<220> FEATURE:
<221> NAME/KEY: MISC_FEATURE
```

```
<222> LOCATION: (42)..(42)
<223> OTHER INFORMATION: Xaa is A, D, E, G, K, Q, R, T or V
<220> FEATURE:
<221> NAME/KEY: MISC_FEATURE
<222> LOCATION: (43)..(43)
<223> OTHER INFORMATION: Xaa is E, G, H, I, K, L, N, R, S, T, V, W or Y
<220> FEATURE:
<221> NAME/KEY: MISC_FEATURE
<222> LOCATION: (44)..(44)
<223> OTHER INFORMATION: Xaa is F, H, K, L, T, V, W or Y
<220> FEATURE:
<221> NAME/KEY: MISC_FEATURE
<222> LOCATION: (45)..(45)
<223> OTHER INFORMATION: Xaa is I, K, L, M, R, S, T, V or W
<220> FEATURE:
<221> NAME/KEY: MISC_FEATURE
<222> LOCATION: (46)..(46)
<223> OTHER INFORMATION: Xaa is A, D, E, G, I, K, L, M, N, Q, S, T, V
      or W
<220> FEATURE:
<221> NAME/KEY: MISC_FEATURE
<222> LOCATION: (47)..(47)
<223> OTHER INFORMATION: Xaa is D, F, H, I, K, M, R, S, T, V or Y
<220> FEATURE:
<221> NAME/KEY: MISC_FEATURE
<222> LOCATION: (48)..(48)
<223> OTHER INFORMATION: Xaa is A, C, E, F, G, H, I, K, L, M, R, S, T,
      V, W or Y
<220> FEATURE:
<221> NAME/KEY: MISC_FEATURE
<222> LOCATION: (49)..(49)
<223> OTHER INFORMATION: Xaa is I, K, M, N, P, Q, R or W
<220> FEATURE:
<221> NAME/KEY: MISC_FEATURE
<222> LOCATION: (50)..(50)
<223> OTHER INFORMATION: Xaa is D, I, N, P, S or T
<220> FEATURE:
<221> NAME/KEY: MISC_FEATURE
<222> LOCATION: (51)..(51)
<223> OTHER INFORMATION: Xaa is A, F, G, H, I, K, L, M, Q, R, S, T or W
<220> FEATURE:
<221> NAME/KEY: MISC_FEATURE
<222> LOCATION: (52)..(52)
<223> OTHER INFORMATION: Xaa is A, F, L, M, R, V, W or Y
<220> FEATURE:
<221> NAME/KEY: MISC_FEATURE
<222> LOCATION: (53)..(53)
<223> OTHER INFORMATION: Xaa is A, E, F, G, H, I, M, N, Q, T, V, W or Y
<220> FEATURE:
<221> NAME/KEY: MISC_FEATURE
<222> LOCATION: (54)..(54)
<223> OTHER INFORMATION: Xaa is A, G, H, I, L, M, N, P, S, T or V
<220> FEATURE:
<221> NAME/KEY: MISC_FEATURE
<222> LOCATION: (55)..(55)
<223> OTHER INFORMATION: Xaa is A, C, F, G, M, P, T, W or Y
<220> FEATURE:
<221> NAME/KEY: MISC_FEATURE
<222> LOCATION: (56)..(56)
<223> OTHER INFORMATION: Xaa is A, F, I, K, L, M or V
<220> FEATURE:
<221> NAME/KEY: MISC_FEATURE
<222> LOCATION: (57)..(57)
<223> OTHER INFORMATION: Xaa is K, L, W or Y
<220> FEATURE:
<221> NAME/KEY: MISC_FEATURE
<222> LOCATION: (58)..(58)
<223> OTHER INFORMATION: Xaa is A, G, K, M, Q, R, S, V or W
<220> FEATURE:
<221> NAME/KEY: MISC_FEATURE
<222> LOCATION: (59)..(59)
<223> OTHER INFORMATION: Xaa is A, D, I, L, M, T, V or W
<220> FEATURE:
<221> NAME/KEY: MISC_FEATURE
<222> LOCATION: (60)..(60)
<223> OTHER INFORMATION: Xaa is A, D, E, F, G, H, I, L, M, P, S, T, V,
      W or Y
<220> FEATURE:
<221> NAME/KEY: MISC_FEATURE
```

```
<222> LOCATION: (61)..(61)
<223> OTHER INFORMATION: Xaa is F, G, N or Q
<220> FEATURE:
<221> NAME/KEY: MISC_FEATURE
<222> LOCATION: (62)..(62)
<223> OTHER INFORMATION: Xaa is C, N or Y
<220> FEATURE:
<221> NAME/KEY: MISC_FEATURE
<222> LOCATION: (63)..(63)
<223> OTHER INFORMATION: Xaa is A, C, F, H, I, K, L, M, P, T, V, W or Y
<220> FEATURE:
<221> NAME/KEY: MISC_FEATURE
<222> LOCATION: (64)..(64)
<223> OTHER INFORMATION: Xaa is E, F, L or M
<220> FEATURE:
<221> NAME/KEY: MISC_FEATURE
<222> LOCATION: (65)..(65)
<223> OTHER INFORMATION: Xaa is D, F, H, M, N or W
<220> FEATURE:
<221> NAME/KEY: MISC_FEATURE
<222> LOCATION: (66)..(66)
<223> OTHER INFORMATION: Xaa is A, G, S or W
<220> FEATURE:
<221> NAME/KEY: MISC_FEATURE
<222> LOCATION: (67)..(67)
<223> OTHER INFORMATION: Xaa is F, K, L, V, W or Y
<220> FEATURE:
<221> NAME/KEY: MISC_FEATURE
<222> LOCATION: (68)..(68)
<223> OTHER INFORMATION: Xaa is K, L, M or W
<220> FEATURE:
<221> NAME/KEY: MISC_FEATURE
<222> LOCATION: (69)..(69)
<223> OTHER INFORMATION: Xaa is F, H, I, K, Q, R, T or Y
<220> FEATURE:
<221> NAME/KEY: MISC_FEATURE
<222> LOCATION: (70)..(70)
<223> OTHER INFORMATION: Xaa is A, F, G, I, L or M
<220> FEATURE:
<221> NAME/KEY: MISC_FEATURE
<222> LOCATION: (71)..(71)
<223> OTHER INFORMATION: Xaa is Q or R
<220> FEATURE:
<221> NAME/KEY: MISC_FEATURE
<222> LOCATION: (72)..(72)
<223> OTHER INFORMATION: Xaa is Q or R
<220> FEATURE:
<221> NAME/KEY: MISC_FEATURE
<222> LOCATION: (73)..(73)
<223> OTHER INFORMATION: Xaa is A, K, L or M
<220> FEATURE:
<221> NAME/KEY: MISC_FEATURE
<222> LOCATION: (74)..(74)
<223> OTHER INFORMATION: Xaa is F, G, H, K, L, R, V, W or Y
<220> FEATURE:
<221> NAME/KEY: MISC_FEATURE
<222> LOCATION: (75)..(75)
<223> OTHER INFORMATION: Xaa is I, K, M, N or R
<220> FEATURE:
<221> NAME/KEY: MISC_FEATURE
<222> LOCATION: (76)..(76)
<223> OTHER INFORMATION: Xaa is A, D, F, G, H, I, K, L, M, N, Q, R, V,
      W or Y
<220> FEATURE:
<221> NAME/KEY: MISC_FEATURE
<222> LOCATION: (77)..(77)
<223> OTHER INFORMATION: Xaa is F, G, Q, R or S
<220> FEATURE:
<221> NAME/KEY: MISC_FEATURE
<222> LOCATION: (78)..(78)
<223> OTHER INFORMATION: Xaa is E, G, H, L, M, N, P, Q, T, V or Y
<220> FEATURE:
<221> NAME/KEY: MISC_FEATURE
<222> LOCATION: (79)..(79)
<223> OTHER INFORMATION: Xaa is A, I, L, M, S, T, V, W or Y
<220> FEATURE:
<221> NAME/KEY: MISC_FEATURE
<222> LOCATION: (80)..(80)
<223> OTHER INFORMATION: Xaa is E, G, M, N, S or T
```

```
<220> FEATURE:
<221> NAME/KEY: MISC_FEATURE
<222> LOCATION: (81)..(81)
<223> OTHER INFORMATION: Xaa is A, D, E, F, G, H, I, K, L, M, N, P, Q,
      R, S, T, V, W or Y
<220> FEATURE:
<221> NAME/KEY: MISC_FEATURE
<222> LOCATION: (82)..(82)
<223> OTHER INFORMATION: Xaa is D, E, F, G, I, K, L, N, P, Q, R, S, W
      or Y
<220> FEATURE:
<221> NAME/KEY: MISC_FEATURE
<222> LOCATION: (83)..(83)
<223> OTHER INFORMATION: Xaa is A, D, E, G, P, Q or W
<220> FEATURE:
<221> NAME/KEY: MISC_FEATURE
<222> LOCATION: (84)..(84)
<223> OTHER INFORMATION: Xaa is A, F, G, H, I, K, L, V or Y
<220> FEATURE:
<221> NAME/KEY: MISC_FEATURE
<222> LOCATION: (85)..(85)
<223> OTHER INFORMATION: Xaa is A, D, E, F, G, H, I, K, L, M, N, P, Q,
      R, S, T, V, W or Y
<220> FEATURE:
<221> NAME/KEY: MISC_FEATURE
<222> LOCATION: (86)..(86)
<223> OTHER INFORMATION: Xaa is A, D, E, F, G, H, R, S, T, V, W or Y
<220> FEATURE:
<221> NAME/KEY: MISC_FEATURE
<222> LOCATION: (87)..(87)
<223> OTHER INFORMATION: Xaa is F, H, I, K, L, M, Q or V
<220> FEATURE:
<221> NAME/KEY: MISC_FEATURE
<222> LOCATION: (88)..(88)
<223> OTHER INFORMATION: Xaa is A, H, N, P, R, S or W
<220> FEATURE:
<221> NAME/KEY: MISC_FEATURE
<222> LOCATION: (89)..(89)
<223> OTHER INFORMATION: Xaa is H, L, Q, R, V or Y
<220> FEATURE:
<221> NAME/KEY: MISC_FEATURE
<222> LOCATION: (90)..(90)
<223> OTHER INFORMATION: Xaa is A, D, G, L, P, Q, R or Y
<220> FEATURE:
<221> NAME/KEY: MISC_FEATURE
<222> LOCATION: (91)..(91)
<223> OTHER INFORMATION: Xaa is C, F, H, I, K, L, P, R, T, V or Y
<220> FEATURE:
<221> NAME/KEY: MISC_FEATURE
<222> LOCATION: (92)..(92)
<223> OTHER INFORMATION: Xaa is C, F, G, I, K, L, M, N, P, Q, S, T, V,
      W or Y
<220> FEATURE:
<221> NAME/KEY: MISC_FEATURE
<222> LOCATION: (93)..(93)
<223> OTHER INFORMATION: Xaa is A, D, E, F, G, H, I, K, L, M, N, Q, R,
      S, T, V, W or Y
<220> FEATURE:
<221> NAME/KEY: MISC_FEATURE
<222> LOCATION: (94)..(94)
<223> OTHER INFORMATION: Xaa is A, C, D, E, G, I, K, L, M, N, Q, R, S,
      T, V or Y
<220> FEATURE:
<221> NAME/KEY: MISC_FEATURE
<222> LOCATION: (95)..(95)
<223> OTHER INFORMATION: Xaa is A, C, D, F, H, I, L, M, P, T, V, W or Y
<220> FEATURE:
<221> NAME/KEY: MISC_FEATURE
<222> LOCATION: (96)..(96)
<223> OTHER INFORMATION: Xaa is H, I, K, N, P, Q, R, T or V
<220> FEATURE:
<221> NAME/KEY: MISC_FEATURE
<222> LOCATION: (97)..(97)
<223> OTHER INFORMATION: Xaa is C, D, E, G, L, M, P, R, S or V
<220> FEATURE:
<221> NAME/KEY: MISC_FEATURE
<222> LOCATION: (98)..(98)
<223> OTHER INFORMATION: Xaa is A, C, F, G, I, K, L, Q, T, V or W
<220> FEATURE:
```

```
<221> NAME/KEY: MISC_FEATURE
<222> LOCATION: (99)..(99)
<223> OTHER INFORMATION: Xaa is E, F, G, I, L, M or W
<220> FEATURE:
<221> NAME/KEY: MISC_FEATURE
<222> LOCATION: (100)..(100)
<223> OTHER INFORMATION: Xaa is A, E, G, H, K, P, Q, R or V
<220> FEATURE:
<221> NAME/KEY: MISC_FEATURE
<222> LOCATION: (101)..(101)
<223> OTHER INFORMATION: Xaa is A, D, E, G, H, I, K, P, R, S or V
<220> FEATURE:
<221> NAME/KEY: MISC_FEATURE
<222> LOCATION: (102)..(102)
<223> OTHER INFORMATION: Xaa is A, C, F, I, L, M, T, V or Y
<220> FEATURE:
<221> NAME/KEY: MISC_FEATURE
<222> LOCATION: (103)..(103)
<223> OTHER INFORMATION: Xaa is I, K or R
<220> FEATURE:
<221> NAME/KEY: MISC_FEATURE
<222> LOCATION: (104)..(104)
<223> OTHER INFORMATION: Xaa is A, C, D, E, F, G, H, I, K, L, M, N, P,
     Q, R, S, V, W or Y
<220> FEATURE:
<221> NAME/KEY: MISC_FEATURE
<222> LOCATION: (105)..(105)
<223> OTHER INFORMATION: Xaa is C, F, H, I, M, R, S, W or Y
<220> FEATURE:
<221> NAME/KEY: MISC_FEATURE
<222> LOCATION: (106)..(106)
<223> OTHER INFORMATION: Xaa is A, E, H, K, L, M, R or V
<220> FEATURE:
<221> NAME/KEY: MISC_FEATURE
<222> LOCATION: (107)..(107)
<223> OTHER INFORMATION: Xaa is A, E, F, G, I, K, L, M, N, Q, R, S, V
     or Y
<220> FEATURE:
<221> NAME/KEY: MISC_FEATURE
<222> LOCATION: (108)..(108)
<223> OTHER INFORMATION: Xaa is A, D, E, G, I, K, L, Q, R or T
<220> FEATURE:
<221> NAME/KEY: MISC_FEATURE
<222> LOCATION: (109)..(109)
<223> OTHER INFORMATION: Xaa is C, E, F, H, L, N, R, V or Y
<220> FEATURE:
<221> NAME/KEY: MISC_FEATURE
<222> LOCATION: (110)..(110)
<223> OTHER INFORMATION: Xaa is A, D, E, F, G, H, I, K, L, M, N, P, R,
     S, T, V, W or Y
<220> FEATURE:
<221> NAME/KEY: MISC_FEATURE
<222> LOCATION: (111)..(111)
<223> OTHER INFORMATION: Xaa is D, I, L, R, S, V, W or Y
<220> FEATURE:
<221> NAME/KEY: MISC_FEATURE
<222> LOCATION: (112)..(112)
<223> OTHER INFORMATION: Xaa is A, C, D, G, H, I, K, L or V
<220> FEATURE:
<221> NAME/KEY: MISC_FEATURE
<222> LOCATION: (113)..(113)
<223> OTHER INFORMATION: Xaa is C, E, F, K, L, Q, R, T or V
<220> FEATURE:
<221> NAME/KEY: MISC_FEATURE
<222> LOCATION: (114)..(114)
<223> OTHER INFORMATION: Xaa is A, D, E, G, I, K, L, M, N, P, Q, R, S,
     T, V, W or Y
<220> FEATURE:
<221> NAME/KEY: MISC_FEATURE
<222> LOCATION: (115)..(115)
<223> OTHER INFORMATION: Xaa is A, D, G, I, L, M, P, R, T, W or Y

<400> SEQUENCE: 276

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
         20                  25                  30
```

```
Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa
        115

<210> SEQ ID NO 277
<211> LENGTH: 20
<212> TYPE: PRT
<213> ORGANISM: Artificial Sequence
<220> FEATURE:
<223> OTHER INFORMATION: Synthetic

<400> SEQUENCE: 277

Lys Glu Lys Tyr Ile Ala Ala Met Leu Arg Ala Ile Gly Asp Ile Phe
1               5                   10                  15

Asn Ala Ile Met
            20
```

US 9,750,814 B2

POLYPEPTIDES TO INHIBIT EPSTEIN BARR VIRAL PROTEIN BHRF1 AND B CELL LYMPHOMA FAMILY PROTEINS

CROSS REFERENCE

This application claims priority to U.S. Provisional Patent Application Ser. No. 62/232,936 filed Sep. 25, 2015, and is a continuation in part of PCT application PCT/US2015/020155 filed Mar. 12, 2015, which claims priority to U.S. Provisional Patent Application Ser. No. 61/951,988 filed Mar. 12, 2014, each incorporated by reference herein in its entirety.

FEDERAL FUNDING STATEMENT

This invention was made with U.S. government support under P41 GM103533 awarded by the National Institutes of Health, under HDTRA1-10-1-0040 awarded by the Defense Threat Reduction Agency, and under DGE-1256082 awarded by the National Science Foundation. The U.S. Government has certain rights in the invention.

BACKGROUND

Following virus infection, cells may undergo apoptosis to prevent further virus spread in the host. This has spurred viruses to evolve counteracting mechanisms to prevent host cell death, and during latent infection these factors may contribute to the development of cancer. This includes multiple cancers associated with Epstein-Barr virus (EBV), in particular Burkitt's lymphoma (BL).

Apoptosis and cell survival are regulated by the homeostatic balance of B cell lymphoma-2 (Bcl-2) family proteins (reviewed in (Martinou and Youle, 2011)), which fall in to three classes. The 'executioners', Bak and Bax, initiate apoptosis by increasing mitochondrial outer membrane permeability and facilitating the release of mitochondrial cytochrome c to the cytosol, which activates downstream signaling. Six human pro-survival Bcl-2 proteins (Bcl-2, Bcl-$X_L$, Bcl-B, Mcl-1, Bcl-w and Bfl-1) inhibit this process. Counterbalancing these are numerous pro-apoptotic BH3-only proteins (BOPs), including Bim. These factors share an approximately 26 residue Bcl-2 homology 3 (BH3) motif, an amphipathic α-helical element which binds a hydrophobic groove on the surface of the canonical Bcl-2 fold. Cellular stresses activate pro-apoptotic BOPs, which bind and inhibit pro-survival Bcl-2 members, and directly interact with Bak and Bax to favor mitochondrial permeabilization. Conversely, pro-survival Bcl-2 proteins dampen apoptotic triggers and enhance chemoresistance by sequestering BOPs or directly inhibiting Bak and Bax. Increased expression of pro-survival Bcl-2 proteins is a common feature of many cancers.

Epstein-Barr virus encodes a pro-survival Bcl-2 homologue, BHRF1, which prevents lymphocyte apoptosis during initial infection by sequestering pro-apoptotic BOPs (especially Bim), and interacting directly with the executioner Bak (Desbien et al., 2009; Kvansakul et al., 2010) (Altmann and Hammerschmidt, 2005) (Henderson et al., 1993). Even though BHRF1 is under the control of an early lytic cycle promoter, low levels of constitutive expression have been observed in some cases of EBV-positive BL when the virus is latent, and it has been speculated that BHRF1 may be a necessary viral factor for lymphomagenesis (Kelly et al., 2009; Leao et al., 2007; Watanabe et al., 2010).

SUMMARY OF THE INVENTION

In a first aspect, the invention provides polypeptides comprising an amino acid sequence having at least 50% amino acid sequence identity over its length relative to the amino acid sequence of SEQ ID NO.:1, wherein the polypeptide selectively binds to a protein selected from the group consisting of Epstein Barr protein BHFR1, and B cell lymphoma family proteins selected from the group consisting of myeloid cell leukemia 1 (Mcl-1), B-cell lymphoma 2 (Bcl-2), Bcl-2-like protein 1 (BCL2L1/Bcl-XL), Bcl-2-like protein 10 (BCL2L10/Bcl-B), Bcl-2-like protein A1 (A1/Bfl-1), and Bcl-2-like protein 2 (BCL2L2/Bcl-w). In one embodiment, the polypeptide comprises an amino acid sequence having at least 50% amino acid sequence identity over its length relative to the amino acid sequence selected from the group consisting of SEQ ID NOS:2-6 and 265. In various further embodiments, the polypeptide comprises an amino acid sequence selected from the group consisting of SEQ ID NOS: 7-13 and 276, wherein the polypeptide binds to a specific target. In a further embodiment, the polypeptides further comprise a cell-penetrating peptide and/or an antibody or antibody fragment.

In another aspect, the invention provides pharmaceutical composition, comprising a polypeptide of the invention and a pharmaceutically acceptable carrier. In one embodiment, the pharmaceutical composition further comprises an antibody. In another embodiment, the carrier comprises a polymer, such as a polymer comprising a hydrophilic block and an endosomolytic block, or a stimuli-responsive polymer.

In various further embodiments, the invention provides recombinant nucleic acids encoding a polypeptide of the invention, recombinant expression vectors comprising the nucleic acid of the invention operatively linked to a promoter, and recombinant host cells comprising the recombinant expression vectors of the invention.

In another aspect, the invention provides methods for treating an Epstein-Barr virus-related diseases comprising administering to a subject in need thereof a therapeutically effective amount of one or more of the polypeptides of the invention, or salts thereof, pharmaceutical compositions thereof, a recombinant nucleic acid encoding the one or more polypeptides, a recombinant expression vector comprising the recombinant nucleic acids, and/or a recombinant host cells comprising the recombinant expression vector, to treat Epstein-Barr virus related diseases wherein the polypeptide or encoded polypeptide selectively inhibits BHRF1.

In further aspect, the invention provides methods for treating cancer, comprising administering to a subject in need thereof a therapeutically effective amount of one or more of the polypeptides of the invention, salts thereof, a pharmaceutical composition thereof, a recombinant nucleic acid encoding the one or more polypeptides, a recombinant expression vector comprising the recombinant nucleic acid, and/or a recombinant host cell comprising the recombinant expression vector, to treat cancer, wherein the polypeptide or encoded polypeptide selectively inhibits one or more of Mcl-1, Bcl-2, BCL2L1/Bcl-XL, BCL2L10/Bcl-B, A1/Bfl-1, and BCL2L2/Bcl-w.

In another aspect, the invention provides methods for determining the Bcl-2 phenotype of a tumor, comprising contacting tumor cells, tumor cell lysates or tumor cellular components with one or more polypeptides selected from the group consisting of SEQ ID NOS: 1-6, 8-12, 262-273, or 276, under conditions suitable to promote apoptosis signaling in cells of the tumor that express a BCL2 homolog targeted by the one or more polypeptides; and determining Bcl-2 dependency of the tumor based on the polypeptide that causes apoptosis or apoptotic signaling in the cells of the tumor.

DETAILED DESCRIPTION OF THE INVENTION

Figure 1:
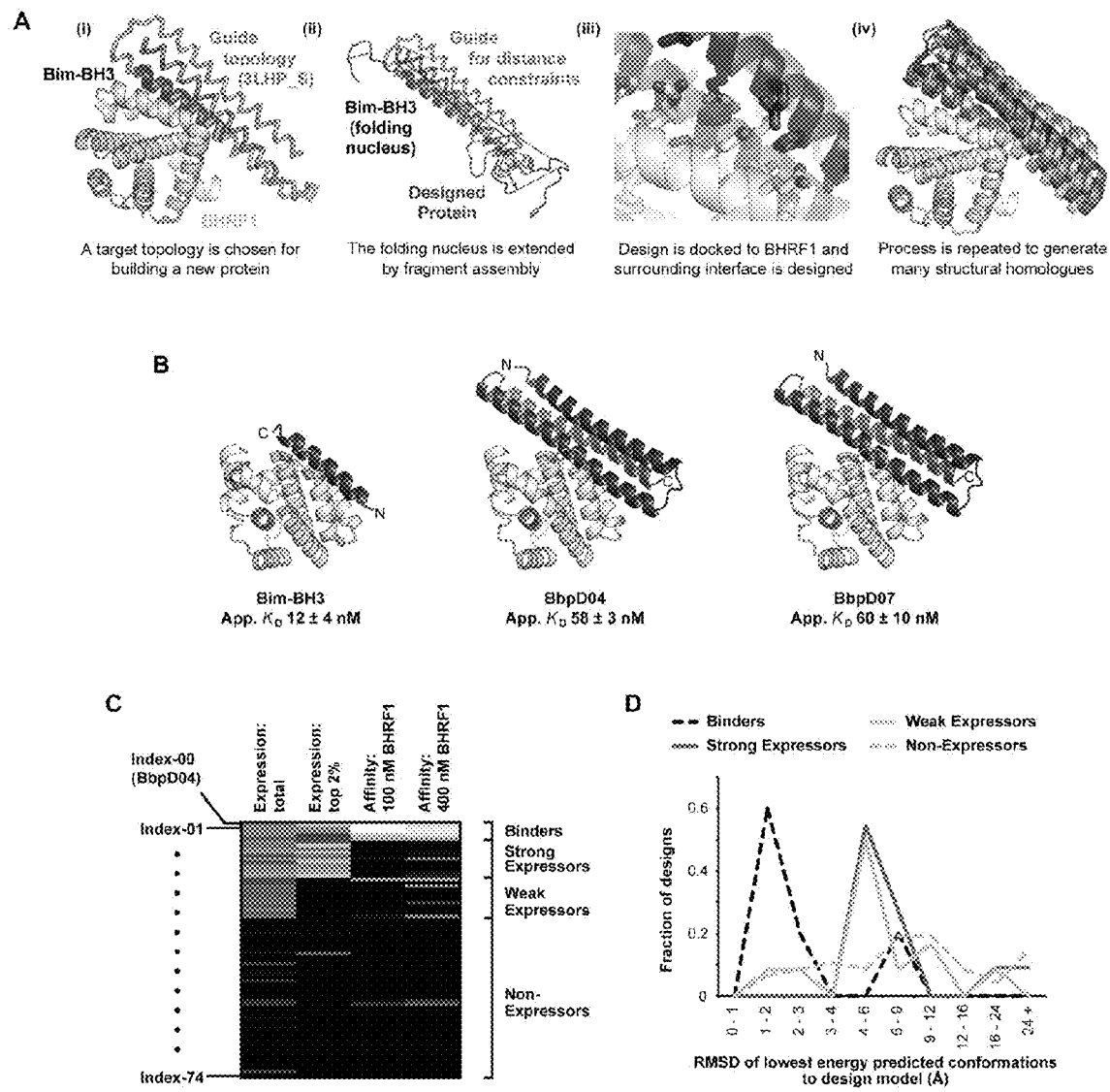
FIG. 1. De novo protein assembly protocol. (A) A scaffold (grey ribbon) is aligned to the Bim-BH3 motif (black) bound to BHRF1 (white) (i). The Bim-BH3 peptide is extended on both ends and a new protein structure (black tube) is built using fragment-based assembly (ii), followed by rounds of minimization and sequence design. The newly assembled protein is docked to BHRF1 and the surrounding interface is designed (iii). Many designs are generated that are filtered by multiple criteria (iv). (B) Computational models of designed proteins BbpD04 and BbpD07 (black) that bind BHRF1 (white). Apparent affinities (m NiNTA-agarose and analyzed on a Coomassie-stained SDS-polyacrylamide electrophoretic gel. An arrow indicates the expected MW of the designed proteins at 15 kD. (E) CD spectra of BbpD04 and its variants (10 μM in PBS) were collected at 25° C. in the presence of guanidinium hydrochloride. The fraction of protein folded was monitored by the change in CD signal at 222 nm. (F-H) BbpD04 and its variants were digested with proteases of different substrate specificities: trypsin (F), chymotrypsin (G) and elastase (H). Shown is mean±range for 3 repeats. Also see FIG. 7H. (I) Summary of all mutations made to BbpD04 during affinity maturation.

Within this application, unless otherwise stated, the techniques utilized may be found in any of several well-known references such as: Molecular Cloning: A Laboratory Manual (Sambrook, et al, 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2$^{nd}$ Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), and the Ambion 1998 Catalog (Ambion, Austin, Tex.)

As used herein and unless otherwise indicated, the terms "a" and "an" are taken to mean "one", "at least one" or "one or more". Unless otherwise required by context, singular terms used herein shall include pluralities and plural terms shall include the singular.

All scientific and technical terms used in this application have meanings commonly used in the art unless otherwise specified.

All embodiments of any aspect of the invention can be used in combination, unless the context clearly dictates otherwise.

In a first aspect, the present invention provides polypeptides comprising or consisting of an amino acid sequence having at least 50% amino acid sequence identity over their length relative to the amino acid sequence of SEQ ID NO.: 1, wherein the polypeptide selectively binds to a protein selected from the group consisting of Epstein Barr protein BHFR1, and B cell lymphoma family proteins selected from the group consisting of myeloid cell leukemia 1 (Mcl-1), B-cell lymphoma 2 (Bcl-2), Bcl-2-like protein 1 (BCL2L1/Bcl-XL), Bcl-2-like protein 10 (BCL2L10/Bcl-B), Bcl-2-like protein A1 (A1/Bfl-1), and Bcl-w.

```
                                             SEQ ID NO: 1
ADPKKVLDKAKDQAENRVRELKQKLEELYKEARKLDLTQEMRRKLELR

YIAAMLMAIGDIYNAIRQAKQEADKLKKAGLVNSQQLDELKRRLEELK

EEASRKARDYGREFQLKLEY (BINDI; Target: BHFR1)
```

The polypeptides of the invention are high-affinity (as low as picomolar affinity), specific protein inhibitors of BHRF1 and B cell lymphoma (BCL) family proteins. And can be used, for example, in methods of treating cancer and Epstein-Barr virus-related diseases. Rather than repurposing an existing natural protein of known structure, the polypeptides of the invention were designed de novo for optimum BHRF1 or and BCL family protein interactions, and are shown herein to trigger apoptosis in relevant cancer lines and slow BL progression in an animal model in the examples herein. This work therefore represents a major bioengineering accomplishment; the creation of an entirely new class of designer polypeptides and their demonstrated therapeutic potential from the ground up.

The polypeptides of the invention have at least 50% amino acid sequence identity over their length relative to the amino acid sequence of SEQ ID NO.: 1, which was designed as shown in the examples that follow to selectively and at very high affinity bind to Epstein Barr protein BHFR1. The inventors have carried out saturation mutagenesis on the polypeptide of SEQ ID NO:1 to identify modifiable residues. Furthermore, the inventors have demonstrated that polypeptides of the invention can be modified for selective binding against BCL family proteins. In various embodiments, the polypeptides of the invention have at least 55%, 60%, 66%, 70%, 75%, 80%, 85%, 90%, 95%, 98%, or 100% identity over their length relative to the amino acid sequence of SEQ ID NO:1. As will be understood by those of skill in the art, the polypeptides may include additional residues at the N-terminus, C-terminus, or both that are not present in SEQ ID NO:1; these additional residues are not included in determining the percent identity of the polypeptides of the invention relative to the reference polypeptide (i.e.: SEQ ID NO:1 in this case).

The polypeptides selectively bind to a protein selected from the group consisting of Epstein Barr protein BHFR1, and B cell lymphoma family proteins selected from the group consisting of myeloid cell leukemia 1 (Mcl-1), B-cell lymphoma 2 (Bcl-2), Bcl-2-like protein 1 (BCL2L1/Bcl-XL), Bcl-2-like protein 10 (BCL2L10/Bcl-B), Bcl-2-like protein A1 (A1/Bfl-1), and Bcl-w. As used herein, "selectively binds" or "specifically binds" refers to the ability of a polypeptide of the invention to bind to its target, such as a BHRF1 molecule or BCL family member, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Selective binding can be influenced by, for example, the affinity and avidity of the polypeptide agent and the concentration of polypeptide agent. The person of ordinary skill in the art can determine appropriate conditions under which the polypeptides described herein selectively bind the targets using any suitable methods, such as titration of a polypeptide agent in a suitable cell binding assay, or as described in the examples that follow. A polypeptide specifically bound to a target is not displaced by a non-similar competitor. In certain embodiments, a polypeptide is said to selectively bind an antigen when it preferentially recognizes its target antigen in a complex mixture of proteins and/or macromolecules.

In one embodiment, the polypeptide comprises or consists of an amino acid sequence having at least 50% amino acid sequence identity over its length relative to the amino acid sequence selected from the group consisting of SEQ ID NOS:2-6 and 265.

```
                                             SEQ ID NO: 2
ADPKKVLDKAKDQAENRVRELKQVLEELYKEARKLDLTQEMRKKLIERY

AAAIIRAIGDINNAIYQAKQEAEKLKKAGLVNSQQLDELLRRLDELQKE

ASRKANEYGREFELKLEY
(MINDI, also referred to as αMCL1; Target: Mcl-1)

SEQ ID NO: 3
ADPKKVLDKAKDEAENRVRELKQRLEELYKEARKLDLTQEMRQELVDKA

RAASLQANGDIFYAILRALAEAEKLKKAGLVNSQQLDELKRRLEELAEE

ARRKAEKLRDEFRLKLEY
(2-INDI,, also referred to as αBCL2; Target:
Bcl-2)

SEQ ID NO: 4
ADPKKVLDKAKDRAENVVRKLKKELEELYKEARKLDLTQEMRDRIRRT

AIAARFQAHGDIFHAIKHAKEEARKLKKAGLVNSQQLDELKRRLRELDE

EAEQRAEKLGKEFRLKLEY
(XINDI, also referred to as αBCLXL; Target:
BCL2L1/Bcl-XL)

SEQ ID NO: 5
ADPKKILDKAKDQVENRVRELKQELERLYKEARKLDLTQEMRRKLHVR

YIEAMLKAIAAIMNAIAQAENEADKLKKAGLVNSQQLDELRRRLEELTE

EAAQKAHDYGRELQLKLEY
```

(10-INDI, also referred to as αBCLB; Target:
BCL2L10/Bcl-B)

```
                                        SEQ ID NO: 6
ADPKKVLDKAKDQAENRVRELKQKLEELYKEARKLDLTQEKRKKLEVA

TLGAVLAAHGDILNAIMQAKEEADKLKKAGLVNSQQLDELKRRLEELKE

EALRKASDYGNEFHLKRRY
```
(FINDI, also referred to as αBFL1;
Target: A1/Bfl-1)

```
                                      SEQ ID NO: 265
DPKKVFDELKDRAENNVRRLKQKLEELYKEARKKDLTQEEREKLKTKYK

TAMQLAALAAEGDIMNALLKARKLHKNGQVNEQQLEELARRLMELAKEA

FQKAKDYANEFKYKLEY
```
(WINDI, also referred to as αBCLW, previously W-ECM01)

The polypeptide of each of SEQ ID NOS:2-6 and 262-273 shares very high levels of sequence identity with BIND1 (SEQ ID NO:1), but were designed by the inventors as selective inhibitors of different BCL-family members, as described in detail in the examples that follow. These differing specificities allow use of the polypeptides in methods to treat cancer with different Bcl phenotypes, as well as to determine the Bcl-2 phenotype of a tumor. The BCL-family member target for each of SEQ ID NOS: 2-6 and 262-273 are provided above. The amino acid sequence of the respective targets for each of SEQ ID NOS:1-6 and 262-273 are shown below:

BHRF1 (Target for SEQ ID NO: 1)
```
                                       (SEQ ID NO: 67)
AYSTREILLALCIRDSRVHGNGTLHPVLELAARETPLRLSPEDTVVLRY

HVLLEEIIERNSETFTETWNRFITHTEHVDLDFNSVFLEIFHRGDPSLG

RALAWMAWCMHACRTLCCNQSTPYYVVDLSVRGMLEASEGLDGWIHQQG

GWSTLIEDNIPGS
```

Mcl-1 (Target for SEQ ID NO: 1)
```
                                       (SEQ ID NO: 68)
GSDELYRQSLEIISRYLREQATGAKDTKPMGRSGATSRKALETLRRVGD

GVQRNHETAFQGMLRKLDIKNEDDVKSLSRVMIHVFSDGVTNWGRIVTL

ISFGAFVAKHLKTINQESCIEPLAESITDVLVRTKRDWLVKQRGWDGFV

EFFHVEDLEGG
```

Bcl-2 (Target for SEQ ID NO: 3)
```
                                       (SEQ ID NO: 69)
AHAGRTGYDNREIVMKYIHYKLSQRGYEWDAGDVGAAPPGAAPAPGIFS

SQPGHTPHPAASRDPVARTSPLQTPAAPGAAAGPALSPVPPVVHLTLRQ

AGDDFSRRYRRDFAEMSSQLHLTPFTARGRFATVVEELFRDGVNWGRIV

AFFEFGGVMCVESVNREMSPLVDNIALWMTEYLNRHLHTWIQDNGGWDA

FVELYGPSMR
```

Bcl-XL (Target for SEQ ID NO: 4)
```
                                       (SEQ ID NO: 70)
SQSNRELVVDFLSYKLSQKGYSWSQFSDVEENRTEAPEGTESEMETPSA

INGNPSWHLADSPAVNGATGHSSSLDAREVIPMAAVKQALREAGDEFEL

RYRRAFSDLTSQLHITPGTAYQSFEQVVNELFRDGVNWGRIVAFFSFGG

ALCVESVDKEMQVLVSRIAAWMATYLNDHLEPWIQENGGWDTFVELYGN

NAAAESRK
```

Bcl-B (Target for SEQ ID NO: 5)
```
                                       (SEQ ID NO: 71)
ADPLRERTELLLADYLGYCAREPGTPEPAPSTPEAAVLRSAAARLRQIH

RSFFSAYLGYPGNRFELVALMADSVLSDSPGPTWGRVVTLVTFAGTLLE

RGPLVTARWKKWGFQPRLKEQEGDVARDCQRLVALLSSRLMGQHRAWLQ

AQGGWDGFCHFFRTPFP
```

Bfl-1 (Target for SEQ ID NO: 6)
```
                                       (SEQ ID NO: 72)
TDSEFGYIYRLAQDYLQCVLQIPQPGSGPSKTSRVLQNVAFSVQKEVEK

NLKSCLDNVNVVSVDTARTLFNQVMEKEFEDGIINWGRIVTIFAFEGIL

IKKLLRQQIAPDVDTYKEISYFVAEFIMNNTGEWIRQNGGWENGFVKKF

EPKSG
```

Bcl-w (Target for SEQ ID NOS: 262-273):
Various isoforms of Bcl-w exist. Exemplary embodiments are:

```
                                      (SEQ ID NO: 274)
MATPASAPDTRALVADFVGYKLRQKGYVCGAGPGEGPAADPLHQAMRAA

GDEFETRFRRTFSDLAAQLHVTPGSAQQRFTQVSDELFQGGPNWGRLVA

FFVFGAALCAESVNKEMEPLVGQVQEWMVAYLETQLADWIHSSGGWAEF

TALYGDGALEEARRLREGNWASVRTVLTGAVALGALVTVGAFFASK (SEQ ID NO: 275)
MATPASAPDTRALVADFVGYKLRQKGYVCGAGPGEGPAADPLHQAMRAA

GDEFETRFRRTFSDLAAQLHVTPGSAQQRFTQVSDELFQGGPNWGRLVA

FFVFGAALCAESVNKEMEPLVGQVQEWMVAYLETQLADWIHSSGGWELE

AIKARVREMEEEAEKLKELQNEVEKQMNMSPPPGNAGPVIMSIEEKMEA

DARSIYVGNVDYGATAEELEAHFHGCGSVNRVTILCDKFSGHPKGFAYI

EFSDKESVRTSLALDESLFRGRQIKVIPKRTNRPGISTTDRGFPRARYR

ARTTNYNSSRSRFYSGFNSRPRGRVYRGRARATSWYSPY
```

The inventors have carried out saturation mutagenesis on the polypeptides according to each of SEQ ID NOS:3-6 and 264, while the polypeptide of SEQ ID NO:2 shares 84% identity and 93% similarity to the polypeptide of SEQ ID NO:1, and therefore likely has a similar tolerance for sequence variations, especially at the majority of positions not making interfacial contacts with its target. In various embodiments, the polypeptides of the invention have at least 55%, 60%, 66%, 70%, 75%, 80%, 85%, 90%, 95%, 98%, or 100% identity over their length relative to the amino acid sequence of SEQ ID NO:1-6 and 262-273. As will be understood by those of skill in the art, the polypeptides may include additional residues at the N-terminus, C-terminus, or both that are not present in SEQ ID NOS:1-6 and 262-273; these additional residues are not included in determining the percent identity of the polypeptides of the invention relative to the reference polypeptide (i.e.: SEQ ID NOS:1-6 and 262-273 in this case).

In one embodiment, the polypeptide comprises or consists of an amino acid sequence according to SEQ ID NO: 7, wherein the polypeptide binds to BHFR1.

(SEQ ID NO: 7)
(A/E/G/H/I/K/M/P/R/S/T/V/W/Y) (A/C/D/E/F/G/H/I/K/L/
M/N/P/Q/R/S/T/V/W/Y) (A/C/D/E/F/G/H/K/L/M/N/P/Q/R/
S/T/V/W/Y) (A/E/G/H/I/K/M/N/P/Q/R/T/V/W) (F/G/I/K/L/
Q/R/T/V/W) (A/F/G/I/L/P/S/V/W) (A/D/E/G/I/L/M/Q/R/S/
T/V/W/Y) (A/C/D/F/G/I/K/L/N/P/Q/R/S/V/W/Y) (H/K/L/N/
Q/R/W) (A/H/S/T) (A/D/E/G/H/K/N/Q/R/S/T/Y) (A/D/E/F/
G/H/K/L/M/N/Q/R/S/T/V/W/Y) (D/E/G/I/K/L/M/N/Q/R/S/
T/V/W/Y) (A/C/I/L/M/N/Q/S/T/V) (A/D/E/M/N/R/V/W/Y)
(A/D/F/G/H/I/K/L/M/N/P/Q/R/S/T/V/W/Y) (A/C/E/G/H/I/
K/L/M/P/R/S/T/V) (A/I/K/M/T/V) (A/C/D/E/F/G/K/L/M/N/
Q/R/T/V/W/Y) (A/D/E/F/G/I/K/L/M/N/Q/R/S/T/V/W/Y)
(F/H/I/L/M/Q/T/Y) (A/C/H/I/K/Q/R) (A/C/E/F/G/H/I/M/
N/Q/R/S/T/W/Y) (A/D/G/H/I/K/N/Q/R/T/Y) (I/L/M/Q) (A/
C/D/E/G/I/K/N/Q/R/S/T/V/W) (A/C/D/E/F/G/H/I/K/L/M/
N/Q/R/S/T/V/W/Y) (C/F/H/I/K/L/M/N/P/R/T/V/Y) (A/D/E/
H/I/L/P/Q/R/W/Y) (A/E/F/G/H/K/L/M/N/Q/R/S/T/W/Y) (A/
D/E/F/G/H/I/K/L/M/N/Q/R/S/T/V/W/Y) (A/F/G/H/K/L/N/
P/R/S/T/Y) (F/H/I/K/L/M/P/Q/R/T/V/Y) (C/H/I/K/L/M/Q/
R/S/T/V/Y) (A/D/E/F/G/H/I/K/L/M/N/P/Q/R/S/T/V/W) (A/
C/D/E/G/H/K/L/M/N/Q/R/S/T/V/W/Y) (A/D/E/F/H/I/K/L/
M/N/P/Q/R/S/T/V/W/Y) (A/D/E/G/K/N/P/Q/R/S/T) (A/D/E/
G/K/N/P/Q/R/S/T/V) (A/D/E/F/G/H/I/K/L/M/N/P/Q/R/S/T
/V) (F/G/H/K/M/N/Q/R/T/V/W/Y) (K/R) (R) (K/R) (F/G/I/
L/Q/V/W/Y) (D/E/M/N/Q/T) (F/L/M/W) (R) (E/F/W/Y) (I)
(A/G) (A/F/I/Q) (D/H/L/M/N/W) (I/L) (G/I/M/S/V) (A/C/F/
G/I/L/M/P/S/T/V) (A/I/M/S/T/V) (G) (D) (I/L/M) (F/M/W/
Y) (A/D/F/G/I/L/M/N/Q/S/T/V/W) (A/F/I/L/M/T/V/Y) (A/
H/I/M/Y) (R/Y) (A/F/I/K/L/M/Q/R/V/W/Y) (A/G) (K/Q/R)
(A/F/G/I/K/L/N/Q/R/S/T/V/W/Y) (A/D/E/F/G/H/I/K/L/M/
N/Q/R/S/T/V/W/Y) (A/G/I/M/S) (A/D/E/F/G/H/I/L/M/Q/S/
T/V/W/Y) (F/K/R/Y) (A/F/L/M/R/W/Y) (A/F/H/K/N/R/S/T/
Y) (I/K/N/R/W) (A/F/G/H/I/K/L/M/N/Q/R/S/T/V/W/Y) (A/
D/G/H/Q/R/S/T) (A/K/L/R/T/V/W/Y) (I/L/M/V) (A/D/E/K/
N/Q/R/S/T) (D/E/G/K/M/P/Q/R/S/T/V) (A/D/E/F/H/I/L/N/
Q/R/S/T/V) (D/E/H/M/N/Q/T/Y) (A/F/G/H/L/M/R/T/V/W/Y)
(D/E/F/G/I/K/L/N/Q/S/T/V/W/Y) (A/E/F/I/K/L/M/Q/T/W)
(A/F/I/L/M/T/V) (A/I/K/Q/R/V) (A/G/I/K/L/M/N/Q/R/S/
T/V/W/Y) (A/C/D/E/G/H/K/L/N/Q/R/S/T/V/Y) (I/L) (A/D/
E/H/I/M/N/Q/T) (A/C/D/E/F/G/H/I/K/L/M/N/Q/R/S/T/V/
Y) (A/L/T/V) (K/Q/R) (A/D/E/G/H/Q/S/T/V) (A/D/E/F/H/K/

-continued
M/N/P/Q/R/S/W/Y) (A/S/V) (A/G/N/Q/S/T) (K/R) (K/R) (A/
I/M/N/S/T/V) (D/K/N/R) (A/D/E/F/G/H/K/L/M/N/R/T/V/W/
Y) (A/E/G/H/I/T/Y) (D/G/S) (K/Q/R) (A/D/E/F/G/H/K/L/R/
S/V/W) (F) (D/E/H/M/Q) (A/D/F/I/L/P/Q/R) (K/Q) (A/H/K/
L/M/P/R/S/T/V/Y) (D/E/P/R/T) (D/E/G/H/K/Q/R/T/Y)

(Target: BHRF1)

This embodiment is based on saturation mutagenesis studies described in the examples that follow, in which all residues of SEQ ID NO:1 were tested to identify allowed sequence variability for the designed proteins that retained function (i.e.: BHFR1 binding).

In another embodiment, the polypeptide comprises or consists of an amino acid sequence according to SEQ ID NO: 8, wherein the polypeptide binds to Bcl-2.

(SEQ ID NO: 8)
(A/E/G/P/S/T/V) (A/D/E/G/H/K/N/S/T/V/Y) (A/E/F/I/K/
L/P/Q/R/S/T/V) (E/H/K/N) (D/E/K/M/Q) (D/V) (C/D/L/Y)
(D/L/N/W/Y) (E/K/Q/T/V) (A/C/F/I/L/M/P/S/T/V/W) (F/G/
K/M/N/Q/S) (D/E/H/N/P) (E/F/H/K/R/V) (A/C/D/F/H/I/L/
M/P/W) (E/F/S) (K/N/R/W/Y) (C/K/N/R) (M/P/V) (P/R) (A/C/
E/F/G/H/I/K/L/M/N/R/S/T/V/Y) (F/K/L/M/R/V/Y) (K/N)
(K/P/Q/R/W) (K/R) (F/I/K/L/R/W/Y) (E/M/T) (E/H/I/R/
W) (I/L/N) (C/G/H/Y) (E/K/N) (E/M/R/T/W) (A/F/I/L/M/R/)
T/V/W/Y) (R(K) (E/H/I/L/P/T/Y) (D/E/N/V/Y) (A/E/L/M/V)
(A/I/N/R/T) (H/P/Q) (D/E/V) (M/R) (D/H/P/Q/R/Y) (H/K/Q/
V) (E/L/W) (K/L/M/V) (A/C/D/E/F/G/H/K/L/M/N/R/T/V/W)
(C/D/F/H/I/L/M/V/W/Y) (K) (A/G/H/K/N/Q/R/T/W/Y) (A/D/
E/G/L/M/R/V/W) (A/G) (A/N/R) (D/H/I/K/M/N/R/S/W) (L/N)
(A/K/Q) (A/C/F/H/K/L/M/N/Q/S/V/W/Y) (A/G/H/N/S/Y) (G)
(D/N) (C/E/F/G/I/L/M/N/Q/T) (F) (Y) (A/F/T) (D/I/R) (L/
M) (C/I/K/L/R/V) (A) (G/I/L/M/N/R/W/Y) (A/F/M/W/Y) (E/
S) (A/C/F/L/M/W) (E/F/S/T/W) (K/M) (L) (K/V/W) (I/K) (A/
K) (G) (L/M/S) (A/M/V) (A/K/N/R) (Q/S) (L/Q/R) (C/F/Q/W)
(I/L/T) (A/D/I/L/M/Q/R/V/W/Y) (E) (F/L/Q/V) (K/L) (L/R)
(H/K/L/Q/R) (D/I/K/L/N/R/T/V) (D/E/Q) (E/W) (D/L/N/P/
S) (A/H/I/Q/V) (E) (D/E/F) (A/P/V) (A/C/F/G/K/R/V/Y) (L/
Q/R/V) (K) (A/D/E/F/G/H/I/K/L/M/N/Q/R/S/T/V/W/Y) (A/
D/E/G/P/S) (K/P/Q/S) (A/F/I/L/V/W) (D/G/I/K/M/Q/R/T/
W) (A/D/E/H/K/N/R/V/Y) (C/E/H/K/P/R/W) (C/F/H/Q/R/W)
(H/R) (G/L/N/P/Q/R/S) (H/K/N/P) (A/C/F/I/L/M/P/Q/R/S/
W) (A/C/E/G/H/K/N/Q/R/S/V/Y) (D/F/H/N/S/Y)

(Target: Bcl-2)

This embodiment is based on saturation mutagenesis studies described in the examples that follow, in which all residues of SEQ ID NO:39 were tested to identify allowed sequence variability for the designed proteins that retained function (i.e.: Bcl-2 binding).

In another embodiment, the polypeptide comprises or consists of an amino acid sequence according to SEQ ID NO:9, and wherein the polypeptide binds to binds to Bcl-2-like protein 1.

(SEQ ID NO: 9)

(A/E/G/P/R/S/T/V) (A/D/E/G/H/N/S/V/Y) (A/L/P/Q/R/S/T) (A/E/I/K/N/Q/R/T) (C/K/N/Q/R) (G/I/M/S/V/W/Y) (C/G/I/L) (D/F/H/M/N/S/T/V/Y) (K) (A/E/H/Q/V/W/Y) (C/G/K/Q/R) (D/E/L/M/P/R/S/W/Y) (R/S) (A/D/F/G/H/L/M/N/R/V/Y) (E/R) (C/H/K/N) (A/G/T/V) (K/P/R/V) (H/P/R/Y) (E/K/N/Q/T/W) (F/H/L/R/Y) (K) (G/H/K/M/N/Q/V) (A/C/E/F/G/H/I/K/L/M/N/P/Q/R/S/V/W/Y) (L/P) (A/D/E/G/K/N/P/V/Y) (E/G/I/K/L/M/R/S/V/W) (E/F/G/I/K/L/M/Q/R/S/T/V/Y) (F/H/N/Y) (C/K/N/R) (A/C/D/E/F/G/H/I/K/L/M/N/P/Q/R/S/T/V/W/Y) (A/G/S/T/V) (R) (F/K/N) (L/R/W/Y) (A/C/D/E/H/I/K/L/M/P/Q/R/T/V/W) (A/L/M/N) (K/N/T) (H/I/K/Q/R/S) (E/F/G/H/I/K/M/N/P/R/T/V/W/Y) (F/I/M) (E/R) (A/D/F/G/N/P/R/W) (Q/R/Y) (F/I/K/L/M/N/R/V/W/Y) (R) (L/M/P/R/T) (A/I/K/L/Q/R/S/T/V/Y) (A) (F/I/L/W/Y) (A/E/G/I/L/M/T/V) (A/H/I/K/L/M/N/Q/R/W) (R) (F/I/W/Y) (A/G/K/P/Q/R/W) (A/F/H/I/K/L/M/P/S/T/V/W) (F/H) (A/G) (D) (D/E/F/I/L/Y) (F) (A/C/D/F/G/H/L/R/S/V/W/Y) (A/F/L/S/T/V/W) (A/D/E/G/I/K/L/R/S/W/Y) (H/I/K/L/M/R/T) (A/D/E/G/H/I/K/L/P/Q/R/S/T/V/W/Y) (A/F/N/R/W) (A/D/G/H/I/K/L/M/N/P/R/S/T) (A/D/E/F/G/K/L/M/R/S/T/W/Y) (A/C/E/F/G/I/P/Q/R/S/T/V/W) (A/G/P/R/T) (R) (K) (K/L/M/P/Q/R/V) (K/R) (K) (A/K/T/W) (G/I/K/L/R/S) (E/G/I/K/L/M/R/S) (K/N/V/W) (G/N/W) (K/Q/R/S/Y) (K/Q) (F/K/L/Q/R/W/Y) (C/L/S/Y) (D/E/G/K/R/T) (E/K/R/W/Y) (I/L/M/R) (K/L/N) (R) (L/R) (G/H/L/R/T/V/Y) (A/E/F/G/H/I/K/L/M/Q/R/S/T/V/W/Y) (E) (E/K/L/M/S/Y) (D/F/I/P/S/T/V/Y) (E/L/S) (C/E/H/M/Q/R) (A/G/K/M/Q/T) (A/E/F/H/I/K/L/Q/T/V/Y) (A/D/L/Q/T/W) (R) (A/C/I/K/L/V) (A/E/G/K/Q/V) (A/C/K/L/M/S) (L/Y) (G/W) (K/R/W) (E/N/R/W) (C/F/I/V) (A/D/E/F/G/H/I/K/L/M/N/Q/R/S/T/V/W/Y) (F/L/M/R/T) (K) (K/L/M/P) (A/D/E/G/K/Q/V) (C/D/F/H/L/N/S/Y) (Target:BCL2L1/Bcl-XL)

This embodiment is based on saturation mutagenesis studies described in the examples that follow, in which all residues of SEQ ID NO:44 were tested to identify allowed sequence variability for the designed proteins that retained function (i.e.: BCL2L1/Bcl-XL binding).

In another embodiment, the polypeptide comprises an amino acid sequence according to SEQ ID NO: 10, wherein the polypeptide binds to Bcl-2-like protein 10.

(SEQ ID NO: 10)

(A/D/E/F/M/S/T/V) (A/D/E/G/H/L/M/N/R/S/Y) (C/F/G/L/P/Q/R/S/T/V) (E/G/I/K/N/Q/R/S/T/W) (A/E/F/K/L/N/P/Q/T/W) (A/D/F/I/S/V) (G/L/M/P/Q/T/V) (A/D/E/G/H/N/R/S/T/W/Y) (A/E/F/I/K/L/N/Q/R/T/Y) (A/E) (E/G/K/L/M/N/Q/R/S/T) (A/C/D/E/F/G/H/N/V/Y) (F/G/H/K/P/Q/R/V) (A/C/E/G/L/S/T/V) (A/C/D/E/K/S/W/Y) (D/I/K/N/T) (A/C/F/H/L/M/N/R/S/T/V/Y) (V) (A/C/G/H/K/R/S/T) (A/D/E/G/K/Q/V/W/Y) (L/M/P/T) (A/E/F/I/K/N/Q/T/Y) (A/H/K/N/P/Q/R/V) (A/C/D/E/F/G/H/I/K/L/M/Q/R/T/V/Y) (L/M/P/R) (D/E/F/G/I/K/M/N/R) (C/H/L/R/S) (L/M/N/R) (C/D/H/N/S/Y) (K/M/N/Q/T/W) (A/D/E/F/G/K/L/M/P/Q/T/W) (A/E/G/M/P/S/T) (C/H/I/L/N/R) (D/G/H/K/N/Q/T) (L/M/Q/R) (A/D/H/K/N/Q/R/T/V/Y) (L/M/P/Q/R) (A/G/N/P/T) (F/G/H/K/L/M/P/Q/R/T/W/Y) (A/D/E/G/K/Q) (C/F/I/K/L/M/R/S/V/W) (C/G/H/L/P/R/S) (A/C/D/F/G/H/I/L/N/P/Q/R/V/W/Y) (K) (L) (A/C/D/E/F/G/H/I/L/M/N/P/Q/S/T/V/W/Y) (F/H/I/K/L/M/P/R/T/V/W) (D/E/G/Q/R) (F/Y) (I/L) (A/D/E/G/H/I/K/L/M/N/P/Q/R/S/T/V/Y) (A/G/I/T) (M/N) (I/L) (F/G/K/M/P/S) (A) (I) (A/C/F/G/P/R/S/W) (A/C/D/E/F/G/H/I/K/L/M/N/P/Q/R/S/T/V/W/Y) (I/W) (A/L/M/P/S/T/V/W) (A/G/M/N/P/Q/S) (A/F/I/L/P) (I/R) (A/E/F/L/W/Y) (F/N/Q/Y) (A) (C/E/G/H/N/R/S/T/V/W/Y) (I/N) (E) (A/K/R/V) (D/F/G/H/K/M/N/Q/R/S/T/V/W/Y) (E/K) (K/L) (K) (E/H/K) (A) (D/G) (C/F/G/L/M/P/Q/R/S/V/W) (A/C/D/F/G/I/V/Y) (D/H/I/K/N/S/T/Y) (A/C/F/I/L/N/P/S/T/Y) (E/F/H/K/L/P/Q/R) (A/E/H/K/P/Q/R) (A/K/L/M/P/Q/R/V) (A/D/E/G/L/N/R/V/Y) (E/G/K/Q) (L/M/P/R/T) (A/C/G/H/P/Q/R) (C/G/I/L/P/R/V) (C/F/H/P/R/S/V/Y) (F/L/M/P/Q/R) (A/D/E/G/H/I/K/L/M/N/P/Q/R/S/T/V/Y) (D/E/G/I/K/L/P/R/V) (A/E/G/K/L/M/P/R/T/V) (A/C/E/G/M/P/Q/S/T/V) (A/D/E/G/H/K/N/Q/R/S/T/Y) (C/D/E/F/G/M/Q/S/V/W) (A/D/F/H/M/P/Q/S/T/V) (A/D/G/S/T/V) (A/C/D/E/G/H/I/L/M/N/Q/R/S/T/V/Y) (A/E/G/I/K/M/R/S/T) (A/E/F/G/S/T) (D/H/K/M/N/P/Q/R) (A/C/D/E/G/L/N/Q/S/V/Y) (C/D/F/H/T/Y) (C/D/G/L) (C/E/H/L/R/S/T/Y) (D/E/K/P/T) (C/F/I/L/S/V/Y) (E/F/H/K/Q/R/S/Y) (H/I/L/N/P/Q/R/S/T) (A/E/H/I/K/N/Q/Y) (E/L/M/P/Q/V) (D/E/G/H/K/L/N/S/V/W) (C/D/G/H/L/R/Y) (Target: BCL2L10/Bcl-B)

This embodiment is based on saturation mutagenesis studies described in the examples that follow, in which all residues of SEQ ID NO:52 were tested to identify allowed sequence variability for the designed proteins that retained function (i.e.: BCL2L10/Bcl-B binding).

In another embodiment the polypeptide comprises or consists of an amino acid sequence according to SEQ ID NO: 11, wherein the polypeptide binds to Bcl-2-like protein A1 (A1/Bfl-1).

(SEQ ID NO: 11)
(A/D/F/G/H/K/L/M/P/R/S/T/V/W/Y) (A/C/D/E/F/G/H/I/
L/M/N/P/Q/S/T/V/W/Y) (A/C/D/F/G/I/K/L/P/Q/R/S/T/V/
W/Y) (C/D/E/F/I/K/L/M/N/Q/R/T/V/W/Y) (E/H/I/K/M/N/P/
Q/R/T) (A/D/E/F/G/I/V) (A/E/F/H/L/M/P/Q/R/T/V/W/Y)
(A/C/D/E/G/H/I/K/L/M/N/P/R/S/V/W/Y) (A/C/D/E/F/G/H/
I/K/L/M/N/P/Q/R/S/T/V/W/Y) (A/E/F/G/H/I/L/M/N/P/S/
T/V/W/Y) (E/F/I/K/L/M/N/Q/T/V/W/Y) (A/D/E/G/H/I/K/L/
M/N/R/V/W/Y) (C/D/E/H/I/K/L/M/P/Q/W/Y) (A/C/E/F/G/I/
L/M/N/Q/S/T/V/W/Y) (A/C/D/E/F/G/K/L/M/N/S/V/Y) (A/D/
E/G/H/I/K/N/Q/S/T/V/W) (A/H/I/L/P/R/S/T/V) (A/D/G/H/
M/S/T/V) (A/C/E/G/H/L/M/R/T/W) (A/D/E/F/G/H/I/K/L/M/
N/P/Q/R/S/T/V/W/Y) (A/F/G/H/I/K/L/M/N/P/Q/R/S/T/V/
W/Y) (E/G/H/I/K/L/M/N/Q/R/T/W/Y) (A/D/E/H/K/M/N/Q/R/
S/T/W) (K) (A/C/E/F/G/H/I/K/L/M/P/Q/R/S/T/V/W/Y) (A/
C/D/E/F/G/H/K/L/M/Q/R/S/V/W/Y) (A/D/E/F/G/H/I/K/L/
M/N/Q/R/S/T/V/W/Y) (I/L/S/T/V) (A/C/D/F/G/H/I/L/M/P/
R/S/T/V/W/Y) (H/I/K/N/Q/T/Y) (A/C/D/E/F/G/H/I/K/L/M/
N/P/Q/R/S/T/V/W/Y) (A/C/D/F/G/H/I/L/M/P/R/S/V/W/Y)
(C/H/K/M/N/R/S/T/Y) (K/L/N/R) (F/H/I/L/P/R) (A/D/E/F/
G/H/I/K/L/M/N/P/Q/R/S/T/V/W/Y) (A/D/E/F/H/I/K/L/M/
N/P/Q/R/S/T/V/W) (A/D/E/F/G/H/I/K/M/N/P/Q/S/T/V/Y)
(A/E/G/H/I/K/L/M/N/P/Q/S/T/V) (A/D/E/F/G/K/N/Y) (A/
F/G/H/I/K/L/M/P/S/T/W/Y) (A/C/D/E/F/G/H/I/L/M/N/P/
Q/R/S/V/W/Y) (A

-continued

SEQ ID NO: 12

| Residue | Allowable Residues |
|---|---|
| I13 | D/E/G/I/K/L/M/N/Q/R/S/T/V/W/Y |
| A14 | A/C/I/L/M/N/Q/S/T/V |
| E15 | A/D/E/M/N/R/V/W/Y |
| N16 | A/D/F/G/H/I/K/L/M/N/P/Q/R/S/T/V/W/Y |
| R17 | A/C/E/G/H/I/K/L/M/P/R/S/T/V |
| V18 | A/I/K/M/T/V |
| R19 | A/C/D/E/F/G/K/L/M/N/Q/R/T/V/W/Y |
| E20 | A/D/E/F/G/I/K/L/M/N/Q/R/S/T/V/W/Y |
| L21 | F/H/I/L/M/Q/T/Y |
| K22 | A/C/H/I/K/Q/R |
| Q23 | A/C/E/F/G/H/I/M/N/Q/R/S/T/W/Y |
| K24 | A/D/G/H/I/K/N/Q/R/T/Y/V |
| L25 | I/L/M/Q |
| E26 | A/C/D/E/G/I/K/N/Q/R/S/T/V/W |
| E27 | A/C/D/E/F/G/H/I/K/L/M/N/Q/R/S/T/V/W/Y |
| F28 | C/F/H/I/K/L/M/N/P/R/T/V/Y |
| Y29 | A/D/E/H/I/L/P/Q/R/W/Y |
| K30 | A/E/F/G/H/K/L/M/N/Q/R/S/T/W/Y |
| E31 | A/D/E/F/G/H/I/K/L/M/N/Q/R/S/T/V/W/Y |
| A32 | A/F/G/H/K/L/N/P/R/S/T/Y |
| M33 | F/H/I/K/L/M/P/Q/R/T/V/Y |
| K34 | C/H/I/K/L/M/Q/R/S/T/V/Y |
| L35 | A/D/E/F/G/H/I/K/L/M/N/P/Q/R/S/T/V/W |
| D36 | A/C/D/E/G/H/K/M/N/Q/R/S/T/V/W/Y |
| L37 | A/D/E/F/G/H/I/K/L/M/N/P/Q/R/S/T/V/W/Y |
| T38 | A/D/E/G/K/N/P/Q/R/S/T |
| Q39 | A/D/E/G/K/N/P/Q/R/S/V |
| E40 | A/D/E/F/G/H/I/K/L/M/N/P/Q/R/S/T/V |
| M41 | F/G/H/K/L/M/N/Q/R/T/V/W/Y |
| R42 | K/R |
| R43 | K |
| K44 | K/R |
| L45 | F/G/I/L/Q/V/W/Y |
| M46 | D/E/M/N/Q/T/I |
| L47 | F/L/M/W/E |
| R48 | R |
| W49 | E/F/W/Y |
| I50 | A |
| A51 | A/G |
| A52 | A/F/I/Q |
| M53 | D/H/L/M/N/W/I |
| L54 | I/L |
| M55 | G/I/M/S/V/R |
| A56 | A/C/F/G/I/L/M/P/S/T/V |
| I57 | A/I/M/S/T/V |
| G58 | G |
| D59 | D |
| I60 | I/L/M |
| F61 | F/M/W/Y/N |
| N62 | A/D/F/G/I/L/M/N/Q/S/T/V/W |
| A63 | A/F/I/L/M/T/V/Y |
| I64 | A/H/I/M/Y |
| R65 | R/Y |
| Q66 | A/F/I/K/L/M/Q/R/V/W/Y |
| A67 | A/G |
| K68 | K/Q/R |
| Q69 | A/F/G/I/K/L/N/Q/R/S/T/V/W/Y |
| E70 | A/D/E/F/G/H/I/K/L/M/N/Q/R/S/T/V/W/Y |
| A71 | A/G/I/M/S |
| D72 | A/D/E/F/G/H/I/L/M/Q/S/T/V/W/Y |
| K73 | F/K/R/Y |
| L74 | A/F/L/M/R/W/Y |
| K75 | A/F/H/K/N/R/S/T/Y |
| K76 | I/K/N/R/W |
| A77 | A/F/G/H/I/K/L/M/N/Q/R/S/T/V/W/Y |
| G78 | A/D/G/H/Q/R/S/T |
| L79 | A/K/L/R/T/V/W/Y |
| V80 | I/L/M/V |
| N81 | A/D/E/K/N/Q/R/S/T |
| S82 | D/E/G/K/M/P/Q/R/S/T/V |
| Q83 | A/D/E/F/H/I/L/N/Q/R/S/V |
| Q84 | D/E/H/M/N/Q/T/Y |
| L85 | A/F/G/H/L/M/R/T/V/W/Y |
| D86 | D/E/F/G/I/K/L/N/Q/S/T/V/W/Y |
| E87 | A/E/F/I/K/L/M/Q/T/W |

-continued

SEQ ID NO: 12

| Residue | Allowable Residues |
|---|---|
| L88 | A/F/I/L/M/T/V |
| K89 | A/I/K/Q/R/V/L |
| R90 | A/G/I/K/L/M/N/Q/R/S/T/V/W/Y |
| R91 | A/C/D/E/G/H/K/L/N/Q/R/S/T/V/Y |
| L92 | I/L |
| E93 | A/D/E/H/I/M/N/Q/T |
| E94 | A/C/D/E/F/G/H/I/K/L/M/N/Q/R/S/T/V/Y |
| L95 | A/L/T/V |
| K96 | K/Q/R |
| E97 | A/D/E/G/H/Q/S/T/V |
| E98 | A/D/E/F/H/K/M/N/P/Q/R/S/W/Y |
| A99 | A/S/V |
| S100 | A/G/N/Q/S/T |
| R101 | K/R |
| K102 | K/R |
| A103 | A/I/M/N/S/T/V |
| R104 | D/K/N/R |
| D105 | A/D/E/F/G/H/K/L/M/N/R/T/V/W/Y |
| Y106 | A/E/G/H/I/T/Y |
| G107 | D/G/S |
| R108 | K/Q/R |
| E109 | A/D/E/F/G/H/K/L/R/S/V/W |
| F110 | F |
| Q111 | D/E/H/M/Q |
| L112 | A/D/F/I/L/P/Q/R |
| K113 | K/Q |
| L114 | A/H/K/L/M/P/R/S/T/V/Y |
| E115 | D/E/P/R/T |
| Y116 | D/E/G/H/K/Q/R/T/Y |

In another embodiment, the polypeptide comprises or consists of the amino acid sequence selected from the group consisting of SEQ ID NOS: 1-6.

In another embodiment the polypeptide comprises or consist of an amino acid sequence having at least 50% identity to the amino acid sequence of SEQ ID NO:13.

SEQ ID NO.: 13
ADWKKVLDKAKDIAENRVREIKQKLEEFYKKAMKLDLTQEMRRKLMLE
WIAAMLMAIGDIFNAIEQAKQEADKLKKAGQVNSQLLDELKRRLEELKE
EASRKCHDYGREFQLKLEY (BbpD04)

As shown in the examples that follow, the polypeptide of SEQ ID NO:13 is a selective high affinity binder of Epstein Barr protein BHFR1. The inventors have carried out saturation mutagenesis on the polypeptide of SEQ ID NO:13 to identify modifiable residues. In various embodiments, the polypeptides of this embodiment have at least 55%, 60%, 66%, 70%, 75%, 80%, 85%, 90%, 95%, 98%, or 100% identity over their length relative to the amino acid sequence of SEQ ID NO:13. As will be understood by those of skill in the art, the polypeptides may include additional residues at the N-terminus, C-terminus, or both that are not present in SEQ ID NO:1; these additional residues are not included in determining the percent identity of the polypeptides of the invention relative to the reference polypeptide (i.e.: SEQ ID NO:13 in this case).

In one embodiment, the polypeptide comprises at least one conservative amino acid substitution corresponding to residues 3, 13, 21, 28, 31, 33, 46, 48, 49, 61, 62, 65, 79, 84, 103, and 104 of the amino acid sequence of SEQ ID NO: 13.

As used herein, "conservative amino acid substitution" means amino acid or nucleic acid substitutions that do not alter or substantially alter polypeptide or polynucleotide function or other characteristics. A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In a further embodiment, the polypeptide includes the substitutions K31E, E48R, and E65R relative to SEQ ID NO:13. In another embodiment, the polypeptide includes the substitutions I21L, Q79L, L84Q, and H104R relative to SEQ ID NO:13. In a further embodiment, the polypeptide includes the substitution C103A relative to SEQ ID NO:13. In a still further embodiment, the polypeptide includes substitutions W3P, I13Q, F28L, M33R, M46E, W49Y, and F61Y relative to SEQ ID NO:13. In another embodiment, the polypeptide includes the substitution N62S relative to SEQ ID NO:13. These embodiments may be combined in any suitable combination.

In another embodiment, the polypeptide comprises or consists of a polypeptide having at least 50%, 60%, 70%, 80%, 90%, 95%, 98%, 99%, or 100% amino acid sequence identity over their length relative to the amino acid sequence of SEQ ID NO: 276, wherein the polypeptide selectively binds to Bcl-w.

| SEQ ID NO: 276 WINDI Allowable Residues | |
|---|---|
| Residue | Allowable Residues |
| 1 | C/D/E/K/L/M/N/R/S/V/W/Y |
| 2 | A/D/E/G/H/L/N/P/Q/R/T/W |
| 3 | A/C/F/G/H/I/K/M/Q/R/T/V/Y |
| 4 | D/F/G/I/K/M/N/R/S/T/V/W |
| 5 | I/L/M/N/T/V/W/Y |
| 6 | E/F/I/L/Q/T/V/W/Y |
| 7 | A/C/D/F/L/W/Y |
| 8 | D/E/H/I/V |
| 9 | A/E/H/L/Y |
| 10 | A/H/I/K/M/N/Q/R/S/T/Y |
| 11 | C/D/E/G/H/K/M/Q/R/S/T/W |
| 12 | A/D/E/G/L/N/Q/R/S/V/W |
| 13 | A/C/F/H/K/L/M/N/S/T/V |
| 14 | A/D/E/F/G/H/I/L/M/Q/S/V/W/Y |
| 15 | A/E/G/H/M/N/Q/R/W/Y |
| 16 | A/F/L/M/N/S/V/W/Y |
| 17 | F/G/H/I/K/M/Q/R/T/V |
| 18 | A/C/E/H/K/L/N/Q/R/S/V/W |
| 19 | I/M/N/Q/R |
| 20 | A/F/G/I/K/L/M/P/T/V/W/Y |
| 21 | I/K/N/S/T/W |
| 22 | A/F/G/H/I/K/L/M/N/P/Q/R/S/V/W/Y |
| 23 | I/K/L/R/V |
| 24 | A/D/F/H/K/L/M/R/S/V |
| 25 | A/C/D/E/G/H/L/M/S/V/W |
| 26 | A/D/E/F/G/H/I/L/M/Q/R/S/V/W/Y |
| 27 | A/F/G/I/K/L/M/Y |
| 28 | F/H/I/K/L/Q/S/V/W/Y |
| 29 | A/F/G/H/I/K/M/N/P/Q/R/S/T/V/W/Y |
| 30 | D/E/G/H/L/M/N/Q/S/V/W/Y |
| 31 | A/F/G/M/P/S/V/Y |
| 32 | A/E/G/H/I/M/N/P/Q/R/T |
| 33 | A/H/I/K/M/P/R/T/V/W/Y |

| SEQ ID NO: 276 WINDI Allowable Residues | |
|---|---|
| Residue | Allowable Residues |
| 34 | A/E/G/H/I/K/N/P/R/S/T/W |
| 35 | A/C/D/E/G/H/K/L/M/N/P/R/S/T/V/W/Y |
| 36 | A/D/E/F/K/L/R/S |
| 37 | G/R/S/T |
| 38 | A/E/G/H/K/L/P/Q/S/V/W |
| 39 | A/D/E/G/I/K/M/N/P/Q/R/S/T/V/W/Y |
| 40 | A/D/E/G/I/R/W/Y |
| 41 | H/K/L/Q/R/Y |
| 42 | A/D/E/G/K/Q/R/T/V |
| 43 | E/G/H/I/K/L/N/R/S/T/V/W/Y |
| 44 | F/H/K/L/T/V/W/Y |
| 45 | I/K/L/M/R/S/T/V/W |
| 46 | A/D/E/G/I/K/L/M/N/Q/S/T/V/W |
| 47 | D/F/H/I/K/M/R/S/T/V/Y |
| 48 | A/C/E/F/G/H/I/K/L/M/R/S/T/V/W/Y |
| 49 | I/K/M/N/P/Q/R/W |
| 50 | D/I/N/P/S/T |
| 51 | A/F/G/H/I/K/L/M/Q/R/S/T/W |
| 52 | A/F/L/M/R/V/W/Y |
| 53 | A/E/F/G/H/I/M/N/Q/T/V/W/Y |
| 54 | A/G/H/I/L/M/N/P/S/T/V |
| 55 | A/C/F/G/M/P/T/W/Y |
| 56 | A/F/I/K/L/M/V |
| 57 | K/L/W/Y |
| 58 | A/G/K/M/Q/R/S/V/W |
| 59 | A/D/I/L/M/T/V/W |
| 60 | A/D/E/F/G/H/I/L/M/P/S/T/V/W/Y |
| 61 | F/G/N/Q |
| 62 | C/D/Y |
| 63 | A/C/F/H/I/K/L/M/P/T/V/W/Y |
| 64 | E/F/L/M |
| 65 | D/F/H/M/N/W |
| 66 | A/G/S/W |
| 67 | F/K/L/V/W/Y |
| 68 | K/L/M/W |
| 69 | F/H/I/K/Q/R/T/Y |
| 70 | A/F/G/I/L/M |

SEQ ID NO: 276 WINDI Allowable Residues

| Residue | Allowable Residues |
|---|---|
| 71 | Q/R |
| 72 | I/K/R/T |
| 73 | A/K/L/M |
| 74 | F/G/H/K/L/R/V/W/Y |
| 75 | I/K/M/N/R |
| 76 | A/D/F/G/H/I/K/L/M/N/Q/R/V/W/Y |
| 77 | F/G/Q/R/S |
| 78 | E/G/H/L/M/N/P/Q/T/V/Y |
| 79 | A/I/L/M/S/T/V/W/Y |
| 80 | E/G/M/N/S/T |
| 81 | A/D/E/F/G/H/I/K/L/M/N/P/Q/R/S/T/V/W/Y |
| 82 | D/E/F/G/I/K/L/N/P/Q/R/S/W/Y |
| 83 | A/D/E/G/P/Q/W |
| 84 | A/F/G/H/I/K/L/V/Y |
| 85 | A/D/E/F/G/H/I/K/L/M/N/P/Q/R/S/T/V/W/Y |
| 86 | A/D/E/F/G/H/R/S/T/V/W/Y |
| 87 | F/H/I/K/L/M/Q/V |
| 88 | A/H/N/P/R/S/W |
| 89 | H/L/Q/R/V/Y |
| 90 | A/D/G/L/P/Q/R/Y |
| 91 | C/F/H/I/K/L/P/R/T/V/Y |
| 92 | C/F/G/I/K/L/M/N/P/Q/S/T/V/W/Y |
| 93 | A/D/E/F/G/H/I/K/L/M/N/Q/R/S/T/V/W/Y |
| 94 | A/C/D/E/G/I/K/L/M/N/Q/R/S/T/V/Y |
| 95 | A/C/D/F/H/I/L/M/P/T/V/W/Y |
| 96 | H/I/K/N/P/Q/R/T/V |
| 97 | C/D/E/G/L/M/P/R/S/V |
| 98 | A/C/F/G/I/K/L/Q/T/V/W |
| 99 | E/F/G/I/L/M/W |
| 100 | A/E/G/H/K/P/Q/R/V |
| 101 | A/D/E/G/H/I/K/P/R/S/V |
| 102 | A/C/F/I/L/M/T/V/Y |
| 103 | I/K/R |
| 104 | A/C/D/E/F/G/H/I/K/L/M/N/P/Q/R/S/V/W/Y |
| 105 | C/F/H/I/M/R/S/W/Y |
| 106 | A/E/H/K/L/M/R/V |
| 107 | A/E/F/G/I/K/L/M/N/Q/R/S/V/Y |
| 108 | A/D/E/G/I/K/L/Q/R/T |
| 109 | C/E/F/H/L/N/R/V/Y |
| 110 | A/D/E/F/G/H/I/K/L/M/N/P/R/S/T/V/W/Y |
| 111 | D/I/L/R/S/V/W/Y |
| 112 | A/C/D/G/H/I/K/L/V |
| 113 | C/E/F/K/L/Q/R/T/V |
| 114 | A/D/E/G/I/K/L/M/N/P/Q/R/S/T/V/W/Y |
| 115 | A/D/G/I/L/M/P/R/T/W/Y |

This embodiment is based on saturation mutagenesis studies described in the examples that follow, in which all possible single amino acid substitutions of SEQ ID NO: 264 were tested to identify allowed sequence variability for the designed proteins that retained function (i.e.: Bcl-w binding).

In preferred embodiments, the polypeptide of SEQ ID NO: 276 include polypeptides with one or more (i.e.: 1, 2, 3, 4, 5, 6, 7, 8, 9, 10, 11, 12, 13, 14, 15, or 16 of the following specific amino acid residues: 10L, 20N, 20Q, 47D, 47T, 54E, 54H, 54Q, 55I, 55L, 55M, 55S, 55T, 55V, 60I, 60M, 60T, 60V, 61E, 64F, 64I, 64L, 64M, 65I, 65L, 65M, 77R, 86R, 93M, 93T, 94V, 98D, 100E, and 111K. In further preferred embodiments, the polypeptides of SEQ ID NO: 276 have 1, 2, 3, 4, 5, 6, 7, 8, or all 9 of the following specific amino acid residues: 10L, 47T, 54Q, 55L, 61E, 64I, 65M, 93M, and 111K.

As noted above, the polypeptides of the invention may include additional residues at the N-terminus, C-terminus, or both. Such residues may be any residues suitable for an intended use, including but not limited to detection tags (i.e.: fluorescent proteins, antibody epitope tags, etc.), linkers, ligands suitable for purposes of purification (His tags, etc.), and peptide domains that add functionality to the polypeptides. In one embodiment, the polypeptide of the invention further comprises a cell penetrating peptide. Cell penetrating peptides are useful, for example, to facilitate uptake of the polypeptides by cells, and are known to those of skill in the art. Non-limiting examples of such cell penetrating peptides that can be used with the polypeptides of the invention include:

TAT:
(SEQ ID NO: 14)
GRKKRRQRRRPPQ;

penetratin:
(SEQ ID NO: 15)
RQIKIWFQNRRMKWKK;

MAP:
(SEQ ID NO: 16)
KLALKLALKALKAALKLA;

transportan/TP10:
(SEQ ID NO: 17)
GWTLNS/AGYLLGKINLKALAALAKKIL;

VP22
(SEQ ID NO: 18)

```
                    -continued
NAKTRRHERRRKLAIER;

polyarginine:
                                        (SEQ ID NO: 19)
R_n, n >7;

MPG:
                                        (SEQ ID NO: 20)
GALFLGFLGAAGSTMGA;

Pep-1:
                                        (SEQ ID NO: 21)
KETWWETWWTEWSQPKKKRKV;

pVEC:
                                        (SEQ ID NO: 22)
LLIILRRRIRKQAHAHSK;

YTA2:
                                        (SEQ ID NO: 23)
YTAIAWVKAFIRKLRK;

YTA4:
                                        (SEQ ID NO: 24)
IAWVKAFIRKLRKGPLG;

M918:
                                        (SEQ ID NO: 25)
MVTVLFRRLRIRRACGPPRVRV;
and CADY:
                                        (SEQ ID NO: 26)
GLWRALWRLLRSLWRLLWRA.
```

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, glycosylation, or may be produced as an Fc-fusion or in deimmunized variants. Such linkage can be covalent or non-covalent as is understood by those of skill in the art.

In another aspect, the invention provides pharmaceutical composition, comprising a polypeptide of any embodiment or combination of embodiments of the invention, and a pharmaceutically acceptable carrier. The pharmaceutical compositions of the invention can be used, for example, in the methods of the invention described below. The pharmaceutical composition may comprise in addition to the polypeptide of the invention (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides of the invention may be the sole active agent in the pharmaceutical composition, or the composition may further comprise one or more other active agents suitable for an intended use, including but not limited to anti-HA and anti-NA antibodies. As used herein, the term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In one embodiment, the pharmaceutical compositions further comprise an antibody, or antibody fragment. In this embodiment, the antibody or antibody fragment adds functionality to the composition by, for example, helping target the composition to a cell type that has a cell surface receptor to which the antibody selectively binds. As a result, compositions of this embodiment are particularly useful for therapeutic applications. As will be understood by those of skill in the art, any suitable antibody or fragment thereof can be employed that targets a cell or tissue of interest. The antibody or fragment may be recombinantly expressed as part of the polypeptide, may be linked to the polypeptide directly (such as by a covalent linkage or non-covalent interaction), or may not be directly linked to the polypeptide at all (i.e.: present in the same composition, but unlinked).

In another embodiment, the pharmaceutical carrier may comprise a polymer. Any suitable polymer may be used that is pharmaceutically acceptable and which does not interfere with function of the polypeptide. In one embodiment, the polymer is a block polymer and comprises a hydrophilic block and an endosomolytic block. Any suitable hydrophilic block and endosomlytic blocks may be used. In one embodiment, the hydrophilic block comprises polyethylene glycol methacrylate. In another embodiment, the endosomolytic block comprises a diethylaminoethyl methacrylate-butyl methacrylate copolymer. In a further embodiment, the polymer is a stimuli-responsive polymer that responds to one or more stimuli selected from the group consisting of pH, temperature, UV-visible light, photo-irradiation, exposure to an electric field, ionic strength, and the concentration of certain chemicals by exhibiting a property change. As used herein, a "stimuli-responsive polymer" is a polymer that changes its associative properties in response to a stimulus. The stimuli-responsive polymer responds to changes in external stimuli such as the pH, temperature, UV-visible light, photo-irradiation, exposure to an electric field, ionic strength, and the concentration of certain chemicals by exhibiting property change. The chemicals could be polyvalent ions such as calcium ion, polyions of either charge, or enzyme substrates such as glucose. For example, a temperature-responsive polymer may be responsive to changes in temperature by exhibiting a LCST in aqueous solution. A stimuli-responsive polymer may be a multi-responsive polymer, where the polymer exhibits property change in response to combined simultaneous or sequential changes in two or more external stimuli. The stimuli-responsive polymers may be synthetic or natural polymers that exhibit reversible conformational or physico-chemical changes such as folding/unfolding transitions, reversible precipitation behavior, or other conformational changes to in response to stimuli, such as to changes in temperature, light, pH, ions, or pressure. Representative stimuli-responsive polymers include temperature-sensitive polymers, pH-sensitive polymers, and light-sensitive polymers.

In a further aspect, the present invention provides isolated nucleic acids encoding a polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In another aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting host cells is well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In various embodiments, the expression vector may comprise a plasmid, viral-based vector, or any other suitable expression vector.

In a further aspect, the present invention provides host cells that comprise the recombinant expression vectors disclosed herein, wherein the host cells can be either prokaryotic or eukaryotic. The cells can be transiently or stably engineered to incorporate the expression vector of the invention, using standard techniques in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium. Methods to recover polypeptide from cell free extracts or culture medium are well known to the person skilled in the art.

In another aspect, the invention provides methods of treating an Epstein-Barr virus-related disease comprising administering to a subject in need thereof a therapeutically effective amount of one or more of the polypeptides of the invention that selectively inhibits BHRF1, or salts thereof, pharmaceutical compositions thereof, a recombinant nucleic acid encoding the one or more polypeptides, a recombinant expression vector comprising the recombinant nucleic acids, and/or a recombinant host cells comprising the expression vector, to treat and/or limit the Epstein-Barr virus related disease.

Epstein-Barr virus encodes a pro-survival Bcl-2 homologue, BHRF1, which prevents lymphocyte apoptosis during initial infection by sequestering pro-apoptotic BOPs (especially Bim), and interacting directly with the executioner Bak (Desbien et al., 2009; Kvansakul et al., 2010) (Altmann and Hammerschmidt, 2005) (Henderson et al., 1993). Even though BHRF1 is under the control of an early lytic cycle promoter, low levels of constitutive expression have been observed in some cases of EBV-positive BL when the virus is latent, and it has been speculated that BHRF1 may be a necessary viral factor for lymphomagenesis (Kelly et al., 2009; Leao et al., 2007; Watanabe et al., 2010). Thus, inhibitors of BHRF1 can be used to treat and/or limit development of Epstein-Barr virus related disease, as is evidenced by the examples that follow.

In various embodiments, the Epstein-Barr virus-related disease is selected from the group comprising of infectious mononucleosis, Burkitt's lymphoma, Hodgkin's lymphoma, non-Hodgkin's lymphoma, mantle cell lymphoma, nasopharyngeal carcinoma, multiple sclerosis, Parkinson's disease, dementia with Lewy bodies, and multiple system atrophy. In other embodiments, the Epstein-Barr virus-related disease is a cancer selected from the group consisting of Burkitt's lymphoma, Hodgkin's lymphoma, non-Hodgkin's lymphoma, mantle cell lymphoma, or nasopharyngeal carcinoma.

In various embodiments, polypeptides for use in this aspect of the invention are selected from polypeptides comprising or consisting of the amino acid sequence of SEQ ID NOS: 1 and 7, including any embodiments thereof such as, but not limited to, further including cell penetrating peptides or antibodies.

In another aspect, the invention provides methods for treating cancer, comprising administering to a subject in need thereof a therapeutically effective amount of one or more of the polypeptides that selectively inhibits one or more of Mcl-1, Bcl-2, BCL2L1/Bcl-XL, BCL2L10/Bcl-B, A1/Bfl-1, and Bcl-w, or salts thereof, a pharmaceutical composition thereof, a recombinant nucleic acid encoding the one or more polypeptides, a recombinant expression vector comprising the recombinant nucleic acid, and/or a recombinant host cell comprising the recombinant expression vector, to treat cancer in the subject.

Apoptosis and cell survival are regulated by the homeostatic balance of B cell lymphoma-2 (Bcl-2) family proteins. The 'executioners', Bak and Bax, initiate apoptosis by increasing mitochondrial outer membrane permeability and facilitating the release of mitochondrial cytochrome c to the cytosol, which activates downstream signaling. Six human pro-survival Bcl-2 proteins (Bcl-2, Bcl-$X_L$, Bcl-B, Mcl-1, Bcl-w and Bfl-1) inhibit this process. Cellular stresses activate pro-apoptotic BOPs, which bind and inhibit pro-survival Bcl-2 members, and directly interact with Bak and Bax to favor mitochondrial permeabilization. Conversely, pro-survival Bcl-2 proteins dampen apoptotic triggers and enhance chemoresistance by sequestering BOPs or directly inhibiting Bak and Bax. Increased expression of pro-survival Bcl-2 proteins is a common feature of many cancers. Thus, the polypeptides of the present invention, which bind to and inhibit the pro-survival Bcl-2 proteins, can be used to treat cancer.

In various embodiments, polypeptides for use in this aspect of the invention are selected from polypeptides comprising or consisting of the amino acid sequence of SEQ ID NOS: 1-6, 8-12, 262-273 and 276, including any embodiments thereof such as, but not limited to, further including cell penetrating peptides or antibodies.

The methods may be used alone or in conjunction with other therapies for treating cancer, such as chemotherapy, radiation therapy, and/or surgical removal of the tumor. In one embodiment, the polypeptides permit reduced (sub-therapeutic) dosages of current therapies; in another embodiment, such a combination therapy permits the use of otherwise sub-therapeutic dosages of the polypeptide of the invention; these embodiments can be combined. In these various embodiments, the methods may be used to overcome tumor resistance to the treatment.

As used herein, the phrase "therapeutically effective amount", "effective amount" or "effective dose" refers to an amount that provides a therapeutic benefit in the treatment, prevention, or management of Epstein-Barr virus and Epstein-Barr related diseases, or cancer. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "treat," "treatment," or "treating," means to reverse, alleviate, ameliorate, inhibit, slow down or stop the progression or severity of a symptom or condition of the disorder being treated. The term "treating" includes reducing or alleviating at least one adverse effect or symptom of a condition. Treatment is generally "effective" if one or more symptoms are reduced. Alternatively, treatment is "effective" if the progression of a condition is reduced or halted. That is, "treatment" may include not just the improvement of symptoms, but also a cessation or slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor or malignancy, delay or slowing of tumor growth and/or metastasis, and an increased lifespan as compared to that expected in the absence of treatment.

As used herein, the term "administering," refers to the placement of a therapeutic into a subject by a method or route deemed appropriate. The therapeutic can be administered by any appropriate route which results in an effective treatment in the subject including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Dosage regimens can be adjusted to provide the optimum desired response (e.g., a therapeutic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

In another aspect, the invention provides methods for determining the Bcl-2 phenotype of a tumor, comprising contacting tumor cells, tumor cell lysates or tumor cellular components with one or more polypeptides selected from the group consisting of SEQ ID NOS: 1-6, 8-12, 262-273 and 276 under conditions suitable to promote apoptosis signaling in cells of the tumor that express a bcl-2 homologue targeted by the one or more polypeptides; and determining bcl-2 dependency of the tumor based on the polypeptide that causes apoptosis or apoptotic signaling in the cells of the tumor.

The methods of this aspect of the invention can be used, for example, to determine an appropriate polypeptide inhibitor of the invention to treat a tumor, by identifying the bcl-2 dependency of the tumor. In one embodiment, the method comprises contacting tumor cells, tumor cell lysates or tumor cellular components with each of the polypeptides of SEQ ID NOS:1-6 and 262-273, or each of the polypeptides of SEQ ID NOS:8-12 and 276, which permits simultaneously determining the bcl-2 dependency of the tumor for each of the Bcl-2 family proteins.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

EXAMPLES

The Epstein-Barr virus (EBV), also called human herpesvirus 4 (HHV-4), is a virus of the herpes family. Epstein-Barr virus has been implicated in several diseases that include infectious mononucleosis, Burkitt's lymphoma, Hodgkin's lymphoma, non-Hodgkin's lymphoma, mantle cell lymphoma, nasopharyngeal carcinoma and multiple sclerosis. The Epstein-Barr virus has been implicated also in disorders related to alpha-synuclein aggregation, such as Parkinson's disease, dementia with Lewy bodies, and multiple system atrophy. As used herein, "Epstein-Barr related diseases" are any diseases related to or caused by Epstein-Barr virus, including those listed immediately above.

Pro-survival Bcl-2 proteins share a common domain that resembles a cupped hand, with a characteristic hydrophobic surface groove that clasps one side of an amphipathic BH3 domain helix (Czabotar et al., 2007; Kvansakul et al., 2010; Liu et al., 2003). Rigidifying BH3 peptides by use of hydrocarbon staples, disulfides or lactam bridges on the non-interactive back side of the helix can reduce the entropic penalty of a partially-folded peptide acquiring a rigid helical conformation upon binding, and improves BH3 peptide affinity (Azzarito et al., 2013). We reasoned that building a folded structure around a BH3 peptide would similarly pre-stabilize the bound helical conformation. In previous work, interacting residues of the BH3 domain were grafted to the surface of a minimal structured peptide, but after directed evolution these folded peptides displayed only moderate affinity and specificity, and did not always bind to the correct interaction site on the target Bcl-2 protein (Chin and Schepartz, 2001; Gemperli et al., 2005). We instead sought to incorporate the interacting residues of the BH3 domain on the exposed surface of a larger 3-helix bundle, which makes additional contacts extending beyond the BH3 motif. This much larger interaction footprint provides opportunity for making many new contacts to increase affinity and specificity.

Creating New Proteins for Optimized Interactions with the BHRF1 Ligand-Binding Groove.

Current protein design methods nearly always involve the repurposing of an existing protein of known structure from the PDB. This protein of known structure acts as a scaffold on which new side chains can be grafted to an assumed rigid backbone by site-directed mutagenesis. The grafted residues form a new functional site for binding to a target protein of interest. However, designed proteins from side chain grafting are limited by the rigid backbone of the scaffold, and may have suboptimal steric complementarity for binding to the target surface. To escape this constraint, we used a computational method (Correia et al., 2014) that builds a new de novo protein with an amino acid sequence unseen in nature that incorporates the Bim-BH3 motif. A helical bundle scaffold protein of known structure is used only as a topology guide. From the crystal structure of Bim-BH3 bound by BHRF1, the Bim-BH3 helix acts as a folding nucleus, around which protein fragments from the PDB are assembled to build a new protein of matching topology to the guiding scaffold (3LHP chain S (Correia et al., 2010)). Cα-Cα atom-pair distances from the scaffold constrain the assembling protein to within a defined deviation threshold (3.0 Å root mean square deviation, RMSD). Thousands of designed proteins were computationally generated to form a family of structural homologues, all with unique sequences and slightly different backbone structures (FIG. 1).

The designed proteins were docked to the BHRF1 surface via alignment of the incorporated Bim-BH3 motif, and surrounding interface residues (within 8 Å) were then further designed, as the incorporated Bim-BH3 motif provides only a fraction of the interaction surface, and many additional contacts across an expansive interface should be designed. Scaffold residues surrounding the graft site were designed to minimize the energy of the modeled bound complex in the ROSETTA energy function (Kuhlman et al., 2003) (Leaver-Fay et al., 2011). BHRF1 interface residues, which normally reach over the backside of the Bim-BH3 helix, were simultaneously repacked to alternative low energy rotamers compatible with the new designed interface.

The proteins were filtered both for stability of the monomer (by computed monomer energy, packing based on RosettaHoles (Sheffler and Baker, 2009) and for the lowest number of buried unsatisfied hydrogen bonding atoms) and for interface quality (high shape complementarity, computed binding energy and a low number of buried unsatisfied hydrogen bonding atoms). From thousands of computer-assembled proteins, a small number of designs were selected for further manual modifications, synthetic E. coli codon-optimized genes were constructed, and those proteins that were expressed and soluble in E. coli were tested by yeast surface display for binding to BHRF1 (Table 1). Two structural homologues of PDB 3LHP chain S were designed with apparent $K_D$s 58-60 nM (BbpD04 and BbpD07; FIG. 1B and Tables 1 and 2). These designs were 'seeded' by a fifteen-residue fragment of the Bim-BH3 motif of which nine side chains contacting the BHRF1 surface were kept fixed. Other residues, primarily on the backside of the motif and buried in the protein core, were designed to minimize the calculated potential energy. The equivalent 3LHP_S fixed backbone graft (i.e. side chain grafting) described in the methods failed (Table 1). Thus backbone modification by in silico refolding can be critical for shaping scaffolds to precisely fit against a desired target.

TABLE 1

Summary of designs based on a seeded ab initio fragment assembly strategy.

| Design Name | Topology Guide | Site † | Expressed and soluble in E. coli ¶ | Binds 400 nM BHRF1 * |
|---|---|---|---|---|
| BbpD01 (S103A) | 3LHP(S) | Bim: 56-70 Scaffold: 54-68 | − | |
| BbpD02 | | | (−) | |
| BbpD03 (A60V) | | | − | |
| BbpD04 | | | (−) | |
| BbpD05 | | | + | Yes: 58 ± 3 nM |
| BbpD06 | | | − | |
| BbpD07 | | | + | No |
| | | | + | Yes: 60 ± 10 nM |

Summary of designs based on a side chain-grafting strategy.

| Design Name | Scaffold | Grafted Bim-BH3 Residues § | Designed Residues § | $K_D$ BHRF1 |
|---|---|---|---|---|
| BbpG1 BbpG1.D | 3LHP(S) | V55W, R56I, G57A, E60L, R63I, V64G, A65D, R67F | None E45D, E46Q, I48K, K49H, D50Q, L52V, K53H, I54Y, E58L, Q61E, R71E, T102R, D103W, I106F, K107Q, E110T, L113A, A114K, | − − |

TABLE 1-continued

E117A,
L120A,
T121Q

† Indicates the region of Bim-BH3 from crystal structure 2WH6 that was used to nucleate ab initio folding, and the site within the topology guide where the Bim-BH3 folding nucleus was located.
¶ E. coli BL21(DE3) cells cultured in terrific broth to an OD(600 nm) ~0.5 were induced with 0.1 mM IPTG overnight at 20° C. and protein expression investigated by SDS-PAGE.
* Designs were expressed on the yeast surface and incubated with 400 nM monomeric BHRF1-biotin, washed, and stained with anti-myc-FITC (expression) and streptavidin-PE (binding).
§ The native scaffold residue (identity and number) is given first, followed by the amino acid type it was mutated to.

In Silico Folding Probability Correlates with Binding Activity

Figure 2:
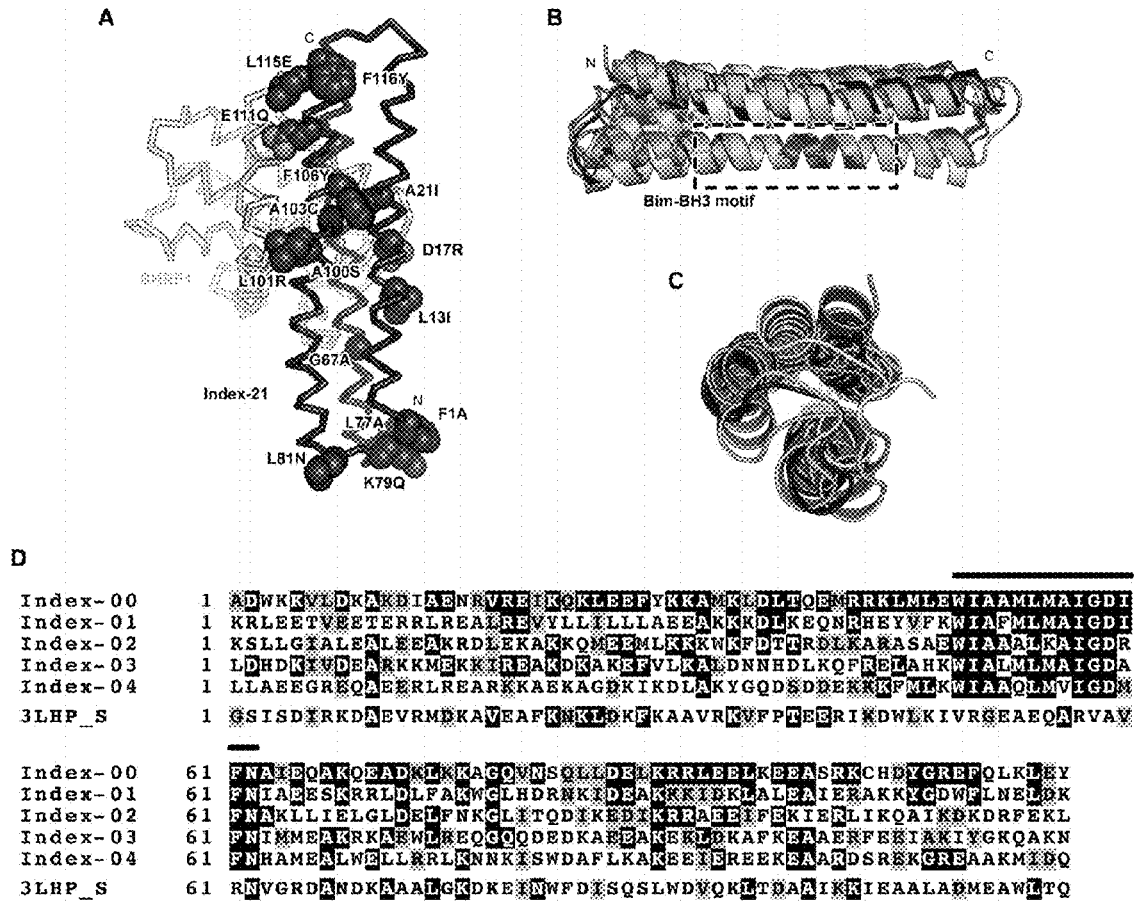
Figure 3:
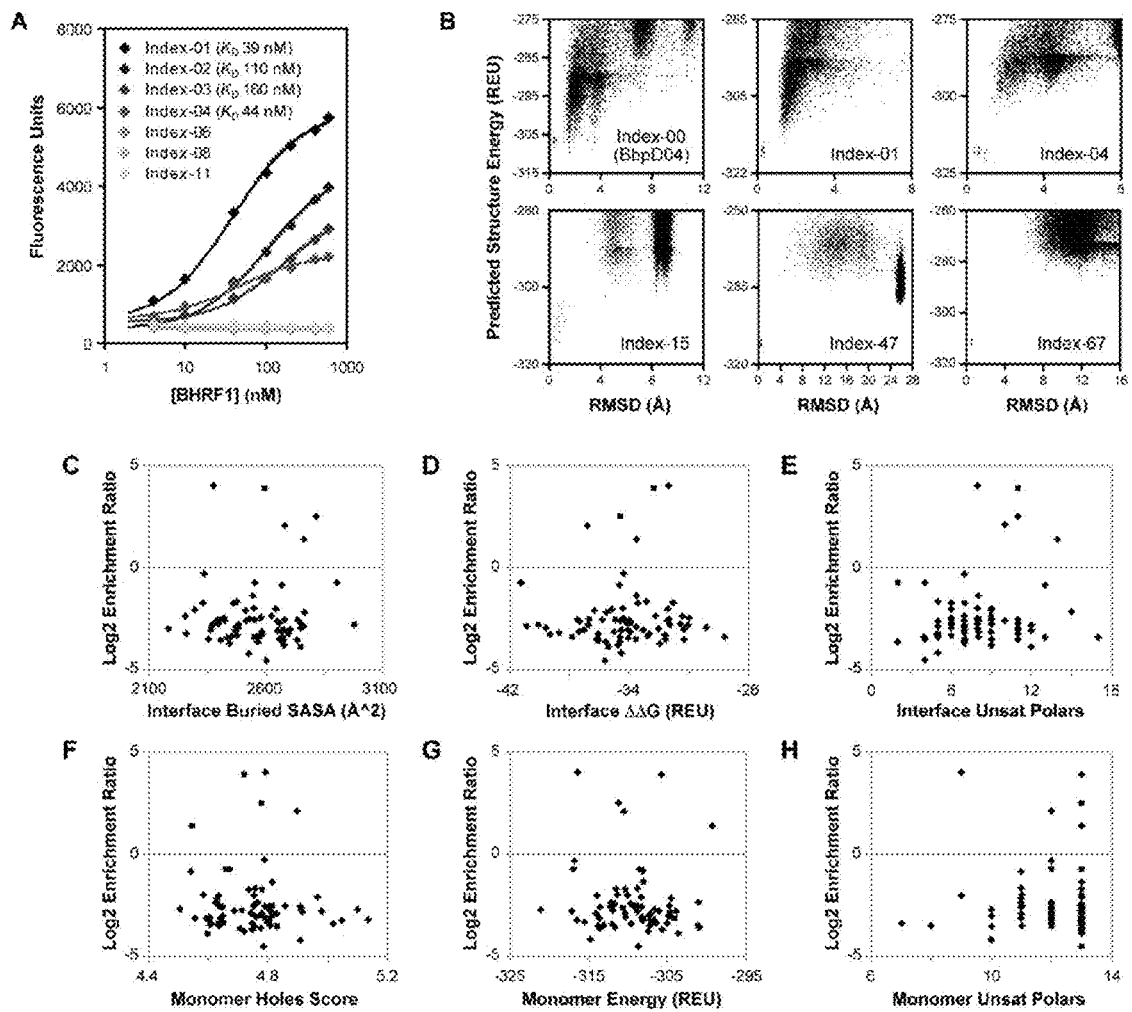

The success rate for designing functional proteins is low, and computational design still requires substantial human intervention to choose and modify the designs prior to experimental validation. For example, working design BbpD04 contained 15 human-introduced mutations out of 116 total residues from its inactive computational 'precursor' (FIG. 2A). These mutations increased packing within the hydrophobic core and hydrophilicity of the exposed surface. This motivated us to test a library of designs 'direct from the computer', without any human modifications. Using the Bim-BH3 motif as a seed for ab initio protein assembly, 5,000 proteins were designed as described for BbpD04 and BbpD07 above (i.e. the guiding scaffold was 3LHP chain S and the Bim-BH3 incorporation site spanned residues 54-67). This was reduced to 74 designs (Indexes-01 to 74) after filtering for strong interface binding energy, low monomer folding energy and a low number of buried unsatisfied hydrogen bonding atoms. Barcoded genes were synthesized (Table 3) and the library transformed in to yeast for surface display ($6 \times 10^5$ transformants). BbpD04 (Index-00) was included as a positive control, and the computational precursor for BbpD04 (Index-21; prior to human modification) was also present. The library was sorted by a single round of FACS for cells expressing surface protein (FIG. 1C; lane 1), for the 2% of cells with highest expression (lane 2), and for cells showing binding signal after incubation with 100 nM (lane 3) or 400 nM BHRF1 (lane 4). DNA from the naive and post-sorted populations was harvested and sequenced by Illumina deep sequencing, and the recovery of each designed sequence determined. A minority of designs (Indexes-00 to 27) were enriched following sorting for expression, and just five designs (Indexes-00 to 04) were highly expressed and enriched after sorting for BHRF1 interaction (FIG. 1C). While the four new functional designs share the same 3-helix topology, the structural details and sequences differ considerably (FIG. 2A-D). BHRF1 binding was validated on clonal yeast populations (FIG. 3A).

TABLE 3

Sequences of seeded ab initio designs tested by high throughput library sorting. Enrichment ratios following yeast display and sorting are indicated.

```
Index 00 (Design BbpD04) DNA Barcode: AGTCATTGCAGTCATTGC (SEQ ID NO: 167)
GADWKKVLDKAKDIAENRVREIKQKLEEFYKKAMKLDLTQEMRRKLMLEWIAAMLMAIG
DIFNAIEQAKQEADKLKKAGQVNSQLLDELKRRLEELKEEASRKCHDYGREFQLKLEYG
(SEQ ID NO: 92)
Log₂ Enrichment Ratios: Expression 1.13, High Expression 2.54, 100 nM BHRF1 3.92, 400 nM
BHRF1 3.19

Index 01 DNA Barcode: TCAACTGGTTCAACTGGT (SEQ ID NO: 168)
GKRLEETVEETERRLREALREVYLLILLLAEEAKKKDLKEQNRHEYVFKWIAFMLMAIGDIF
NIAEESKRRLDLFAKWGLHDRNKIDEAKKKIDKLALEAIERAKKYGDWFLNELDKG (SEQ ID
NO: 93)
Log₂ Enrichment Ratios: Expression 1.16, High Expression 1.23, 100 nM BHRF1 4.02, 400 nM
BHRF1 3.54

Index 02 DNA Barcode: TTAAGCCTGTTAAGCCTG (SEQ ID NO: 169)
GKSLLGIALEALEEAKRDLEKAKKQMEEMLKKKWKFDTTRDLKARASAEWIAAALKAIGD
RFNAKLLIELGLDELFNKGLITQDIKEDIKRRAEEIFEKIERLIKQAIKDKDRFEKLG (SEQ ID
NO: 94)
Log₂ Enrichment Ratios: Expression 1.13, High Expression 1.08, 100 nM BHRF1 3.92, 400 nM
BHRF1 3.43

Index 03 DNA Barcode: TTAGACCACTTAGACCAC (SEQ ID NO: 170)
GLDHDKIVDEARKKMEKKIREAKDKAKEFVLKALDNNHDLKQFRELAHKWIALMLMAIGD
AFNIMMEAKRKAEWLREQGQQDEDKAEEAKEKLDKAFKEAAERFEEIAKIYGKQAKNG
(SEQ ID NO: 95)
Log₂ Enrichment Ratios: Expression 1.10, High Expression -0.16, 100 nM BHRF1 2.52, 400 nM
BHRF1 3.17

Index 04 DNA Barcode: GCTATCATCGCTATCATC (SEQ ID NO: 171)
GLLAEEGREQAEERLREARKKAEKAGDKIKDLAKYGQDSDDEKKKFMLKWIAAQLMVIGD
MFNHAMEALWELLRRLKNNKISWDAFLKAKEEIEREEKEAARDSREKGREAAKMIDQG
(SEQ ID NO: 96)
Log₂ Enrichment Ratios: Expression 0.40, High Expression 0.07, 100 nM BHRF1 2.11, 400 nM
BHRF1 1.96

Index 05 DNA Barcode: ACAGCTTCAACAGCTTCA (SEQ ID NO: 172)
GKDADKKKDEAKKKAEWKEREVFERLEKMEWKKRKDSVSKDDARKFTLKWIADDLELIG
DLFNLKEEAREVAEDAARNNQITEEQREEDEKDLEKLAKEHSWRAAYRGKLKAKEFWEG
(SEQ ID NO: 97)
Log₂ Enrichment Ratios: Expression 1.07, High Expression 0.31, 100 nM BHRF1 -2.50, 400 nM
BHRF1 -0.83

Index 06 DNA Barcode: TCCAACATGTCCAACATG (SEQ ID NO: 173)
GRSANDILKQFLEMLQEALRKFDEKKNKIEDEWKQFDLSTQRREEATHKWIAAALMAIGDM
```

TABLE 3-continued

Sequences of seeded ab initio designs tested by high throughput library sorting.
Enrichment ratios following yeast display and sorting are indicated.

FNALRWALEEALKAKLKNLQSSDDLKEAIERMMKLMLEKAQEIQEKGRELADKIEQG (SEQ
ID NO: 98)
Log$_2$ Enrichment Ratios: Expression 0.86, High Expression 2.77, 100 nM BHRF1 −2.35, 400 nM
BHRF1 −1.45

Index 07 DNA Barcode: CTGAACTGACTGAACTGA (SEQ ID NO: 174)
GEEFKKKLKKWEEWLLKATNEAENQARNMWQKAEQTDLEDQQRIRAVDFWIAIALMAIGD
KFNADQEGDEEFEKYKKKGRASEDKIKEAKDERDRAKKRWEQFVKEAGERAFRGEQLG
(SEQ ID NO: 99)
Log$_2$ Enrichment Ratios: Expression 1.33, High Expression 0.72, 100 nM BHRF1 −2.79, 400 nM
BHRF1 −1.16

Index 08 DNA Barcode: TGACGCATTTGACGCATT (SEQ ID NO: 175)
GWDARRALKYVYERMREDLEYARNQIDNMEDRADQYDARTEERKEFTKRWIALALMLIGD
GFNAFERAKEWIDDGKNNNQRSSDEADYAKDEALKFIFYAAFEARRKGDELDKKAEGG
(SEQ ID NO: 100)
Log$_2$ Enrichment Ratios: Expression 1.53, High Expression 2.32, 100 nM BHRF1 −3.06, 400 nM
BHRF1 −0.80

Index 09 DNA Barcode: GGAATCGATGGAATCGAT (SEQ ID NO: 176)
GKEAKKRIQEALEEAKRKAEKLLREHEKKKKEHLLGDKRDREKTEETDKWIAEALMLIGDIF
NLYMKFEWEKEREKKLGLLREEEEKEVEDEAKDAYLKALKLAYLVSKKGHEVAELG (SEQ
ID NO: 101)
Log$_2$ Enrichment Ratios: Expression 0.18, High Expression 0.86, 100 nM BHRF1 −2.55, 400 nM
BHRF1 −2.05

Index 10 DNA Barcode: GAAGGCTATGAAGGCTAT (SEQ ID NO: 177)
GDSDDDDLKDALLRMLWAAAQAIYHSLENMERKEKFDMHFEEERRDTLQWIADALRAIGD
AFNEMMRRRRELEKKRENNIISEQRARLYEEFLKRFAEWASRELAKAGKKEANKLNEG (SEQ
ID NO: 102)
Log$_2$ Enrichment Ratios: Expression 1.30, High Expression 1.47, 100 nM BHRF1 −0.72, 400 nM
BHRF1 0.62

Index 11 DNA Barcode: GACGTTACAGACGTTACA (SEQ ID NO: 178)
GNILDEAKDEMREEMEKLWKKFKDEVEEERKEAEREEKHFQERAELTKRWIARALMAIGD
MFNRFREAKEKLEKRRELGLISEEDARKALLLLEEFMRRMAEFAKKLGDDLMRDAEKG
(SEQ ID NO: 103)
Log$_2$ Enrichment Ratios: Expression 0.34, High Expression 2.13, 100 nM BHRF1 −2.62, 400 nM
BHRF1 −1.55

Index 12 DNA Barcode: AGTGGCATAAGTGGCATA (SEQ ID NO: 179)
GEDDDKVLKWALEALRKVLDEAKEKLEKLKKYTDGDGFGEDYRREFFRKWIAIALEAIGDIF
NIMMEALQKADKHKKLNTHDSQKADEAKEKIKKFADEAEERAKELAKKGEAWLLKG (SEQ
ID NO: 104)
Log$_2$ Enrichment Ratios: Expression 1.13, High Expression 1.08, 100 nM BHRF1 −2.56, 400 nM
BHRF1 −1.37

Index 13 DNA Barcode: TAGATCGAGTAGATCGAG (SEQ ID NO: 180)
GSKWEEDREKAKREAEKKLDEAKDKLDLYKDFALRFDASDELKTKWTLEWIALALEMIGD
VFNYALEAKEFAEKKARNNLLLDDLKDLYKLYLALLAKEESKKAIEEGDKLREAIEKG (SEQ
ID NO: 105)
Log$_2$ Enrichment Ratios: Expression 1.19, High Expression 1.58, 100 nM BHRF1 −3.07, 400 nM
BHRF1 −1.60

Index 14 DNA Barcode: CCTTGAGAACCTTGAGAA (SEQ ID NO: 181)
GLSADDLFDYAEDRMREGWKDFEELAGEAEKKAKEHTLSDQERREATEKWIAAALELIGDA
FNAIRWAEELGKLYVKLNLDDKQKVEELKKKLEERAKEEAQKARKRGDKLEDLADSG (SEQ
ID NO: 106)
Log$_2$ Enrichment Ratios: Expression 1.32, High Expression 1.78, 100 nM BHRF1 −2.91, 400 nM
BHRF1 −0.65

Index 15 DNA Barcode: CATGTCTCACATGTCTCA (SEQ ID NO: 182)
GNDRDQIEEYHRERMDEELDRAKKRLEELKKLWEKLDGDDLMKFFWTFKWIAESLKIIGDL
FNRLLRTWEFABEALKKGIGFDEKKAEEEAKERAYERAAEAAWKAAKLSREMREFLLKG (SEQ
ID NO: 107)
Log$_2$ Enrichment Ratios: Expression 1.60, High Expression 2.73, 100 nM BHRF1 −2.77, 400 nM
BHRF1 −0.71

Index 16 DNA Barcode: CATCTGCTACATCTGCTA (SEQ ID NO: 183)
GNSADDILDEARDRHERTALWAKDQEDNLKDEAEKGDIGTEQLIRLTMKWIAIQLMAIGDAF
NFAMEAKKKLDLLKKLNLVQAQKLEEAKERADKFEKKADQLSSKFGREMARDLAQG (SEQ
ID NO: 108)
Log$_2$ Enrichment Ratios: Expression 0.13, High Expression −2.21, 100 nM BHRF1 1.40, 400 nM
BHRF1 1.61

Index 17 DNA Barcode: CCATCTTAGCCATCTTAG (SEQ ID NO: 184)
GRSAEIMREILEKQAEDDAKKIRDIAQKWKERRKRYDPRDEEREEEVEKWIAFALMAIGDIFN

TABLE 3-continued

Sequences of seeded ab initio designs tested by high throughput library sorting.
Enrichment ratios following yeast display and sorting are indicated.

LARWALLQARWERRWNLSHEDEGKNHEENVKDAEDRAHWKAREAAREGAKMSWEG
(SEQ ID NO: 109)
Log$_2$ Enrichment Ratios: Expression 0.20, High Expression -3.24, 100 nM BHRF1 -3.41, 400 nM BHRF1 -2.54

Index 18 DNA Barcode: TTGCCGATTTTGCCGATT (SEQ ID NO: 185)
GGTEDDIKDLAEKWRDDMKKEFLREFLRIKEWTKYWGWREEGRKLATLRWIALSLMHIGD
LFNLKELAKKLVDDIKKKGLEHEERAERAREEAEKIMEKAAKLDSILSKLAAKLIEEG (SEQ
ID NO: 110)
Log$_2$ Enrichment Ratios: Expression 0.69, High Expression -1.70, 100 nM BHRF1 -1.36, 400 nM BHRF1 0.98

Index 19 DNA Barcode: CACGATTCTCACGATTCT (SEQ ID NO: 186)
GERVEEILRKMLDDALLHFLEHRDDARERKERGERHQPRDEEREELSHDWIAAALMAIGDIF
NAKLRAEERAEEFLKWGLRSQDDKKELEERAKEAAKIALKWAEEAGKEADEAEKAG (SEQ
ID NO: 111)
Log$_2$ Enrichment Ratios: Expression 0.40, High Expression -2.28, 100 nM BHRF1 -2.97, 400 nM BHRF1 -1.98

Index 20 DNA Barcode: AGAATTGCCAGAATTGCC (SEQ ID NO: 187)
GLRFEEIERYAREEADKIADEAKERFEKLKKLFLWLTDKDEERLKMTHLWIAGALEAIGDLF
NAAELAKELAEKAARLTSQDANRRDEARKKIDEAEKEAADKVSKAAKEAAKFFEQG (SEQ
ID NO: 112)
Log$_2$ Enrichment Ratios: Expression 0.54, High Expression -1.99, 100 nM BHRF1 -3.87, 400 nM BHRF1 -3.65

Index 21 DNA Barcode: ATTAGTCGGATTAGTCGG (SEQ ID NO: 188)
GFDWKKVLDKAKDLAENDVREAKQKLEEFYKKAMKLDLTQEMRRKLMLEWIAAMLMAIG
DIFNAIEQGKQEADKLKKLGKVLSQLLDELKRRLEELKEEAALKAHDFGREFELKLLFG (SEQ
ID NO: 113)
Log$_2$ Enrichment Ratios: Expression 0.49, High Expression -1.20, 100 nM BHRF1 -3.38, 400 nM BHRF1 -2.81

Index 22 DNA Barcode: GATGACTTCGATGACTTC (SEQ ID NO: 189)
GSSAEDLRDWARDQHEKDVDKMEKRLRLLYFELARKDFNEEELKKATEKWIAAALDAIGD
HFNAALKARLLARDAAKKGLIDRNKLDEVEKMAELFEELGERKAALKGREFLRWVLLG
(SEQ ID NO: 114)
Log$_2$ Enrichment Ratios: Expression 0.59, High Expression -3.19, 100 nM BHRF1 -3.03, 400 nM BHRF1 -2.40

Index 23 DNA Barcode: ATCGATCTCATCGATCTC (SEQ ID NO: 190)
GEDEEKDHKDTEEKARRLHERARDMLDKVKDLEEKTDAQDNERRRATHDWIAAALMMIG
DAFNSFEDTKRRAEKKRELNLISEDEAKEKIKRAEELRKRIYELLKKAAEFAREAEKGG (SEQ
ID NO: 115)
Log$_2$ Enrichment Ratios: Expression 0.78, High Expression -1.37, 100 nM BHRF1 -1.72, 400 nM BHRF1 -0.17

Index 24 DNA Barcode: TGTCTAGTGTGTCTAGTG (SEQ ID NO: 191)
GELAREAAEEAHRRVEEDARDAKNRLDEFKKRYKITQLSKSDISRATALWIAAALDAIGDIFN
AKQKAEKILGLWYKLGLVQLQEFLEKEDKARYHWQAALERAFEAGRDMLEVAAYG (SEQ
ID NO: 116)
Log$_2$ Enrichment Ratios: Expression 0.48, High Expression -1.95, 100 nM BHRF1 -3.02, 400 nM BHRF1 -2.95

Index 25 DNA Barcode: GGATGTTCTGGATGTTCT (SEQ ID NO: 192)
GANHEDAIWEALYKAEDAFKDHLKEIEIYREFSEKFWPLDDYKDNLRAHWIAAALAAIGDW
FNVFFEAELKFREAKRKNLRSEDDIKKYRWRLFKALDIAIDLADRVGDEAEKAERLG (SEQ
ID NO: 117)
Log$_2$ Enrichment Ratios: Expression 0.95, High Expression -1.01, 100 nM BHRF1 -2.90, 400 nM BHRF1 -1.53

Index 26 DNA Barcode: ATGGTGTCTATGGTGTCT (SEQ ID NO: 193)
GRFAERLFKKMLIKQLLNTQYFRDQLKQLKDRSKKYDASDDDKDEATHRWIAFALMAIGDV
FNDKLEIELLIELFAKYGLVHEEERKEFRKRLDEFEKIFRKWLDELKKLALEALNQG (SEQ ID
NO: 118)
Log$_2$ Enrichment Ratios: Expression 0.50, High Expression -1.87, 100 nM BHRF1 -2.74, 400 nM BHRF1 -2.00

Index 27 DNA Barcode: CTCAGATCACTCAGATCA (SEQ ID NO: 194)
GLDGDYLMDEAFKFIERERERAEEEAKKMYELAEKGKYYEERKTKATKFWIALALEMIGDF
FNFEMWFRKYAEKNRENNQRREDLLRRWELLLRFQAWDAAERARELGKRLELWFKKG
(SEQ ID NO: 119)
Log$_2$ Enrichment Ratios: Expression 0.71, High Expression -2.21, 100 nM BHRF1 -0.72, 400 nM BHRF1 0.86

Index 28 DNA Barcode: CTACGACATCTACGACAT (SEQ ID NO: 195)
GKEGSRLREEAERRGLRKLLEVILRWLEDALRMIYGQDKDEDRKEATHRWIADALELIGDIF

TABLE 3-continued

Sequences of seeded ab initio designs tested by high throughput library sorting.
Enrichment ratios following yeast display and sorting are indicated.

NALLEAFIKMELARRFGLLEEQRARDEKKKALERAEEFSKRARELGEKLTQILEGG (SEQ ID
NO: 120)
Log$_2$ Enrichment Ratios: Expression -2.87, High Expression -4.25, 100 nM BHRF1 -4.52, 400 nM
BHRF1 -2.85

Index 29 DNA Barcode: CTAGGTGTACTAGGTGTA (SEQ ID NO: 196)
GEVAKDLAKLAIDLAKKLMLLFWWFFELFKLFAKFTDEWQEWKARGTAFWIALSLAAIGDF
FNARRRAELQAREGKQKGLTTEEKEKRWREHLKEAWEKLEKISRLAFLFAQEAENQG (SEQ
ID NO: 121)
Log$_2$ Enrichment Ratios: Expression -1.14, High Expression -2.44, 100 nM BHRF1 -1.66, 400 nM
BHRF1 -2.43

Index 30 DNA Barcode: AAGTTGACCAAGTTGACC (SEQ ID NO: 197)
GSRWFDAEDKMRERKDRAILQLLFMLWIIFYILWYGDDTEEAKRKAMAAWIALALIGIGDIF
NAEAEFLEELERAIKQGQVSDQLKEELLKRMEDDKRDLEKRLYEFLLKALLQWMQG (SEQ
ID NO: 122)
Log$_2$ Enrichment Ratios: Expression -1.26, High Expression -1.69, 100 nM BHRF1 -2.58, 400 nM
BHRF1 -4.10

Index 31 DNA Barcode: AAGGCCATTAAGGCCATT (SEQ ID NO: 198)
GDQADKIKDKIKDEAKKKADEFKKRLEQFREYLEKVYSDDLKEIYLTIFWIALALMLIGDAF
NEKMLLEWEFKERKKRNLRHEEELKEEKKKREEAEKALEWASKYASQVGKEAAEEG (SEQ
ID NO: 123)
Log$_2$ Enrichment Ratios: Expression -2.65, High Expression -3.58, 100 nM BHRF1 -3.55, 400 nM
BHRF1 -4.21

Index 32 DNA Barcode: TGGCTTCTATGGCTTCTA (SEQ ID NO: 199)
GGDENKLKDYVKDEIERGLNEIEDLARKIEQLARRFFPKDEERMKFTMWWIAAALMAIGDIF
NAKEYARERAEEIRRKGLRREEEARRIEKFIEEEAEKAAKKAAKLGDHLAEELFRG (SEQ ID
NO: 124)
Log$_2$ Enrichment Ratios: Expression -0.75, High Expression -0.86, 100 nM BHRF1 -2.00, 400 nM
BHRF1 -2.56

Index 33 DNA Barcode: GTCTTCTGAGTCTTCTGA (SEQ ID NO: 200)
GKQWQEAFEEARRRIEEKAREFEDRAKKEALLHLFFIPHDKEIADNSKKWIAWALMLIGDIFN
LEEEAAERARRHVKRGEISEDDAKQIRKRLQEQAKRAAWWMRYWGEESAKFAFIG (SEQ
ID NO: 125)
Log$_2$ Enrichment Ratios: Expression -2.15, High Expression -3.65, 100 nM BHRF1 -4.18, 400 nM
BHRF1 -3.85

Index 34 DNA Barcode: TGCTCACAATGCTCACAA (SEQ ID NO: 201)
GKFKKLFENYAELFARWVADKGKKLAEELREKAEKGLKLQKLWLIFTMIWIAIMLMSIGDA
FNLALLAELWVQAAKNYGWLRDNEADEAEDRVRKFADEASRRALEKGLEALRKILEG (SEQ
ID NO: 126)
Log$_2$ Enrichment Ratios: Expression -3.29, High Expression -4.31, 100 nM BHRF1 -3.41, 400 nM
BHRF1 -2.21

Index 35 DNA Barcode: ATAGCTGAGATAGCTGAG (SEQ ID NO: 202)
GGDGVKELEEELEKRKDEKKNKAEDRIKKFKDEAKYADDRTEDKEKLAHRWIALALDIIGDA
FNLKEEARRRFLRHKFRGELDDSKKEYAEKEMKRFEDDVEKDAEELAQKAKEAFKEG (SEQ
ID NO: 127)
Log$_2$ Enrichment Ratios: Expression -2.24, High Expression -3.49, 100 nM BHRF1 -3.51, 400 nM
BHRF1 -3.29

Index 36 DNA Barcode: AAGTCAGAGAAGTCAGAG (SEQ ID NO: 203)
GYTKEWIRDRAKEELDRFADEAKDKADKIRDDFEKRDDKNQIAAELTKKWIAAELEAIGDA
FNRAEEAKERLKKLLKLGLTRKEEAEEAAEKLEKLEKEASEKLSKIAHEVSKHDDQG (SEQ
ID NO: 128)
Log$_2$ Enrichment Ratios: Expression -2.73, High Expression -3.32, 100 nM BHRF1 -3.60, 400 nM
BHRF1 -3.65

Index 37 DNA Barcode: TATTGCCTCTATTGCCTC (SEQ ID NO: 204)
GDFWLKAIEIAGGRMLERARESWYRALYFILMVKLFYPSDDLRRIFTLRWIAESLKLIGDAFN
LFELARELLELYYKYGWITLEKALKALWILLKLEEIFSKASKDLGERLAEEIERG (SEQ ID NO:
129)
Log$_2$ Enrichment Ratios: Expression -1.72, High Expression -3.52, 100 nM BHRF1 -3.13, 400 nM
BHRF1 -2.14

Index 38 DNA Barcode: GCTTATGGTGCTTATGGT (SEQ ID NO: 205)
GEKLKKLAEEELEKKFRKLFFILKDELDRAYLIALKTQVQRQELARDTKLWIAVALMIIGDLFN
AEIQGKELRDKLIKKNQVEEQKAKEFWKKWEEVKQRAEELIKKGGEMVERLADYG (SEQ
ID NO: 130)
Log$_2$ Enrichment Ratios: Expression -0.73, High Expression 0.48, 100 nM BHRF1 -1.71, 400 nM
BHRF1 -1.46

Index 39 DNA Barcode: GCTGTATACGCTGTATAC (SEQ ID NO: 206)
GKKYLKAARLALYLLWEAYLRGYLNLLLDELEAEFFDPHDERKIRYTINWIADALMLIGDLF TABLE 3-continued Sequences of seeded ab initio designs tested by high throughput library sorting.
Enrichment ratios following yeast display and sorting are indicated.

NARLKMEKALWELKKEGKLREEDYEKMERLFRKWMELAFKWLEHFREMAEKAKKKG
(SEQ ID NO: 131)
Log$_2$ Enrichment Ratios: Expression -1.76, High Expression -2.01, 100 nM BHRF1 -2.08, 400 nM
BHRF1 -2.01

Index 40 DNA Barcode: GAATCCTCAGAATCCTCA (SEQ ID NO: 207)
GNEAEQRREEFKEIMEKKKDEAEKKSEKIKRLALAFDLSDDDKTKATDEWIAISLEIIGDAFN
FGEGLKDEAKRRKKRGLKRDEEVDKFEKIAEQAIEELRKLAEEADERGAKHLRDG (SEQ ID
NO: 132)
Log$_2$ Enrichment Ratios: Expression -2.67, High Expression -3.15, 100 nM BHRF1 -3.70, 400 nM
BHRF1 -4.69

Index 41 DNA Barcode: CATCAGTGTCATCAGTGT (SEQ ID NO: 208)
GEQEDKVKERAKRGALERAREMFEKMRKAIYLAELYINNDEGKTKLTDRWIAFALMMIGDI
FNIALEARLEALKLVLKGLRSQEDAEKVKKLAEEAEREAAKRAAKLGDKMDEKEHEG (SEQ
ID NO: 133)
Log$_2$ Enrichment Ratios: Expression -0.27, High Expression -1.86, 100 nM BHRF1 -2.17, 400 nM
BHRF1 -2.39

Index 42 DNA Barcode: ACCTGTAACACCTGTAAC (SEQ ID NO: 209)
GQQEEQFIEDFKKEVLRAADDAKDDMEKRAEEFLKKDGDDNEKKRKILKWIADALEAIGDL
FNAAQEAKRRAELYFKLGLLKKERKEEAEEEAEKAKEEASKKLHKAAREARIKMEKG (SEQ
ID NO: 134)
Log$_2$ Enrichment Ratios: Expression -3.04, High Expression -3.00, 100 nM BHRF1 -3.63, 400 nM
BHRF1 -3.15

Index 43 DNA Barcode: CCGTAATTGCCGTAATTG (SEQ ID NO: 210)
GKKAEEVLKEARKLHEAQLRYAYLMMKDWREKKQQEEKQTQREEKWTAWWIALMLMAI
GDIFNFAEWAKEELDKLREKGLVEKKKAEEAKEKAEKLAEEASRRASEFAQLFAKWDKEG
(SEQ ID NO: 135)
Log$_2$ Enrichment Ratios: Expression -2.29, High Expression -1.97, 100 nM BHRF1 -2.44, 400 nM
BHRF1 -3.04

Index 44 DNA Barcode: CCAAGCAATCCAAGCAAT (SEQ ID NO: 211)
GESGEWILEKTREKIERAIRDAEKKLRLIILLIRLFHPGDDLRALFAAIWIAAELELIGDIFNEKQ
DAEEKFKELLKKNQFRWEELWRKWLILEWIFQKARRKSKELAERAKKAFDFG (SEQ ID NO:
136)
Log$_2$ Enrichment Ratios: Expression -0.78, High Expression -3.17, 100 nM BHRF1 -3.29, 400 nM
BHRF1 -3.16

Index 45 DNA Barcode: TAGCGTACTTAGCGTACT (SEQ ID NO: 212)
GYSLDDFLKLAKLLAELLKRFIRKEAERLRELKEWLLDTTLGRLILTLEWIAIELMIIGDIFNAK
MLLDKFAKYAEWLGLMKEEEAKQAKKLAKLLLDEVKDEARKKADDGEKFAEEG (SEQ ID
NO: 137)
Log$_2$ Enrichment Ratios: Expression -2.31, High Expression -2.28, 100 nM BHRF1 -2.44, 400 nM
BHRF1 -3.17

Index 46 DNA Barcode: GCAACTATGGCAACTATG (SEQ ID NO: 213)
GRDGERVVKWAKNQHENTVDEAKDKMDNQEDEMRKKNADDEKLRKETHKWIAFALEAIG
DVFNDAMQAFELLERFKKFGQQEQKKLDEFKEKVERLAREASRKLTYLGKRFALDIESG
(SEQ ID NO: 138)
Log$_2$ Enrichment Ratios: Expression -0.31, High Expression -3.37, 100 nM BHRF1 -3.41, 400 nM
BHRF1 -3.60

Index 47 DNA Barcode: CTGTCGTAACTGTCGTAA (SEQ ID NO: 214)
GWSADWIKDQAKELMLRAAEEMKKRADEEEKKFKYKQFTTEFLTKATMRWIALALMAIGD
VFNVLMWALEWAKRMAKLNQYRKEELEKAKEEAAKKLAEKAARRITEIGREAEQKALKG
(SEQ ID NO: 139)
Log$_2$ Enrichment Ratios: Expression -2.07, High Expression -2.42, 100 nM BHRF1 -3.13, 400 nM
BHRF1 -2.79

Index 48 DNA Barcode: TTACTGACGTTACTGACG (SEQ ID NO: 215)
GEKGKEKAQKFRDIIKDILEEAIRLAKDLAEDAKKFDLKLEKLLEATLKWIAAALMAIGDLFN
FKDLAEKEVRERHDRGEISSDRRDKYEKEAREGADEAAKELSKLAKIAEKKILEG (SEQ ID
NO: 140)
Log$_2$ Enrichment Ratios: Expression -2.24, High Expression -3.39, 100 nM BHRF1 -2.80, 400 nM
BHRF1 -2.33

Index 49 DNA Barcode: CGTATGATGCGTATGATG (SEQ ID NO: 216)
GWSKDWVLEWLREKLEEIDREALWKFILIWIEKMLGVDDDEQRRKDAAKWIAGSLEAIGDIF
NAMMWAKRLLEWLEKANLVRREELEKAKQKAEEELAKKAALRAAIYSKIAEEWLWKG
(SEQ ID NO: 141)
Log$_2$ Enrichment Ratios: Expression -2.07, High Expression -3.05, 100 nM BHRF1 -2.70, 400 nM
BHRF1 -1.22

Index 50 DNA Barcode: ATCGGTAGTATCGGTAGT (SEQ ID NO: 217)
GKRAEELREEAEERAKEAFKETEQKLREVEERSRQTLARDEELRKAALLWIAAALMGIGDLF

TABLE 3-continued

Sequences of seeded ab initio designs tested by high throughput library sorting. Enrichment ratios following yeast display and sorting are indicated.

NKKEKGKEALEKEEKNGKRRTERAEREKERLEKEVSREAQRFKKKGEEEEKKHKYG (SEQ
ID NO: 142)
Log$_2$ Enrichment Ratios: Expression -2.93, High Expression -2.75, 100 nM BHRF1 -3.79, 400 nM
BHRF1 -3.47

Index 51 DNA Barcode: GATCAACTGGATCAACTG (SEQ ID NO: 218)
GWTALWLKDFTEQEARKKFREALYYGWMMAMRALEHQLQADELAMWTALWIAAMLEAI
GDMFNDKLRAEKYALLLIWLNLYHKDIAEKWREEHEEKLKEALQEMFEAAEKFDKFAKFG
(SEQ ID NO: 143)
Log$_2$ Enrichment Ratios: Expression -1.53, High Expression -2.24, 100 nM BHRF1 -2.53, 400 nM
BHRF1 -2.43

Index 52 DNA Barcode: AGTCTACCTAGTCTACCT (SEQ ID NO: 219)
GNDKEKFREDVKKKAKYALWKLKKLADEAKERALKFDPSEEMKREFTLEWIAWALEAIGDI
FNAWLDGKKYADEAKKQGKARKEEAEETKKEATRIAKEAHEKASELARKILYHMLLG (SEQ
ID NO: 144)
Log$_2$ Enrichment Ratios: Expression -0.35, High Expression -3.17, 100 nM BHRF1 -0.83, 400 nM
BHRF1 -0.20

Index 53 DNA Barcode: ATGATCGGTATGATCGGT (SEQ ID NO: 220)
GHVAEEEIRRFLRKAEKVLQEARRKMEKRRREAEEHDTTTWLLARGTIEWIADALMLIGDAF
NFRREAYIRGELYKKFGLIREDDLKDRLKEADQRLDEFAKKMALFGLELHLRLREG (SEQ ID
NO: 145)
Log$_2$ Enrichment Ratios: Expression -0.27, High Expression -2.43, 100 nM BHRF1 -0.29, 400 nM
BHRF1 0.40

Index 54 DNA Barcode: GTGCAATGTGTGCAATGT (SEQ ID NO: 221)
GDKHEEAKEEAEKKFEKLRIEARLKAEWLKKAGKYGLQLQELWAKLSDYWIAFALEIIGDLF
NFLEEHKEKIEKDLKKGEALDDRADDILKDLEKKAKEVSKHAMKLGREAQQFIELG (SEQ ID
NO: 146)
Log$_2$ Enrichment Ratios: Expression -1.26, High Expression -1.71, 100 nM BHRF1 -3.22, 400 nM
BHRF1 -2.24

Index 55 DNA Barcode: TGAATGCCATGAATGCCA (SEQ ID NO: 222)
GEEAEKLIKEAKDKFEDLREKAEELLYKMWLIRYLSSKDTKRGEIYTKKWIAIMLMMIGDAF
NMALRARLYLEERRKRGEKHEEEAEEKERRARWEQEDAYKKAKKGAKRARLYDKLG (SEQ
ID NO: 147)
Log$_2$ Enrichment Ratios: Expression -1.78, High Expression -1.88, 100 nM BHRF1 -2.69, 400 nM
BHRF1 -3.29

Index 56 DNA Barcode: AACAGTCCAAACAGTCCA (SEQ ID NO: 223)
GESAEKWRERLREKAGYWAEYAFWLADEAEKRAKIYSASSERRAEWTMRWIAIALAAIGD
VFNEGQKADEKFDELKKQNKRSDDDLDDYKDKFKEEVEKALRKLLKAGDKIADLAEQG
(SEQ ID NO: 148)
Log$_2$ Enrichment Ratios: Expression -2.62, High Expression -3.45, 100 nM BHRF1 -3.49, 400 nM
BHRF1 -3.81

Index 57 DNA Barcode: TCCTAACGTTCCTAACGT (SEQ ID NO: 224)
GDLKEELKERAKKIIRRALDEAKDAEDLIKKEAEKRYVTTEMATKFVAWWIAGALMIIGDIF
NAAREVKERAEKALKWGVLSQDDIKELLLELENLEQEAKERAKEFGEKAEKFKKMG (SEQ
ID NO: 149)
Log$_2$ Enrichment Ratios: Expression -0.83, High Expression -3.04, 100 nM BHRF1 -1.97, 400 nM
BHRF1 -2.85

Index 58 DNA Barcode: AGCAGATGTAGCAGATGT (SEQ ID NO: 225)
GEKAKKLEEYAREEIERALREGGDLMEEEREFGEKTELTTEWKHRAMAYWIAAALMIIGDG
FNALQFIEEEGRKFIRKGEFARQKIEEHKERAKERLEKALKQAKKRGDELDRFARLG (SEQ ID
NO: 150)
Log$_2$ Enrichment Ratios: Expression -0.99, High Expression -2.52, 100 nM BHRF1 -2.36, 400 nM
BHRF1 -2.11

Index 59 DNA Barcode: GTATCAGTCGTATCAGTC (SEQ ID NO: 226)
GITLEKLWKEAKEKIRKREDEALLKAEWFKKKANNVLDLNDMKAKMTAKWIALALMAIGD
IFNYLLETEIKARLLVRLGLFRQEEAEKKKEEAKEEAIKSSRNIAKRGEEAAKQMEQG (SEQ
ID NO: 151)
Log$_2$ Enrichment Ratios: Expression -1.98, High Expression -2.63, 100 nM BHRF1 -2.86, 400 nM
BHRF1 -2.36

Index 60 DNA Barcode: AATCGTGGAAATCGTGGA (SEQ ID NO: 227)
GRQEDEIKDEATKRALEILQKLEQKVRKAKKFAKYGLLLQRWWAWITKVWIAAALDAIGD
AFNLGEELKRILEELRRRGLSSEEKAQEIKNWIEWLEKWVAIMAKLFGEELEKQFKQG (SEQ
ID NO: 152)
Log$_2$ Enrichment Ratios: Expression -0.86, High Expression -3.77, 100 nM BHRF1 -2.91, 400 nM
BHRF1 -2.63

Index 61 DNA Barcode: CTCGTAATGCTCGTAATG (SEQ ID NO: 228)
GEHLDELLLKLLWLAIQFAERAKLTIELWKLWGKITQSYNEWAEKAARDWIAAALMIIGDM

TABLE 3-continued

Sequences of seeded ab initio designs tested by high throughput library sorting.
Enrichment ratios following yeast display and sorting are indicated.

FNHKQKAEEEAKKFAKKGLKRKEELEELLKKLEEFIKRAKKLIKETAQKHEEASKMG (SEQ
ID NO: 153)
Log$_2$ Enrichment Ratios: Expression -1.82, High Expression -2.20, 100 nM BHRF1 -2.79, 400 nM
BHRF1 -3.54

Index 62 DNA Barcode: TTCAGTGAGTTCAGTGAG (SEQ ID NO: 229)
GKLGEELREDAEKKGEEDMRRFERRIREIKRKLKFGYDFEQRKREATHKWIAFALEMIGDAF
NFAQKLERALELFKKWNIYSEDDLRELKKRFEEAKEKLKKFADRIRDEGLKAVLLG (SEQ ID
NO: 154)
Log$_2$ Enrichment Ratios: Expression -1.89, High Expression -2.70, 100 nM BHRF1 -3.21, 400 nM
BHRF1 -2.65

Index 63 DNA Barcode: GTAAGTCACGTAAGTCAC (SEQ ID NO: 230)
GDDKEKVKDYAKKRALEDVLRAKELAEKFIDEAKKSDHSKQNERQYIIAWIAFMLMAIGDV
FNAMMEAKRLAELLKRLGLRRWEEAEEVKQKAEELAEEASRLLADLGKDFAKKIEQG (SEQ
ID NO: 155)
Log$_2$ Enrichment Ratios: Expression -0.98, High Expression -2.63, 100 nM BHRF1 -2.52, 400 nM
BHRF1 -2.41

Index 64 DNA Barcode: CTTATCCAGCTTATCCAG (SEQ ID NO: 231)
GLSGDDAEDFARQEIEKRAREAEEKARKLIWLASKYDAKREEALKFHLRWIAFALMMIGDA
FNAEEIAREMLEIARELGLTREEEAKEKLEKIRRKKETEASKKMAERGRRLDNQANNG (SEQ
ID NO: 156)
Log$_2$ Enrichment Ratios: Expression -1.81, High Expression -2.68, 100 nM BHRF1 -3.51, 400 nM
BHRF1 -1.68

Index 65 DNA Barcode: AGGACAGTTAGGACAGTT (SEQ ID NO: 232)
GNDLKDIARQIEEQAKKALDDMAKLIRELAEKKAEKFYPSKDDIRRLTHYWIAAALMAIGDAF
NRLQEARRRAEWLRKWGLRREEEAEKAKKEAEERHERAKELAHKMGDEMEEKLKRG (SEQ
ID NO: 157)
Log$_2$ Enrichment Ratios: Expression -3.11, High Expression -2.45, 100 nM BHRF1 -3.20, 400 nM
BHRF1 -2.31

Index 66 DNA Barcode: GTCATGCATGTCATGCAT (SEQ ID NO: 233)
GRSKDDATKEAWERLERLLKEFKEKAEKLRDKAQAHYVYKQFALKVTILWIAWALKLIGD
AFNFIEEAEKKMRENRERNLISEDDAREEKRKLEEFARRASKKANKIGDDLDRQLELG (SEQ
ID NO: 158)
Log$_2$ Enrichment Ratios: Expression -0.97, High Expression -2.30, 100 nM BHRF1 -2.03, 400 nM
BHRF1 -2.49

Index 67 DNA Barcode: TTCACCGTATTCACCGTA (SEQ ID NO: 234)
GNRSEEVKELMRELAERVLLKFRWRADEMNKEKDKKYDKEELKRELTEKWIAFALDAIGDL
FNAAELAKKLADLFKKGTGFLEERLERRKEEIEKLEEKGSRKVSYEGRREAEKIESG (SEQ ID
NO: 159)
Log$_2$ Enrichment Ratios: Expression -1.41, High Expression -3.44, 100 nM BHRF1 -3.48, 400 nM
BHRF1 -3.44

Index 68 DNA Barcode: TAGTACGCTTAGTACGCT (SEQ ID NO: 235)
GVSIEWAFDFLENKAEEDAREARRLAQKLAEEFFKHSAREEDRAKLTKKWIAVALMIIGDIF
NVEQFTKQQGEEFVKRGLRSEDDFKEYLRKMEEKKEEAERIAKRAKDDMLKARDLG (SEQ
ID NO: 160)
Log$_2$ Enrichment Ratios: Expression -2.49, High Expression -2.65, 100 nM BHRF1 -2.57, 400 nM
BHRF1 -3.63

Index 69 DNA Barcode: TCGTTGAAGTCGTTGAAG (SEQ ID NO: 236)
GEQAEKALRRAKRRAKWGLDDAKDILDDIEAEIRWYYPRDEERFKFVDRWIAAMLMVIGDL
FNAKREALERALRLMRKGLISQDQFKKFMEKLEKIILWGKFQARKLGREKESEITQG (SEQ ID
NO: 161)
Log$_2$ Enrichment Ratios: Expression -2.56, High Expression -2.78, 100 nM BHRF1 -3.25, 400 nM
BHRF1 -3.99

Index 70 DNA Barcode: CATTAACGCCATTAACGC (SEQ ID NO: 237)
GLLWLAIILKAEELARKKDDEAEERIRRLEDEKRKGDPGTLGEAERTDRWIAIMLMAIGDAF
NVMLEAKEEAEKLEKLGLVHKELLEKVKEEAERLFERSSDNFEEAAKRADDMEKEG (SEQ
ID NO: 162)
Log$_2$ Enrichment Ratios: Expression -1.16, High Expression -2.58, 100 nM BHRF1 -3.02, 400 nM
BHRF1 -3.13

Index 71 DNA Barcode: TAGTGGCAATAGTGGCAA (SEQ ID NO: 238)
GERAERARDWAKDQMDDELEKAREKLWKLAFIAFKFYLKLELLFKLMFRWIAIMLEAIGDF
FNVWAIAKRWLERYKLQNNIRKEEIEKAKERAKKLYEEAADKAAKLGRFYMKLLTSG (SEQ
ID NO: 163)
Log$_2$ Enrichment Ratios: Expression -2.79, High Expression -3.00, 100 nM BHRF1 -2.58, 400 nM
BHRF1 -3.07

Index 72 DNA Barcode: ACCGTAAGAACCGTAAGA (SEQ ID NO: 239)
GGSYDDIADLAKKLHKKIAEEAKKKIDELLKEAFEDKPYEEEFAKKMFKWIAIALMAIGDLF TABLE 3-continued Sequences of seeded ab initio designs tested by high throughput library sorting.
Enrichment ratios following yeast display and sorting are indicated.

NAAELAKRLAEDLKKDNNRDENKAEEAKQRAEQFEKEGAEELAKKGEEAAKKLAGG (SEQ
ID NO: 164)
Log$_2$ Enrichment Ratios: Expression -2.19, High Expression -3.48, 100 nM BHRF1 -3.34, 400 nM
BHRF1 -3.47

Index 73 DNA Barcode: GACGAGATTGACGAGATT (SEQ ID NO: 240)
GKDLDEIIDEARKEMDDDADDGKKKAEKLLKLHAGTNHSQDDFNEAHRRWIAVALEEIGDL
FNAALRAWRKIEEEIRKNQRRKEEAEKAKEKVSKEYERASRKAAELGKEFEERVEQG (SEQ
ID NO: 165)
Log$_2$ Enrichment Ratios: Expression -0.07, High Expression -2.31, 100 nM BHRF1 -3.14, 400 nM
BHRF1 -2.27

Index 74 DNA Barcode: TACGAAGTCTACGAAGTC (SEQ ID NO: 241)
GTDHQAFDEWARRELERIVEEARERAERLREWIEQKDASREELTKFFAIWIAISLMAIGDLFN
VKEQAKRLAELLEFLGLQRKEEIEKSKKNAEKLADEAMKKASKLDAKVEKELMQG (SEQ ID
NO: 166)
Log$_2$ Enrichment Ratios: Expression -1.92, High Expression -2.09, 100 nM BHRF1 -3.38, 400 nM
BHRF1 -2.62

Standard metrics for assessing interface quality (FIG. 3C-E) or monomer stability (FIG. 3F-H) did not distinguish the working designs. We hypothesized that many of the failed designs (Indexes-05 to 74) may simply not fold to the designed conformation. The design calculations find the lowest energy sequence for a given structure, but there is no guarantee that the lowest energy state of that designed sequence is the intended target structure. The likelihood of a protein folding depends on many factors, including the probability of an amino acid stretch adopting the correct secondary structure, the formation of a well-packed hydrophobic core, and a single native conformation of lowest energy amongst a vast assortment of alternative states. We used ROSETTA ab initio structure prediction to assess the likelihood that the designed sequence folds to the designed target conformation. Many folding simulations were carried out to give tens of thousands of possible structures (called decoys) that map out a protein energy landscape. An ideal protein would have an energy funnel from distant high-energy conformers towards a low energy folded state, and therefore a small mean RMSD between the lowest energy decoys and the intended designed conformation (plotted in FIG. 1D). Representative energy landscapes are plotted in FIG. 3B. A high calculated probability of correct folding is a common attribute of designs that bind BHRF1 (FIG. 1D). Notably, the human-modified BbpD04/Index-00 control sequence was predicted to fold, but its nonfunctional computational precursor Index-21 was not. This "forward folding" method should be broadly useful in future design efforts.

Enhanced Affinity and Specificity of a BHRF1-Binding Protein Through Improved Electrostatic Complementarity To illuminate BHRF1 biology, the designed protein should not only bind with high affinity, but do so specifically. Design BbpD04, a de novo designed protein without sequence homologues identified by BLAST (Altschul et al., 1997), bound BHRF1 with moderate affinity (apparent KD=58±3 nM) and reasonable specificity, and was therefore chosen for further optimization.

Figure 4:
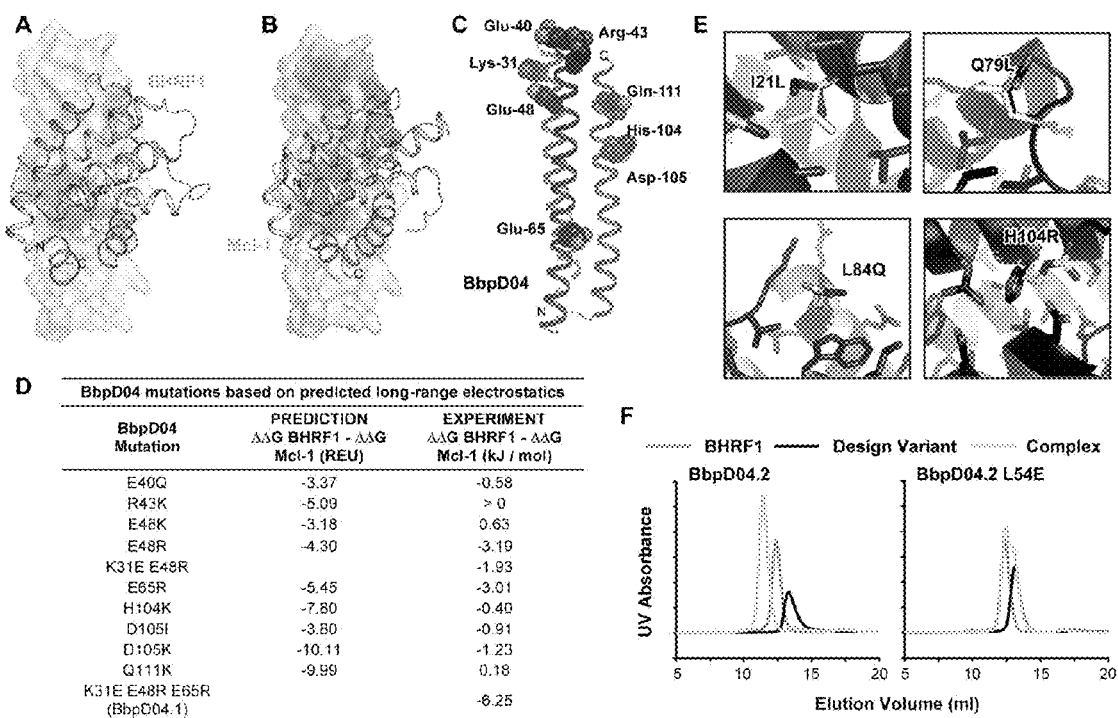

Design BbpD04 binds BHRF1 tighter than all human prosurvival Bcl-2 proteins with the exception of Mcl-1 (Table 2). Based on a Poisson-Boltzmann electrostatics model (Whitehead et al.), the computed electric field experienced by BbpD04 when bound to BHRF1 is markedly more negative than when bound to Mcl-1 (FIG. 4A-B). We therefore introduced nine point substitutions to eight residues of BbpD04 to specifically increase electrostatic complementarity for BHRF1 (FIG. 4C). Six decreased the $K_D$(BHRF1)/$K_D$(Mcl-1) ratio as predicted (FIG. 4D). However, putting many of these beneficial mutations together in combination generally caused a loss in yeast surface expression, possibly indicating poor protein stability. The variant BbpD04.1 containing the best two point mutations (E48R and E65R), together with a third compensatory mutation (K31E) to preserve a putatively stabilizing salt-bridge, bound BHRF1 slightly tighter (apparent $K_D$=8±4 nM) than any of the other human prosurvival Bcl-2 proteins (Table 2).

TABLE 2

| Protein | BHRF1 | Bcl-2 | Bcl-w | Mcl-1 | Bfl-1 | Bcl-X$_L$ | Bcl-B |
|---|---|---|---|---|---|---|---|
| Apparent dissociation constants (nM; mean ± SE, n = 3-6) from yeast surface display titrations | | | | | | | |
| Bim-BH3 | 12 ± 4 | 2.02 ± 0.08 | 2.1 ± 0.1 | 0.6 ± 0.2 | 2.1 ± 0.3 | 3 ± 1 | 12.2 ± 0.1 |
| BbpD07 | 60 ± 10 | 76 ± 7 | — | 3.1 ± 0.3 | >100 | — | >100 |
| BbpD04 | 58 ± 3 | — | — | 17 ± 7 | >100 | — | — |
| BbpD04.1 | 8 ± 4 | 110 ± 20 | 14 ± 5 | 30 ± 10 | >100 | 25 ± 1 | — |
| BbpD04.2 | 0.6 ± 0.2 | 33 ± 4 | 40 ± 10 | 26 ± 4 | 70 ± 20 | 31 ± 2 | — |
| BbpD04.3 | 0.54 ± 0.01 | 20 ± 2 | 34 ± 3 | 19 ± 1 | 32 ± 6 | 34 ± 7 | — |
| BINDI | 0.9 ± 0.2 | 45 ± 7 | 60 ± 10 | 21.6 ± 0.8 | >100 | >100 | — |
| Accurate dissociation constants (nM; mean ± SD, n = 4-6) measured by BLI | | | | | | | |
| Bim-BH3 | 7 ± 3 | 0.75 ± 0.09 | 20 ± 10 | 0.17 ± 0.02 | 0.61 ± 0.04 | 1.56 ± 0.09 | 7 ± 2 |

TABLE 2-continued

| Protein | BHRF1 | Bcl-2 | Bcl-w | Mcl-1 | Bfl-1 | Bcl-X$_L$ | Bcl-B |
|---|---|---|---|---|---|---|---|
| BINDI | 0.22 ± 0.05 | 2,100 ± 100 | 870 ± 40 | 40 ± 10 | 2,600 ± 800 | 810 ± 80 | >10,000 |
| BINDI N62S | 0.16 ± 0.08 | 30,000 ± 10,000 | 4,600 ± 400 | 230 ± 40 | 4,000 ± 2,000 | 8,000 ± 2,000 | 50,000 ± 10,000 |

Enhanced Affinity and Specificity of the Designed Protein Via Mutations Distant from the Interface To optimize the design, the BbpD04.1 gene was diversified by error prone-PCR (average error rate 1.3 amino acid substitutions per clone) and a subsequent yeast display library of 2×10$^6$ transformants was sorted by three rounds of fluorescence-activated cell sorting (FACS). During each sort, the library was incubated with 5 nM biotinylated BHRF1 and 15 nM of each unlabeled human Bcl-2 protein as competitors to favor selectivity. Five mutated sites were identified that increased binding signal in the final sorted population: two mutations at the designed interface (H104R, predicted to enhance electrostatic complementarity, and N62S, predicted to improve specificity based on sequence-fitness landscape mapping described below), while three mutations were distal from the interface and might alter protein stability (shown later). I21V/L slightly alters packing in the hydrophobic core, Q79L increases hydrophobic interactions buttressing the second connecting loop, and L84Q forms a stabilizing hydrogen bond to the loop backbone. The mutations were mixed combinatorially (72 protein variants) in a yeast display library with 1×10$^6$ transformants that was further sorted for affinity and specificity. Over two rounds of sorting, the library was incubated with 1 nM biotinylated BHRF1 and 8 nM of each unlabeled human Bcl-2 protein, and the top one percent of cells based on binding signal intensity relative to surface expression were selected. Of 20 clones sequenced from the final sorted library, there were 12 unique sequences. The poor convergence in such a low complexity library suggests many sequences had similar binding signals under the yeast display conditions.

Screening a number of clones, we identified one (BbpD04.2 with four mutations: I21L, Q79L, I84Q and H104R, see FIG. 4E) that was monodisperse and monomeric by size exclusion chromatography (SEC) after protein purification from *E. coli*. BbpD04.2 eluted as a higher molecular weight (MW) complex by SEC when mixed with BHRF1, indicating their interaction in solution (FIG. 4F). A single point mutation of a conserved Bim leucine buried within the hydrophobic interface, L62E, severely diminishes binding of Bim-BH3 to all Bcl-2 family members (data not shown). The equivalent mutation of BbpD04.2, L54E, similarly abolishes the interaction of BbpD04.2 with BHRF1 observed by SEC (FIG. 4F).

Figure 5:
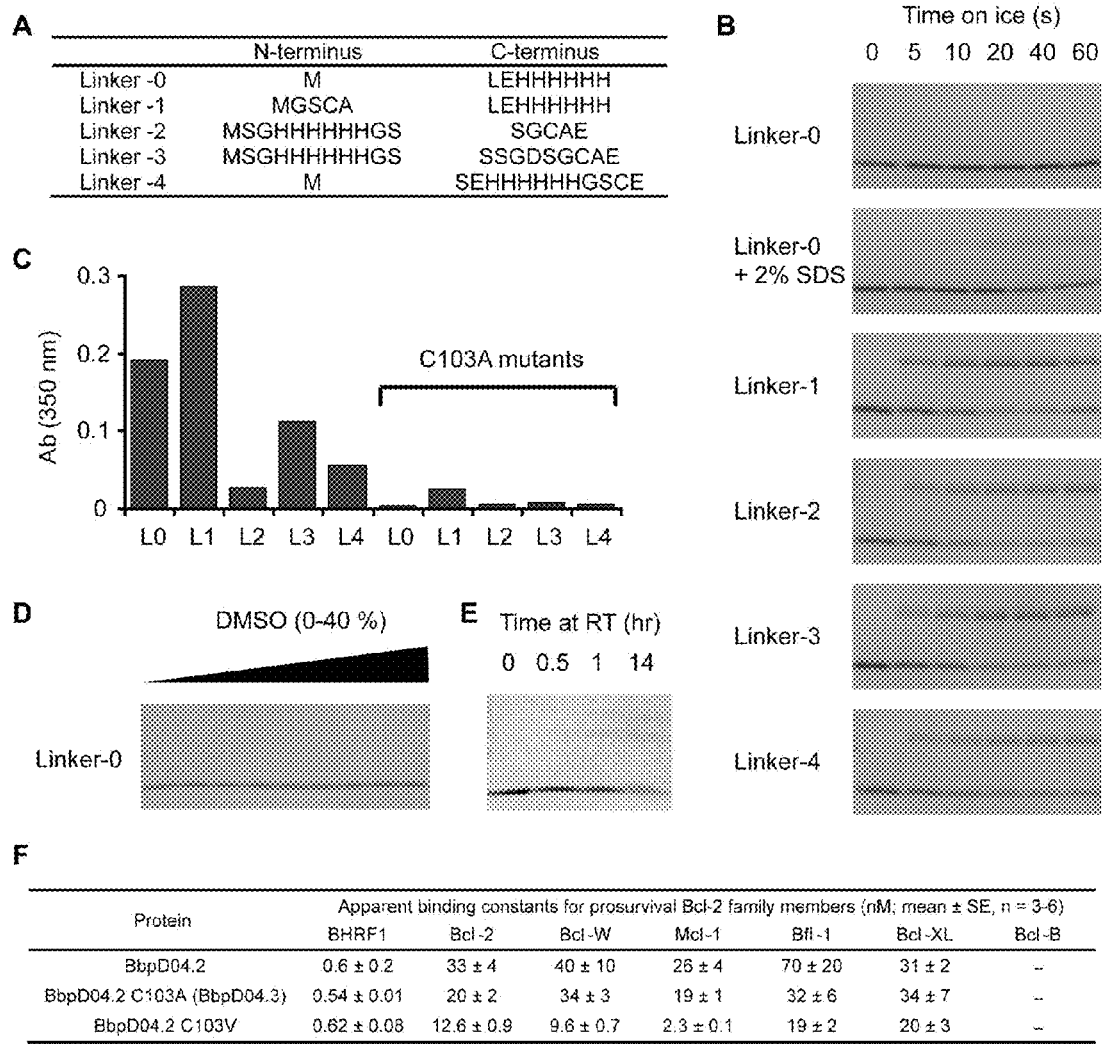

Conjugation of various chemical agents to exposed cysteine residues can allow intracellular delivery, fluorescence detection or surface immobilization for affinity measurements, as described below. BbpD04.2 was incompatible with single labeling of an added terminal cysteine residue, due to the presence of a second internal cysteine (FIG. 5). Short peptide linkers containing single cysteines were genetically fused to the BbpD04.2 termini (FIG. 5A) and found to react in seconds with polyethylene glycol (PEG)-maleimide, producing a higher MW product with reduced electrophoretic mobility (FIG. 5B). BbpD04.2 has an internal buried cysteine, which becomes exposed for PEG-maleimide conjugation in the presence of the harsh detergent SDS, indicating the protein is folded and the hydrophobic core is generally shielded from solvent unless chemically denatured. However, when cysteine-linker BbpD04.2 proteins were conjugated to HPDP-biotin for longer incubations (4 h) at room temperature, the proteins would subsequently aggregate when mixed with tetrameric streptavidin. We hypothesized that, in addition to the exposed terminal cysteine, the internal cysteine was weakly conjugated under these conditions to form aggregated streptavidin-complexes. Mutation of the internal cysteine (C103A) markedly diminished aggregation (FIG. 5C). BbpD04.2 C103A (called BbpD04.3) had only a small loss of affinity and specificity (FIG. 5F), and was therefore chosen for further experiments.

Interface Interactions and Folded Structure are Both Critical

To probe the sequence-fitness landscape of the designed protein, site-specific saturation mutagenesis according to the protocol of (Procko et al., 2013) was used to independently diversify every codon of the BbpD04.3 gene to NNK (N is any base, K is G or T), producing a library of (116 positions)×(20 amino acids+stop codon)=2,436 protein variants. The variants were expressed by yeast surface display (2.5× 10$^6$ transformants) and the library was sorted by a single round of FACS for the 1% of cells with highest binding signal for 400 pM biotinylated BHRF1 (FIG. 6A). Alternatively, the library was sorted for affinity and specificity (yeast were incubated with 400 pM biotinylated BHRF1 and 8 nM of an equimolar mixture of unlabeled human Bcl-2 proteins as competitors; FIG. 6B). DNA was extracted from the naive and post-sorted yeast populations, the BbpD04.3 gene amplified as two fragments to provide full sequencing coverage, and the samples were deep sequenced using Illumina MiSeq sequencing. The frequency of each protein variant is compared between the naive/pre-sorted and enriched/post-sorted populations to calculate an enrichment ratio, which acts as a proxy for the affinity/specificity fitness of each substitution (Fowler et al., 2010; McLaughlin et al., 2012; Procko et al., 2013; Whitehead et al., 2012).

The BbpD04.3 affinity sequence-fitness landscape reveals the critical nature of the incorporated Bim-BH3 motif, with most substitutions of interface residues being depleted (FIG. 6A). In addition, substitutions to proline, which can break regular helical secondary structure, are depleted across the first, second and third helical spans of the designed helical bundle fold (FIG. 6A). Substitutions to aspartate, a short and charged amino acid, are depleted within the hydrophobic core as anticipated (FIG. 6A). The BbpD04.3 affinity-specificity sequence-fitness landscape, in which unlabeled Bcl-2 proteins were included as competitors for BHRF1 binding, is similar (FIG. 6B).

Figure 14:
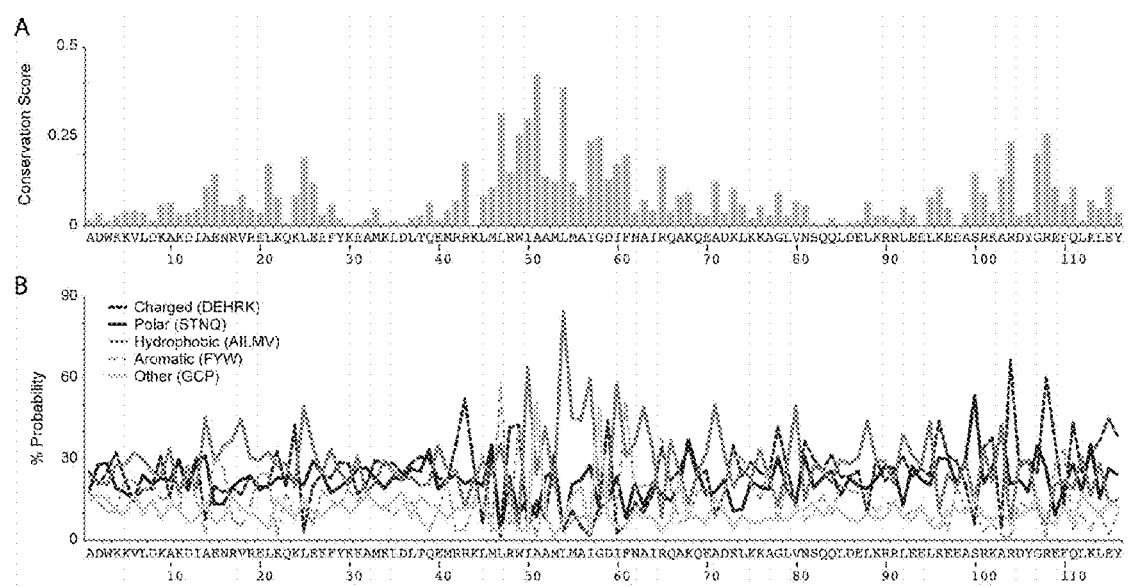
FIG. 14. (A) Based on the experimental enrichment ratios for all single amino acid substitutions of BbpD04.3, a conservation score was calculated for all residue positions. SEQ ID NO: 73 (B) Beginning with a hypothetical population of BbpD04.3 variants that evenly spans all single amino acid substitutions, we applied the experimental enrichment ratios to evolve our population in silico. The probability of finding a particular amino acid at any given position was then calculated. This analysis gives an indication of the tolerated sequence diversity in BbpD04.3/BINDI SEQ ID NO: 74.

Using the sequence-fitness landscape for BHRF1 affinity, we are able to determine the allowed sequence variation of BbpD04.3. The most conserved residues for BHRF1 interaction are found within the second helix of BbpD04.3 and span the incorporated Bim-BH3 motif (FIG. 14A). Residues near the BbpD04.3 C-terminus that also contact BHRF1 are similarly conserved. We applied our experimental enrichment ratios to a hypothetical population that evenly covered all single amino acid substitutions at a given residue, and from the evolved population calculated the probability of finding each amino acid. This analysis reveals that significant diversity is tolerated for any single amino acid substitution, except at critically conserved residues (FIG. 14B and Table 4). Presumably the tolerance for any two amino acid substitutions would be less, less again for three substitutions and so forth, but it is clear that some positions have little preference for amino acid type. A large number of BbpD04.3 sequence variants can therefore maintain the folded structure and favorable binding to a target BCL2 protein.

TABLE 4

Allowed sequence variability in BbpD04.3 from single site saturation mutagenesis

Figure 6:
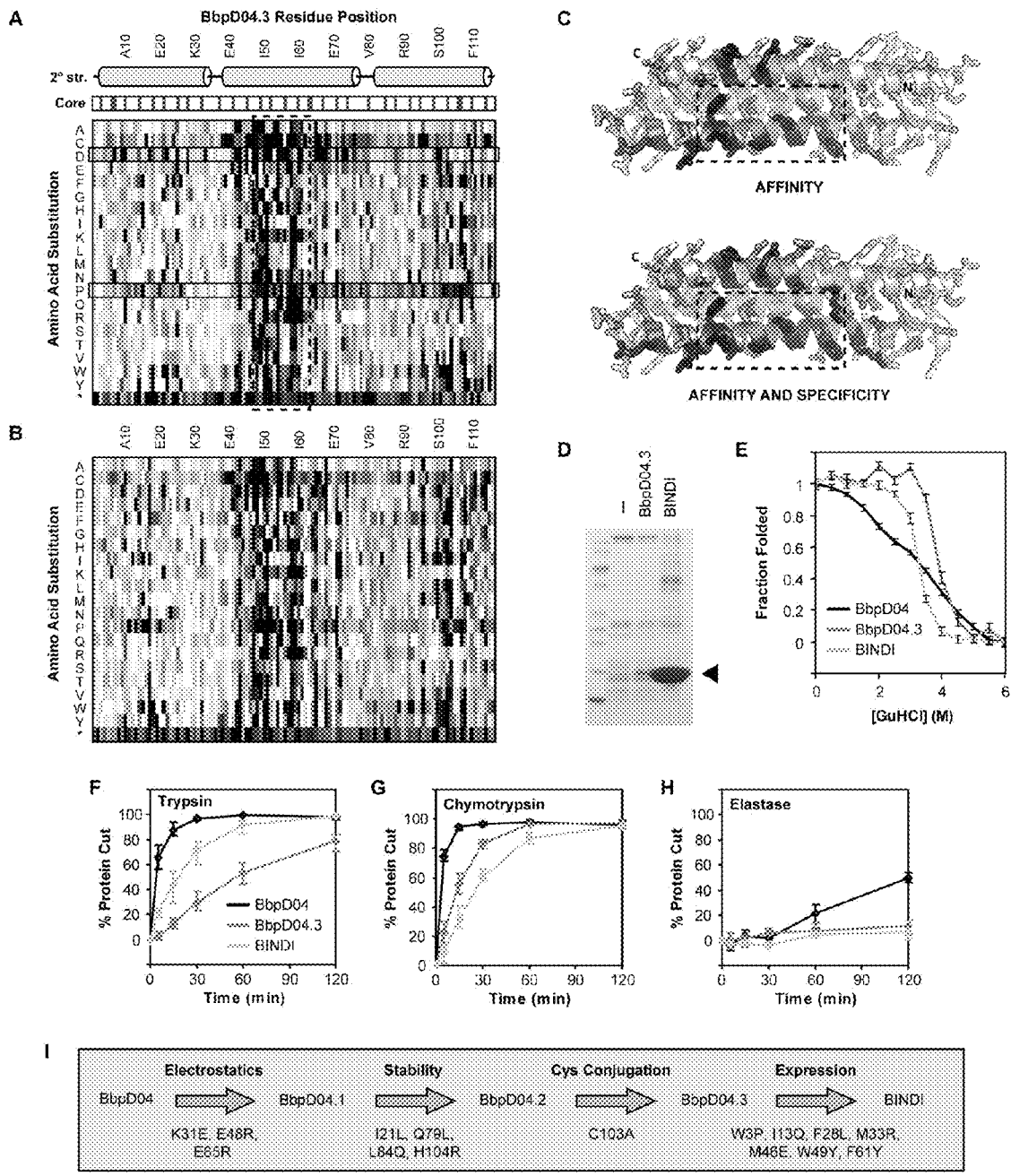
Figure 7:
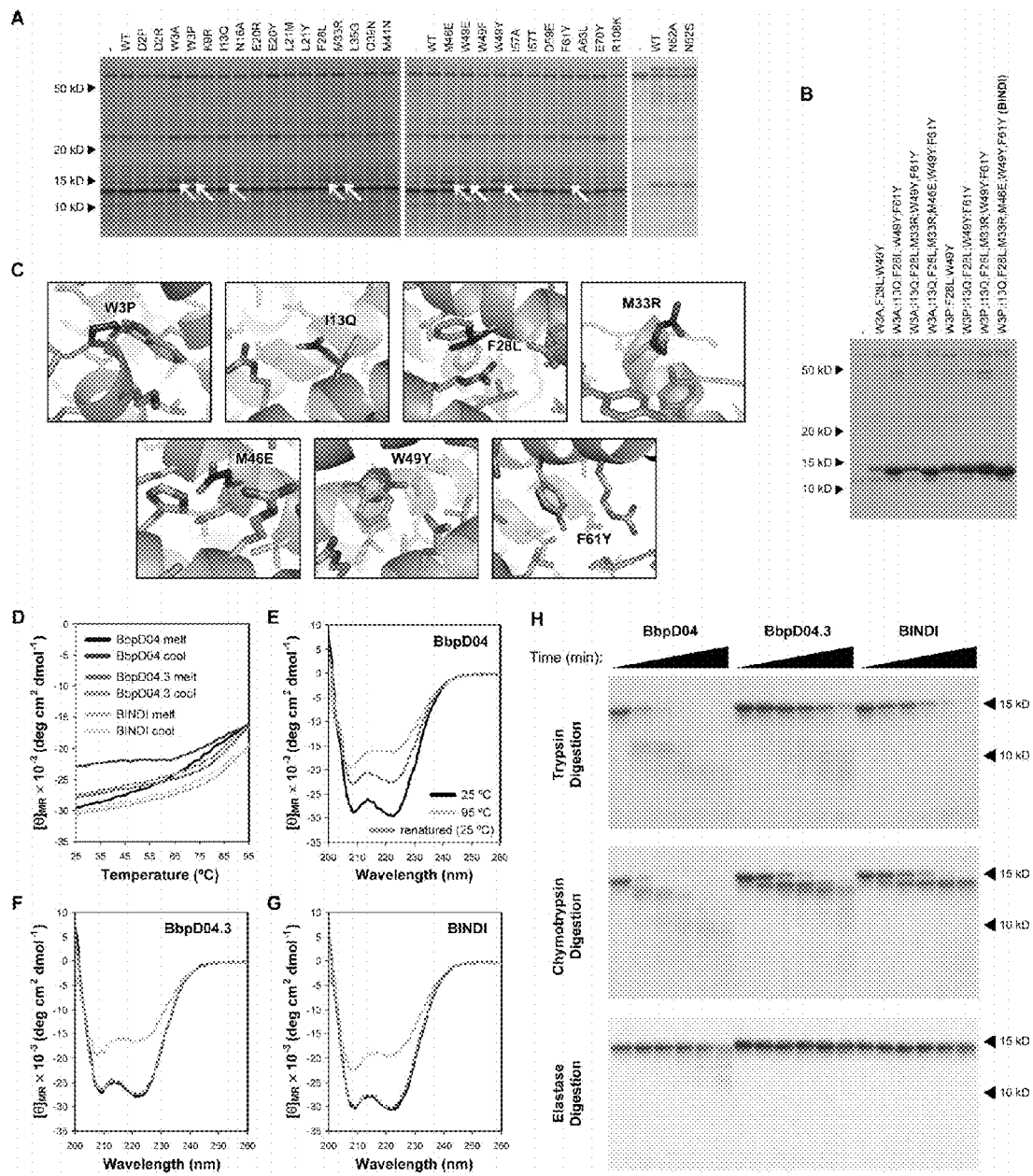
FIG. 7. BINDI has increased bacterial expression and protein stability. (A) BbpD04.3 point mutants were expressed overnight at 22° C. in E. coli Rosetta 2 cells. Cells were harvested, the C-terminally 6his-tagged proteins precipitated with NiNTA-agarose to partially remove background bands, and analyzed on Coomassie-stained SDS-polyacrylamide electrophoretic gels. White arrows indicate mutations with elevated expression. (B) As in (A), with mutations now combined to provide a large increase in expression. (C) Computational model of BHRF1-bound BbpD04.3. Combined mutations in variant BINDI are highlighted with dark sticks. (D) Molar ellipticity at 222 nm as the protein is heated and cooled. Substantial helical structure remains at 95° C. Evolved variants BbpD04.3 and BINDI fully renature. (E) Molar ellipticity of original design BbpD04 as a function of wavelength, recorded at 25° C., 95° C., and after cooling back to 25° C. (F) As in (E), measured for variant BbpD04.3. (G) As in (E), measured for variant BINDI. (H) Protease-susceptibility of BbpD04 and affinity-matured variants BbpD04.3 and BINDI. Protein substrates were incubated for 0, 5, 15, 30, 60, and 120 minutes with protease at 37° C., reactions were terminated with inhibitors, and proteolysis followed on Coomassie-stained SDS-polyacrylamide gels.

| Residue | Conserv. score | % Probability ||||
|---|---|---|---|---|---|
| | | Charged DEHRK agarose precipitation (FIG. 7A). Nine mutations were identified: W3A and W3P increase helical propensity of the initiating residue in the starting helix; I13Q, M33R, F61Y, W49E/Y and M46E decrease surface hydrophobicity; and F28L slightly increases packing in the hydrophobic core while again reducing surface hydrophobicity (the lowest energy Phe rotamer at this position is predicted to point towards solvent, while Leu is directed inwards to the core in the crystal structure described below). Because the mutations are generally surface-exposed at distinct sites on a long helical bundle, we reasoned they could likely be combined without negative interference (FIG. 7B). A BbpD04.3 variant with seven mutations—W3P, I13Q, F28L, M33R, M46E, W49Y and F61Y (FIG. 7C)—had significantly increased bacterial expression and improved specificity with no significant change in BHRF1 affinity by yeast surface display (FIG. 6D and Table 2). This variant is named BHRF1-INhibiting Design acting Intracellularly (BINDI).

The increased expression of BINDI compared to BbpD04.3 is not due to enhanced protein stability; both BbpD04.3 and BINDI undergo cooperative unfolding at high concentrations (>3 M) of the chemical denaturant guanidinium hydrochloride measured by circular dichroism (CD) spectroscopy (FIG. 6E). However, the original design, BbpD04, has nearly linear loss of CD signal over a 0 to 6 M range of guanidinium hydrochloride (FIG. 6E). The absence of a cooperative melting transition is associated with molten globules that lack a rigid core or single native conformation. While BbpD04, BbpD04.3 and BINDI have high thermostability and retain partly α-helical CD spectra at 95° C., only the evolved BbpD04.3 and BINDI fully renature when the heated protein solutions are cooled (FIG. 7D-G). Further, the original BbpD04 design is sensitive to rapid hydrolysis by proteases, which require unfolded substrate backbone to access the enzyme active site (FIGS. 6F-H and 7H). BbpD04.3 and BINDI are similarly resistant to protease digestion with differences attributable to sequence variation (i.e. trypsin cuts after lys or arg residues that are more abundant in BINDI, and chymotrypsin cuts after aromatic residues that are more abundant in BbpD04.3). Increased affinity for BHRF1 following in vitro evolution correlates with enhanced protein stability. A summary of all mutations introduced in the original design is provided in FIG. 6I.

The Designed BINDI Protein has High Affinity and Specificity

Figure 8:
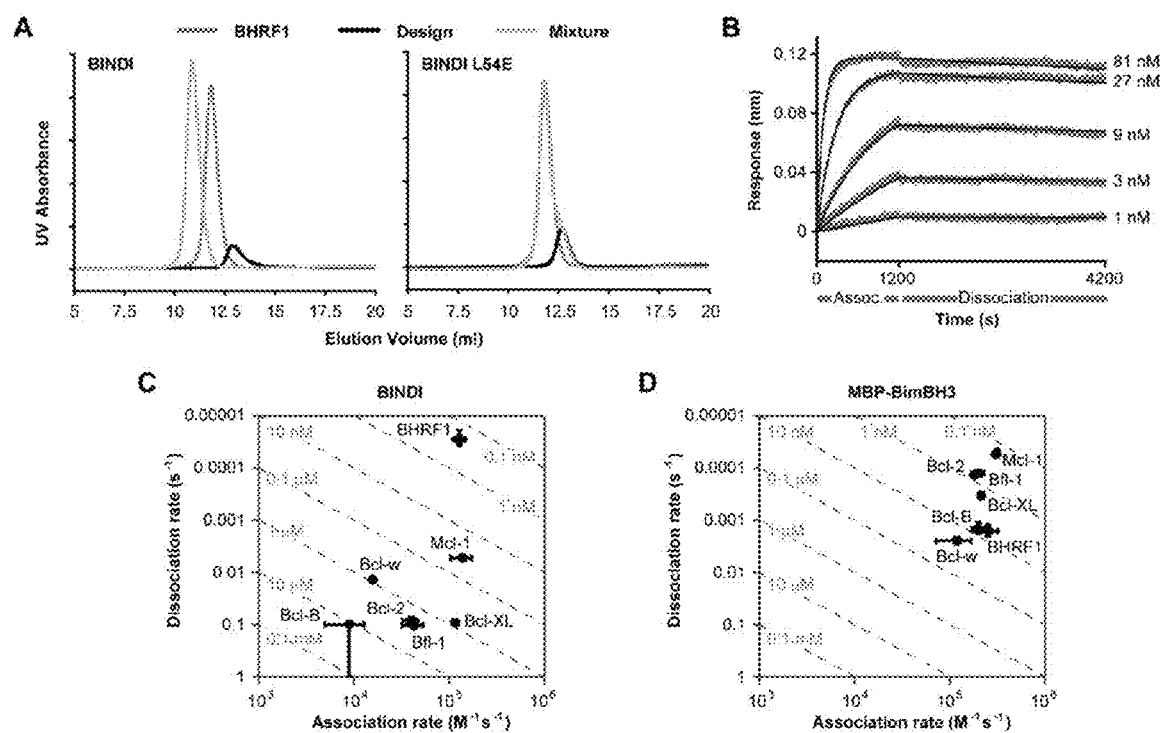
FIG. 8. BINDI binds BHRF1 with high affinity and specificity. (A) BINDI or knockout mutant BINDI L54E were mixed with BHRF1 and separated by SEC. A shift in elution volume upon mixing BINDI and BHRF1 is abrogated by the knockout mutation. (B) Biotinylated BHRF1 was immobilized to a BLI sensor and the interaction with BINDI was measured at the indicated concentrations. (C) BLI kinetic analysis of BINDI interactions with BHRF1 (as in panel B) and human Bcl-2 proteins. (D) BLI kinetic analysis of interactions between the Bim-BH3 motif fused to the C-terminus of maltose-binding protein (MBP) and Bcl-2 proteins immobilized to the sensor surface.

Apparent dissociation constants by yeast surface display are useful approximations, but may be artificially tight due to avidity effects or ligand rebinding to a dense receptor surface, or may be artificially weak if binding equilibrium is not reached during the incubation time. The BINDI•BHRF1 interaction was therefore further characterized by alternative methods. BINDI eluted as a higher molecular weight complex by SEC when mixed with BHRF1 in solution, whereas BINDI L54E with a knockout mutation in the designed interface did not (FIG. 8A). Using bio-layer interferometry (BLI) to measure the kinetic rate constants, BINDI•BHRF1 was found to form an extraordinarily tight complex ($K_D$ 220±50 pM) with a slow dissociation rate ($k_{off}$=[2.8±0.9]× $10^{-5}$ $s^{-1}$) (FIG. 8B-C). BINDI bound human Mcl-1 with $K_D$ 40±10 nM (180-fold increase compared to BHRF1), Bcl-2 with $K_D$ 2.1±0.1 µM (10,000-fold increase), Bcl-w with $K_D$ 870±40 nM (4,000-fold increase), Bfl-1 with $K_D$ 2.6±0.8 µM (12,000-fold increase), Bcl-B with $K_D$>10 µM (>45,000-fold increase) and Bcl-$X_L$ with $K_D$ 810±80 nM (4,000-fold increase). Compared to the measured affinities of Bcl-2 proteins for Bim-BH3 (FIG. 8D) and to other published values (Dutta et al., 2013; Dutta et al., 2010; Gemperli et al., 2005; Lessene et al., 2013) (Tse et al., 2008) (Caria et al., 2012; Flanagan and Letai, 2008; Kvansakul et al., 2010), the affinity and specificity of BINDI for BHRF1 is considerably greater than any previously described BHRF1 ligand, and is similar to or exceeds that of any other protein, peptide or drug designed to specifically bind a Bcl-2 family protein.

Figure 9:
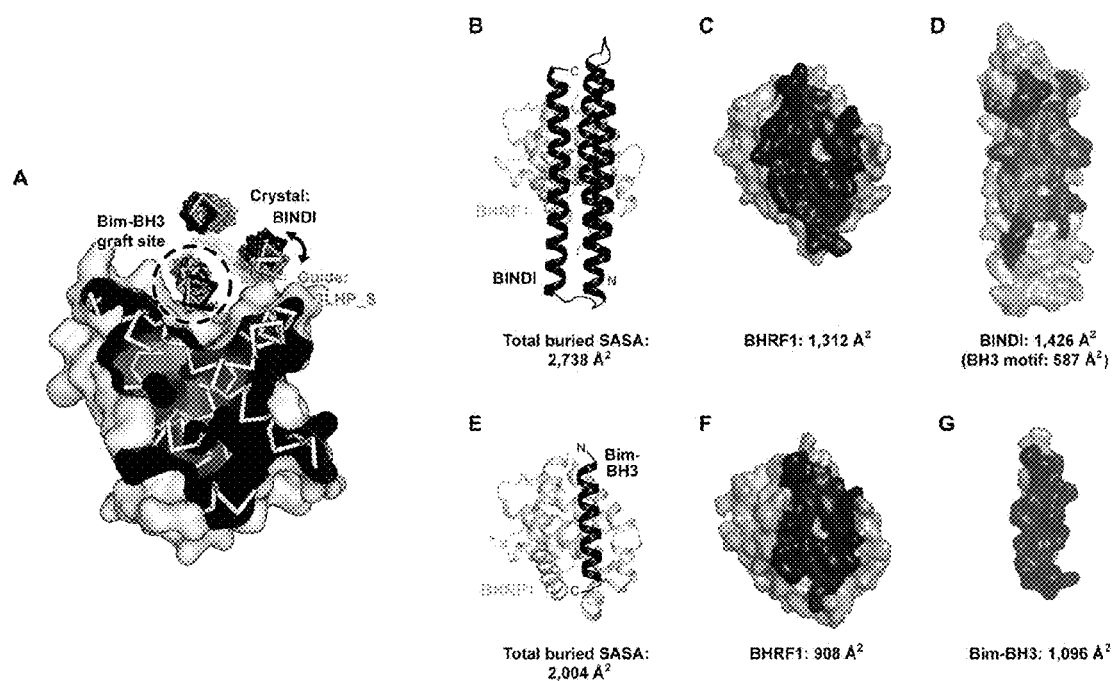
FIG. 9. Structural basis for exceptional affinity and specificity of BINDI. (A) Slice through the crystal structure of BINDI (black ribbon) bound to BHRF1 (white ribbon with surface). The guiding scaffold 3LHP_S (grey) is aligned to BINDI at the Bim-BH3 incorporation site. A direct graft of the BH3 motif into 3LHP_S at this position causes clashes elsewhere with the BHRF1 surface. (B) Crystal structure of BINDI (black) bound to BHRF1 (white). (C) The surface of BHRF1, with the buried contact surface in BHRF1•BINDI shaded black. (D) The surface of BINDI, with the buried contact surface in BHRF1•BINDI shaded. Buried residues from the incorporated Bim-BH3 motif are dark grey. Buried residues in the surrounding designed surface are black. (E) The crystal structure (PDB 2WH6) of Bim-BH3 (black) bound to BHRF1 (white). (F) The surface of BHRF1, with the buried contact surface in BHRF1 •Bim-BH3 shaded black. (G) The surface of Bim-BH3, with the buried contact surface in BHRF1•Bim-BH3 black.

BINDI incorporates the Bim-BH3 motif within a de novo designed fold guided by the topology of PDB 3LHP chain S. The direct graft of Bim-BH3 interaction residues to the equivalent site within the 3LHP_S scaffold (design BbpG1) failed to bind BHRF1. Even after extensive design of the surrounding interaction surface (design BbpG1.D), the grafted protein did not bind BHRF1. While 3LHP_S is structurally similar to BINDI, it is nonetheless a poor steric fit for the BHRF1 binding groove in this design protocol. Aligning the graft site within 3LHP_S to the Bim-BH3 motif of BINDI in the BINDI•BHRF1 structure demonstrates how the C-terminal helix of the grafted design comes too close to the BHRF1 surface, such that side chains would clash (FIG. 9A). This simple structural alignment demonstrates why building new proteins with unique backbone atom positions can be essential for designing productive interactions. BINDI has an ideal structure and amino acid sequence found after computationally filtering thousands of potential designs for optimum interactions with BHRF1.

Figure 10:
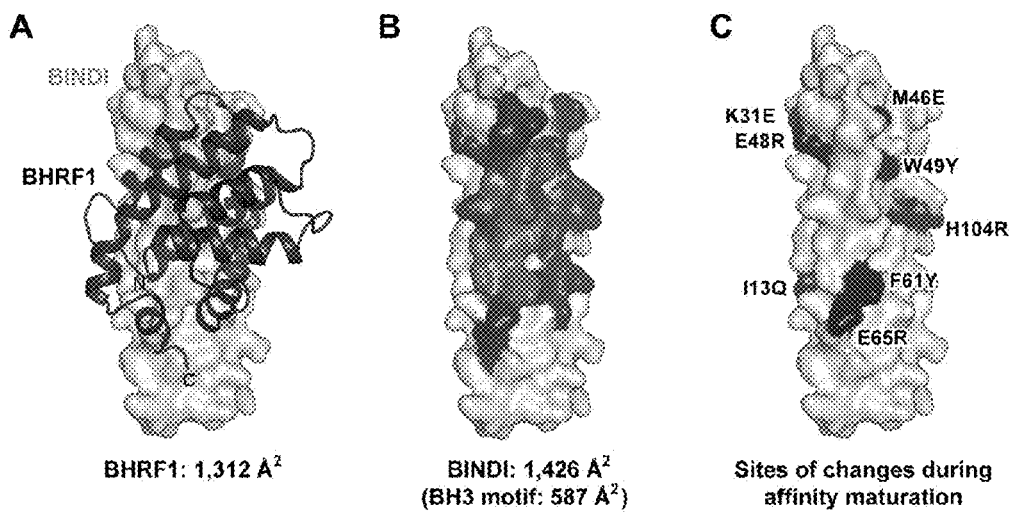
FIG. 10. Mutations within the incorporated Bim-BH3 motif are not the major source of the exceptional specificity of BINDI. (A) Crystal structure of BINDI (surface) bound to BHRF1 (black ribbon). The buried contact surface areas are indicated below. (B) The surface of BINDI, with the buried contact surface shaded. Buried residues from the incorporated Bim-BH3 motif are dark grey. Buried residues in the surrounding designed surface are black. (C) Residues of BINDI that changed during affinity maturation are black. Only two residues at the edge of the incorporated Bim-BH3 motif were substituted (W49Y and F61Y). (D) Sequences of the Bim-BH3 motif and equivalent regions in BbpD04 and BINDI. Residues of Bim-BH3 that were fixed in the design of BbpD04 are shaded. Based on these sequences, two 26-residue peptides were fused to maltose-binding protein (MBP): BimBH3-W57Y-F69Y and BimBH3-5*. These have mutations to the Bim-BH3 motif based on changes during affinity maturation of BINDI. (E) MBP-peptide fusions were tested by BLI for binding to Bcl-2 proteins. Neither peptide had the affinity or specificity for BHRF1 of BINDI.

Compared to the native Bim-BH3 interaction, BINDI contacts an additional 404 Å$^2$ on the surface of BHRF1 (FIG. 9B-G). Residues from the incorporated Bim-BH3 motif account for just 587 Å$^2$ of the BINDI surface buried in the complex, whereas surrounding designed residues account for 839 Å$^2$. Only two residues at the periphery of the incorporated Bim-BH3 motif changed during the final round of affinity maturation (the conservative W49Y and F61Y substitutions), while all residues in the core of the motif remained unchanged (FIG. 10A-C). Introducing these two mutations into a Bim-BH3 peptide, or mutating the Bim-BH3 peptide at all five positions within the BH3 region that distinguish nonspecific BbpD04 from specific BINDI, failed to achieve the high affinity and specificity of BINDI (FIG. 10D-E). The extraordinary specificity of BINDI is therefore accomplished through interactions across an expansive interface, extending well beyond the central Bim-BH3 residues.

BINDI Triggers Apoptosis Preferentially in an EBV-Infected Cell Line

Figure 11:
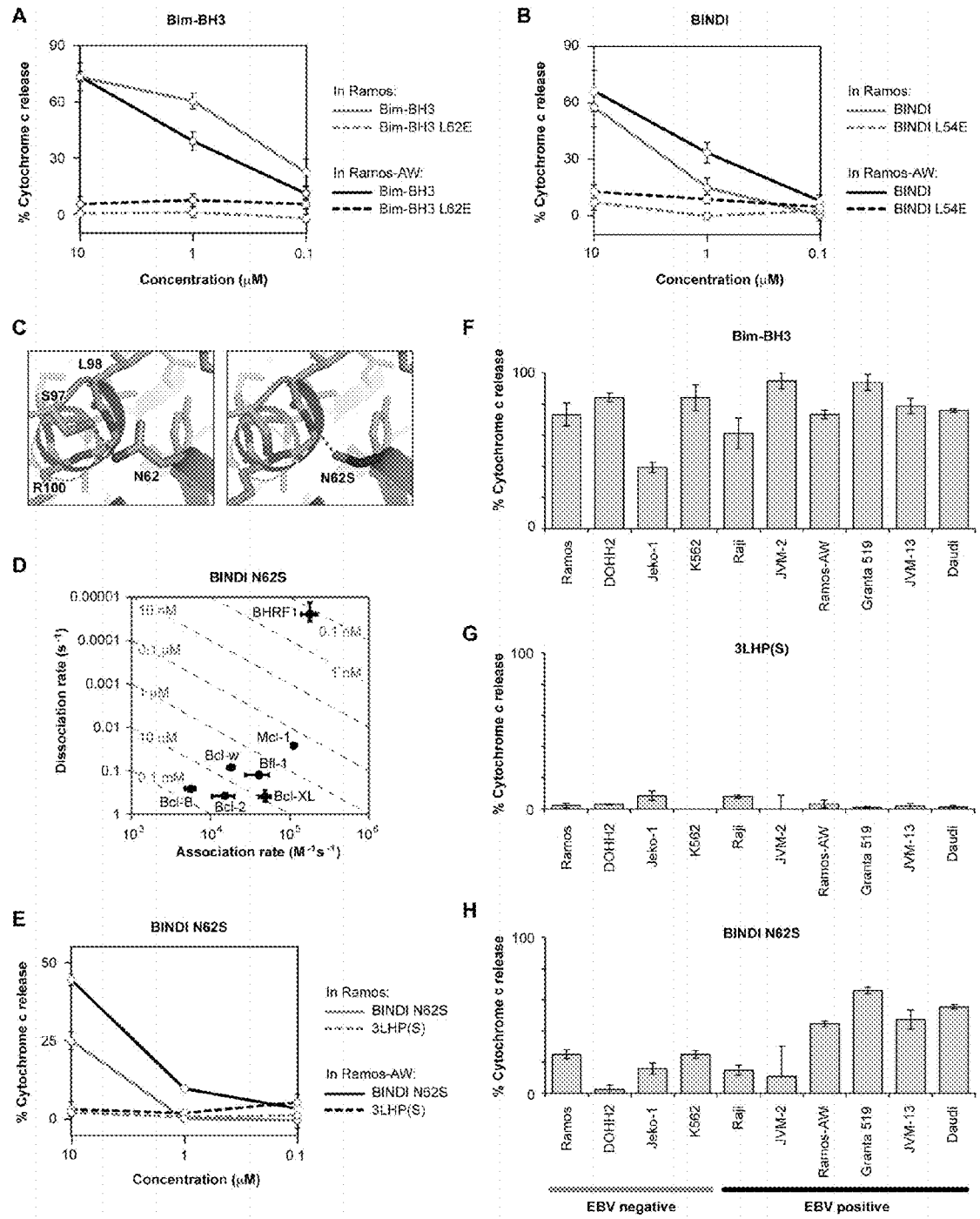
FIG. 11. BINDI triggers apoptosis in an EBV-positive cell line. (A) Cytochrome c release from mitochondria harvested from Ramos (EBV-negative) or Ramos-AW cells (EBV-positive) treated with Bim-BH3 peptide. Bim-BH3 L62E has a knockout mutation in the binding interface. Mean±SD, n=4, for all panels. (B) As in (A), with mitochondria treated with BINDI protein. BINDI L54E has the equivalent interface mutation as Bim-BH3 L62E. (C) At left, the crystal structure of BINDI bound to BHRF1 showing the interaction of Asn62 with the N-terminus of helix α6. At right, BINDI mutation N62S is predicted to maintain interface interactions. (D) BLI kinetic analysis of BINDI N62S interactions with Bcl-2 proteins. (E) Cytochrome c release from Ramos and Ramos-AW mitochondria treated with BINDI N62S or inactive guide scaffold 3LHP(S). (F-H) Mitochondria were harvested from four EBV-negative and six EBV-positive lines. Cytochrome c release was measured after treatment with 10 μM Bim-BH3 peptide (F), guide scaffold 3LHP(S) (G), or BINDI N62S (H).

We tested whether inhibition of BHRF1 via steric occlusion of the BH3-binding groove with BINDI could induce mitochondrial cytochrome c release in the EBV-positive BL cell line Ramos-AW. Ramos-AW expresses BHRF1 at very low levels (Leao et al., 2007), and therefore presents a challenging biological target that likely expresses much higher levels of off-target endogenous Bcl-2 family proteins. BINDI was applied to mitochondria isolated from both Ramos-AW and the EBV-negative parental line Ramos (Andersson and Lindahl, 1976). BINDI elicited greater cytochrome c release from Ramos-AW mitochondria (FIG. 11B), indicating an EBV-associated factor is likely a BINDI target. Strikingly, the non-specific Bim-BH3 peptide had opposite behavior; mitochondria from EBV-negative Ramos cells were more sensitive to Bim-BH3 treatment than those from EBV-positive Ramos-AW cells (FIG. 11A). Indeed, EBV-positive cell lines are widely reported as more resistant to nonselective apoptotic stimuli (Ishii et al., 1995; Kvansakul et al., 2010; Leao et al., 2007), making the enhanced activity of BINDI against Ramos-AW cells all the more significant.

While significantly weaker than the picomolar affinity of BINDI for BHRF1, the moderate affinity for Mcl-1 is likely the reason BINDI still triggers apoptosis in the EBV-negative Ramos cell line. It is possible that the enhanced toxicity of BINDI towards Ramos-AW reflects increased Mcl-1-dependency in this line, rather than expression of EBV BHRF1. To rule out this possibility, we tested a variant, BINDI N62S, with even greater specificity. During affinity maturation, the N62S mutation was found to enhance specificity both in the error-prone PCR-based library and in the comprehensive site-specific saturation mutagenesis library (FIG. 6). However, the N62S mutation simply wasn't present in clone BbpD04.2 isolated from the combinatorial library, and neither did this mutation improve expression of soluble protein in bacteria, the criterion used for combining mutations to generate BINDI. Asn62 of BINDI (Asn70 in Bim-BH3) hydrogen bonds to the N-terminus of BHRF1 helix α6, and serine at this position is predicted to similarly interact at the interface (FIG. 11C). BINDI N62S still binds BHRF1 with extraordinarily tight affinity ($K_D$ 160±80 pM), but now with even better specificity (Table 2 and FIG. 11D). Most notably, the affinity for Mcl-1 is diminished six-fold ($K_D$ 230±40 nM). Like parental BINDI, the N62S variant has enhanced apoptotic activity against EBV-positive Ramos-AW (FIG. 11E). Indeed, BINDI N62S, with greater specificity amongst the Bcl-2 family for BHRF1, has even greater discrimination between Ramos and Ramos-AW cells (FIGS. 11B and 11E). The enhanced activity of BINDI to initiate cytochrome c release preferentially in EBV-positive cells is therefore due to BHRF1 inhibition.

Expression profiling of EBV-positive BLs has revealed distinct subgroups (Kelly et al., 2013; Watanabe et al., 2010), and BHRF1 may not be important for cell survival in all cases. Mitochondria were isolated from six EBV-positive and four EBV-negative cancer lines. Bim-BH3 peptide triggered cytochrome c release (FIG. 11F), whereas the inactive guide scaffold 3LHP(S) had no effect (FIG. 11G; we switched from the L54E knockout mutation to using the scaffold 3LHP(S) as a generic negative control suitable for comparison to any BINDI variant). Incubation with BINDI N62S induced high cytochrome c release in four EBV-positive lines (FIG. 11H): BL lines Ramos-AW and Daudi, mantle cell lymphoma line Granta 519, and B-prolymphocytic leukemia JVM-13. Two of the EBV-positive lines had low levels of cytochrome c release similar to EBV-negative cells: BL line Raji and mantle cell lymphoma line JVM-2. Hence only a subset of EBV-positive cancer lines are dependent on BHRF1 for survival.

Figure 12:
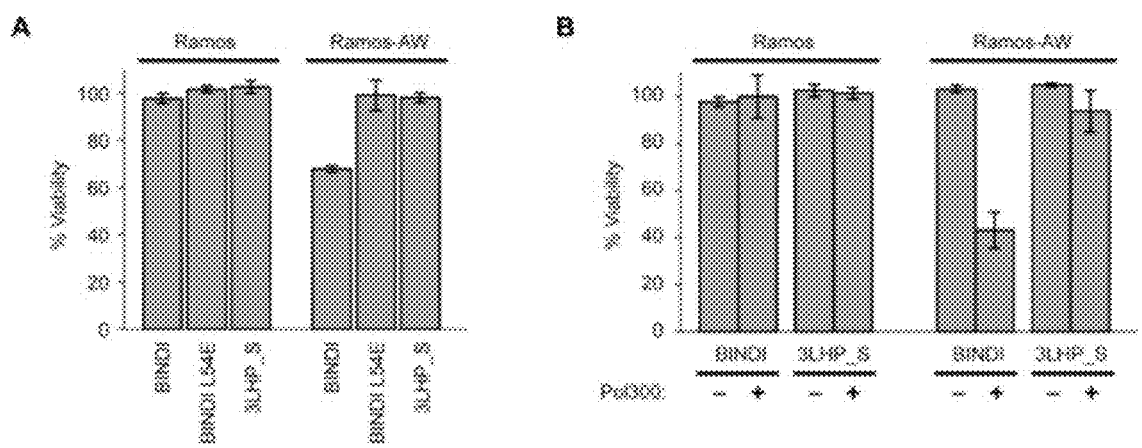
FIG. 12. Intracellular delivery of BINDI induces cell death in an EBV-positive cancer line in vitro. (A) Cells were incubated with 4 μM antennapedia peptide-fusions of BINDI, BINDI-L54E or 3LHP chain S. Cell viability after 24 h was assessed by quantifying metabolic activity. (B) Cells were incubated with sub-lethal doses (2 μM) of antennapedia peptide-fused proteins. Diblock copolymer Pol300 was conjugated to the proteins via a terminal cysteine for enhanced endosomal escape. Cell viability (mean±SD, n=3) was measured after 24 hours.

Treatment of EBV-Positive B Lymphoma in a Xenograft Mouse Model by Intracellular Delivery of BINDI BINDI was genetically fused with a C-terminal antennapedia peptide for non-specific cellular uptake and intracellular delivery in vitro. BINDI-antennapedia applied to the growth medium at 4 μM selectively killed 40% of EBV-positive Ramos-AW cells, with no measurable death of EBV-negative Ramos cells (FIG. 12A). Antennapedia-fused proteins concentrate in endocytic organelles and escape to the cytosol with low efficiency (Duvall et al., 2010). To enhance endosomal escape, BINDI-antennapedia was conjugated via a terminal cysteine to a diblock copolymer carrier, Pol300, containing a hydrophilic first block for stability and a pH-responsive endosomolytic second block (Duvall et al, 2010; Mamganiello et al., 2012; Convertine et al., 2010). A lower 2 μM dose of BINDI-antennapedia induced 60% cell death preferentially in Ramos-AW cells when conjugated to the Pol300 polymeric carrier for enhanced cytosolic delivery (FIG. 12B). Our data suggest inhibition of BHRF1 can effectively kill EBV-positive BL.

Figure 13:
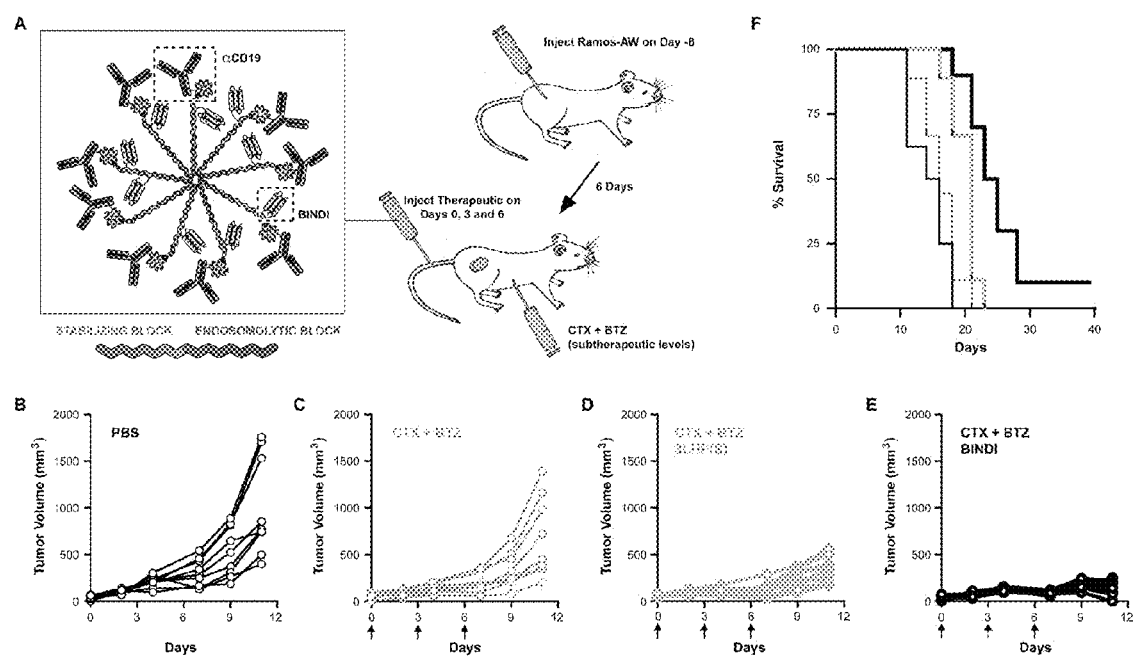
FIG. 13. Treatment of EBV-positive B lymphoma xenograft tumors by intracellular delivery of BINDI in vivo. (A) Schematic representation of the copolymer-based treatment. Pol950 has stabilizing and endosomolytic blocks and forms a micelle at physiological pH. The stabilizing block couples to αCD19 and BINDI. Nude mice with subcutaneous Ramos-AW xenografts were treated on days 0, 3 and 6 with Pol950 (300 mg/kg): αCD19 (15 mg/kg): BINDI or 3LHP (S) (105 mg/kg). Mice were injected 30 minutes prior to each treatment with CTX (35 mg/ml) and BTZ (0.5 mg/ml). (B-E) Tumor growth is plotted for each individual mouse until day 11 when the first mice are euthanized. (B) PBS control treatment, black, n=8; (C) chemo-only, grey, n=9; (D) 3LHP(S)-copolymer treatment, n=9; (E) BINDI-copolymer treatment, n=10. (F) Kaplan-Meier survival plot. There is a significant increase in survival with treatment (log-rank test $\chi^2$=46, P<0.0001).

Intracellular delivery of proteins in vivo is exceptionally challenging, with no efficient artificial methods currently available. Taking inspiration from the entry mechanisms of natural viruses, we developed an antibody-copolymer-based formulation to deliver BINDI to the cytosolic compartment of B cells within an animal. BINDI is coupled via a C-terminal cysteine to diblock copolymer Pol950 synthesized by reversible addition-fragmentation chain transfer. The copolymer's hydrophilic first block is composed of polyethylene glycol methacrylate (MA) for stability in the host, pyridyldisulfide MA for cysteine conjugation to BINDI, and biotin-hydroxylethyl MA for coupling to streptavidin-antiCD19 (αCD19; human monoclonal CAT-13.1E10-SA). The endosomolytic second block is composed of diethylaminoethyl MA and butyl MA. The entire complex of copolymer:αCD19:BINDI forms large micelles that disassociate at low pH to expose membrane-destabilizing groups (FIG. 13A). CD19 is a rapidly internalizing surface antigen, and bound αCD19-complex is endocytosed. Copolymer allows escape from the acidic endosome, and presumably BINDI is then released in the reducing cytosolic environment.

Subcutaneous Ramos-AW xenograft tumors were established in nude BALB/c mice. The mice were treated intravenously on days 0, 3 and 6 with antibody-copolymer coupled to the inactive scaffold 3LHP(S) or to BINDI. Thirty minutes prior to each treatment, cyclophosphamide (CTX) and bortezomib (BTZ) were injected intraperitoneally at subtherapeutic doses to prime cells for apoptosis (O'Connor et al., 2006). The treatments were nontoxic, with no substantial change in mouse body weight.

The intracellular delivery of BINDI to the B lymphoma xenograft slowed tumor progression and prolonged survival. Tumors grew rapidly in the untreated/PBS and chemo-only control groups (FIG. 13B-C), with mean tumor sizes of 1080±500 mm$^3$ and 680±410 mm$^3$, respectively, at day 11 when the first mice were euthanized due to excessive tumor burden. Due to the therapeutic effects of αCD19 coupled to an endosomolytic polymer, both scaffold 3LHP(S) and BINDI treatment groups had reduced tumor sizes, though volumes were significantly smaller (unpaired t test, P=0.003) in the BINDI (140±60 mm$^3$) than 3LHP(S) (330±140 mm$^3$) treatment group (FIG. 13D-E). Lifespan was extended in the BINDI-treated mice compared to the scaffold treatment (log-rank test, P=0.006), with median survival of 15 days for PBS treatment, 16 days for chemo-only, and 21 days for 3LHP(S) treatment, extending to 24 days following BINDI treatment (FIG. 13F). In addition to validating BHRF1 as a therapeutic target in EBV-positive B lymphoma, our data represent the first demonstration that a de novo computationally-designed protein can treat cancer in a preclinical model.

Figure 15:
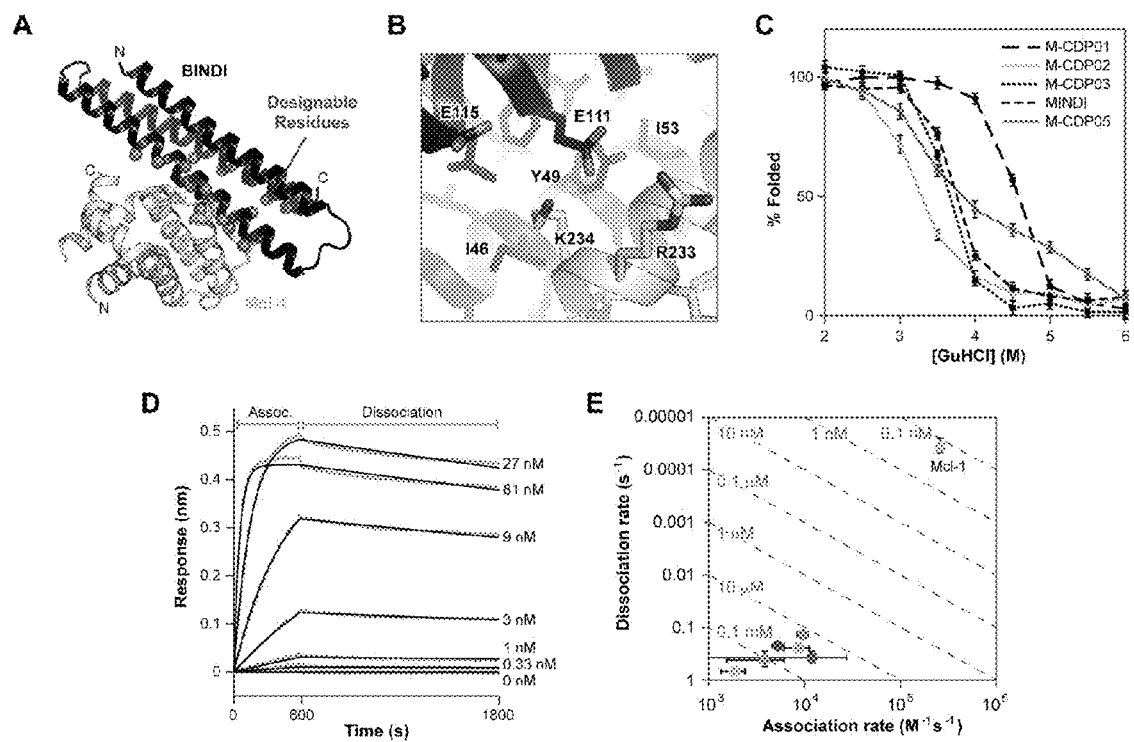
FIG. 15. (A) BINDI (black) was docked to the hydrophobic binding groove of Mcl-1 (white) by alignment to a bound BH3 peptide (not shown). The docked configuration is computationally designed. (B) Designed ionic interactions in MINDI. (C) Chemical denaturation measured by following loss of CD signal (222 nm). (D) BLI titration experiment for accurate $K_D$ determination. Biotinylated Mcl-1 was immobilized to a streptavidin-coated sensor and incubated with the indicated concentrations of soluble MINDI. Raw data is grey, fitted curves are black. (E) Isoaffinity plot from BLI titrations of MINDI interactions with BCL2 family members (only Mcl-1 is labeled).
Figure 16:
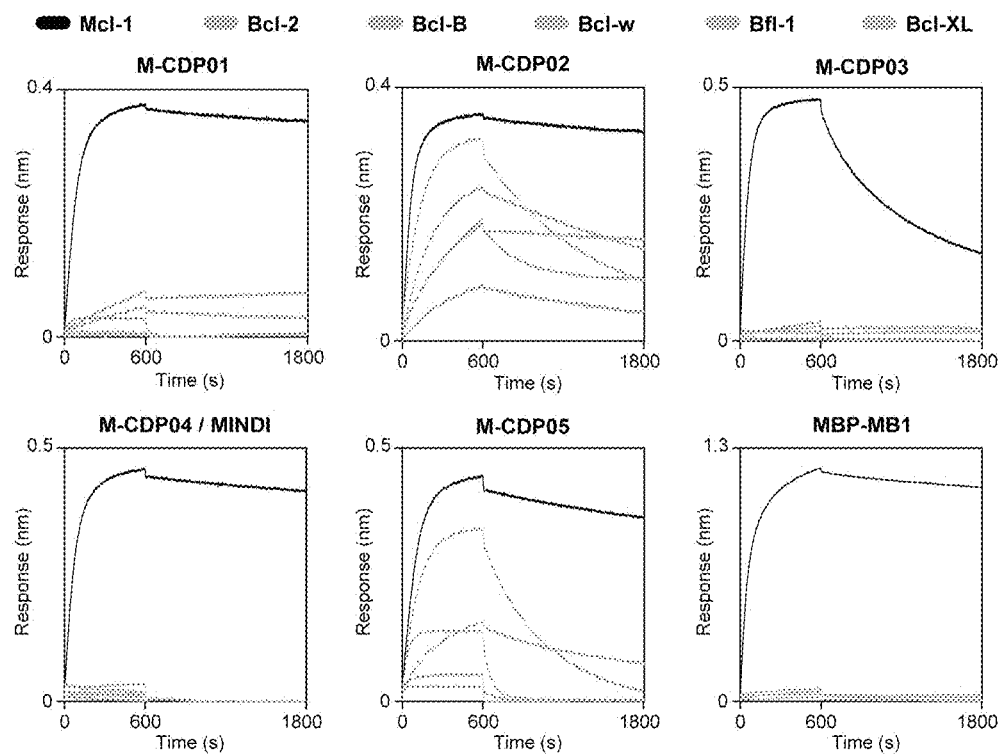
FIG. 16. Qualitative measurements of binding by BLI analysis at a single analyte concentration. The BCL2 proteins are biotinylated and immobilized on streptavidin-sensors. The sensors are dipped for 600 s in 50 nM of the indicated designed Mcl-1 binding proteins, followed by incubation in buffer to monitor dissociation. Mcl-1-specific peptide MB1 was purified as a MBP fusion and used as a positive control.

BCL2 family proteins share similar sequences (>50% similarity between any two family members) and similar structures (~3 Å RMSD). It therefore seemed likely that the BINDI protein, having high complementarity with the binding pocket of BHRF1, could serve as an excellent scaffold for engineering new specificities to other BCL2 proteins. Since earlier variants of BINDI prior to exhaustive optimization bound Mcl-1 with high affinity, we began by repurposing the BINDI protein as a Mcl-1 binder. First, BINDI (PDB 4OYD chain D) was 'docked' into the hydrophobic binding cavity of existing crystallographic models of Mcl-1. In these models, Mcl-1 is bound to nonspecific BH3 peptides from Bim (PDBID 2PQK), Bax (PDBID 3PK1), or the Mcl-1 specific peptide MB7 (PDBID 3KZ0). The bound peptide was used to align the BH3-equivalent residues of BINDI. The docked complex was then designed (FIG. 15A-B). Residues of BINDI within 8 Å of the interface were computationally mutated to minimize the bound proteins' energy, keeping critical residues shared with Bim-BH3 fixed. Since design calculations use repeated random sampling, the process is done numerous times to give different possible sequences. Genes encoding six Mcl1-targeted computationally designed proteins, M-CDP01 to M-CDP06, were synthesized (Tables 5 and 6) and five expressed in *E. coli*. The affinities of the five proteins for BCL2 family members were tested by biolayer interferometry (BLI), with the specific Mcl-1-binding peptide MB1 tested as a positive control. All five proteins had tight affinity for Mcl-1 due to slow off rates, and two appeared to be highly specific (FIG. 16). This is despite only interactions with Mcl-1 being designed; specificity was achieved without explicitly designing against interactions with other BCL2 proteins.

When exposed to chemical denaturants and measuring the loss of helical structure by CD, two partially-specific binders (M-CDP02 and M-CDP05) unfolded over broad denaturant concentration ranges, suggestive of poorly packed or 'molten' cores (FIG. 15C). Binders specific for just Mcl-1 have narrow, cooperative unfolding transitions. A well-packed structure therefore appears to be necessary for specificity. We chose highly specific M-CDP04 (subsequently called MINDI for Mcl-1-inhibiting design acting intracellularly) for accurate determination of binding affinities in BLI experiments (FIG. 15D-E). MINDI bound Mcl1 with 150±60 pM affinity, with over ten thousand-fold weaker affinity for other BCL2 family members.

We sought to evolve a partially-specific Mcl-1 binder (M-CDP02) to specifically associate with single BCL2 proteins. However, this approach enriched for mutations that damaged regions of structure (data not shown). Since our aim is to engineer specific binders that are compact and well-folded, we abandoned directed evolution at this point and instead explicitly designed proteins to bind each BCL2 family member.

The structure of BINDI (PDB 4OYD chain D) was docked into the BH3 binding cavity in the structures of Bax-BH3-bound Bcl-2 (PDB 2XA0), small molecule inhibitors bound to Bcl-2 (PDBs 4AQ3, 4IEH and 4LVT), Bim-BH3-bound Bcl-XL (PDB 1PQ1; structure of mouse Bcl-XL, which is 97% identical to the human sequence), modified Bim peptides bound to Bcl-XL (PDBs 2YQ6 and 2YQ7), Bax-bound Bcl-XL (PDB 3PL7), a Puma-derived αβ peptide bound to Bcl-XL (PDB 4BPK), Bim-bound Bcl-B (PDB 4B4S), and Bak-bound Bfl-1 (PDB 3I1H). Critical interaction residues from the peptide ligand were grafted to the BINDI scaffold, or alternatively, residues of the BINDI BH3-like motif were kept fixed (Tables 5 and 6). Then, surrounding residues at the edges of the interface were computationally designed. The designed proteins were filtered for favorable binding energies, shape complementarity with the Bcl-2 homolog's BH3 binding cavity, and minimal buried unsatisfied polar atoms. Codon-optimized genes were synthesized and the proteins were expressed and purified from *E. coli*.

TABLE 5

Computationally designed derivatives of BINDI

| Design | Target PDB | PDB description | Residues kept fixed (numbered as on BINDI scaffold) | Residues borrowed from | Binds target? | Binding energy (ddg) | Shape complementarity (Sc) | Buried unsatisfied polar atoms (unsat) |
|---|---|---|---|---|---|---|---|---|
| 2-CDP01 | 2XA0 | Bcl-2·Bax-BH3 | L54, I57, G58, D59, F61 | Bad-BH3 | + | −35.2669 | 0.509289 | 10 |
| 2-CDP02 | 2XA0 | Bcl-2·Bax-BH3 | L54, I57, G58, D59, F61 | Bad-BH3 | + | −41.0808 | 0.529427 | 9 |
| 2-CDP03 | 4AQ3 | Bcl-2·phenylacyl sulfonamide | A51, L54, G58, D59 | BINDI | + | −29.2064 | 0.580547 | 2 |
| 2-CDP04 | 4IEH | Bcl-2/Bcl-XL·N-heteroaryl sulfonamide | Y49, A51, L54, G58, D59, N62 | BINDI | − | −24.6658 | 0.528941 | 7 |
| 2-CDP05 | 4IEH | Bcl-2/Bcl-XL·N-heteroaryl sulfonamide | A51, L54, G58, D59 | BINDI | − | −17.011 | 0.554712 | 5 |
| 2-CDP06 | 4LVT | Bcl-2·navitoclax | L54, G58, D59 | BINDI | + | −25.7035 | 0.467105 | 5 |
| 2-CDP07 | 4LVT | Bcl-2·navitoclax | L54, G58, D59, N62 | BINDI | + | −25.7202 | 0.466163 | 11 |
| X-CDP01 | 1PQ1 | Bcl-XL·Bim-BH3 | I50, A51, L54, G58, D59 | Bim-BH3 | + | −40.5426 | 0.613795 | 9 |
| X-CDP02 | 1PQ1 | Bcl-XL·Bim-BH3 | Y49, I50, A51, L54, G58, D59 | Bim-BH3, BINDI | + | −37.9138 | 0.575281 | 7 |
| X-CDP03 | 2YQ6 | Bcl-XL·BimSAHB | I50, A51, L54, I57, G58, D59, N62 | Bim-BH3 | + | −32.0914 | 0.622902 | 8 |
| X-CDP04 | 2YQ6 | Bcl-XL·BimSAHB | Y49, I50, A51, L54, I57, G58, D59, N62 | Bim-BH3, BINDI | + | −34.2881 | 0.554852 | 4 |
| X-CDP05 | 2YQ6 | Bcl-XL·BimSAHB | Y49, I50, A51, L54, I57, G58, D59, N62 | BINDI | + | −32.6508 | 0.603245 | 11 |

TABLE 5-continued

Computationally designed derivatives of BINDI

| Design | Target PDB | PDB description | Residues kept fixed (numbered as on BINDI scaffold) | Residues borrowed from | Binds target? | Binding energy (ddg) | Shape complementarity (Sc) | Buried unsatisfied polar atoms (unsat) |
|---|---|---|---|---|---|---|---|---|
| X-CDP06 | 2YQ7 | Bcl-XL·BimLOCK | A52, I54, F57, G58, D59, F61 | XG10 peptide[1] | + | −44.9274 | 0.643131 | 6 |
| X-CDP07 | 2YQ7 | Bcl-XL·BimLOCK | A52, I54, F57, G58, D59, F61 | XG10 peptide[1] | + | −47.9744 | 0.61353 | 4 |
| X-CDP08 | 2YQ7 | Bcl-XL·BimLOCK | A52, I54, F57, G58, D59, F61 | XG10 peptide[1] | + | −31.7966 | 0.631045 | 7 |
| X-CDP09 | 3PL7 | Bcl-XL·Bax-BH3 | L50, S51, L54, K55, I57, G58, D59, D62 | Bax-BH3 | − | −24.8947 | 0.637508 | 7 |
| X-CDP10 | 4BPK | Bcl-XL·Puma-α/β-foldamer | I50, A51, L54, G58, D59 | BINDI | + | −40.6185 | 0.587325 | 3 |
| X-CDP11 | 4BPK | Bcl-XL·Puma-α/β-foldamer | Y49, I50, A51, L54, I57, G58, D59, N62 | BINDI | + | −31.2246 | 0.549465 | 4 |
| M-CDP01 | 2PQK | Mcl-1·Bim-BH3 | E47, I50, A51, L54, R55, I57, G58, D59, F61, N62 | Bim-BH3 | + | −38.3045 | 0.665342 | 8 |
| M-CDP02 | 2PQK | Mcl-1·Bim-BH3 | E47, I50, A51, L54, R55, I57, G58, D59, F61, N62 | Bim-BH3, BINDI | + | −37.4996 | 0.678787 | 8 |
| M-CDP03 | 3KZ0 | Mcl-1·MB7 | E47, A50, A51, I54, R55, I57, G58, D59, N61, N62, Y65 | MB7 peptide | + | −31.2833 | 0.660599 | 11 |
| M-CDP04 | 3KZ0 | Mcl-1·MB7 | E47, A50, A51, I54, R55, I57, G58, D59, N61, N62, Y65; Y49 | MB7 peptide; BINDI | + | −31.1976 | 0.656449 | 5 |
| M-CDP05 | 3PK1 | Mcl-1·Bax-BH3 | T47, L50, S51, L54, I57, G58, D59, L61, D62, M65 | Bax-BH3 | + | −30.7442 | 0.694437 | 5 |
| F-CDP01 | 3I1H | Bfl-1·Bak-BH3 | I50, A51, L54, I57, G58, D59, N62 | Bak-BH3 | + | −28.74 | 0.671393 | 5 |
| B-CDP01 | 4B4S | Bcl-B·Bim-BH3 | I50, A51, L54, I57, G58, D59, N62 | Bim-BH3 | + | −29.0724 | 0.700157 | 5 |
| W-CDP01 | 1PQ1* | Bcl-XL·Bim-BH3 | L54, I57, G58, D59, F61, N62 | Bim-BH3 | + | −29.6374 | 0.563108 | 7 |
| W-CDP02 | 2YJ1* | Bcl-XL·Puma-α/β-foldamer | L54, I57, G58, D59, F61, N62 | Bim-BH3 | + | −28.4893 | 0.557322 | 10 |
| W-CDP03 | 3FDL* | Bcl-XL·Bim-BH3 | L54, I57, G58, D59, F61, N62 | Bim-BH3 | + | −29.7158 | 0.532155 | 4 |

*Bcl-w models were generated by threading the aligned Bcl-w sequence onto the crystal structure of the Bcl-2 pro-survival homolog with indicated PDBID
[1]XG10 is a synthetic peptide designed for specificity to Bcl-xL, as described in Dutta et al., 2010.

TABLE 6

Sequences of computationally designed proteins (CDPs) prior to experimental optimization and evolved combinatorial mutants (ECM) selected for BLI screening.

```
> M-CDP01 (Target: Mcl-1)
ADPKKVLDKAKDQAENRVRELKQELEELYKKARKLDLTQEERRKLEEEAIAALLRAIGDIYN
AIQQALNEADKLKKAGLVNSQQLDELKRRLEELKKEASKKARDYGLEFFEKLDY (SEQ ID NO: 28)

> M-CDP02 (Target: Mcl-1)
ADPKKVLDKAKDQAENRVRELKQELEELYKEARKLDLTQEERRKLEESYIAAMLRAIGDIFN
AIMQAKNEADKLKKAGLVNSQQLDELRRRLEELRKEASLKAEDYGREFQEKLEY (SEQ ID NO: 29)

> M-CDP03 (Target: Mcl-1)
ADPKKVLDKAKDQAENRVRELKQDLERLYKEARKLDLTQEMRRKLQEKAAAAMIRAIGDI
NNAIYQALQEADKLKKAGLVNSQQLDELKRRLEELQKEASRKAQAYGEEFMLKLEY (SEQ ID NO: 30)
```

TABLE 6-continued

Sequences of computationally designed proteins (CDPs) prior to experimental optimization and evolved combinatorial mutants (ECM) selected for BLI screening.

```
> M-CDP04 (Target: Mcl-1)
ADPKKVLDKAKDQAENRVRELKQVLEELYKEARKLDLTQEMRKKLIERYAAAIIRAIGDINN
AIYQAKQEAEKLKKAGLVNSQQLDELLRRLDELQKEASRKANEYGREFELKLEY (SEQ ID NO: 2)

> M-CDP05 (Target: Mcl-1)
ADPKKVLDKAKDQAENRVRELKQKLEELYKEARKLDLTQEERHRLETKALSALLAAIGDIL
DAIMQALQEAAKLKKAGLVNSQQLDELKRRLEELRKEASRKARDYGREFWLKLDY (SEQ ID NO: 32)

> M-CDP06 (Target: Mcl-1)
ADPKKVLDKAKDQAENRVRELKQKLEELYKEARKLDLTQEEREKLKTKYLSAMLAAIGDIL
DAIMQALNEAQKLKKAGLVNSQQLDELKRRLEELRKEASRKARDYGREFELKLDY (SEQ ID NO: 33)

> 2-CDP01 (Target: Bcl-2)
ADPKKVLDKAKDQAENVVRLKQELEELYKEARKLDLTQDMREKIKLRAEAAELQAIGDIF
QAILQAKMEAKKLYDAGLVNSQQLDELKRRLEELAKEAEDRAAKLGKEFLQKLEYG (SEQ ID NO: 34)

> 2-CDP02 (Target: Bcl-2)
ADPKKVLDKAKDRAENAVRELKQKLEELYKEARKLDLTQDMRNKLIMKAIAAELRAIGDIF
QAILEAKAEAKKLLDAGLVNSQQFDELKRRLEELEEEAAERARKLGDEFRQKLEYG (SEQ ID NO: 35)

> 2-CDP03 (Target: Bcl-2)
ADPKKVLDKAKDQAENRVRELKQKLEELYKEARKLDLTQEMRRELKERALAARLQAVGDI
FYAILQAKSEADKLKKAGLVNSQQLDELKRRLEELAEEAQRKARDYGIEFALKLEY (SEQ ID NO: 36)

> 2-CDP04 (Target: Bcl-2)
ADPKKVLDKAKDQAENRVRELKQKLEELYKEARKLDLTQEMREKLQEQALAAWLNAAGDI
IEAISRALQEADKLKKAGLVNSQQLDELKRRLEELAEEAARKAEKYGEEFKKKLEY (SEQ ID NO: 37)

> 2-CDP05 (Target: Bcl-2)
ADPKKVLDKAKDQAENRVRELKQKLEELYKEARKLDLTQEMRAELNARFAAATLAAAGDII
NAISEALAEADKLKKAGLVNSQQLDELKRRLEELAQEAERKAEEYGQEFLLKLEY (SEQ ID NO: 38)

> 2-CDP06 (Target: Bcl-2)
ADPKKVLDKAKDEAENRVRELKQKLEELYKEARKLDLTQEMRQELVDKARAASLQASGDIF
YAILRALAEAEKLKKAGLVNSQQLDELKRRLEELAEEARRKAEKLGDEFRLKLEY (SEQ ID NO: 39)

> 2-CDP07 (Target: Bcl-2)
ADPKKVLDKAKDDAENRVRELKQKLEELYKEARKLDLTQEERDELKLKAIAASLQASGDIY
NAILRALEEARKLKKAGLVNSQQLDELKRRLEELAEEAQRKANKLGDEFRLKLEY (SEQ ID NO: 40)

> X-CDP01 (Target: Bcl-xL)
ADPKKVLDKAKDQAENRVRELKQKLEELYKEARKLDLTQEMRRELQARYIAAMLAAAGDI
MEAIQQAKNEADKLKKAGLVNSQQLDELKRRLEELAKEAARKAEDYGREFQLKLEY (SEQ ID NO: 41)

> X-CDP02 (Target: Bcl-xL)
ADPKKVLDKAKDQAENRVRELKQKLEELYKEARKLDLTQEMRKELVARYIAAMLAAAGDI
VQAIQDAKNEADKLKKAGLVNSQQLDELKRRLEELAKEAARKATDYGREFQLKLEY (SEQ ID NO: 42)

> X-CDP03 (Target: Bcl-xL)
ADPKKVLDKAKDQAENRVRELKQKLEELYKEARKLDLTQEMRRELRNRAIAAILQAIGDLL
NAIQQAKDEADKLKKAGLVNSQQLDELKRRLEELQNEAAEKAADYGEEFWLKLEY (SEQ ID NO: 43)

> X-CDP04 (Target: Bcl-xL)
ADPKKVLDKAKDQAENRVRELKQKLEELYKEARKLDLTQEDRKRLLLQYIAAMLAAIGDLE
NAIRWAKREADKLKKAGLVNSQQLDELKRRLEELAKEAAEKAADYGEEFNLKLEY (SEQ ID NO: 44)

> X-CDP05 (Target: Bcl-xL)
ADPKKVLDKAKDQAENRVRELKQKLEELYKEARKLDLTQEMRRQLRDQYIAAMLAAIGDL
LNAIMQAKREADKLKKAGLVNSQQLDELKRRLEELEEEAAQKAADYGQEFLLKLEY (SEQ ID NO: 45)

> X-CDP06 (Target: Bcl-xL)
ADPKKVLDKAKDRAENRVRELKKKLEKLYKEARKLDLTQEQRNKIINAAMAAMIAAFGDIF
HAIQEAKEEAKKLKKAGLVNSQQLDELKRRLDELDEEAAQRAEKLGKEFNLKFEY (SEQ ID NO: 46)

> X-CDP07 (Target: Bcl-xL)
ADPKKVLDKAKDRAENVVRKLKKELEELYKEARKLDLTQEMRDRIRLAAIAARIAAFGDIFH
AIMEALEEARKLKKAGLVNSQQLDELKRRLEELDEEAAQRAEKLGKEFELKLEY (SEQ ID NO: 47)

> X-CDP08 (Target: Bcl-xL)
ADPKKVLDKAKDRAENRVRKLKKELEKLYKEARKLDLTQEQRDRIINAAIAAMIAAFGDIFH
AIMEAKEEARKLKKAGLVNSQQLDELKRRLDELDEEAAQRAEKLGKEFRLKFEY (SEQ ID NO: 48)

> X-CDP09 (Target: Bcl-xL)
ADPKKVLDKAKDQAENRVRELKQKLEELYKEARKLDLTQEMRKKLIQKALSALLKAIGDIL
DAIARAKAEADKLKKAGLVNSQQLDELKRRLEELLKEAARKALDYGREFWLKLEY (SEQ ID NO: 49)
```

TABLE 6-continued

Sequences of computationally designed proteins (CDPs) prior to experimental optimization and evolved combinatorial mutants (ECM) selected for BLI screening.

> X-CDP10 (Target: Bcl-xL)
ADPKKVLDKAKDQAENRVRELKQKLEELYKEARKLDLTQEMRRELRERYIAAMLAAAGDL
WYAITQAKREADKLKKAGLVNSQQLDELKRRLEELLEEAARKAEDYGEEFRLKLEY (SEQ ID NO: 50)

> X-CDP11 (Target: Bcl-xL)
ADPKKVLDKAKDQAENRVRELKQKLEELYKEARKLDLTQEMRRELRDRYIAAMLAAIGDLF
NAIQWAKQEADKLKKAGLVNSQQLDELKRRLEELAEEAARKAEDYGEEFKLKLEY (SEQ ID NO: 51)

> 10-CDP01 (Target: Bcl-B)
ADPKKVLDKAKDQAENRVRELKQELERLYKEARKLDLTQEMRRKLEWRYIAAMLKAIGDIL
NAIAQAENEADKLKKAGLVNSQQLDELRRRLEELAKEAARKAHDYGREFQLKLEY (SEQ ID NO: 52)

> F-CDP01 (Target: Bfl-1)
ADPKKVLDKAKDQAENRVRELKQKLEELYKEARKLDLTQEMRKKLQYAAIGAMLAAIGDI
LNAIMQAKQEADKLKKAGLVNSQQLDELKRRLEELKEEALRKAHDYGSEFYLKLEY (SEQ ID NO: 53)

> X-ECM01 (Target: Bcl-xL)
ADPKKVLDKAKDRAENVVRKLKKELEELYKEARKLDLTQEMRDRIRRAAIAARIQAHGDIF
HAIKHALREARKLKKAGLVNSQQLDELKRRLEELDEEAEQRAEKLGKEFELKLEYG (SEQ ID NO: 54)

> X-ECM02 (Target: Bcl-xL)
ADPKKVLDKAKDRAENVVRKLKKELEELYKEARKLDLTQEMRDRIRRTAIAARFQAHGDIF
HAIKEAKREARKLKKAGLVNSQQLDELKRRLEELDEEAEQRAEKLGKEFELKLEYG (SEQ ID NO: 55)

> X-ECM03 (Target: Bcl-xL)
ADPKKVLDKAKDRAENVVRKLKKELEELYKEARKLDLTQEMRDRIRRAAIAARFAAHGDIF
HAIKEAKEEARKLKKAGLVNSQQLDELKRRLRELDEEAEQRAEKLGKEFRLKLEYG (SEQ ID NO: 56)

> X-ECM04(XINDI) (Target: Bcl-xL)
ADPKKVLDKAKDRAENVVRKLKKELEELYKEARKLDLTQEMRDRIRRTAIAARFQAHGDIF
HAIKHAKEEARKLKKAGLVNSQQLDELKRRLRELDEEAEQRAEKLGKEFRLKLEYG (SEQ ID NO: 4)

> 10-ECM01 (Target: Bcl-B)
ADPKKILDKAKDQVENRVRELKQELERLYKEARKLDLTQEMRRKLHVRYIAAMLKAIAAIL
NAIAQAENEADKLKKAGLVNSQQLDELRRRLEELTEEAAQKAHDYGREFQLKLEYG (SEQ ID NO: 58)

> 10-ECM02 (Target: Bcl-B)
ADPKKILDKAKDQVENRVRELKQELERLYKEARKLDLTQEMRRKLHVRYIAAMLKAIASIL
NAIAQAENEADKLKKAGLVNSQQLDELRRRLEELTEEAAQKAHDYGREFQLKLEYG (SEQ ID NO: 59)

> 10-ECM03 (Target: Bcl-B)
ADPKKILDKAKDQVENRVRELKQELERLYKEARKLDLTQEMRRKLHVRYIAAMLKAIADIL
NAIAQAENEADKLKKAGLVNSQQLDELRRRLEELTEEAARKAHDYGREFQLKLEYG (SEQ ID NO: 60)

> 10-ECM04 (Target: Bcl-B)
ADPKKILDKAKDQVENRVRELKQELERLYKEARKLDLTQEMRRKLHWRYIAAMLKAIADIL
NAIAQAENEADKLKKAGLVNSQQLDELRRRLEELTEEAARKAHDYGREFQLKLEYG (SEQ ID NO: 61)

> F-ECM01 (Target: Bfl-1)
ADPKKVLDKAKDQAENRVRELKQKLEELYKEARKLDLTQEMRKKLEIAALGAVLAAHGDI
LNAIMQAKEEADKLKKAGLVNSQQLDELKRRLEELKEEALRKASDYGKEFHLKRQYG (SEQ ID NO: 62)

> F-ECM02 (Target: Bfl-1)
ADPKKVLDKAKDQAENRVRELKQKLEELYKEARKLDLTQEMRKKLEIAALGAVLAAHGDI
LNAIMQAKEEADKLKKAGLVNSQQLDELKRRLEELKEEALRKASDYGKEFHLKRRYG (SEQ ID NO: 63)

> F-ECM03 (Target: Bfl-1)
ADPKKVLDKAKDQAENRVRELKQKLEELYKEARKLDLTQEMRKKLEVAALGAVLAAHGDI
LNAIMQAKEEADKLKKAGLVNSQQLDELKRRLEELKEEALRKASDYGKEFHLKRQYG (SEQ ID NO: 64)

> F-ECM04 (Target: Bfl-1)
ADPKKVLDKAKDQAENRVRELKQKLEELYKEARKLDLTQEMRKKLEVAALGAVLAAHGDI
LNAIMQAKEEADKLKKAGLVNSQQLDELKRRLEELKEEALRKASDYGKEFHLKRRYG (SEQ ID NO: 65)

> F-ECM05 (Target: Bfl-1)
ADPKKVLDKAKDQAENRVRELKQKLEELYKEARKLDLTQEMRKKLQIAALGAMLAAIGDIL
NAIMQAKEEADKLKKAGLVNSQQLDELKRRLEELKEEALRKASDYGKEFHLKRQYG (SEQ ID NO: 66)

> F-ECM06 (Target: Bfl-1)
ADPKKVLDKAKDQAENRVRELKQKLEELYKEARKLDLTQEMRKKLQIAALGAMLAAIGDIL
NAIMQAKEEADKLKKAGLVNSQQLDELKRRLEELKEEALRKASDYGSEFHLKREYG (SEQ ID NO: 31)

> F-ECM07 (Target: Bfl-1)
ADPKKVLDKAKDQAENRVRELKQKLEELYKEARKLDLTQEMRKKLQIAALGAMLAAIGDIL
NAIMQAKEEADKLKKAGLVNSQQLDELKRRLEELKEEALRKASDYGSEFHLKLEYG (SEQ ID NO: 57)

TABLE 6-continued

Sequences of computationally designed proteins (CDPs) prior to experimental optimization and evolved combinatorial mutants (ECM) selected for BLI screening.

```
> W-CDP01 (Target: Bcl-w)
DPKKVFDKAKDKAENQVRYLKQRLEELYKEARKKDLTQEQRRKLKEKYLAAKLAAILAAIG
DAFNALAEARELHKQGKVNKQQLDELAKRLDRLAEEAIQKAEDYAREFAYKLEY (SEQ ID NO: 262)

> W-CDP02 (Target: Bcl-w)
DPKKVLDKARDQALKRLEEMRKKLEESYKEARKKDLTQEERRKLEEKYAEAMKRAAEDIY
NMIQQALKEAEKEKKAGQVNSQQLDKLREDLNNKLIAAALAAIGDAFNMAANLRT (SEQ ID NO: 263)

> W-CDP03 (Target: Bcl-w)
DPKKVFDEAKDRAENNVRRLKQKLEELYKEARKKDLTQEEREKLKEKYKTAMAAAALAAI
GDAFNALLKARKLHKNGQVNEQQLEELARRLQELAKEAFQKAKDYANEFEYKLEY (SEQ ID NO: 264)

> W-ECM01 (Target: Bcl-w; also referred to as WINDI, or αBCLW)
DPKKVFDELKDRAENNVRRLKQKLEELYKEARKKDLTQEEREKLKTKYKTAMQLAALAAE
GDIMNALLKARKLHKNGQVNEQQLEELARRLMELAKEAFQKAKDYANEFKYKLEY (SEQ ID NO: 265)

> W-ECM02 (Target: Bcl-w)
DPKKVFDELKDRAENNVRQLKQKLEELYKEARKKDLTQEEREKLKDKYKTAMHIAALAAE
GDIMNALLKARKLHKRGQVNEQQLRELARRLMELAKEAFQKAKDYANEFKYKLEY (SEQ ID NO: 266)

> W-ECM03 (Target: Bcl-w)
DPKKVFDELKDRAENNVRRLKQKLEELYKEARKKDLTQEEREKLKTKYKTAMHIAALAAE
GDIINALLKARKLHKRGQVNEQQLRELARRLMELAKEAFQKAKDYANEFEYKLEY (SEQ ID NO: 267)

> W-ECM04 (Target: Bcl-w)
DPKKVFDELKDRAENNVRNLKQKLEELYKEARKKDLTQEEREKLKDKYKTAMQIAALAAE
GDIMNALLKARKLHKNGQVNEQQLRELARRLMELAKEAFQKAKDYANEFKYKLEY (SEQ ID NO: 268)

> W-ECM05 (Target: Bcl-w)
DPKKVFDELKDRAENNVRNLKQKLEELYKEARKKDLTQEEREKLKTKYKTAMAIAALAAE
GDLLNALLKARKLHKRGQVNEQQLRELARRLMELAKEAFQKAKDYANEFKYKLEY (SEQ ID NO: 269)

> W-ECM50 (Target: Bcl-w)
DPKKVFDELKDRAENNVRRLKQKLEELYKEARKKDLTQEEREKLKTKYKTAMAIAALAAE
GDIMNALLKARKLHKRGQVNEQQLRELARRLMELAKEAFQKAKDYANEFKYKLEY (SEQ ID NO: 270)

> W-ECM60 (Target: Bcl-w)
DPKKVFDELKDRAENNVRRLKQKLEELYKEARKKDLTQEEREKLKTKYKTAMAAAALAAE
GDAFNALLKARKLHKRGQVNEQQLRELARRLMELAKEAFQKAKDYANEFKYKLEY (SEQ ID NO: 271)

> W-ECM70 (Target: Bcl-w)
DPKKVFDELKDRAENNVRRLKQKLEELYKEARKKDLTQEEREKLKEKYKTAMAAAALAAE
GDAFNALLKARKLHKNGQVNEQQLRELARRLMELAKEAFQKAKDYANEFKYKLEY (SEQ ID NO: 272)

> W-ECM80 (Target: Bcl-w)
DPKKVFDELKDRAENNVRRLKQKLEELYKEARKKDLTQEEREKLKEKYKTAMAAAALAAE
GDAFNALLKARKLHKNGQVNEQQLRELARRLMELAKEAFQKAKDYANEFEYKLEY (SEQ ID NO: 273)
```

Figure 17:
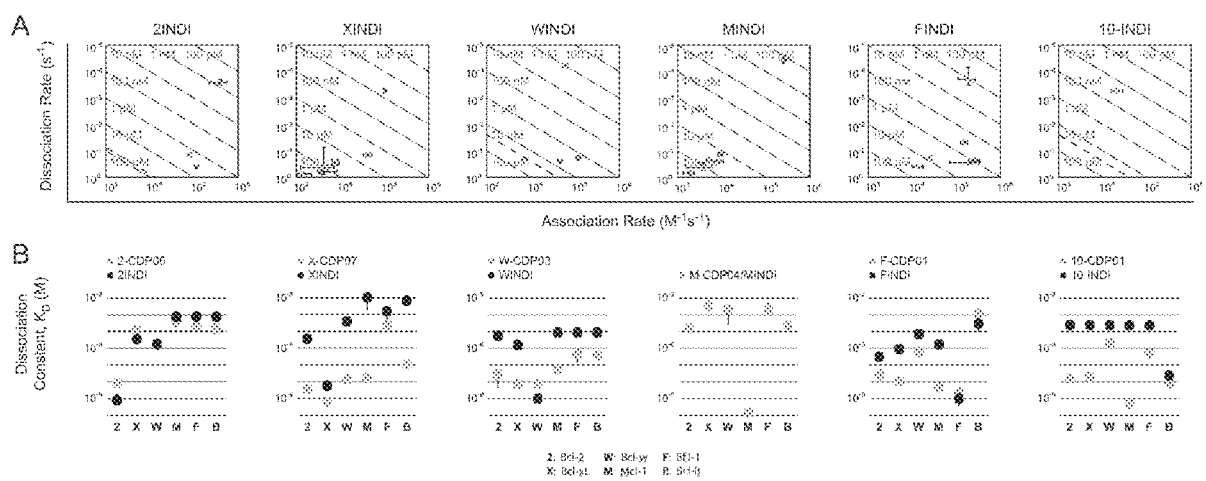
FIG. 17. Quantitative BLI analysis of optimized designs binding each BCL2 protein. For a given binding pair, the biotinylated BCL2 protein was immobilized on the surface of streptavidin-coated sensors, incubated with a range of concentrations of soluble designed protein (association), and then placed back in buffer (dissociation). Data were fitted with analysis software. (A) The determined on- and off-rates are plotted, where dashed lines indicate where binding was too weak to be accurately measured. Weak interactions that fall below the dashed lines are not plotted. (B) $K_D$s of pre-optimized computational designs compared to optimized variants are plotted. $K_D$s can also be found in Table 10 (mean+/−SD; n=3).

Initial screening by BLI indicated designed proteins generally bound their intended targets with nanomolar affinity and moderate specificity, but lacked the exceptional specificity of MINDI for Mcl-1 or BINDI for BHRF1. The designed proteins were therefore now improved by directed evolution. Selecting individual designs with promising partial specificity for each target BCL2 protein, the genes were diversified at every codon position to encode all possible single amino acid substitutions, and the libraries were transformed into yeast as Aga2p fusions for surface display. Each library was selected by one round of FACS for high affinity binding to the intended target (biotinylated for detection with streptavidin-phycoerythrin), with the other five human BCL2 proteins (unlabeled) added to the binding reaction as competitors to favor specific interactions. The pre- and post-sort populations were deep sequenced and enrichment ratios for all single amino acid substitutions calculated. From these sequence-fitness landscapes, mutations were chosen that were highly enriched during selection (Table 7). In the cases of the designed Bcl-XL, Bcl-B, and Bfl-1 binders, these enriching mutations were then combined in a combinatorial library that was selected by five (Bcl-XL binder) or three (Bfl-1 and Bcl-B binders) rounds of FACS to find variants with significantly improved affinity and/or specificity, each round under more stringent conditions including lower concentrations of target Bcl-2 paralogue and/or higher concentrations of competitors (Tables 7 and 8). Another round of directed evolution was required to further improve specificity of the Bfl-1 and Bcl-B binders. In these cases, the most specific evolved combinatorial mutants (10-ECM01 and F-ECM04) were diversified by error prone PCR, expressed on the yeast cell surface and selected as previously (Tables 7 and 8). In the case of the designed Bcl-2 binder, the computationally designed protein 2-CDP06 bound Bcl-2 with high affinity prior to in vitro evolution. Therefore, 20 point mutants indicating improved affinity and specificity in the sequence-fitness landscape were screened by BLI in lieu of further evolution. Point mutants that improved affinity for Bcl-2 while diminishing affinity for other paralogues were combined. Ultimately protein variants were found that bind each BCL2 paralogue with high affinity and specificity (FIG. 17 and Table 9).

TABLE 7

Design and directed evolution of BCL2-protein specific binders

| Name of Final Variant | Target | Name of Original Computational Design | Combinatorial library created | | No combinatorial library | | Additional mutations from error prone-PCR library |
|---|---|---|---|---|---|---|---|
| | | | SSM mutations included in combinatorial library | Mutations in isolated clone from combinatorial library | SSM-guided point mutants screened | Point mutants combined for final design | |
| MINDI | Mcl-1 | M-CDP04 | NA | NA | NA | NA | NA |
| 2-INDI | Bcl-2 | 2-CDP06 | NA | NA | E20N, K24R, V46E, V46R, D47F, D47W, R50D, R50L, R50M, S53D, S53K, S53R, S57H, S57N, L68R, R100F, R100K, R100N, G107M, G107R | K24R, S57N, G107R | NA |
| XINDI | Bcl-XL | X-CDP07 | E24R, L28K, D43R, L47R, A48E, A48K, A48Q, A48T, I54F, A55Q, F57H, M65H, M65K, M65R, E66H, E66K, E66R, L68K, L68N, L68R, E69R, E70R, E93K, E93R, D96T, A100E, A100K, A100Q, E111R | L47R, A48T, I54F, A55Q, F57H, M65K, E66H, L68K, E93R, A100E, E111R | NA | NA | NA |
| 10-INDI | Bcl-B/ BCL2L10 | 10-CDP01 | I6V, A14V, N16K, E20F, L21V, E46H, E46Q, E46Y, W47F, W47I, W47L, W47V, Y49F, I50L, A51E, A51I, A51K, A51R, L54I, G58A, G58S, D59A, D59K, D59N, D59S, D59T, A63L, A63V, E93K, A96T, K97E, R101Q | V6I, A14V, E46H, W47V, G58A, D58A, A96T, K97E, R101Q | NA | NA | A51E, L61M, F110L |
| FINDI | Bfl-1 | F-CDP01 | Q46S, Q46E, Y47I, Y47V, I50K, I50L, I50M, M53C, M53I, M53V, L54N, I57F, I57H, I57L, I57N, I57S, I57T, Q69E, H104E, H104R, H104S, H104T, S108K, S108N, Y111H, Y111K, Y111W, L114R, | Q46E, Y47V, I50L, M53V, I57H, Q69E, H104S, S108K, L114R, E115R | NA | NA | M41K, A49T, N108K |

TABLE 7-continued

Design and directed evolution of BCL2-protein specific binders

| Name of Final Variant | Target | Name of Original Computational Design | Combinatorial library created | | No combinatorial library | | |
|---|---|---|---|---|---|---|---|
| | | | SSM mutations included in combinatorial library | Mutations in isolated clone from combinatorial library | SSM-guided point mutants screened | Point mutants combined for final design | Additional mutations from error prone-PCR library |
| WINDI | Bcl-w | W-CDP03 | E115G, E115Q, E115R A9L, R19N, R19Q, E46D, E46T, A53E, A53H, A53Q, A54I, A54L, A54M A54S, A54T, A54V, A59I, A59M, A59T, A59V, I60E, A63F, A63I, A63L, A63M, F64I, F64L, F64M, N76R, E85R, Q92M, Q92T, E93V, E97D, F99E, E110K | A9L, E46T, A53Q, A54L, I60E, A63I, F64M, Q92M, E110K | NA | NA | NA |

TABLE 8

Sort conditions for SSM, combinatorial and error-prone PCR libraries

| Library | Sort | Incubation conditions | |
|---|---|---|---|
| | | Target concentration (nM) | Competitor concentration (nM) |
| 2-CDP06 SSM | 1 | 0.5 | 40 |
| 2-CDP06 SSM | 2 | 0.25 | 40 |
| X-CDP07 SSM | 1 | 2 | 4 |
| X-CDP07 SSM | 2 | 2 | 4 |
| X-CDP07 combinatorial | 1 | 1 | 8 |
| X-CDP07 combinatorial | 2 | 0.5 | 32 |
| X-CDP07 combinatorial | 3 | 0.35 | 64 |
| X-CDP07 combinatorial | 4 | 0.2 | 100 |
| X-CDP07 combinatorial | 5 | 0.1 | 200 |
| 10-CDP01 SSM | 1 | 4 | 8 |
| 10-CDP01 SSM | 2 | 4 | 8 |
| 10-CDP combinatorial | 1 | 4 | 8 |
| 10-CDP combinatorial | 2 | 2 | 8 |
| 10-CDP combinatorial | 3 | 2 | 16 |
| 10-CDP combinatorial | 4 | 2 | 16 |
| 10-ECM01 error-prone PCR | 1 | 0.5 | 40 |
| 10-ECM01 error-prone PCR | 2 | 0.2 | 40 |
| 10-ECM01 error-prone PCR | 3 | 0.2 | 40 |
| 10-ECM01 error-prone PCR | 4 | 0.1 | 40 |
| 10-ECM01 error-prone PCR | 5 | 0.1 | 40 |
| F-CDP01 SSM | 1 | 4 | 4 |
| F-CDP01 SSM | 2 | 4 | 4 |
| F-CDP01 combinatorial | 1 | 4 | 8 |
| F-CDP01 combinatorial | 2 | 2 | 8 |
| F-CDP01 combinatorial | 3 | 2 | 16 |
| F-CDP01 combinatorial | 4 | 2 | 16 |
| F-ECM04 error-prone PCR | 1 | 0.75 | 40 |
| F-ECM04 error-prone PCR | 2 | 0.5 | 40 |
| F-ECM04 error-prone PCR | 3 | 0.5 | 40 |
| F-ECM04 error-prone PCR | 4 | 0.5 | 40 |
| F-ECM04 error-prone PCR | 5 | 0.5 | 40 |
| W-CDP03 SSM | 1 | 2 | 8 |
| W-CDP03 SSM | 2 | 0.5 | 2 |
| W-CDP03 combinatorial | 1 | 0.5 | 2 |
| W-CDP03 combinatorial | 2 | 0.15 | 3 |
| W-CDP03 combinatorial | 3 | 0.05 | 20 |
| W-CDP03 combinatorial | 4 | 0.05 | 40 |
| W-CDP03 combinatorial | 5 | 0.05 | 80 |

TABLE 9

Sequences of BINDI derivatives that specifically bind BCL2 family members

Name: MINDI Target: Mcl-1
ADPKKVLDKAKDQAENRVRELKQVLEELYKEARKLDLTQEMRKKLIERY
AAAIIRAIGDINNAIYQAKQEAEKLKKAGLVNSQQLDELLRRLDELQKE
ASRKANEYGREFELKLEY (SEQ ID NO: 2)

Name: 2-INDI Target: Bcl-2
ADPKKVLDKAKDEAENRVRELKQRLEELYKEARKLDLTQEMRQELVDKA
RAASLQANGDIFYAILRALAEAEKLKKAGLVNSQQLDELKRRLEELAEE
ARRKAEKLRDEFRLKLEY (SEQ ID NO: 3)

Name: XINDI Target: Bcl-XL
ADPKKVLDKAKDRAENVVRKLKKELEELYKEARKLDLTQEMRDRIRRTA
IAARFQAHGDIFHAIKHAKEEARKLKKAGLVNSQQLDELKRRLRELDEE
AEQRAEKLGKEFRLKLEY (SEQ ID NO: 4)

TABLE 9-continued

Sequences of BINDI derivatives that specifically
bind BCL2 family members

Name: 10-INDI Target: Bcl-B/BCL2L10
ADPKKILDKAKDQVENRVRELKQELERLYKEARKLDLTQEMRRKLHVRY
IEAMLKAIAAIMNAIAQAENEADKLKKAGLVNSQQLDELRRRLEELTEE
AAQKAHDYGRELQLKLEY (SEQ ID NO: 5)

Name: FINDI Target: Bfl-1
ADPKKVLDKAKDQAENRVRELKQKLEELYKEARKLDLTQEKRKKLEVAT
LGAVLAAHGDILNAIMQAKEEADKLKKAGLVNSQQLDELKRRLEELKEE
ALRKASDYGNEFHLKRRY (SEQ ID NO: 6)

Name: WINDI Target: Bcl-w
ADPKKVFDELKDRAENNVRRLKQKLEELYKEARKKDLTQEEREKLKTKY
KTAMQLAALAAEGDIMNALLKARKLHKNGQVNEQQLEELARRLMELAKE
AFQKAKDYANEFKYKLEY (SEQ ID NO: 265)

Figure 18:
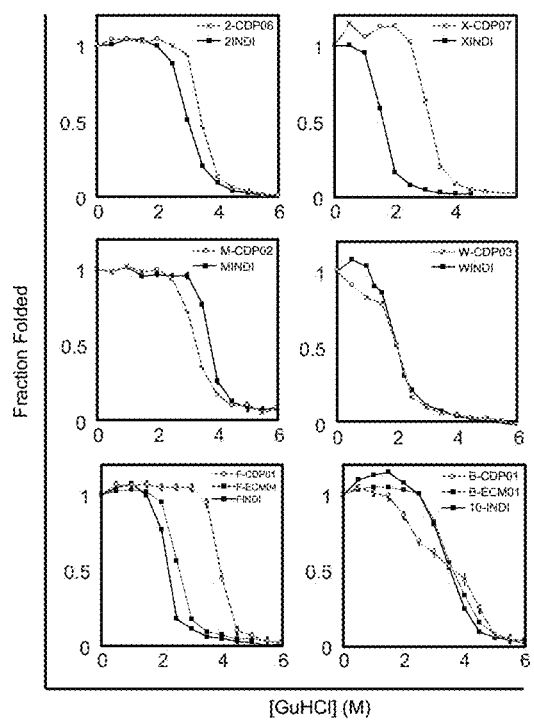
FIG. 18. Computationally designed proteins 2-CDP06 (A), X-CDP07 (B), 10-CDP01 (C), F-CDP01 (D) and W-CDP03 (E) and their experimentally optimized derivatives 2-INDI (A), XINDI (B), 10-ECM01 and 10-INDI (C), F-ECM04 and FINDI (D) and WINDI (E) were denatured with guanidinium hydrochloride. Loss of CD signal at 222 nm was used to calculate the fraction folded.

The final variants that specifically bind Bcl-2, Bcl-XL, Bcl-B/BCL2L10, and Bfl-1 with high affinity are named 2-INDI, XINDI, 10-INDI and FINDI, respectively. Based on BLI measurements at multiple analyte concentrations (FIG. 17), 2-INDI binds Bcl-2 with $K_D$ 0.839±0.005 nM and >2,000-fold weaker affinity for the next tightest binding BCL2 family protein; XINDI binds Bcl-XL with $K_D$ 5.59±0.03 nM and >660-fold weaker affinity for other BCL2 proteins; 10-INDI binds Bcl-B with 24.7±0.1 nM affinity, and 1000-fold specificity; and FINDI binds Bfl-1 with $K_D$ 0.91±0.01 nM and >350-fold specificity (Table 10). These affinities and specificities are similar or better than other engineered peptides or small molecule ligands of BCL2 family proteins. When exposed to the chemical denaturant guanidinium hydrochloride, all the optimized inhibitors had sharp unfolding transitions as measured by loss of CD absorbance for helical structure (FIG. 18). For 2-INDI, XINDI and FINDI, the protein stabilities were slightly to moderately decreased from the original computational designs. However, unfolding was still a cooperative reaction over narrow guanidinium concentrations, suggestive of a well-packed protein core.

Figure 19:
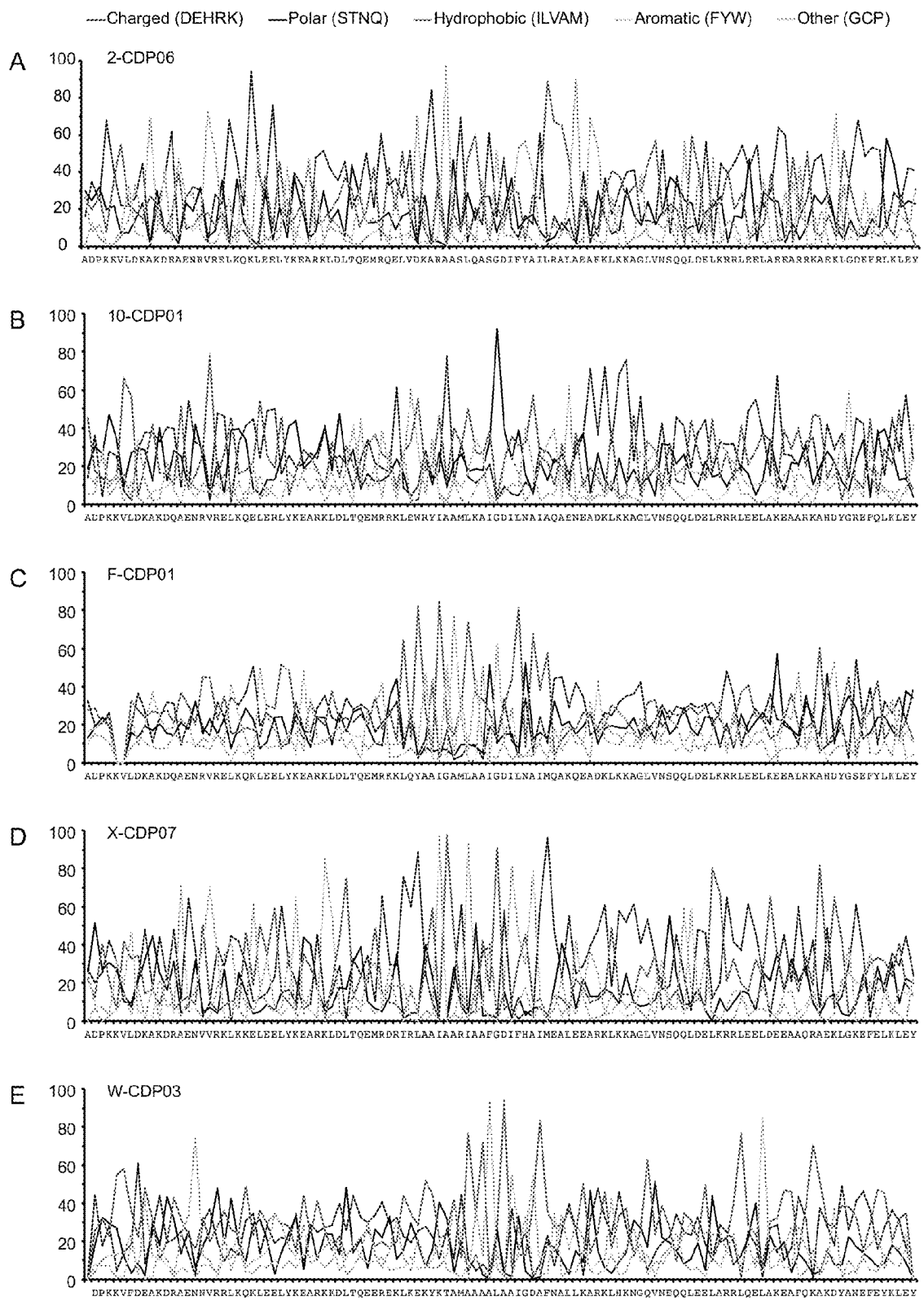
FIG. 19. Beginning with a hypothetical population of diverse protein variants, we applied experimental enrichment ratios for all single amino acid substitutions to evolve our population in silico. The probability of finding a particular amino acid at any given position was then calculated. This analysis gives an indication of the tolerated sequence diversity in the protein. (A) 2-CDP06 (optimized to 2-INDI) (SEQ ID NO: 39), (B) 10-CDP01 (optimized to 10-INDI) (SEQ ID NO: 52), (C) F-CDP01 (optimized to FINDI) (SEQ ID NO: 53), (D) X-CDP07 (optimized to XINDI) (SEQ ID NO: 47), and (E) W-CDP03 (optimized to WINDI) (SEQ ID NO: 264).

Using the experimental sequence-fitness landscapes described above, we could determine the allowed sequence variability for the designed proteins (FIG. 19, Tables 11-20). While our saturation mutagenesis data are for the original computational designs, they nonetheless likely capture the capacity of the final optimized variants to tolerate mutations. As described for BINDI earlier, sequence conservation varies across the protein sequence, and while some positions are reasonably conserved for high affinity and specific interaction with a BCL2 family member, other positions are not. The BINDI scaffold is able to tolerate many mutations while preserving function. The different BCL2 inhibitors differ from each other by as many as 39 mutations, yet when any of the sequences is queried against GenBank for homologues by BLAST (E-value threshold 0.1), the proteins are found to be related only to each other, without homologous natural proteins. We have therefore designed an unnatural protein scaffold that can be easily repurposed for binding any BCL2 family member. Any modified version of BINDI or its derivatives will similarly belong to our designed protein family but lack homology to any natural protein, and should therefore be covered by the claims in this patent.

Figure 20:
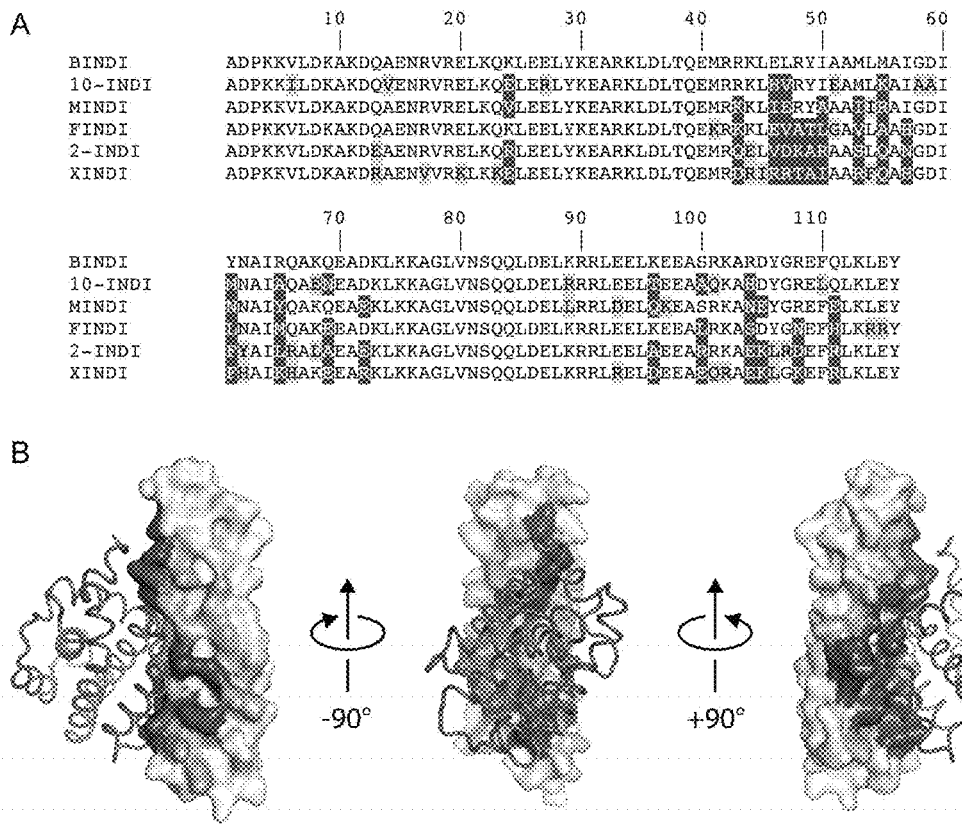
FIG. 20. (A) Sequence alignment of specific BCL2 protein binders. Differences from BINDI, the original designed binder targeting viral BHRF1 that was repurposed for binding other BCL2 family members, are highlighted (from top to bottom SEQ ID NOs: 1, 5, 2, 6, 3, and 4). The Bcl-w binder, WINDI, has been excluded as it binds its target via a shifted interaction surface. Residues that differ from BINDI in one or two sequences are shaded grey, while residues that differ in three or more of the derived binders are shaded black. (B) Sequence variation amongst the INDI family is mapped to the structure of BINDI (surface representation) bound to BHRF1 (ribbon).

An alignment of the optimized binders demonstrates that some amino acids differ in just one or a couple of the proteins, while other residues diverge among most of the binders and are likely strong determinants of specificity (FIG. 20A). When mapped to the structure of BHRF1-bound BINDI, residues that differ in just a couple of the binders tend to be localized to the extreme edges of the interface where there is minimal direct contact, with a few positions in the very center of the interface that are conserved for binding across the BCL2 family (FIG. 20B). By comparison, the primary specificity-determining residues are localized around the interface core at sites of direct contact (FIG. 20B). Our interface can therefore be divided into three regions from the center outwards: (i) a conserved core for binding all BCL2 family members, (ii) a region that prin-

TABLE 10

$K_D$ values for designed binder-BCL2 protein interactions

|  | Mcl-1 | Bcl-2 | Bcl-XL | Bcl-B | Bfl-1 | Bcl-w | Specificity |
|---|---|---|---|---|---|---|---|
| MINDI | 0.15 ± 0.06 | 14,200 ± 700 | 400,000 ± 100,000 | 40,000 ± 10,000 | 30,000 ± 10,000 | 200,000 ± 200,000 | 93,000 |
| 2-INDI | >75 μM | 0.839 ± 0.005 | 3,500 ± 200 | >75 μM | >75 μM | 1,850 ± 80 | 2210 |
| 2-CDP06 | >50 μM | 8.9 ± 0.9 | 12,000 ± 2,000 | >50 μM | >50 μM | 1,670 ± 40 | 190 |
| XINDI | >50 μM | 3,700 ± 100 | 5.59 ± 0.03 | >50 μM | >50 μM | 40,000 ± 6,000 | 660 |
| X-CDP07 | 174.2 ± 0.2 | 3.81 ± 0.04 | 0.590 ± 0.003 | 107 ± 3 | >50 μM | 14.89 ± 0.06 | 6.46 |
| 10-INDI | >25 μM | >25 μM | >25 μM | 24.7 ± 0.1 | >25 μM | >25 μM | 1010 |
| 10-ECM01 | 3,650 ± 60 | 12,500 ± 700 | 7,800 ± 300 | 77 ± 7 | 2,380 ± 80 | 19,000 ± 1,000 | 31 |
| 10-CDP01 | 0.47 ± 0.07 | 14 ± 4 | 16 ± 2 | 9 ± 1 | 250 ± 100 | 900 ± 700 | 0.05 |
| FINDI | 1,700 ± 100 | 321 ± 20 | 900 ± 100 | 31,000 ± 6,000 | 0.91 ± 0.01 | 7,400 ± 600 | 350 |
| F-ECM04 | 255 ± 8 | 100 ± 1 | 540 ± 20 | 4,000 ± 1,000 | 1.1 ± 0.3 | 3,800 ± 100 | 91 |
| F-CDP01 | 4.6 ± 0.7 | 20 ± 11 | 9 ± 1 | 210,000 ± 74,000 | 2.6 ± 0.4 | 590 ± 40 | 1.8 |
| W-CDP03 | 55.3 ± 0.8 | 18.8 ± 2 | 7.43 ± 0.08 | 400 ± 8 | 400 ± 20 | 8.00 ± 0.08 | 0.9 |
| WINDI | >25 μM | 5700 ± 900 | 1,610 ± 61 | >25 μM | >25 μM | 1.013 ± 0.005 | 1590 | cipally determines specific interactions, and (iii) an extreme periphery that can offer an occasional specificity contact.

TABLE 11

Allowed sequence variability in 2-CDP06 from single site saturation mutagenesis

| Residue | Conservation score | % Probability | | | | |
|---|---|---|---|---|---|---|
| | | Charged DEHRK | Polar STNQ | Hydrophobic ILVAM | Aromatic FYW | Other GCP |
| A1 | 0.35 | 16 | 30 | 27 | 0 | 26 |
| D2 | 0.2 | 35 | 25 | 20 | 13 | 8 |
| P3 | 0.13 | 25 | 32 | 27 | 4 | 12 |
| K4 | 0.27 | 68 | 20 | 8 | 2 | 2 |
| K5 | 0.24 | 40 | 22 | 37 | 1 | 1 |
| V6 | 0,3 | 22 | 7 | 55 | 5 | 10 |
| L7 | 0.24 | 22 | 7 | 23 | 15 | 33 |
| D8 | 0.2 | 26 | 14 | 19 | 33 | 7 |
| K9 | 0.16 | 45 | 23 | 15 | 11 | 5 |
| A10 | 0.58 | 0 | 1 | 27 | 69 | 2 |
| K11 | 0.18 | 21 | 30 | 23 | 17 | 9 |
| D12 | 0.34 | 36 | 9 | 7 | 7 | 41 |
| E13 | 0.21 | 62 | 8 | 17 | 10 | 3 |
| A14 | 0.37 | 4 | 2 | 40 | 47 | 6 |
| E15 | 0.23 | 27 | 24 | 10 | 27 | 13 |
| N16 | 0.18 | 32 | 19 | 11 | 29 | 9 |
| R17 | 0.19 | 30 | 32 | 17 | 8 | 13 |
| V18 | 0.57 | 2 | 5 | 18 | 2 | 72 |
| R19 | 0.35 | 28 | 8 | 11 | 2 | 51 |
| E20 | 0.18 | 23 | 36 | 19 | 10 | 12 |
| L21 | 0.64 | 69 | 1 | 4 | 27 | 0 |
| K22 | 0.39 | 47 | 36 | 7 | 1 | 8 |
| Q23 | 0.31 | 22 | 14 | 9 | 17 | 38 |
| K24 | 0.81 | 94 | 4 | 1 | 0 | 0 |
| L25 | 0.48 | 41 | 1 | 2 | 55 | 1 |
| E26 | 0.36 | 26 | 30 | 38 | 1 | 5 |
| E27 | 0.45 | 76 | 4 | 10 | 8 | 3 |
| L28 | 0.29 | 21 | 21 | 45 | 8 | 5 |
| Y29 | 0.24 | 16 | 5 | 11 | 26 | 43 |
| K30 | 0.36 | 40 | 37 | 15 | 1 | 8 |
| E31 | 0.22 | 33 | 21 | 23 | 19 | 4 |
| A32 | 0.3 | 3 | 4 | 44 | 47 | 1 |
| R33 | 0.33 | 48 | 8 | 12 | 1 | 31 |
| K34 | 0.32 | 52 | 30 | 14 | 1 | 3 |
| L35 | 0.2 | 42 | 13 | 19 | 15 | 10 |
| D36 | 0.22 | 36 | 20 | 26 | 11 | 8 |
| L37 | 0.32 | 46 | 6 | 37 | 3 | 8 |
| T38 | 0.31 | 20 | 44 | 30 | 2 | 3 |
| Q39 | 0.25 | 30 | 27 | 11 | 1 | 30 |
| E40 | 0.23 | 50 | 11 | 19 | 3 | 13 |
| M41 | 0.18 | 21 | 13 | 43 | 8 | 15 |
| R42 | 0.31 | 61 | 15 | 4 | 10 | 11 |
| Q43 | 0.37 | 33 | 18 | 42 | 1 | 5 |
| E44 | 0.21 | 37 | 9 | 21 | 29 | 5 |
| L45 | 0.25 | 26 | 17 | 51 | 1 | 6 |
| V46 | 0.15 | 52 | 19 | 16 | 5 | 8 |
| D47 | 0.59 | 2 | 0 | 27 | 70 | 1 |
| K48 | 0.28 | 49 | 28 | 9 | 11 | 3 |
| A49 | 0.47 | 84 | 3 | 1 | 11 | 1 |
| R50 | 0.21 | 26 | 3 | 39 | 25 | 6 |
| A51 | 0.95 | 0 | 0 | 1 | 0 | 98 |
| A52 | 0.3 | 20 | 46 | 18 | 11 | 5 |
| S53 | 0.37 | 70 | 9 | 8 | 11 | 2 |
| L54 | 0.36 | 3 | 29 | 47 | 13 | 8 |
| Q55 | 0.48 | 21 | 15 | 60 | 0 | 4 |
| A56 | 0.33 | 12 | 27 | 24 | 35 | 3 |
| S57 | 0.56 | 61 | 27 | 4 | 4 | 4 |
| G58 | 0.4 | 16 | 8 | 23 | 2 | 51 |
| D59 | 0.31 | 48 | 19 | 11 | 16 | 6 |
| I60 | 0.31 | 10 | 37 | 30 | 17 | 6 |
| F61 | 0.37 | 5 | 10 | 29 | 53 | 4 |
| Y62 | 0.38 | 17 | 15 | 3 | 57 | 9 |
| A63 | 0.34 | 12 | 17 | 28 | 40 | 2 |
| I64 | 0.39 | 61 | 8 | 26 | 5 | 0 |
| L65 | 0.61 | 1 | 3 | 89 | 2 | 5 |
| R66 | 0.35 | 16 | 5 | 67 | 0 | 12 |
| A67 | 0.43 | 8 | 13 | 65 | 7 | 6 |
| L68 | 0.29 | 15 | 8 | 46 | 24 | 8 |
| A69 | 0.61 | 2 | 1 | 6 | 90 | 1 |
| E70 | 0.26 | 40 | 27 | 26 | 2 | 5 |
| A71 | 0.4 | 4 | 2 | 19 | 69 | 5 |
| E72 | 0.33 | 10 | 30 | 5 | 52 | 3 |
| K73 | 0.28 | 37 | 16 | 30 | 16 | 2 |
| L74 | 0.23 | 18 | 7 | 40 | 8 | 27 |
| K75 | 0.3 | 30 | 9 | 39 | 22 | 0 |
| K76 | 0.33 | 40 | 31 | 26 | 1 | 1 |
| A77 | 0.31 | 41 | 17 | 33 | 4 | 5 |
| G78 | 0.27 | 14 | 11 | 30 | 6 | 39 |
| L79 | 0.27 | 14 | 24 | 45 | 11 | 6 |
| V80 | 0.18 | 13 | 12 | 57 | 15 | 4 |
| N81 | 0.29 | 52 | 19 | 17 | 10 | 3 |
| S82 | 0.21 | 7 | 37 | 23 | 11 | 21 |
| Q83 | 0.25 | 38 | 33 | 19 | 0 | 8 |
| Q84 | 0.33 | 9 | 25 | 1 | 56 | 9 |
| L85 | 0.39 | 11 | 23 | 60 | 0 | 6 |
| D86 | 0.24 | 12 | 7 | 41 | 37 | 2 |
| E87 | 0.25 | 56 | 19 | 6 | 1 | 18 |
| L88 | 0.43 | 2 | 22 | 25 | 48 | 4 |
| K89 | 0.26 | 45 | 27 | 23 | 4 | 2 |
| R90 | 0.29 | 40 | 3 | 40 | 4 | 14 |
| R91 | 0.26 | 45 | 17 | 20 | 6 | 12 |
| L92 | 0.35 | 54 | 15 | 29 | 0 | 1 |
| E93 | 0.44 | 42 | 47 | 4 | 1 | 6 |
| E94 | 0.36 | 55 | 3 | 8 | 22 | 12 |
| L95 | 0.29 | 21 | 29 | 12 | 1 | 36 |
| A96 | 0.34 | 31 | 25 | 39 | 3 | 1 |
| E97 | 0.36 | 64 | 24 | 3 | 3 | 5 |
| E98 | 0.32 | 60 | 3 | 4 | 30 | 4 |
| A99 | 0.41 | 4 | 12 | 48 | 0 | 35 |
| R100 | 0.28 | 16 | 4 | 20 | 43 | 17 |
| R101 | 0.34 | 26 | 11 | 51 | 0 | 11 |
| K102 | 0.22 | 46 | 28 | 8 | 2 | 16 |
| A103 | 0.3 | 49 | 23 | 6 | 20 | 2 |
| E104 | 0.29 | 24 | 29 | 17 | 1 | 30 |
| K105 | 0.57 | 12 | 11 | 5 | 0 | 73 |
| L106 | 0.2 | 8 | 3 | 52 | 33 | 3 |
| G107 | 0.26 | 41 | 14 | 31 | 9 | 5 |
| D108 | 0.26 | 68 | 6 | 15 | 8 | 3 |
| E109 | 0.22 | 49 | 6 | 6 | 10 | 30 |
| F110 | 0.3 | 53 | 15 | 8 | 20 | 5 |
| R111 | 0.31 | 52 | 10 | 6 | 9 | 23 |
| L112 | 0.27 | 10 | 58 | 12 | 1 | 19 |
| K113 | 0.38 | 29 | 45 | 6 | 2 | 18 |
| L114 | 0.13 | 24 | 21 | 28 | 9 | 17 |
| E115 | 0.11 | 42 | 25 | 13 | 8 | 12 |
| Y116 | 0.37 | 41 | 23 | 0 | 31 | 6 |

TABLE 12

Allowed sequence variability in X-CDP07 from single site saturation mutagenesis

| Residue | Conservation score | % Probability | | | | |
|---|---|---|---|---|---|---|
| | | Charged DEHRK | Polar STNQ | Hydrophobic ILVAM | Aromatic FYW | Other GCP |
| A1 | 0.31 | 27 | 25 | 22 | 0 | 25

TABLE 12-continued

Allowed sequence variability in X-CDP07 from single site saturation mutagenesis

| Residue | Conservation score | % Probability Charged DEHRK | Polar STNQ | Hydrophobic ILVAM | Aromatic FYW | Other GCP |
|---|---|---|---|---|---|---|
| K11 | 0.22 | 44 | 25 | 8 | 1 | 22 |
| D12 | 0.19 | 22 | 17 | 26 | 28 | 8 |
| R13 | 0.36 | 48 | 31 | 7 | 5 | 10 |
| A14 | 0.44 | 12 | 4 | 11 | 71 | 3 |
| E15 | 0.24 | 64 | 8 | 13 | 5 | 10 |
| N16 | 0.16 | 37 | 32 | 9 | 7 | 15 |
| V17 | 0.55 | 2 | 5 | 50 | 1 | 41 |
| V18 | 0.53 | 10 | 7 | 11 | 2 | 70 |
| R19 | 0.31 | 39 | 4 | 5 | 18 | 34 |
| K20 | 0.25 | 29 | 27 | 8 | 34 | 2 |
| L21 | 0.47 | 45 | 0 | 11 | 42 | 2 |
| K22 | 0.21 | 42 | 26 | 6 | 7 | 19 |
| K23 | 0.34 | 30 | 15 | 46 | 0 | 9 |
| E24 | 0.23 | 10 | 4 | 19 | 62 | 3 |
| L25 | 0.29 | 12 | 5 | 50 | 16 | 16 |
| E26 | 0.26 | 15 | 9 | 34 | 9 | 33 |
| E27 | 0.27 | 23 | 6 | 60 | 5 | 6 |
| L28 | 0.34 | 60 | 15 | 15 | 6 | 4 |
| Y29 | 0.25 | 29 | 16 | 9 | 36 | 9 |
| K30 | 0.55 | 20 | 9 | 5 | 1 | 65 |
| E31 | 0.19 | 6 | 44 | 35 | 11 | 3 |
| A32 | 0.25 | 9 | 40 | 28 | 6 | 17 |
| R33 | 0.26 | 45 | 17 | 18 | 2 | 18 |
| K34 | 0.77 | 8 | 5 | 1 | 85 | 0 |
| L35 | 0.37 | 14 | 8 | 19 | 55 | 4 |
| D36 | 0.13 | 29 | 18 | 43 | 6 | 5 |
| L37 | 0.4 | 2 | 17 | 75 | 0 | 7 |
| T38 | 0.17 | 33 | 31 | 12 | 10 | 14 |
| Q39 | 0.27 | 24 | 39 | 24 | 5 | 8 |
| E40 | 0.1 | 34 | 10 | 20 | 26 | 10 |
| M41 | 0.34 | 10 | 7 | 49 | 30 | 3 |
| R42 | 0.33 | 65 | 5 | 15 | 8 | 7 |
| D43 | 0.17 | 30 | 13 | 10 | 19 | 28 |
| R44 | 0.26 | 29 | 35 | 9 | 18 | 8 |
| I45 | 0.64 | 76 | 1 | 4 | 19 | 0 |
| R46 | 0.4 | 60 | 4 | 16 | 1 | 19 |
| L47 | 0.8 | 89 | 4 | 5 | 0 | 2 |
| A48 | 0.24 | 24 | 40 | 29 | 5 | 1 |
| A49 | 0.41 | 10 | 23 | 59 | 4 | 4 |
| I50 | 0.64 | 0 | 1 | 2 | 97 | 0 |
| A51 | 0.57 | 0 | 1 | 98 | 0 | 1 |
| A52 | 0.26 | 20 | 28 | 46 | 3 | 3 |
| R53 | 0.38 | 61 | 8 | 10 | 1 | 19 |
| I54 | 0.65 | 0 | 2 | 3 | 94 | 1 |
| A55 | 0.43 | 19 | 52 | 5 | 4 | 21 |
| A56 | 0.39 | 36 | 3 | 42 | 10 | 8 |
| F57 | 0.44 | 39 | 3 | 16 | 40 | 1 |
| G58 | 0.83 | 2 | 2 | 91 | 0 | 6 |
| D59 | 0.37 | 58 | 16 | 6 | 17 | 3 |
| I60 | 0.56 | 6 | 2 | 11 | 81 | 0 |
| F61 | 0.33 | 2 | 12 | 31 | 44 | 10 |
| H62 | 0.32 | 5 | 3 | 45 | 29 | 17 |
| A63 | 0.64 | 2 | 7 | 10 | 80 | 1 |
| I64 | 0.21 | 61 | 7 | 11 | 12 | 8 |
| M65 | 0.64 | 96 | 1 | 2 | 0 | 0 |
| E66 | 0.23 | 47 | 18 | 14 | 7 | 14 |
| A67 | 0.3 | 23 | 41 | 12 | 22 | 2 |
| L68 | 0.3 | 55 | 26 | 7 | 1 | 11 |
| E69 | 0.18 | 25 | 7 | 22 | 43 | 4 |
| E70 | 0.17 | 29 | 22 | 17 | 12 | 19 |
| A71 | 0.4 | 39 | 13 | 10 | 1 | 37 |
| R72 | 0.24 | 48 | 13 | 12 | 2 | 25 |
| K73 | 0.33 | 61 | 17 | 15 | 4 | 4 |
| L74 | 0.24 | 18 | 15 | 49 | 4 | 14 |
| K75 | 0.28 | 58 | 9 | 14 | 13 | 6 |
| K76 | 0.28 | 52 | 25 | 14 | 7 | 3 |
| A77 | 0.45 | 62 | 10 | 14 | 11 | 4 |
| G78 | 0.21 | 41 | 8 | 29 | 5 | 18 |
| L79 | 0.26 | 53 | 9 | 23 | 1 | 14 |
| V80 | 0.22 | 34 | 11 | 35 | 17 | 2 |
| N81 | 0.25 | 17 | 20 | 6 | 32 | 26 |
| S82 | 0.31 | 18 | 55 | 11 | 9 | 6 |
| Q83 | 0.24 | 45 | 25 | 16 | 7 | 7 |
| Q84 | 0.33 | 24 | 9 | 5 | 59 | 3 |
| L85 | 0.45 | 6 | 9 | 9 | 17 | 59 |
| D86 | 0.13 | 48 | 17 | 12 | 10 | 13 |
| E87 | 0.2 | 47 | 5 | 9 | 34 | 6 |
| L88 | 0.52 | 12 | 0 | 81 | 2 | 5 |
| K89 | 0.54 | 20 | 12 | 67 | 0 | 0 |
| R90 | 0.31 | 65 | 5 | 21 | 1 | 7 |
| R91 | 0.36 | 41 | 10 | 32 | 1 | 16 |
| L92 | 0.18 | 37 | 16 | 19 | 12 | 16 |
| E93 | 0.29 | 61 | 14 | 16 | 6 | 2 |
| E94 | 0.25 | 46 | 6 | 32 | 10 | 6 |
| L95 | 0.11 | 25 | 26 | 24 | 19 | 7 |
| D96 | 0.51 | 3 | 21 | 66 | 6 | 4 |
| E97 | 0.3 | 25 | 36 | 35 | 0 | 3 |
| E98 | 0.18 | 45 | 16 | 15 | 9 | 14 |
| A99 | 0.26 | 21 | 33 | 30 | 0 | 16 |
| A100 | 0.4 | 60 | 20 | 15 | 4 | 0 |
| Q101 | 0.19 | 24 | 29 | 34 | 8 | 6 |
| R102 | 0.19 | 43 | 10 | 19 | 16 | 13 |
| A103 | 0.53 | 6 | 4 | 82 | 2 | 6 |
| E104 | 0.36 | 49 | 12 | 26 | 0 | 13 |
| K105 | 0.36 | 7 | 14 | 65 | 4 | 11 |
| L106 | 0.31 | 13 | 4 | 42 | 22 | 18 |
| G107 | 0.31 | 29 | 3 | 3 | 26 | 38 |
| K108 | 0.38 | 61 | 9 | 10 | 20 | 0 |
| E109 | 0.25 | 35 | 24 | 19 | 20 | 1 |
| F110 | 0.3 | 3 | 10 | 31 | 35 | 21 |
| E111 | 0.13 | 23 | 28 | 33 | 15 | 1 |
| L112 | 0.24 | 19 | 14 | 32 | 19 | 15 |
| K113 | 0.24 | 36 | 31 | 23 | 6 | 3 |
| L114 | 0.25 | 29 | 9 | 41 | 3 | 17 |
| E115 | 0.36 | 44 | 22 | 19 | 0 | 14 |
| Y116 | 0.31 | 25 | 20 | 13 | 24 | 18 |

TABLE 13

Allowed sequence variability in 10-CDP01 from single site saturation mutagenesis

| Residue | Conservation score | % Probability Charged DEHRK | Polar STNQ | Hydrophobic ILVAM | Aromatic FYW | Other GCP |
|---|---|---|---|---|---|---|
| A1 | 0.25 | 14 | 19 | 45 | 16 | 5 |
| D2 | 0.2 | 36 | 30 | 18 | 11 | 5 |
| P3 | 0.21 | 4 | 27 | 14 | 26 | 29 |
| K4 | 0.23 | 28 | 47 | 12 | 5 | 9 |
| K5 | 0.16 | 25 | 34 | 14 | 11 | 16 |
| V6 | 0.35 | 7 | 9 | 66 | 16 | 1 |
| L7 | 0.31 | 2 | 27 | 57 | 3 | 11 |
| D8 | 0.24 | 29 | 29 | 3 | 34 | 3 |
| K9 | 0.18 | 38 | 28 | 21 | 12 | 0 |
| A10 | 0.4 | 38 | 12 | 42 | 1 | 7 |
| K11 | 0.18 | 33 | 40 | 16 | 3 | 7 |
| D12 | 0.21 | 40 | 12 | 16 | 22 | 10 |
| Q13 | 0.23 | 40 | 28 | 10 | 8 | 14 |
| A14 | 0.27 | 9 | 25 | 51 | 1 | 14 |
| E15 | 0.25 | 55 | 9 | 8 | 16 | 12 |
| N16 | 0.22 | 33 | 42 | 15 | 8 | 3 |
| R17 | 0.13 | 30 | 25 | 27 | 7 | 11 |
| V18 | 0.47 | 6 | 2 | 79 | 6 | 7 |
| R19 | 0.21 | 48 | 22 | 14 | 4 | 11 |
| E20 | 0.26 | 46 | 6 | 27 | 16 | 5 |
| L21 | 0.46 | 1 | 39 | 46 | 3 | 11 |
| K22 | 0.22 | 32 | 40 | 16 | 12 | 0 |
| Q23 | 0.28 | 41 | 34 | 18 | 0 | 6 |
| E24 | 0.1 | 45 | 8 | 22 | 19 | 6 |

TABLE 13-continued

Allowed sequence variability in 10-CDP01 from single site saturation mutagenesis

| Residue | Conservation score | % Probability Charged DEHRK | Polar STNQ | Hydrophobic ILVAM | Aromatic FYW | Other GCP |
|---|---|---|---|---|---|---|
| L25 | 0.43 | 24 | 5 | 54 | 2 | 14 |
| E26 | 0.21 | 49 | 13 | 26 | 9 | 4 |
| R27 | 0.31 | 50 | 13 | 19 | 5 | 13 |
| L28 | 0.17 | 16 | 24 | 46 | 2 | 12 |
| Y29 | 0.22 | 26 | 41 | 5 | 17 | 11 |
| K30 | 0.17 | 19 | 44 | 17 | 13 | 7 |
| E31 | 0.06 | 21 | 19 | 28 | 14 | 18 |
| A32 | 0.17 | 27 | 22 | 25 | 7 | 19 |
| R33 | 0.2 | 24 | 27 | 18 | 13 | 17 |
| K34 | 0.19 | 40 | 41 | 8 | 0 | 11 |
| L35 | 0.2 | 23 | 18 | 33 | 10 | 17 |
| D36 | 0.19 | 26 | 48 | 14 | 7 | 5 |
| L37 | 0.18 | 21 | 20 | 30 | 11 | 18 |
| T38 | 0.26 | 8 | 29 | 20 | 1 | 42 |
| Q39 | 0.21 | 24 | 8 | 10 | 45 | 13 |
| E40 | 0.15 | 34 | 16 | 32 | 8 | 10 |
| M41 | 0.14 | 22 | 12 | 36 | 20 | 10 |
| R42 | 0.21 | 19 | 13 | 26 | 3 | 39 |
| R43 | 0.08 | 17 | 16 | 24 | 27 | 17 |
| K44 | 0.25 | 61 | 24 | 9 | 4 | 2 |
| L45 | 0.22 | 9 | 16 | 27 | 21 | 27 |
| E46 | 0.34 | 4 | 2 | 33 | 60 | 1 |
| W47 | 0.35 | 10 | 2 | 55 | 29 | 4 |
| R48 | 0.19 | 28 | 24 | 18 | 5 | 25 |
| Y49 | 0.21 | 14 | 10 | 20 | 34 | 21 |
| I50 | 0.14 | 17 | 27 | 46 | 4 | 6 |
| A51 | 0.46 | 78 | 9 | 11 | 0 | 1 |
| A52 | 0.16 | 12 | 22 | 40 | 12 | 14 |
| M53 | 0.14 | 32 | 26 | 31 | 2 | 8 |
| L54 | 0.21 | 14 | 17 | 50 | 1 | 17 |
| K55 | 0.15 | 11 | 19 | 27 | 9 | 35 |
| A56 | 0.11 | 14 | 18 | 26 | 15 | 26 |
| I57 | 0.16 | 21 | 33 | 38 | 6 | 1 |
| G58 | 0.85 | 2 | 92 | 3 | 1 | 2 |
| D59 | 0.24 | 10 | 40 | 23 | 21 | 7 |
| I60 | 0.2 | 5 | 24 | 36 | 25 | 11 |
| L61 | 0.18 | 5 | 39 | 31 | 17 | 9 |
| N62 | 0.21 | 12 | 16 | 32 | 1 | 40 |
| A63 | 0.28 | 8 | 5 | 57 | 10 | 19 |
| I64 | 0.13 | 29 | 23 | 25 | 21 | 2 |
| A65 | 0.13 | 27 | 12 | 22 | 33 | 6 |
| Q66 | 0.14 | 22 | 24 | 10 | 39 | 5 |
| A67 | 0.18 | 26 | 19 | 31 | 3 | 20 |
| E68 | 0.41 | 16 | 11 | 7 | 62 | 5 |
| N69 | 0.18 | 27 | 31 | 37 | 2 | 3 |
| E70 | 0.2 | 37 | 37 | 9 | 13 | 4 |
| A71 | 0.47 | 71 | 6 | 20 | 1 | 2 |
| D72 | 0.08 | 36 | 27 | 13 | 19 | 5 |
| K73 | 0.3 | 72 | 13 | 7 | 4 | 5 |
| L74 | 0.25 | 32 | 7 | 38 | 10 | 12 |
| K75 | 0.31 | 68 | 24 | 3 | 2 | 3 |
| K76 | 0.36 | 76 | 11 | 5 | 5 | 3 |
| A77 | 0.25 | 23 | 18 | 47 | 3 | 8 |
| G78 | 0.33 | 56 | 9 | 5 | 1 | 29 |
| L79 | 0.12 | 13 | 15 | 33 | 16 | 22 |
| V80 | 0.2 | 19 | 5 | 29 | 19 | 28 |
| N81 | 0.17 | 43 | 32 | 8 | 15 | 2 |
| S82 | 0.11 | 10 | 31 | 32 | 10 | 17 |
| Q83 | 0.18 | 46 | 21 | 12 | 6 | 15 |
| Q84 | 0.22 | 41 | 26 | 11 | 2 | 20 |
| L85 | 0.12 | 20 | 15 | 44 | 5 | 17 |
| D86 | 0.15 | 37 | 9 | 29 | 8 | 16 |
| E87 | 0.15 | 44 | 22 | 14 | 7 | 12 |
| L88 | 0.24 | 17 | 14 | 45 | 3 | 21 |
| R89 | 0.16 | 33 | 16 | 14 | 3 | 34 |
| R90 | 0.13 | 31 | 9 | 28 | 6 | 26 |
| R91 | 0.18 | 32 | 16 | 13 | 18 | 22 |
| L92 | 0.29 | 17 | 20 | 42 | 5 | 16 |
| E93 | 0.11 | 49 | 16 | 21 | 5 | 9 |
| E94 | 0.2 | 55 | 5 | 28 | 2 | 11 |
| L95 | 0.2 | 39 | 12 | 37 | 1 | 11 |
| A96 | 0.17 | 15 | 34 | 33 | 4 | 13 |
| K97 | 0.35 | 67 | 17 | 9 | 1 | 6 |
| E98 | 0.25 | 26 | 8 | 39 | 15 | 12 |
| A99 | 0.24 | 25 | 22 | 29 | 19 | 5 |
| A100 | 0.33 | 20 | 21 | 40 | 1 | 18 |
| R101 | 0.1 | 33 | 31 | 20 | 6 | 11 |
| K102 | 0.27 | 35 | 11 | 47 | 0 | 7 |
| A103 | 0.34 | 11 | 19 | 46 | 10 | 13 |
| H104 | 0.2 | 42 | 28 | 13 | 7 | 10 |
| D105 | 0.15 | 29 | 22 | 23 | 10 | 15 |
| Y106 | 0.29 | 37 | 12 | 2 | 34 | 15 |
| G107 | 0.36 | 14 | 7 | 18 | 1 | 59 |
| R108 | 0.22 | 45 | 24 | 13 | 11 | 8 |
| E109 | 0.27 | 43 | 34 | 8 | 4 | 11 |
| F110 | 0.31 | 4 | 5 | 45 | 27 | 19 |
| Q111 | 0.24 | 39 | 37 | 4 | 16 | 4 |
| L112 | 0.19 | 16 | 39 | 30 | 6 | 9 |
| K113 | 0.29 | 45 | 27 | 20 | 7 | 1 |
| L114 | 0.3 | 28 | 13 | 49 | 1 | 8 |
| E115 | 0.22 | 57 | 14 | 16 | 8 | 5 |
| Y116 | 0.31 | 23 | 4 | 8 | 24 | 41 |

TABLE 14

Allowed sequence variability in F-CDP01 from single site saturation mutagenesis

| Residue | Conservation score | % Probability Charged DEHRK | Polar STNQ | Hydrophobic ILVAM | Aromatic FYW | Other GCP |
|---|---|---|---|---|---|---|
| A1 | 0.04 | 33 | 13 | 28 | 17

TABLE 14-continued

Allowed sequence variability in F-CDP01 from single site saturation mutagenesis

| Residue | Conservation score | % Probability Charged DEHRK | Polar STNQ | Hydrophobic ILVAM | Aromatic FYW | Other GCP |
|---|---|---|---|---|---|---|
| Q39 | 0.07 | 31 | 28 | 26 | 2 | 13 |
| E40 | 0.08 | 28 | 19 | 19 | 27 | 7 |
| M41 | 0.1 | 16 | 10 | 34 | 29 | 11 |
| R42 | 0.12 | 21 | 9 | 18 | 42 | 11 |
| K43 | 0.06 | 25 | 35 | 27 | 3 | 10 |
| K44 | 0.18 | 32 | 44 | 12 | 3 | 10 |
| L45 | 0.22 | 8 | 11 | 65 | 5 | 12 |
| Q46 | 0.11 | 26 | 26 | 12 | 7 | 28 |
| Y47 | 0.47 | 3 | 3 | 82 | 3 | 9 |
| A48 | 0.39 | 13 | 8 | 27 | 5 | 47 |
| A49 | 0.29 | 42 | 6 | 5 | 44 | 3 |
| I50 | 0.49 | 2 | 7 | 84 | 6 | 1 |
| G51 | 0.33 | 17 | 7 | 22 | 3 | 51 |
| A52 | 0.48 | 2 | 4 | 14 | 77 | 4 |
| M53 | 0.23 | 3 | 10 | 30 | 23 | 34 |
| L54 | 0.49 | 10 | 10 | 74 | 1 | 6 |
| A55 | 0.37 | 9 | 8 | 36 | 1 | 46 |
| A56 | 0.31 | 2 | 5 | 33 | 51 | 9 |
| I57 | 0.38 | 19 | 51 | 26 | 3 | 0 |
| G58 | 0.39 | 13 | 10 | 12 | 2 | 62 |
| D59 | 0.2 | 33 | 15 | 30 | 12 | 10 |
| I60 | 0.18 | 11 | 15 | 43 | 29 | 1 |
| L61 | 0.39 | 8 | 3 | 81 | 3 | 5 |
| N62 | 0.26 | 34 | 52 | 7 | 4 | 3 |
| A63 | 0.22 | 6 | 13 | 67 | 3 | 11 |
| I64 | 0.1 | 24 | 16 | 38 | 12 | 10 |
| M65 | 0.2 | 11 | 13 | 58 | 17 | 2 |
| Q66 | 0.25 | 44 | 32 | 4 | 1 | 18 |
| A67 | 0.14 | 45 | 19 | 12 | 17 | 6 |
| K68 | 0.07 | 29 | 21 | 17 | 19 | 13 |
| Q69 | 0.12 | 42 | 15 | 18 | 10 | 15 |
| E70 | 0.08 | 34 | 19 | 26 | 10 | 10 |
| A71 | 0.2 | 15 | 26 | 26 | 1 | 32 |
| D72 | 0.13 | 19 | 10 | 16 | 43 | 13 |
| K73 | 0.04 | 26 | 18 | 20 | 11 | 24 |
| L74 | 0.07 | 25 | 19 | 30 | 10 | 15 |
| K75 | 0.05 | 32 | 18 | 26 | 9 | 15 |
| K76 | 0.03 | 35 | 18 | 22 | 16 | 9 |
| A77 | 0.07 | 36 | 23 | 16 | 15 | 9 |
| G78 | 0.13 | 42 | 14 | 12 | 8 | 24 |
| L79 | 0.03 | 17 | 20 | 31 | 19 | 13 |
| V80 | 0.08 | 22 | 12 | 33 | 10 | 22 |
| N81 | 0.07 | 30 | 27 | 19 | 15 | 9 |
| S82 | 0.03 | 23 | 15 | 28 | 23 | 11 |
| Q83 | 0.05 | 30 | 19 | 25 | 20 | 7 |
| Q84 | 0.06 | 28 | 29 | 26 | 8 | 9 |
| L85 | 0.03 | 31 | 18 | 29 | 6 | 16 |
| D86 | 0.05 | 29 | 14 | 26 | 24 | 7 |
| E87 | 0.04 | 31 | 24 | 29 | 6 | 10 |
| L88 | 0.06 | 19 | 24 | 32 | 16 | 10 |
| K89 | 0.07 | 27 | 8 | 23 | 32 | 9 |
| R90 | 0.08 | 48 | 20 | 17 | 5 | 9 |
| R91 | 0.07 | 35 | 8 | 21 | 26 | 10 |
| L92 | 0.09 | 9 | 26 | 37 | 7 | 21 |
| E93 | 0.09 | 21 | 16 | 41 | 8 | 14 |
| E94 | 0.03 | 28 | 22 | 25 | 16 | 10 |
| L95 | 0.02 | 23 | 26 | 23 | 16 | 12 |
| K96 | 0.25 | 36 | 20 | 13 | 30 | 1 |
| E97 | 0.29 | 23 | 57 | 15 | 1 | 5 |
| E98 | 0.06 | 22 | 20 | 23 | 27 | 8 |
| A99 | 0.14 | 18 | 17 | 36 | 22 | 7 |
| L100 | 0.31 | 10 | 14 | 19 | 48 | 9 |
| R101 | 0.12 | 32 | 35 | 18 | 7 | 8 |
| K102 | 0.08 | 24 | 20 | 21 | 20 | 15 |
| A103 | 0.21 | 6 | 14 | 60 | 14 | 5 |
| H104 | 0.35 | 9 | 46 | 9 | 1 | 34 |
| D105 | 0.31 | 12 | 10 | 17 | 8 | 53 |
| Y106 | 0.07 | 20 | 27 | 29 | 9 | 15 |
| G107 | 0.18 | 3 | 35 | 45 | 8 | 10 |
| S108 | 0.21 | 54 | 29 | 3 | 3 | 12 |
| E109 | 0.06 | 22 | 13 | 22 | 29 | 14 |
| F110 | 0.08 | 9 | 16 | 27 | 5 | 13 |
| Y111 | 0.13 | 10 | 24 | 43 | 4 | 20 |
| L112 | 0.07 | 32 | 24 | 12 | 12 | 20 |
| K113 | 0.21 | 26 | 17 | 20 | 3 | 34 |
| L114 | 0.11 | 34 | 12 | 15 | 28 | 10 |
| E115 | 0.13 | 22 | 37 | 22 | 2 | 16 |
| Y116 | 0.13 | 39 | 34 | 12 | 4 | 11 |

TABLE 15

Allowed sequence variability in W-CDP03 from single site saturation mutagenesis

| Residue | Conservation score | % Probability Charged DEHRK | Polar STNQ | Hydrophobic ILVAM | Aromatic FYW | Other GCP |
|---|---|---|---|---|---|---|
| D1 | 0.14 | 20.5 | 18.0 | 19.3 | 27.5 | 14.7 |
| P2 | 0.22 | 44.4 | 18.1 | 25.7 | 3.8 | 8.0 |
| K3 | 0.13 | 17.9 | 32.4 | 32.2 | 10.4 | 7.0 |
| K4 | 0.13 | 28.1 | 29.6 | 23.0 | 12.4 | 6.9 |
| V5 | 0.22 | 4.4 | 26.8 | 54.8 | 13.3 | 0.6 |
| F6 | 0.28 | 13.8 | 12.2 | 58.2 | 14.1 | 1.6 |
| D7 | 0.16 | 18.3 | 3.7 | 36.0 | 23.8 | 18.3 |
| E8 | 0.24 | 61.1 | 8.6 | 22.3 | 3.3 | 4.8 |
| A9 | 0.56 | 8.7 | 2.0 | 48.1 | 40.7 | 0.4 |
| K10 | 0.10 | 25.3 | 30.1 | 30.8 | 12.0 | 1.8 |
| D11 | 0.09 | 43.9 | 17.9 | 10.3 | 11.4 | 16.4 |
| R12 | 0.13 | 19.4 | 43.3 | 20.3 | 6.8 | 10.3 |
| A13 | 0.28 | 21.4 | 31.8 | 42.8 | 1.8 | 2.2 |
| E14 | 0.08 | 25.3 | 13.5 | 31.6 | 23.6 | 6.0 |
| N15 | 0.20 | 13.5 | 25.4 | 23.1 | 33.8 | 4.3 |
| N16 | 0.39 | 2.5 | 6.4 | 15.8 | 73.9 | 1.4 |
| V17 | 0.11 | 30.0 | 17.6 | 32.3 | 12.2 | 7.8 |
| R18 | 0.12 | 37.1 | 25.6 | 19.9 | 10.0 | 7.4 |
| R19 | 0.27 | 19.7 | 47.9 | 28.1 | 1.6 | 2.7 |
| L20 | 0.17 | 9.7 | 19.2 | 36.1 | 12.2 | 22.8 |
| K21 | 0.22 | 16.3 | 42.5 | 25.9 | 10.5 | 4.7 |
| Q22 | 0.06 | 13.0 | 17.9 | 24.6 | 26.6 | 17.9 |
| K23 | 0.21 | 31.0 | 9.5 | 49.1 | 6.0 | 4.4 |
| L24 | 0.20 | 34.5 | 29.2 | 23.4 | 9.7 | 3.1 |
| E25 | 0.25 | 13.7 | 31.2 | 36.1 | 11.7 | 7.3 |
| E26 | 0.09 | 28.9 | 21.0 | 29.5 | 14.4 | 6.2 |
| L27 | 0.19 | 18.9 | 3.0 | 33.8 | 34.4 | 9.9 |
| Y28 | 0.12 | 22.1 | 14.3 | 29.4 | 28.6 | 5.6 |
| K29 | 0.05 | 20.4 | 24.3 | 28.2 | 17.0 | 10.1 |
| E30 | 0.12 | 34.6 | 33.4 | 14.7 | 11.1 | 6.2 |
| A31 | 0.22 | 7.9 | 5.3 | 44.3 | 28.5 | 14.1 |
| R32 | 0.07 | 28.8 | 26.5 | 23.8 | 8.7 | 12.2 |
| K33 | 0.08 | 24.8 | 10.3 | 41.1 | 11.4 | 12.4 |
| K34 | 0.07 | 27.5 | 24.0 | 25.5 | 6.4 | 16.5 |
| D35 | 0.06 | 28.4 | 23.7 | 15.3 | 10.4 | 22.1 |
| L36 | 0.10 | 39.8 | 13.3 | 22.8 | 20.3 | 3.9 |
| T37 | 0.15 | 25.8 | 48.3 | 12.0 | 2.4 | 11.5 |
| Q38 | 0.18 | 43.9 | 13.9 | 17.2 | 6.5 | 18.5 |
| E39 | 0.05 | 32.3 | 21.1 | 21.9 | 13.1 | 11.6 |
| E40 | 0.15 | 30.0 | 5.9 | 25.4 | 29.9 | 8.8 |
| R41 | 0.11 | 33.8 | 26.4 | 17.5 | 12.6 | 9.7 |
| E42 | 0.08 | 40.7 | 22.1 | 19.8 | 6.0 | 11.3 |
| K43 | 0.15 | 29.0 | 33.3 | 16.8 | 16.1 | 4.8 |
| L44 | 0.12 | 32.3 | 10.9 | 20.1 | 30.8 | 5.8 |
| K45 | 0.12 | 22.5 | 15.5 | 43.8 | 11.7 | 6.5 |
| E46 | 0.10 | 19.4 | 29.5 | 34.3 | 5.0 | 11.4 |
| K47 | 0.07 | 25.6 | 18.9 | 28.4 | 21.5 | 5.6 |
| Y48 | 0.24 | 27.8 | 6.6 | 51.9 | 7.1 | 6.5 |
| K49 | 0.22 | 22.8 | 16.0 | 44.8 | 5.5 | 10.8 |
| T50 | 0.21 | 10.6 | 40.6 | 21.5 | 6.9 | 20.4 |
| A51 | 0.13 | 26.2 | 31.7 | 24.2 | 13.1 | 4.9 |
| M52 | 0.23 | 11.0 | 3.5 | 42.3 | 39.3 | 3.9 |

TABLE 15-continued

Allowed sequence variability in W-CDP03 from single site saturation mutagenesis

| Residue | Conservation score | % Probability | | | | |
|---|---|---|---|---|---|---|
| | | Charged DEHRK | Polar STNQ | Hydrophobic ILVAM | Aromatic FYW | Other GCP |
| A53 | 0.29 | 44.3 | 20.2 | 11.5 | 22.7 | 1.3 |
| A54 | 0.36 | 10.7 | 4.7 | 76.4 | 0.2 | 8.0 |
| A55 | 0.21 | 4.6 | 12.9 | 33.3 | 37.5 | 11.7 |
| A56 | 0.24 | 8.0 | 2.6 | 71.7 | 12.5 | 5.3 |
| L57 | 0.66 | 3.9 | 0.4 | 2.1 | 93.0 | 0.6 |
| A58 | 0.18 | 26.4 | 25.0 | 28.6 | 6.1 | 13.9 |
| A59 | 0.68 | 0.4 | 3.7 | 94.7 | 0.8 | 0.5 |
| I60 | 0.57 | 36.8 | 1.3 | 6.5 | 54.6 | 0.8 |
| G61 | 0.25 | 15.1 | 33.1 | 12.8 | 24.0 | 15.1 |
| D62 | 0.27 | 25.4 | 4.7 | 12.8 | 24.0 | 33.1 |
| A63 | 0.46 | 1.3 | 0.3 | 40.0 | 54.2 | 4.2 |
| F64 | 0.70 | 8.4 | 1.5 | 83.5 | 4.6 | 2.0 |
| N65 | 0.20 | 23.1 | 19.4 | 35.2 | 18.8 | 3.6 |
| A66 | 0.24 | 7.1 | 16.4 | 28.1 | 13.9 | 34.5 |
| L67 | 0.23 | 25.6 | 10.2 | 28.6 | 33.8 | 1.8 |
| L68 | 0.34 | 39.8 | 2.9 | 36.4 | 15.7 | 3.3 |
| K69 | 0.17 | 26.6 | 15.0 | 25.9 | 29.3 | 3.2 |
| A70 | 0.21 | 2.5 | 9.4 | 50.0 | 21.9 | 16.1 |
| R71 | 0.40 | 31.2 | 46.5 | 13.9 | 3.8 | 4.6 |
| K72 | 0.27 | 47.9 | 15.0 | 25.3 | 9.0 | 23 |
| L73 | 0.23 | 32.3 | 6.0 | 46.0 | 10.7 | 5.1 |
| H74 | 0.20 | 23.8 | 3.7 | 16.4 | 42.7 | 13.4 |
| K75 | 0.26 | 46.0 | 9.2 | 33.4 | 9.2 | 2.2 |
| N76 | 0.09 | 27.5 | 14.4 | 37.5 | 16.3 | 4.2 |
| G77 | 0.20 | 14.8 | 30.9 | 12.0 | 27.0 | 15.2 |
| Q78 | 0.09 | 18.1 | 27.4 | 26.2 | 9.9 | 18.3 |
| V79 | 0.24 | 5.0 | 17.0 | 62.6 | 12.8 | 2.6 |
| N80 | 0.26 | 14.0 | 51.1 | 23.8 | 1.4 | 9.7 |
| E81 | 0.08 | 19.5 | 21.9 | 38.7 | 12.2 | 7.7 |
| Q82 | 0.08 | 22.1 | 19.4 | 27.5 | 16.9 | 14.1 |
| Q83 | 0.14 | 34.2 | 15.5 | 9.5 | 16.2 | 24.5 |
| L84 | 0.12 | 25.0 | 8.2 | 34.9 | 23.6 | 8.3 |
| E85 | 0.07 | 23.4 | 10.7 | 31.2 | 29.5 | 5.1 |
| E86 | 0.09 | 32.6 | 19.1 | 22.0 | 20.4 | 5.9 |
| L87 | 0.30 | 18.6 | 5.1 | 49.3 | 24.8 | 2.2 |
| A88 | 0.31 | 10.1 | 44.2 | 9.4 | 23.3 | 13.0 |
| R89 | 0.23 | 28.8 | 20.0 | 21.1 | 24.7 | 5.5 |
| R90 | 0.10 | 25.0 | 21.7 | 21.4 | 15.4 | 16.5 |
| L91 | 0.21 | 20.0 | 7.9 | 39.6 | 8.8 | 23.7 |
| Q92 | 0.40 | 1.4 | 12.7 | 76.7 | 6.0 | 3.2 |
| E93 | 0.05 | 25.2 | 21.8 | 28.3 | 19.4 | 5.3 |
| L94 | 0.08 | 18.3 | 39.9 | 24.3 | 6.6 | 11.0 |
| A95 | 0.62 | 2.4 | 1.7 | 7.5 | 84.5 | 3.8 |
| K96 | 0.10 | 27.2 | 23.0 | 30.5 | 5.6 | 13.7 |
| E97 | 0.10 | 28.8 | 14.3 | 32.0 | 7.5 | 17.4 |
| A98 | 0.24 | 10.1 | 19.9 | 46.9 | 16.7 | 6.5 |
| F99 | 0.25 | 16.4 | 4.0 | 45.9 | 27.3 | 6.4 |
| Q100 | 0.19 | 43.7 | 13.7 | 13.5 | 1.3 | 27.8 |
| K101 | 0.12 | 31.5 | 9.0 | 38.9 | 4.6 | 16.0 |
| A102 | 0.32 | 0.6 | 2.8 | 70.7 | 15.7 | 10.1 |
| K103 | 0.28 | 37.3 | 4.2 | 52.0 | 1.6 | 4.9 |
| D104 | 0.04 | 28.1 | 16.1 | 29.3 | 9.7 | 16.9 |
| Y105 | 0.12 | 18.2 | 7.8 | 27.9 | 37.0 | 9.2 |
| A106 | 0.19 | 48.9 | 8.0 | 38.6 | 0.9 | 3.5 |
| N107 | 0.11 | 25.8 | 22.3 | 38.3 | 10.5 | 3.0 |
| E108 | 0.19 | 41.2 | 17.2 | 32.7 | 3.6 | 5.3 |
| F109 | 0.16 | 46.1 | 13.9 | 14.9 | 13.9 | 11.0 |
| E110 | 0.12 | 36.5 | 10.9 | 29.3 | 18.3 | 5.0 |
| Y111 | 0.24 | 16.1 | 6.8 | 47.4 | 25.5 | 4.3 |
| K112 | 0.11 | 27.3 | 8.5 | 45.1 | 5.4 | 13.8 |
| L113 | 0.14 | 36.2 | 18.2 | 19.7 | 16.8 | 9.1 |
| E114 | 0.08 | 31.0 | 14.2 | 31.9 | 16.1 | 6.8 |
| Y115 | 0.10 | 17.3 | 8.8 | 34.7 | 23.3 | 15.9 |

TABLE 16

Allowable residues for BINDI based on experimental saturation mutagenesis data (enrichment ratios of 0 or greater after one round of sorting). (SEQ ID NO: 7)

| Residue | Allowable Residues |
|---|---|
| A1 | A/E/G/H/I/K/M/P/R/S/T/V/W/Y |
| D2 | A/C/D/E/F/G/H/I/K/L/M/N/P/Q/R/S/T/V/W/Y |
| W3 | A/C/D/E/F/G/H/K/L/M/N/P/Q/R/S/T/V/W/Y |
| K4 | A/E/G/H/I/K/M/N/P/Q/R/T/V/W |
| K5 | F/G/I/K/L/Q/R/T/V/W |
| V6 | A/F/G/I/L/P/S/V/W |
| L7 | A/D/E/G/I/L/M/Q/R/S/T/V/W/Y |
| D8 | A/C/D/F/G/I/K/L/N/P/Q/R/S/V/W/Y |
| K9 | H/K/L/N/Q/R/W |
| A10 | A/H/S/T |
| K11 | A/D/E/G/H/K/N/Q/R/S/T/Y |
| D12 | A/D/E/F/G/H/K/L/M/N/Q/R/S/T/V/W/Y |
| I13 | D/E/G/I/K/L/M/N/Q/R/S/T/V/W/Y |
| A14 | A/C/I/L/M/N/Q/S/T/V |
| E15 | A/D/E/M/N/R/V/W/Y |
| N16 | A/D/F/G/H/I/K/L/M/N/P/Q/R/S/T/V/W/Y |
| R17 | A/C/E/G/H/I/K/L/M/P/R/S/T/V |
| V18 | A/I/K/M/T/V |
| R19 | A/C/D/E/F/G/K/L/M/N/Q/R/T/V/W/Y |
| E20 | A/D/E/F/G/I/K/L/M/N/Q/R/S/T/V/W/Y |
| L21 | F/H/I/L/M/Q/T/Y |
| K22 | A/C/H/I/K/Q/R |
| Q23 | A/C/E/F/G/H/I/M/N/Q/R/S/T/W/Y |
| K24 | A/D/G/H/I/K/N/Q/R/T/Y |
| L25 | I/L/M/Q |
| E26 | A/C/D/E/G/I/K/N/Q/R/S/T/V/W |
| E27 | A/C/D/E/F/G/H/I/K/L/M/N/Q/R/S/T/V/W/Y |
| F28 | C/F/H/I/K/M/N/P/R/T/V/Y |
| Y29 | A/D/E/H/I/L/P/Q/R/W/Y |
| K30 | A/E/F/G/H/K/L/M/N/Q/R/S/T/W/Y |
| E31 | A/D/E/F/G/H/I/K/L/M/N/Q/R/S/T/V/W/Y |
| A32 | A/F/G/H/K/L/N/P/R/S/T/Y |
| M33 | F/H/I/K/L/M/P/Q/R/T/V/Y |

TABLE 16-continued

Allowable residues for BINDI based on experimental saturation mutagenesis data (enrichment ratios of 0 or greater after one round of sorting). (SEQ ID NO: 7)

| Residue | Allowable Residues |
|---|---|
| K34 | C/H/I/K/L/M/Q/R/S/T/V/Y |
| L35 | A/D/E/F/G/H/I/K/L/M/N/P/Q/R/S/T/V/W |
| D36 | A/C/D/E/G/H/K/L/M/N/Q/R/S/T/V/W/Y |
| L37 | A/D/E/F/H/I/K/L/M/N/P/Q/R/S/T/V/W/Y |
| T38 | A/D/E/G/K/N/P/Q/R/S/T |
| Q39 | A/D/E/G/K/N/P/Q/R/S/T/V |
| E40 | A/D/E/F/G/H/I/K/L/M/N/P/Q/R/S/T/V |
| M41 | F/G/H/K/L/M/N/Q/R/T/V/W/Y |
| R42 | K/R |
| R43 | R |
| K44 | K/R |
| L45 | F/G/I/L/Q/V/W/Y |
| M46 | D/E/M/N/Q/T |
| L47 | F/L/M/W |
| R48 | R |
| W49 | E/F/W/Y |
| I50 | I |
| A51 | A/G |
| A52 | A/F/I/Q |
| M53 | D/H/L/M/N/W |
| L54 | I/L |
| M55 | G/I/M/S/V |
| A56 | A/C/F/G/I/L/M/P/S/T/V |
| I57 | A/I/M/S/T/V |
| G58 | G |
| D59 | D |
| I60 | I/L/M |
| F61 | F/M/W/Y |
| N62 | A/D/F/G/I/L/M/N/Q/S/T/V/W |
| A63 | A/F/I/L/M/T/V/Y |
| I64 | A/H/I/M/Y |
| R65 | R/Y |
| Q66 | A/F/I/K/L/M/Q/R/V/W/Y |
| A67 | A/G |
| K68 | K/Q/R |
| Q69 | A/F/G/I/K/L/N/Q/R/S/T/V/W/Y |
| E70 | A/D/E/F/G/H/I/K/L/M/N/Q/R/S/T/V/W/Y |
| A71 | A/G/I/M/S |
| D72 | A/D/E/F/G/H/I/L/M/Q/S/T/V/W/Y |
| K73 | F/K/R/Y |
| L74 | A/F/L/M/R/W/Y |
| K75 | A/F/H/K/N/R/S/T/Y |
| K76 | I/K/N/R/W |
| A77 | A/F/G/H/I/K/L/M/N/Q/R/S/T/V/W/Y |
| G78 | A/D/G/H/Q/R/S/T |
| L79 | A/K/L/R/T/V/W/Y |
| V80 | I/L/M/V |
| N81 | A/D/E/K/N/Q/R/S/T |
| S82 | D/E/G/K/M/P/Q/R/S/T/V |
| Q83 | A/D/E/F/H/I/L/N/Q/R/S/T/V |
| Q84 | D/E/H/M/N/Q/T/Y |
| L85 | A/F/G/H/L/M/R/T/V/W/Y |
| D86 | D/E/F/G/I/K/L/N/Q/S/T/V/W/Y |
| E87 | A/E/F/I/K/L/M/Q/T/W |
| L88 | A/F/I/L/M/T/V |
| K89 | A/I/K/Q/R/V |
| R90 | A/G/I/K/L/M/N/Q/R/S/T/V/W/Y |
| R91 | A/C/D/E/G/H/K/L/N/Q/R/S/T/V/Y |
| L92 | I/L |
| E93 | A/D/E/H/I/M/N/Q/T |
| E94 | A/C/D/E/F/G/H/I/K/L/M/N/Q/R/S/T/V/Y |
| L95 | A/L/T/V |
| K96 | K/Q/R |
| E97 | A/D/E/G/H/Q/S/T/V |
| E98 | A/D/E/F/H/K/M/N/P/Q/R/S/W/Y |
| A99 | A/S/V |
| S100 | A/G/N/Q/S/T |
| R101 | K/R |
| K102 | K/R |
| A103 | A/I/M/N/S/T/V |

TABLE 16-continued

Allowable residues for BINDI based on experimental saturation mutagenesis data (enrichment ratios of 0 or greater after one round of sorting). (SEQ ID NO: 7)

| Residue | Allowable Residues |
|---|---|
| R104 | D/K/N/R |
| D105 | A/D/E/F/G/H/K/L/M/N/R/T/V/W/Y |
| Y106 | A/E/G/H/I/T/Y |
| G107 | D/G/S |
| R108 | K/Q/R |
| E109 | A/D/E/F/G/H/K/L/R/S/V/W |
| F110 | F |
| Q111 | D/E/H/M/Q |
| L112 | A/D/F/I/L/P/Q/R |
| K113 | K/Q |
| L114 | A/H/K/L/M/P/R/S/T/V/Y |
| E115 | D/E/P/R/T |
| Y116 | D/E/G/H/K/Q/R/T/Y |

TABLE 17

Allowable residues for 2-INDI based on experimental saturation mutagenesis data (enrichment ratios of −1 or greater after two rounds of sorting). (SEQ ID NO: 8)

| Residue | Allowable Residues |
|---|---|
| A1 | A/E/G/P/S/T/V |
| D2 | A/D/E/G/H/K/N/S/T/V/Y |
| P3 | A/E/F/I/K/L/P/Q/R/S/T/V |
| K4 | E/H/K/N |
| K5 | D/E/K/M/Q |
| V6 | D/V |
| L7 | C/D/L/Y |
| D8 | D/L/N/W/Y |
| K9 | E/K/Q/T/V |
| A10 | A/C/F/I/L/M/P/S/T/V/W |
| K11 | F/G/K/M/N/Q/S |
| D12 | D/E/H/N/P |
| E13 | E/F/H/K/R/V |
| A14 | A/C/D/F/H/I/L/M/P/W |
| E15 | E/F/S |
| N16 | K/N/R/W/Y |
| R17 | C/K/N/R |
| V18 | M/P/V |
| R19 | P/R |
| E20 | A/C/E/F/G/H/I/K/L/M/N/R/S/T/V/Y |
| L21 | F/K/L/M/R/V/Y |
| K22 | K/N |
| Q23 | K/P/Q/R/W |
| K24 | K/R |
| L25 | F/I/K/L/R/W/Y |
| E26 | E/M/T |
| E27 | E/H/I/R/W |
| L28 | I/L/N |
| Y29 | C/G/H/Y |
| K30 | E/K/N |
| E31 | E/M/R/T/W |
| A32 | A/F/I/L/M/R/T/V/W/Y |
| R33 | R |
| K34 | K |
| L35 | E/H/I/L/P/T/Y |
| D36 | D/E/N/V/Y |
| L37 | A/E/L/M/V |
| T38 | A/I/N/R/T |
| Q39 | H/P/Q |
| E40 | D/E/V |
| M41 | M/R |
| R42 | D/H/P/Q/R/Y |
| Q43 | H/K/Q/V |
| E44 | E/L/W |
| L45 | K/L/M/V |
| V46 | A/C/D/E/F/G/H/K/L/M/N/R/T/V/W |
| D47 | C/D/F/H/I/L/M/V/W/Y |
| K48 | K |
| A49 | A/G/H/K/N/Q/R/T/W/Y |
| R50 | A/D/E/G/L/M/R/V/W |
| A51 | A/G |
| A52 | A/N/R |
| S53 | D/H/I/K/M/N/R/S/W |
| L54 | L/N |

TABLE 17-continued

Allowable residues for 2-INDI based on experimental saturation mutagenesis data (enrichment ratios of −1 or greater after two rounds of sorting). (SEQ ID NO: 8)

| Residue | Allowable Residues |
| --- | --- |
| Q55 | A/K/Q |
| A56 | A/C/F/H/K/L/M/N/Q/S/V/W/Y |
| S57 | A/G/H/N/S/Y |
| G58 | G |
| D59 | D/N |
| I60 | C/E/F/G/I/L/M/N/Q/T |
| F61 | F |
| Y62 | Y |
| A63 | A/F/T |
| I64 | D/I/R |
| L65 | L/M |
| R66 | C/I/K/L/R/V |
| A67 | A |
| L68 | G/I/L/M/N/R/W/Y |
| A69 | A/F/M/W/Y |
| E70 | E/S |
| A71 | A/C/F/L/M/W |
| E72 | E/F/S/T/W |
| K73 | K/M |
| L74 | L |
| K75 | K/V/W |
| K76 | I/K |
| A77 | A/K |
| G78 | G |
| L79 | L/M/S |
| V80 | A/M/V |
| N81 | A/K/N/R |
| S82 | Q/S |
| Q83 | L/Q/R |
| Q84 | C/F/Q/W |
| L85 | I/L/T |
| D86 | A/D/I/L/M/Q/R/V/W/Y |
| E87 | E |
| L88 | F/L/Q/V |
| K89 | K/L |
| R90 | L/R |
| R91 | H/K/L/Q/R |
| L92 | D/I/K/L/N/R/T/V |
| E93 | D/E/Q |
| E94 | E/W |
| L95 | D/L/N/P/S |
| A96 | A/H/I/Q/V |
| E97 | E |
| E98 | D/E/F |
| A99 | A/P/V |
| R100 | A/C/F/G/K/R/V/Y |
| R101 | L/Q/R/V |
| K102 | K |
| A103 | A/D/E/F/G/H/I/K/L/M/N/Q/R/S/T/V/W/Y |
| E104 | A/D/E/G/P/S |
| K105 | K/P/Q/S |
| L106 | A/F/I/L/V/W |
| G107 | D/G/I/K/M/Q/R/T/W |
| D108 | A/D/E/H/K/N/R/V/Y |
| E109 | C/E/H/K/P/R/W |
| F110 | C/F/H/Q/R/W |
| R111 | H/R |
| L112 | G/L/N/P/Q/R/S |
| K113 | H/K/N/P |
| L114 | A/C/F/I/L/M/P/Q/R/S/W |
| E115 | A/C/E/G/H/K/N/Q/R/S/V/Y |
| Y116 | D/F/H/N/S/Y |

TABLE 18

Allowable residues for XINDI based on experimental saturation mutagenesis data (enrichment ratios of −1 or greater after two rounds of sorting). (SEQ ID NO: 9)

| Residue | Allowable Residues |
| --- | --- |
| A1 | A/E/G/P/R/S/T/V |
| D2 | A/D/E/G/H/N/S/V/Y |
| P3 | A/L/P/Q/R/S/T |
| K4 | A/E/I/K/N/Q/R/T |

TABLE 18-continued

Allowable residues for XINDI based on experimental saturation mutagenesis data (enrichment ratios of −

TABLE 18-continued

Allowable residues for XINDI based on experimental saturation mutagenesis data (enrichment ratios of −1 or greater after two rounds of sorting). (SEQ ID NO: 9)

| Residue | Allowable Residues |
|---|---|
| A77 | A/K/T/W |
| G78 | G/I/K/L/R/S |
| L79 | E/G/I/K/L/M/R/S |
| V80 | K/N/V/W |
| N81 | G/N/W |
| S82 | K/Q/R/S/Y |
| Q83 | K/Q |
| Q84 | F/K/L/Q/R/W/Y |
| L85 | C/L/S/Y |
| D86 | D/E/G/K/R/T |
| E87 | E/K/R/W/Y |
| L88 | I/L/M/R |
| K89 | K/L/N |
| R90 | R |
| R91 | L/R |
| L92 | G/H/L/R/T/V/Y |
| E93 | A/E/F/G/H/I/K/L/M/Q/R/S/T/V/W/Y |
| E94 | E |
| L95 | E/K/L/M/S/Y |
| D96 | D/F/I/P/S/T/V/Y |
| E97 | E/L/S |
| E98 | C/E/H/M/Q/R |
| A99 | A/G/K/M/Q/T |
| A100 | A/E/F/H/I/K/L/Q/T/V/Y |
| Q101 | A/D/L/Q/T/W |
| R102 | R |
| A103 | A/C/I/K/L/V |
| E104 | A/E/G/K/Q/V |
| K105 | A/C/K/L/M/S |
| L106 | L/Y |
| G107 | G/W |
| K108 | K/R/W |
| E109 | E/N/R/W |
| F110 | C/F/I/Y |
| E111 | A/D/E/F/G/H/I/K/L/M/N/Q/R/S/T/V/W/Y |
| L112 | F/L/M/R/T |

TABLE 18-continued

Allowable residues for XINDI based on experimental saturation mutagenesis data (enrichment ratios of −1 or greater after two rounds of sorting). (SEQ ID NO: 9)

| Residue | Allowable Residues |
|---|---|
| K113 | K |
| L114 | K/L/M/P |
| E115 | A/D/E/G/K/Q/V |
| Y116 | C/D/F/H/L/N/S/Y |

TABLE 19

Allowable residues for 10-INDI based on experimental saturation mutagenesis data (enrichment ratios of −1 or greater after two rounds of sorting). (SEQ ID NO: 10)

| Residue | Allowable Residues |
|---|---|
| A1 | A/D/E/F/M/S/T/V |
| D2 | A/D/E/G/H/L/M/N/R/S/Y |
| P3 | C/F/G/L/P/Q/R/S/T/V |
| K4 | E/G/I/K/N/Q/R/S/T/W |
| K5 | A/E/F/K/L/N/P/Q/T/W |
| V6 | A/D/F/I/S/V |
| L7 | G/L/M/P/Q/T/V |
| D8 | A/D/E/G/H/N/R/S/T/W/Y |
| K9 | A/E/F/I/K/L/N/Q/R/T/Y |
| A10 | A/E |
| K11 | E/G/K/L/M/N/Q/R/S/T |
| D12 | A/C/D/E/F/G/H/N/V/Y |
| Q13 | F/G/H/K/P/Q/R/V |
| A14 | A/C/E/G/L/S/T/V |
| E15 | A/C/D/E/K/S/W/Y |
| N16 | D/I/K/N/T |
| R17 | A/C/F/H/L/M/N/R/S/T/V/Y |
| V18 | V |
| R19 | A/C/G/H/K/R/S/T |
| E20 | A/D/E/G/K/Q/V/W/Y |
| L21 | L/M/P/T |
| K22 | A/E/F/I/K/N/Q/T/Y |
| Q23 | A/H/K/N/P/Q/R/V |
| E24 | A/C/D/E/F/G/H/I/K/L/M/Q/R/T/V/Y |
| L25 | L/M/P/R |
| E26 | D/E/F/G/I/K/M/N/R |
| R27 | C/H/L/R/S |

TABLE 19-continued

Allowable residues for 10-INDI based on experimental saturation mutagenesis data (enrichment ratios of −1 or greater after two rounds of sorting). (SEQ ID NO: 10)

| Residue | Allowable Residues |
|---|---|
| L28 | L/M/N/R |
| Y29 | C/D/H/N/S/Y |
| K30 | K/M/N/Q/T/W |
| E31 | A/D/E/F/G/K/L/M/P/Q/T/W |
| A32 | A/E/G/M/P/S/T |
| R33 | C/H/I/L/N/R |
| K34 | D/G/H/K/N/Q/T |
| L35 | L/M/Q/R |
| D36 | A/D/H/K/N/Q/R/T/V/Y |
| L37 | L/M/P/Q/R |
| T38 | A/G/N/P/T |
| Q39 | F/G/H/K/L/M/P/Q/R/T/W/Y |
| E40 | A/D/E/G/K/Q |
| M41 | C/F/I/K/L/M/R/S/V/W |
| R42 | C/G/H/L/P/R/S |
| R43 | A/C/D/F/G/H/I/L/N/P/Q/R/V/W/Y |
| K44 | K |
| L45 | L |
| E46 | A/C/D/E/F/G/H/I/L/M/N/P/Q/S/T/V/W/Y |
| W47 | F/H/I/K/L/M/P/R/T/V/W |
| R48 | D/E/G/Q/R |
| Y49 | F/Y |
| I50 | I/L |
| A51 | A/D/E/F/G/H/I/K/L/M/N/P/Q/R/S/T/V/Y |
| A52 | A/G/I/T |
| M53 | M/N |
| L54 | I/L |
| K55 | F/G/K/M/P/S |
| A56 | A |
| I57 | I |
| G58 | A/C/F/G/P/R/S/W |
| D59 | A/C/D/E/F/G/H/I/K/L/M/N/P/Q/R/S/T/V/W/Y |
| I60 | I/W |
| L61 | A/L/M/P/S/T/V/W |
| N62 | A/G/M/N/P/Q/S |
| A63 | A/F/I/L/P |
| I64 | I/R |
| A65 | A/E/F/L/W/Y |
| Q66 | F/N/Q/Y |
| A67 | A |
| E68 | C/E/G/H/N/R/S/T/V/W/Y |
| N69 | I/N |
| E70 | E |
| A71 | A/K/R/V |
| D72 | D/F/G/H/K/M/N/Q/R/S/T/V/W/Y |
| K73 | E/K |
| L74 | K/L |
| K75 | K |
| K76 | E/H/K |
| A77 | A |
| G78 | D/G |
| L79 | C/F/G/L/M/P/Q/R/S/V/W |
| V80 | A/C/D/F/G/I/V/Y |
| N81 | D/H/I/K/N/S/T/Y |
| S82 | A/C/F/I/L/N/P/S/T/Y |
| Q83 | E/F/H/K/L/P/Q/R |
| Q84 | A/E/H/K/P/Q/R |
| L85 | A/K/L/M/P/Q/R/V |
| D86 | A/D/E/G/L/N/R/V/Y |
| E87 | E/G/K/Q |
| L88 | L/M/P/R/T |
| R89 | A/C/G/H/P/Q/R |
| R90 | C/G/I/L/P/R/V |
| R91 | C/F/H/P/R/S/V/Y |
| L92 | F/L/M/P/Q/R |
| E93 | A/D/E/G/H/I/K/L/M/N/P/Q/R/S/T/V/Y |
| E94 | D/E/G/I/K/L/P/R/V |
| L95 | A/E/G/K/L/M/P/R/T/V |
| A96 | A/C/E/G/M/P/Q/S/T/V |
| K97 | A/D/E/G/H/K/N/Q/R/S/T/Y |
| E98 | C/D/E/F/G/M/Q/S/V/W |

TABLE 19-continued

Allowable residues for 10-INDI based on experimental saturation mutagenesis data (enrichment ratios of −1 or greater after two rounds of sorting). (SEQ ID NO: 10)

| Residue | Allowable Residues |
|---|---|
| A99 | A/D/F/H/M/P/Q/S/T/V |
| A100 | A/D/G/S/T/V |
| R101 | A/C/D/E/G/H/I/L/M/N/Q/R/S/T/V/Y |
| K102 | A/E/G/I/K/M/R/S/T |
| A103 | A/E/F/G/S/T |
| H104 | D/H/K/M/N/P/Q/R |
| D105 | A/C/D/E/G/L/N/Q/S/V/Y |
| Y106 | C/D/F/H/T/Y |
| G107 | C/D/G/L |
| R108 | C/E/H/L/R/S/T/Y |
| E109 | D/E/K/P/T |
| F110 | C/F/I/L/S/V/Y |
| Q111 | E/F/H/K/Q/R/S/Y |
| L112 | H/I/L/N/P/Q/R/S/T |
| K113 | A/E/H/I/K/N/Q/Y |
| L114 | E/L/M/P/Q/V |
| E115 | D/E/G/H/K/L/N/S/V/W |
| Y116 | C/D/G/H/L/R/Y |

TABLE 20

Allowable residues for FINDI based on experimental saturation mutagenesis data (enrichment ratios of −1 or greater after two rounds of sorting). (SEQ ID NO: 11)

| Residue | Allowable Residues |
|---|---|
| A1 | A/D/E/F/M/S/T/V |
| D2 | A/D/E/G/H/L/M/N/R/S/Y |
| P3 | C/F/G/L/P/Q/R/S/T/V |
| K4 | E/G/I/K/N/Q/R/S/T/W |
| K5 | A/E/F/K/L/N/P/Q/T/W |
| V6 | A/D/F/I/S/V |
| L7 | G/L/M/P/Q/T/V |
| D8 | A/D/E/G/H/N/R/S/T/W/Y |
| K9 | A/E/F/I/K/L/N/Q/R/T/Y |
| A10 | A/E |
| K11 | E/G/K/L/M/N/Q/R/S/T |
| D12 | A/C/D/E/F/G/H/N/V/Y |
| Q13 | F/G/H/K/P/Q/R/V |
| A14 | A/C/E/G/L/S/T/V |
| E15 | A/C/D/E/K/S/W/Y |
| N16 | D/I/K/N/T |
| R17 | A/C/F/H/L/M/N/R/S/T/V/Y |
| V18 | V |
| R19 | A/C/G/H/K/R/S/T |
| E20 | A/D/E/G/K/Q/V/W/Y |
| L21 | L/M/P/T |
| K22 | A/E/F/I/K/N/Q/T/Y |
| Q23 | A/H/K/N/P/Q/R/V |
| K24 | A/C/D/E/F/G/H/I/K/L/M/Q/R/T/V/Y |
| L25 | L/M/P/R |
| E26 | D/E/F/G/I/K/M/N/R |
| E27 | C/H/L/R/S |
| L28 | L/M/N/R |
| Y29 | C/D/H/N/S/Y |
| K30 | K/M/N/Q/T/W |
| E31 | A/D/E/F/G/K/L/M/P/Q/T/W |
| A32 | A/E/G/M/P/S/T |
| R33 | C/H/I/L/N/R |
| K34 | D/G/H/K/N/Q/T |
| L35 | L/M/Q/R |
| D36 | A/D/H/K/N/Q/R/T/V/Y |
| L37 | L/M/P/Q/R |
| T38 | A/G/N/P/T |
| Q39 | F/G/H/K/L/M/P/Q/R/T/W/Y |
| E40 | A/D/E/G/K/Q |
| M41 | C/F/I/K/L/M/R/S/V/W |
| R42 | C/G/H/L/P/R/S |
| K43 | A/C/D/F/G/H/I/L/N/P/Q/R/V/W/Y |
| K44 | K |
| L45 | L |
| Q46 | A/C/D/E/F/G/H/I/L/M/N/P/Q/S/T/V/W/Y |
| Y47 | F/H/I/K/L/M/P/R/T/V/W |
| A48 | D/E/G/Q/R |

TABLE 20-continued

Allowable residues for FINDI based on experimental saturation mutagenesis data (enrichment ratios of −1 or greater after two rounds of sorting). (SEQ ID NO: 11)

| Residue | Allowable Residues |
|---|---|
| A49 | F/Y |
| I50 | I/L |
| G51 | A/D/E/G/H/I/K/L/M/N/P/Q/R/S/T/V/Y |
| A52 | A/G/I/T |
| M53 | M/N |
| L54 | I/L |
| A55 | F/G/K/M/P/S |
| A56 | A |
| I57 | I |
| G58 | A/C/F/G/P/R/S/W |
| D59 | A/C/D/E/F/G/H/I/K/L/M/N/P/Q/R/S/T/V/W/Y |
| I60 | I/W |
| L61 | A/L/M/P/S/T/V/W |
| N62 | A/G/M/N/P/Q/S |
| A63 | A/F/I/L/P |
| I64 | I/R |
| M65 | A/E/F/L/W/Y |
| Q66 | F/N/Q/Y |
| A67 | A |
| K68 | C/E/G/H/N/R/S/T/V/W/Y |
| Q69 | I/N |
| E70 | E |
| A71 | A/K/R/V |
| D72 | D/F/G/H/K/M/N/Q/R/S/T/V/W/Y |
| K73 | E/K |
| L74 | K/L |
| K75 | K |
| K76 | E/H/K |
| A77 | A |
| G78 | D/G |
| L79 | C/F/G/L/M/P/Q/R/S/V/W |
| V80 | A/C/D/F/G/I/V/Y |
| N81 | D/H/I/K/N/S/T/Y |
| S82 | A/C/F/I/L/N/P/S/T/Y |
| Q83 | E/F/H/K/L/P/Q/R |
| Q84 | A/E/H/K/P/Q/R |
| L85 | A/K/L/M/P/Q/R/V |
| D86 | A/D/E/G/L/N/R/V/Y |
| E87 | E/G/K/Q |
| L88 | L/M/P/R/T |
| K89 | A/C/G/H/P/Q/R |
| R90 | C/G/I/L/P/R/V |
| R91 | C/F/H/P/R/S/V/Y |
| L92 | F/L/M/P/Q/R |
| E93 | A/D/E/G/H/I/K/L/M/N/P/Q/R/S/T/V/Y |
| E94 | D/E/G/I/K/L/P/R/V |
| L95 | A/E/G/K/L/M/P/R/T/V |
| K96 | A/C/E/G/M/P/Q/S/T/V |
| E97 | A/D/E/G/H/K/N/Q/R/S/T/Y |
| E98 | C/D/E/F/G/M/Q/S/V/W |
| A99 | A/D/F/H/M/P/Q/S/T/V |
| L100 | A/D/G/S/T/V |
| R101 | A/C/D/E/G/H/I/L/M/N/Q/R/S/T/V/Y |
| K102 | A/E/G/I/K/M/R/S/T |
| A103 | A/E/F/G/S/T |
| H104 | D/H/K/M/N/P/Q/R |
| D105 | A/C/D/E/G/L/N/Q/S/V/Y |
| Y106 | C/D/F/H/T/Y |
| G107 | C/D/G/L |
| S108 | C/E/H/L/R/S/T/Y |
| E109 | D/E/K/P/T |
| F110 | C/F/I/L/S/V/Y |
| Y111 | E/F/H/K/Q/R/S/Y |
| L112 | H/I/L/N/P/Q/R/S/T |
| K113 | A/E/H/I/K/N/Q/Y |
| L114 | E/L/M/P/Q/V |
| E115 | D/E/G/H/K/L/N/S/V/W |
| Y116 | C/D/G/H/L/R/Y |

TABLE 21

Allowable residues for MIND1 (SEQ ID NO: 12)

| Residue | Allowable Residues |
|---|---|
| A1 | A/E/G/H/I/K/M/P/R/S/T/V/W/Y |
| D2 | A/C/D/E/F/G/H/I/K/L/M/N/P/Q/R/S/T/V/W/Y |
| W3 | A/C/D/E/F/G/H/K/L/M/N/P/Q/R/S/T/V/W/Y |
| K4 | A/E/G/H/I/K/M/N/P/Q/R/T/V/W |
| K5 | F/G/I/K/L/Q/R/T/V/W |
| V6 | A/F/G/I/L/P/S/V/W |
| L7 | A/D/E/G/I/L/M/Q/R/S/T/V/W/Y |
| D8 | A/C/D/F/G/I/K/L/N/P/Q/R/S/V/W/Y |
| K9 | H/K/L/N/Q/R/W |
| A10 | A/H/S/T |
| K11 | A/D/E/G/H/K/N/Q/R/S/T/Y |
| D12 | A/D/E/F/G/H/K/L/M/N/Q/R/S/T/V/W/Y |
| I13 | D/E/G/I/K/L/M/N/Q/R/S/T/V/W/Y |
| A14 | A/C/I/L/M/N/Q/S/T/V |
| E15 | A/D/E/M/N/R/V/W/Y |
| N16 | A/D/F/G/H/I/K/L/M/N/P/Q/R/S/T/V/W/Y |
| R17 | A/C/E/G/H/I/K/L/M/P/R/S/T/V |
| V18 | A/I/K/M/T/V |
| R19 | A/C/D/E/F/G/K/L/M/N/Q/R/V/W/Y |
| E20 | A/D/E/F/G/I/K/L/M/N/Q/R/S/T/V/W/Y |
| L21 | F/H/I/L/M/Q/T/Y |
| K22 | A/C/H/I/K/Q/R |
| Q23 | A/C/E/F/G/H/I/M/N/Q/R/S/T/W/Y |
| K24 | A/D/G/H/I/K/N/Q/R/T/Y/V |
| L25 | I/L/M/Q |
| E26 | A/C/D/E/G/I/K/N/Q/R/S/T/V/W |
| E27 | A/C/D/E/F/G/H/I/K/L/M/N/Q/R/S/T/V/W/Y |
| F28 | C/F/H/I/K/L/M/N/P/R/T/V/Y |
| Y29 | A/D/E/H/I/L/P/Q/R/W/Y |
| K30 | A/E/F/G/H/K/L/M/N/Q/R/S/T/W/Y |
| E31 | A/D/E/F/G/H/I/K/L/M/N/Q/R/S/T/V/W/Y |
| A32 | A/F/G/H/K/L/N/P/R/S/T/Y |
| M33 | F/H/I/K/L/M/P/Q/R/T/V/Y |
| K34 | C/H/I/K/L/M/Q/R/S/T/V/Y |
| L35 | A/D/E/F/G/H/I/K/L/M/N/P/Q/R/S/T/V/W |
| D36 | A/C/D/E/G/H/K/L/M/N/Q/R/S/T/V/W/Y |
| L37 | A/D/E/F/H/I/K/L/M/N/P/Q/R/S/T/V/W/Y |
| T38 | A/D/E/G/K/N/P/Q/R/S/T |

TABLE 21-continued

Allowable residues for MIND1 (SEQ ID NO: 12)

| Residue | Allowable Residues |
|---|---|
| Q39 | A/D/E/G/K/N/P/Q/R/S/T/V |
| E40 | A/D/E/F/G/H/I/K/L/M/N/P/Q/R/S/T/V |
| M41 | F/G/H/K/L/M/N/Q/R/T/V/W/Y |
| R42 | K/R |
| R43 | K |
| K44 | K/R |
| L45 | F/G/I/L/Q/V/W/Y |
| M46 | D/E/M/N/Q/T/I |
| L47 | F/L/M/W/E |
| R48 | R |
| W49 | E/F/W/Y |
| I50 | A |
| A51 | A/G |
| A52 | A/F/I/Q |
| M53 | D/H/L/M/N/W/I |
| L54 | I/L |
| M55 | G/I/M/S/V/R |
| A56 | A/C/F/G/I/L/M/P/S/T/V |
| I57 | A/I/M/S/T/V |
| G58 | G |
| D59 | D |
| I60 | I/L/M |
| F61 | F/M/W/Y/N |
| N62 | A/D/F/G/I/L/M/N/Q/S/T/V/W |
| A63 | A/F/I/L/M/T/V/Y |
| I64 | A/H/I/M/Y |
| R65 | R/Y |
| Q66 | A/F/I/K/L/M/Q/R/V/W/Y |
| A67 | A/G |
| K68 | K/Q/R |
| Q69 | A/F/G/I/K/L/N/Q/R/S/T/V/W/Y |
| E70 | A/D/E/F/G/H/I/K/L/M/N/Q/R/S/T/V/W/Y |
| A71 | A/G/I/M/S |
| D72 | A/D/E/F/G/H/I/L/M/Q/S/T/V/W/Y |
| K73 | F/K/R/Y |
| L74 | A/F/L/M/R/W/Y |
| K75 | A/F/H/K/N/R/S/T/Y |
| K76 | I/K/N/R/W |

TABLE 21-continued

Allowable residues for MIND1 (SEQ ID NO: 12)

| Residue | Allowable Residues |
|---|---|
| A77 | A/F/G/H/I/K/L/M/N/Q/R/S/T/V/W/Y |
| G78 | A/D/G/H/Q/R/S/T |
| L79 | A/K/L/R/T/V/W/Y |
| V80 | I/L/M/V |
| N81 | A/D/E/K/N/Q/R/S/T |
| S82 | D/E/G/K/M/P/Q/R/S/T/V |
| Q83 | A/D/E/F/H/I/L/N/Q/R/S/T/V |
| Q84 | D/E/H/M/N/Q/T/Y |
| L85 | A/F/G/H/L/M/R/T/V/W/Y |
| D86 | D/E/F/G/I/K/L/N/Q/S/T/V/W/Y |
| E87 | A/E/F/I/K/L/M/Q/T/W |
| L88 | A/F/I/L/M/T/V |
| K89 | A/I/K/Q/R/V/L |
| R90 | A/G/I/K/L/M/N/Q/R/S/T/V/W/Y |
| R91 | A/C/D/E/G/H/K/L/N/Q/R/S/T/V/Y |
| L92 | I/L |
| E93 | A/D/E/H/I/M/N/Q/T |
| E94 | A/C/D/E/F/G/H/I/K/L/M/N/Q/R/S/T/V/Y |
| L95 | A/L/T/V |
| K96 | K/Q/R |
| E97 | A/D/E/G/H/Q/S/T/V |
| E98 | A/D/E/F/H/K/M/N/P/Q/R/S/W/Y |
| A99 | A/S/V |
| S100 | A/G/N/Q/S/T |
| R101 | K/R |
| K102 | K/R |
| A103 | A/I/M/N/S/T/V |
| R104 | D/K/N/R |
| D105 | A/D/E/F/G/H/K/M/N/R/T/V/W/Y |
| Y106 | A/E/G/H/I/T/Y |
| G107 | D/G/S |
| R108 | K/Q/R |
| E109 | A/D/E/F/G/H/K/L/R/S/V/W |
| F110 | F |
| Q111 | D/E/H/M/Q |
| L112 | A/D/F/I/L/P/Q/R |
| K113 | K/Q |
| L114 | A/H/K/L/M/P/R/S/T/V/Y |

TABLE 21-continued

Allowable residues for MIND1 (SEQ ID NO: 12)

| Residue | Allowable Residues |
|---|---|
| E115 | D/E/P/R/T |
| Y116 | D/E/G/H/K/Q/R/T/Y |

TABLE 22

Allowable residues for WIND1 (SEQ ID NO: 265)

| Residue | Allowable Residues |
|---|---|
| D1 | C/D/E/K/L/M/N/R/S/V/W/Y |
| P2 | A/D/E/G/H/L/N/P/Q/R/T/W |
| K3 | A/C/F/G/H/I/K/M/Q/R/T/V/Y |
| K4 | D/F/G/I/K/M/N/R/S/T/V/W |
| V5 | I/L/M/N/T/V/W/Y |
| F6 | E/F/I/L/Q/T/V/W/Y |
| D7 | A/C/D/F/L/W/Y |
| E8 | D/E/H/I/V |
| A9 | A/E/H/L/Y |
| K10 | A/H/I/K/M/N/Q/R/S/T/Y |
| D11 | C/D/E/G/H/K/M/Q/R/S/T/W |
| R12 | A/D/E/G/L/N/Q/R/S/V/W |
| A13 | A/C/F/H/K/L/M/N/S/T/V |
| E14 | A/D/E/F/G/H/I/L/M/Q/S/V/W/Y |
| N15 | A/E/G/H/M/N/Q/R/W/Y |
| N16 | A/F/L/M/N/S/V/W/Y |
| V17 | F/G/H/I/K/M/Q/R/T/V |
| R18 | A/C/E/H/K/L/N/Q/R/S/V/W |
| R19 | I/M/N/Q/R |
| L20 | A/F/G/I/K/L/M/P/T/V/W/Y |
| K21 | I/K/N/S/T/W |
| Q22 | A/F/G/H/I/K/L/M/N/P/Q/R/S/V/W/Y |
| K23 | I/K/L/R/V |
| L24 | A/D/F/H/K/L/M/R/S/V |
| E25 | A/C/D/E/G/H/L/M/S/V/W |
| E26 | A/D/E/F/G/H/I/L/M/Q/R/S/V/W/Y |
| L27 | A/F/G/I/K/L/M/Y |
| Y28 | F/H/I/K/L/Q/S/V/W/Y |
| K29 | A/F/G/H/I/K/M/N/P/Q/R/S/T/V/W/Y |
| E30 | D/E/G/H/L/M/N/Q/S/V/W/Y |
| A31 | A/F/G/M/P/S/V/Y |

TABLE 22-continued

| Allowable residues for WINDI (SEQ ID NO: 265) | |
|---|---|
| Residue | Allowable Residues |
| R32 | A/E/G/H/I/M/N/P/Q/R/T |
| K33 | A/H/I/K/M/P/R/T/V/W/Y |
| K34 | A/E/G/H/I/K/N/P/R/S/T/W |
| D35 | A/C/D/E/G/H/K/L/M/N/P/R/S/T/V/W/Y |
| L36 | A/D/E/F/K/L/R/S |
| T37 | G/R/S/T |
| Q38 | A/E/G/H/K/L/P/Q/S/V/W |
| E39 | A/D/E/G/I/K/M/N/P/Q/R/S/T/V/W/Y |
| E40 | A/D/E/G/I/R/W/Y |
| R41 | H/K/L/Q/R/Y |
| E42 | A/D/E/G/K/Q/R/T/V |
| K43 | E/G/H/I/K/L/N/R/S/T/V/W/Y |
| L44 | F/H/K/L/T/V/W/Y |
| K45 | I/K/L/M/R/S/T/V/W |
| E46 | A/D/E/G/I/K/L/M/N/Q/S/T/V/W |
| K47 | D/F/H/I/K/M/R/S/T/V/Y |
| Y48 | A/C/E/F/G/H/I/K/L/M/R/S/T/V/W/Y |
| K49 | I/K/M/N/P/Q/R/W |
| T50 | D/I/N/P/S/T |
| A51 | A/F/G/H/I/K/L/M/Q/R/S/T/W |
| M52 | A/F/L/M/R/V/W/Y |
| A53 | A/E/F/G/H/I/M/N/Q/T/V/W/Y |
| A54 | A/G/H/I/L/M/N/P/S/T/V |
| A55 | A/C/F/G/M/P/T/W/Y |
| A56 | A/F/I/K/L/M/V |
| L57 | K/L/W/Y |
| A58 | A/G/K/M/Q/R/S/V/W |
| A59 | A/D/I/L/M/T/V/W |
| I60 | A/D/E/F/G/H/I/L/M/P/S/T/V/W/Y |
| G61 | F/G/N/Q |
| D62 | C/D/Y |
| A63 | A/C/F/H/I/K/L/M/P/T/V/W/Y |
| F64 | E/F/L/M |
| N65 | D/F/H/M/N/W |
| A66 | A/G/S/W |
| L67 | F/K/L/V/W/Y |
| L68 | K/L/M/W |
| K69 | F/H/I/K/Q/R/T/Y |

TABLE 22-continued

| Allowable residues for WINDI (SEQ ID NO: 265) | |
|---|---|
| Residue | Allowable Residues |
| A70 | A/F/G/I/L/M |
| R71 | Q/R |
| K72 | I/K/R/T |
| L73 | A/K/L/M |
| H74 | F/G/H/K/L/R/V/W/Y |
| K75 | I/K/M/N/R |
| N76 | A/D/F/G/H/I/K/L/M/N/Q/R/V/W/Y |
| G77 | F/G/Q/R/S |
| Q78 | E/G/H/L/M/N/P/Q/T/V/Y |
| V79 | A/I/L/M/S/T/V/W/Y |
| N80 | E/G/M/N/S/T |
| E81 | A/D/E/F/G/H/I/K/L/M/N/P/Q/R/S/T/V/W/Y |
| Q82 | D/E/F/G/I/K/L/N/P/Q/R/S/W/Y |
| Q83 | A/D/E/G/P/Q/W |
| L84 | A/F/G/H/I/K/L/V/Y |
| E85 | A/D/E/F/G/H/I/K/L/M/N/P/Q/R/S/T/V/W/Y |
| E86 | A/D/E/F/G/H/R/S/T/V/W/Y |
| L87 | F/H/I/K/L/M/Q/V |
| A88 | A/H/N/P/R/S/W |
| R89 | H/L/Q/R/V/Y |
| R90 | A/D/G/L/P/Q/R/Y |
| L91 | C/F/H/I/K/L/P/R/T/V/Y |
| Q92 | C/F/G/I/K/L/M/N/P/Q/S/T/V/W/Y |
| E93 | A/D/E/F/G/H/I/K/L/M/N/Q/R/S/T/V/W/Y |
| L94 | A/C/D/E/G/I/K/L/M/N/Q/R/S/T/V/Y |
| A95 | A/C/D/F/H/I/L/M/P/T/V/W/Y |
| K96 | H/I/K/N/P/Q/R/T/V |
| E97 | C/D/E/G/L/M/P/R/S/V |
| A98 | A/C/F/G/I/K/L/Q/T/V/W |
| F99 | E/F/G/I/L/M/W |
| Q100 | A/E/G/H/K/P/Q/R/V |
| K101 | A/D/E/G/H/I/K/P/R/S/V |
| A102 | A/C/F/I/L/M/T/V/Y |
| K103 | I/K/R |
| D104 | A/C/D/E/F/G/H/I/K/L/M/N/P/Q/R/S/V/W/Y |
| Y105 | C/F/H/I/M/R/S/W/Y |
| A106 | A/E/H/K/L/M/R/V |

TABLE 22-continued

Allowable residues for WINDI
(SEQ ID NO: 265)

| Residue | Allowable Residues |
| --- | --- |
| N107 | A/E/F/G/I/K/L/M/N/Q/R/S/V/Y |
| E108 | A/D/E/G/I/K/L/Q/R/T |
| F109 | C/E/F/H/L/N/R/V/Y |
| E110 | A/D/E/F/G/H/I/K/L/M/N/P/R/S/T/V/W/Y |
| Y111 | D/I/L/R/S/V/W/Y |
| K112 | A/C/D/G/H/I/K/L/V |
| L113 | C/E/F/K/L/Q/R/T/V |
| E114 | A/D/E/G/I/K/L/M/N/P/Q/R/S/T/V/W/Y |
| Y115 | A/D/G/I/L/M/P/R/T/W/Y |

Experimental Procedures
Computational Methods: General Information

ROSETTA® software can be downloaded from the Rosetta Commons web site, wherein online documentation and ROSETTASCRIPTS® syntax can be found.

Computational Methods: Side Chain Grafting on a Fixed Backbone Toward BHRF1 Binding A suitable helical region of the scaffold protein was aligned to the Bim-BH3 motif of PDB 2WH6 (Bim-BH3•BHRF1) using PyMOL™ (Schrödinger, LLC). The structural alignment was visually inspected for minimal backbone clashes between the scaffold protein and BHRF1 (side chain clashes may be fixed later by sequence design of the scaffold and by rotamer repacking on the target). Based on the structural alignment, scaffold residues were mutated in PyMol™ to the corresponding Bim-BH3 residue within the interface core; this 'grafted' important Bim interaction residues to the scaffold surface by mutation. A new PDB file containing the partially mutated scaffold bound to BHRF1 was saved and used as the input for ROSETTA-based design.

Design with ROSETTA™. An example command line to launch ROSETTA™ (Leaver-Fay et al., 2011) and example recipe/protocol file (Fleishman et al., 2011a) was developed. The design run was launched ten times. The consensus sequence was chosen for experimental validation after minor manual modification (e.g. a less-represented amino acid amongst the set of ten designs may be substituted for the consensus residue based on user preference).

Filtering. Proteins that passed the interface design filters (buried SASA>800 Å2, calculated ΔΔG<−15 REU, unsatisfied buried polar atoms <20) were further filtered based on properties of the unbound designed protein. The lowest scoring 10-20 designs for monomer energy, unsatisfied buried polar atoms, and ROSETTAHOLES™ score were selected for manual inspection. Designs were human modified to increase packing within the hydrophobic core and increase surface hydrophilicity, using the ROSETTA™ graphical user interface FoldIt™ (Cooper et al., 2010). Those designs considered most promising by the human eye were then selected for experimental validation.

For the 'direct-from-computer' designs tested in a high-throughput yeast display library (FIG. 1C), 5,000 structures were initially assembled using the FFL procedure. The lowest scoring 1,000 were designed at the interface, with 423 designs passing the minimum threshold for interface binding energy. From these 423, the 74 designs with the lowest number of buried unsatisfied hydrogen bonding atoms in the unbound monomer were chosen for experimental testing.

Other Computational Methods Toward BHRF1 Binding

Predicted binding probabilities for BbpD04 point mutants were calculated using the method of (Whitehead et al., 2012), with mutations ranked according to specificity improvements based on the electrostatics term in the score function.

Computational Methods: Design Based on the BINDI Scaffold

Input Models

The following crystallographic models of ligand-bound human BCL2 pro-survival homologs, found in the Protein Data Bank, were used to manually graft side chains onto a fixed backbone, as described below: 2PQK (Mcl-1•Bim-BH3), 3PK1 (Mcl-1•Bax-BH3), 3KZ0 (Mcl-1•MB7 peptide), 2XA0 (Bcl-2•Bax-BH3), 4AQ3 (Bcl-2-phenylacylsulfonamide), 4IEH (Bcl-2•sulfonamide), 4LVT (Bcl-2•Navitoclax), 1PQ1 (Bcl-xL•Bim-BH3), 2YQ6 (Bcl-xL•BimSAHB), 2YQ7 (Bcl-xL•BimLOCK), 3PL7 (Bcl-xL•Bax-BH3), 4BPK (Bcl-xL•α/β-Puma-BH3), 4K5A (Bcl-w•DARPin) 3I1H (Bfl-1•Bak-BH3), and 4B4S (Bcl-B•Bim-BH3).

Additional models of Bcl-w were generated for input into an automated motif grafting protocol described below. The Bcl-w sequence was threaded onto structurally analogous positions in existing crystallographic models of other BCL2 homologs. Only models bound to helical motifs were used: 1PQ1, 2BZW (Bcl-xL•Bad-BH3), 2YJ1 (Bcl-xL•α/β-Puma-BH3), 2YQ6, 2YQ7, 3FDL (Bcl-xL•Bim-BH3), 4A1U (Bcl-xL•designed α/β-foldamer), 4A1W (Bcl-xL•designed α/β-foldamer), 4BPK, 4HNJ (Bcl-xL•Puma-BH3), and 4OYD (BHRF1•BINDI). The TM-align software (Zhang, 2005) was used to generate structural alignments. Each new Bcl-w model then underwent constrained backbone and side chain minimization in the presence of the bound helical motif borrowed from the initial crystallographic model. The Bcl-w•helix complex was then aligned to a common 20-amino-acid truncated BH3-motif using PyMOL™ (Schrödinger). New PDB files of each Bcl-w model positioned to bind the common BH3-motif were saved and input as "context" in the automated motif grafting protocol described below.

Additional conformations of the partially-nonspecific Mcl-1-targeting binder, M-CDP02, were sampled by submitting the M-CDP02 sequence to the ROSETTA™ ab initio structure prediction protocol (Rohl et al., 2004). Of 30,200 generated models, any having greater than 2.5 Å RMSD relative to the starting model of M-CDP02 were discarded. 250 models with the most favorable (lowest) total score in ROSETTA™ energy units were input as "scaffolds" for the automated motif grafting protocol described below.

Manual Side-Chain Grafting on a Fixed Backbone

A suitable helical region of the BINDI protein (PDB 4OYD chain B) was aligned to the BH3-motif ligand in crystallographic models of each BCL2 pro-survival homolog, using PyMOL™. If the target structure was bound to an unnatural ligand, such as a small molecule or α/β-foldamer, the model of the pro-survival homolog was first aligned to an alternative structure bound to a helical BH3 motif, which then served as a guide for structural alignment of BINDI. The structural alignment was visually inspected, and any docked configurations with backbone clashes between the scaffold protein and BCL2 homolog were discarded. Side chain clashes were tolerated, as they may be resolved later by sequence design of the scaffold and by rotamer repacking on the target. Important interfacial residues from each BH3-motif were transferred, or grafted, to the aligned BINDI scaffold and kept fixed during the subsequent design protocol. A new PDB file containing the partially mutated scaffold bound to the target homolog was saved and used as the input for ROSETTA™-based design.

Computational Motif Grafting on a Fixed Backbone

Grafting is a 'seeded interface' protein design approach (Correia et al., 2010), in which a small motif of known structure that binds to a target site of interest is used to initiate the protein design process. The motif is then grafted (i.e. embedded) into a larger protein scaffold, which both stabilizes the structure of the small motif and contributes additional favorable interactions with the target protein. We have implemented a new computational grafting protocol as the MOTIFGRAFT™ mover in ROSETTASCRIPTS™, described in detail by Silva et al (2016). The input of MOTIFGRAFT™ is composed of three structures: 1) the motif, which is a protein fragment that is intended for grafting in a new protein scaffold; 2) the context, which is the macromolecule interacting with the motif; and 3) the target scaffolds, which are protein scaffolds that the protocol will use to search insertion points for the motif. The goal of MOTIFGRAFT™ is to find fragments in the target scaffolds that are geometrically compatible with the specified motif(s), and then replace those fragments with the motif(s) itself. In this case, the parameters of grafting were settled to perform full backbone alignment of the input motif, with a maximum RMSD of the backbone of 3.0 Å and RMSD for the endpoints of 2.0 Å. For the input motif "truncatedBH3.pdb" the hotspot residues were defined as: LEU-9, GLY-13, ASP-14, PHE-16 and ASN-17. The protocol was instructed to revert all other residues to their native identities in the target scaffold. No clashes between the grafted design and the context protein were allowed. The following mover was added to the XML script to implement this protocol within the ROSETTASCRIPTS™ framework:

```
<MotifGraft name="motif_grafting"
    context_structure="%%context%%"
    motif_structure="truncatedBH3.pdb"
    RMSD_tolerance="3.0"
    NC_points_RMSD_tolerance="2.0"
    clash_score_cutoff="0"
    clash_test_residue="ALA"
    hotspots="9:12:13:14:16:17"
    combinatory_fragment_size_delta="0:0"
    max_fragment_replacement_size_delta="0:0"
    full_motif_bb_alignment="1"
    allow_independent_alignment_per_fragment="0"
    graft_only_hotspots_by_replacement="0"
    only_allow_if_N_point_match_aa_identity="0"
    only_allow_if_C_point_match_aa_identity="0"
    revert_graft_to_native_sequence="1"
    allow_repeat_same_graft_output="1"/>
```

Plasmids, Gene Synthesis and Mutagenesis

Genes encoding Bcl-2 proteins were synthesized (Genscript) and cloned with C-terminal avi-6his tags (GLN-DIFEAQKIEWHEGSHHHHHH (SEQ ID NO: 75)) into plasmid pET29b (NdeI-XhoI sites; Novagen): human Bcl-2 a.a. 1-207 (Accession No. NP_000624.2), Bcl-w a.a. 1-182 (AAB09055.1), Bfl-1 a.a. 1-153 (C4S mutation; NP_004040), Bcl-B a.a. 11-175 (NP_065129.1), Mcl-1 a.a. 172-327 (Q07820.3), Bcl-$X_L$ a.a. 1-205 (CAA80661), and EBV BHRF1 a.a. 1-161 (YP_401646). For later BLI analysis, Bcl-B and Bfl-1 were genetically fused to C-terminal maltose-binding-protein with an avi-6his tag for improved solution properties. Codon usage was optimized for E. coli expression. Human Bim-BH3 (a.a. 141-166, Accession No. O43521) was cloned into pETCON (NdeI-XhoI sites). The genes for individually-tested designed proteins were assembled from oligos (Hoover and Lubkowski, 2002) and cloned into pET29b (NdeI-XhoI sites) with C-terminal 6his tags for purification from E. coli, or cloned into PETCON (NdeI-XhoI sites; (Fleishman et al., 2011)) for yeast surface expression. Alternative tags were added using PCR methods. Point mutations were made by overlapping PCR (Procko et al., 2013). Error-prone PCR with an average error rate of 1.3 amino acid substitutions per clone used GeneMorph II Random Mutagenesis (Agilent Technologies).

Protein Purification

E. coli BL21* (DE3) (Invitrogen) transformed with the relevant plasmid were grown at 37° C. in terrific broth with 50 µg/ml kanamycin to $OD_{600}$ 0.5-0.8, transferred to 21° C. and expression induced overnight with 0.1 mM IPTG. Centrifuged cells were resuspended in lysis buffer (20 mM Tris-Cl pH 8.0, 20 mM imidazole, 300 mM NaCl, 0.5 mM PMSF) supplemented with 0.2 mg/ml lysozyme and 0.06 mg/ml DNase I, and sonicated. Cleared lysate was incubated with NiNTA-agarose at 4° C. for 1 h and collected in a chromatography column. The resin was washed with 100 CV lysis buffer and protein was eluted with 6 CV elution buffer (20 mM Tris-Cl pH 8.0, 250 mM imidazole, 300 mM NaCl, 0.5 mM PMSF, 0.05% β-mercaptoethanol). Proteins were concentrated using a centrifugal ultrafiltration device (Sartorius) and separated from remaining contaminants by SEC using a Sephacryl-100 16/600 column (GE Healthcare) with running buffer (20 mM Tris-Cl pH 7.5, 150 mM NaCl, 1 mM DTT). Fractions containing pure protein were pooled, concentrated to 5-20 mg/ml based on calculated extinction coefficients for absorbance at 280 nm, and aliquots snap frozen in liquid $N_2$ for storage at −80° C. For animal studies, endotoxin was removed with a high-capacity endotoxin removal spin column (Pierce) and reducing agent was removed with a PD-10 desalting column (GE Healthcare).

Enzymatic Ligand Biotinylation

Purified avi-6his-tagged ligands (20 µM) in reaction buffer (250 mM potassium glutamate, 20 mM Tris-Cl [pH 7.5], 50 mM bicine [pH 8.3], 10 mM ATP, 10 mM MgOAc, 100 µM d-biotin) were enzymatically biotinylated with 150 U/µl BirA (Avidity) at room temperature overnight, followed by purification with NiNTA-agarose and SEC. Biotinylated ligands were stored at 4° C. in 150 mM NaCl, 20 mM Tris-Cl (pH 7.5), 1 mM DTT, 0.02% sodium azide.

Yeast Surface Display

Transformed yeast were cultured, induced and binding of surface displayed protein to biotinylated ligands was assessed by flow cytometry as reported (Chao et al., 2006; Procko et al., 2013). All yeast displayed proteins had C-terminal myc epitope tags for detection with FITC-conjugated anti-myc (Immunology Consultants Laboratory). Binding of biotinylated protein to the yeast surface is detected with phycoerythrin-conjugated streptavidin (Invitrogen).

Deep Sequencing Analysis

Yeast cells were sorted on a BD Influx cytometer operated by Spigot (BD Biosciences) and recovered in SDCAA media at 30° C. overnight. Yeast were lysed with 125 U/ml Zymolase at 37° C. for 5 h, and DNA was harvested (Zymoprep kit from Zymo Research). Genomic DNA was digested with 2 U/µl Exonuclease I and 0.25 U/µl Lambda exonuclease (New England Biolabs) for 90 min at 30° C., and plasmid DNA purified with a QIAquick™ kit (Qiagen). DNA was deep sequenced with a MiSeq™ sequencer (Illumina) and sequences were analyzed with adapted scripts from Enrich (Fowler et al., 2011).

For the library of designs in FIG. 1C, genes were synthesized (Gen9) with barcodes downstream of the stop codon for easy identification during deep sequencing (Table 3). After yeast cell transformation, expression, sorting and plasmid DNA purification, the genes were PCR amplified using primers that annealed to external regions within the plasmid, followed by a second round of PCR to add flanking sequences for annealing to the Illumina flow cell oligonucleotides and a 6-bp sample identification sequence. PCR rounds were 12 cycles each with high-fidelity Phusion polymerase (New England Biolabs). Barcodes were read on a MiSeq™ sequencer using a 50-cycle reagent kit (Illumina). 257,812 sequences passing the chastity filter were read in the naive population (ranging from 260 to 17,192 reads per gene, with a median of 2,492). The sorted populations had 117,720 to 232,195 reads.

For the single-site saturation mutagenesis library (FIG. 6), the BbpD04.3 gene was amplified as two overlapping fragments to provide complete sequencing coverage, and additional flanking DNA for annealing to the Illumina flow cell was added by PCR as described above. Gel-purified DNA was sequenced on a MiSeq™ sequencer using a 300-cycle paired-end reads reagent kit (Illumina). 3,058,244 sequences passing the chastity filter were read for the naive population. Each single amino acid substitution had 10 to 10,856 reads, with a median of 451 reads per mutant, and only mutation E109F was not represented. Parental protein sequences accounted for ~25% of reads. 2,930,499 and 2,548,997 sequences passing the chastity filter were read for the affinity and affinity-specificity sorted populations, respectively.

Analytical Size Exclusion Chromatography

Proteins (20 nmol each) were injected in a 200 µl loop in line with a Superdex-75 10/300 column (GE Healthcare) and separated with running buffer (20 mM Tris-Cl pH 7.5, 150 mM NaCl, 1 mM DTT) at room temperature.

Proteolysis Susceptibility Assay

Substrates (0.5 mg/ml) were incubated at 37° C. with protease (0.01 mg/ml) in 50 mM Tris-HCl (pH 8.0), 10 mM $CaCl_2$. Reactions were terminated with benzamidine (12.5 mM final), PMSF (1.25 mM final) and 4× load dye. Samples were run on 18% SDS-polyacrylamide gels, stained with Coomassie dye, and the decrease in full-length protein quantified using ImageJ software (National Institute of Mental Health).

Circular Dichroism

CD spectra were recorded with a Model 420 spectrometer (AVIV Biomedical) or a J-1500 Circular Dichroism Spectrometer (JASCO). Unless stated otherwise, proteins were at 20 µM in PBS and data were collected at 25° C.

Bio-Layer Interferometry

Data were collected on an Octet RED96 (Forte Bio) and processed using the instrument's integrated software. Enzymatically-biotinylated Bcl-2 proteins (25 nM) in binding buffer (10 mM HEPES [pH 7.4], 150 mM NaCl, 3 mM EDTA, 0.05% surfactant P20, 0.5% non-fat dry milk) were immobilized for 360 s at 30° C. to streptavidin biosensors. Biosensors were dipped in solutions containing the analyte of interest to measure association, and transferred back to empty binding buffer for monitoring dissociation. Kinetic constants were determined from the mathematical fit of a 1:1 binding model.

Cytochrome c Release

Cells (~$10^9$) were equilibrated in 5 ml of homogenization buffer (0.25 M sucrose, 1 mM EGTA, 10 mM HEPES/NaOH, 0.5% BSA, pH 7.4, Roche Complete protease inhibitors) for 5 min. Samples were kept on ice or at 4° C. until assayed. Cells were homogenized under $N_2$ pressure (400 psi) in a steel disruption vessel (Parr Instrument Company) for 10 min, then centrifuged (750 g) for 10 min to remove intact cells. Supernatant was centrifuged again (12,000 g) for 12 min to collect mitochondria. The pellet was resuspended in 300 µl wash buffer (0.25 M sucrose, 1 mM EDTA, 10 mM Tris/HCl pH 7.4). Proteins at the indicated concentrations were incubated with mitochondria (25 µg mitochondrial protein based on BCA assay, Sigma) in 50 µl final volume of experimental buffer (125 mM KCl, 10 mM Tris-MOPS pH 7.4, 5 mM glutamate, 2.5 mM malate, 1 mM $K-PO_4$, 10 µM EGTA-Tris pH 7.4) for 30 min at room temperature. Reaction solutions were centrifuged (18,000 g) for 10 min at 4° C. and cytochrome c release was quantified using a Cytochrome c ELISA kit (Life Technologies). Complete cytochrome c release was quantified by treatment with 0.5% Triton-X100.

Cell Viability Assays, BINDI-Polymer Conjugates

A 25,000 Da diblock copolymer (Pol300) composed of 95% polyethylene glycol methacrylate (300 Da) for stability and 5% pyridyl disulfide methacryate for conjugation in the first block, and 60% diethylaminoethyl methacrylate and 40% butyl methacrylate in the second block, was synthesized by reversible addition-fragmentation chain transfer. Development and characterization of the diblock copolymer will be published in a separate article. After purification, Pol300 was dissolved in ethanol at 100 mg/ml then diluted into PBS at 1 mg/ml and spin filtered to remove ethanol. Proteins with exposed terminal cysteines were incubated with Pol300 at a molar ratio of 2:1 (protein:polymer) overnight. Protein-polymer conjugation was quantified by measuring pyridyl disulfide release and the absorbance of 2-mercaptopyridine at 343 nm with 8,080 $M^{-1}$ $cm^{-1}$ as the extinction coefficient. For cell viability studies, protein and protein-polymer conjugates were incubated with Ramos or Ramos-AW cells in a 96 well round bottom plate with 50,000 cells per well in 100 µl media. Cells were cultured in RPMI 1640 containing L-glutamine and 25 mM HEPES supplemented with 1% penicillin-streptomycin (GIBCO) and 10% fetal bovine serum (Invitrogen) at 37° C. and 5% $CO_2$. After 24 h, cell viability was measured using a Cell-Titer 96 Aqueous One Solution Cell Proliferation Assay, MTS (Promega).

Tissue Culture, BINDI-Polymer Conjugates

Ramos, Ramos-AW, Daudi, Raji, DOHH2, JVM-2, and JVM-13 were grown in RPMI 1640 containing L-glutamine and 25 mM HEPES supplemented with 1% penicillin-streptomycin (GIBCO) and 10% fetal bovine serum (FBS, Invitrogen). Jeko-1 were grown in similar RPMI 1640 media supplemented with 20% FBS. Granta-519 and K562 were grown in Iscove's DMEM supplemented with 10% FBS. All cell lines were maintained in log growth phase at 37° C. and 5% $CO_2$.

Xenograft Mouse Model, BINDI-Polymer Conjugates

To prepare mAb-polymer-protein conjugates, a 44,000 Da diblock copolymer (Pol950) composed of 80% polyethylene glycol methacrylate (950 Da), 10% pyridyl disulfide methacrylate, and 10% biotin-hydroxyethyl methacrylate for mAb-streptavidin conjugation in the first block, and 60% diethylaminoethyl methacrylate and 40% butyl methacrylate in the second block, was synthesized by reversible addition-fragmentation chain transfer. Development and characterization of the Pol950 diblock copolymer will be published in a separate article. Pol950 was dissolved in ethanol at 100 mg/mL, then diluted in PBS at 10 mg/ml and spin filtered to remove ethanol. Proteins were incubated with Pol950 at an equimolar ratio overnight and conjugation was quantified by $A_{343}$ absorbance. αCD19 was conjugated to protein-polymer through the streptavidin linkage at a molar ratio of 90:1 (polymer:mAb).

BALB/c nu/nu mice (6 to 8 weeks old) were used from Harian Sprague-Dawley and housed under protocols approved by the FHCRC Institutional Animal Care and Use Committee. Mice were placed on biotin-free diet (Purina Feed) for the duration of study. To form tumor-xenografts, Ramos-AW cells were resuspended in PBS ($5 \times 10^7$ cells/mL) and injected in the right flank with $10^7$ cells/mouse. Tumors were allowed to grow for 6 days to a volume of 50 mm$^3$. Mice with similar sized tumors were sorted randomly into treatment groups (n=8 to 10). On days 6, 9, and 12, mice were injected intraperitoneally with cyclophosphamide (35 mg/kg) and bortezomib (0.5 mg/kg). After 30 min, mice were injected via tail vein with conjugates at a dose of 15 mg/kg (αCD19), 300 mg/kg (Pol950) and 105 mg/kg (BINDI or 3LHP). Body weight was monitored for toxicity and tumor sizes were measured while blinded to treatment groups. Measurements were performed in the x, y, and z plane using calipers three times a week. Mice were euthanized when tumors reached a volume of 1250 mm$^3$. Tumor volumes and deaths were recorded into Prism (GraphPad Software, Inc.) for statistical analysis and a log-rank (Mantel-Cox) test was performed to determine if survival curves and trends were statistically different (P<0.0001). Significance in tumor volumes was verified by an unpaired t test with Welch's correction.

MEF-Derivative Cell Line Generation

Mouse embryonic fibroblasts were generated from E13-E14.5 embryos derived from CreERT2/Bcl-x$^{fl/fl}$/Mcl-1$^{fl/fl}$ C57BL/6 mice (Kelly et al., 2014) and immortalized (at passage 2-4) with SV40 large T antigen. Retroviral expression constructs in the pMIG vector (Murine Stem Cell Virus-IRES-GFP) expressing each FLAG-tagged pro-survival protein were transiently transfected using LIPOFECTAMINE™ (Invitrogen), into Phoenix ecotropic packaging cells. Filtered virus-containing supernatants were used to infect the MEFs by spin inoculation as previously described (Lee et al., 2008). Cells stably expressing each pro-survival protein were selected by sorting GFP$^{+ve}$ cells 24 hours after spin inoculation and protein expression verified by Western blotting using an anti-FLAG antibody. Following verification of exogenous pro-survival protein expression, each cell line was treated with 1 μM Tamoxifen (Sigma-Aldrich) to enable deletion of endogenous Mcl-1 and Bcl-xL. Deletion of endogenous Mcl-1 and Bcl-xL was shown by Western blotting using anti-Mcl-1 (Rockland Clone, 600-401-394) and anti-Bcl-xL (BD Transduction Laboratories Clone 44/Bcl-x) antibodies. Cells were maintained in DME Kelso medium supplemented with 10% (v/v) fetal bovine serum, 250 mM L-asparagine and 50 mM 2-mercaptoethanol.

HeLa-Derivative Cell Line Generation

HeLa cells were transfected with pSFFV vectors encoding human Mcl-1, Bcl-2, Bcl-xL, or empty vector (Neo) and selected with 1 mg/ml geneticin for 48 hours. Cells were maintained afterwards in DMEM with 10% (v/v) fetal bovine serum (FBS) supplemented with 500 μg/ml geneticin. Increased expression of pro-survival BCL2 proteins was confirmed by Western blotting using anti-Bcl-2, anti-Bcl-xL (Santa Cruz Biotechnology), and anti-Mcl-1 (Cell Signaling) antibodies.

Lentiviral Infection

Inducible αMCL1 and αBFL1 constructs were generated in a lentiviral vector described in Aubrey et al. (2015). Ligand expression is linked via the T2A peptide to mCherry™ fluorescent reporter protein. Lentiviral particles were produced by transient transfection of 293T cells with plasmid DNA along with the packaging constructs pMDL, pRSV-rev and pVSV-G using calcium chloride precipitation. Viral supernatants were then filtered prior to target cell transduction. SW620, HCT-116, DLD1, RKO, HT-29, Caco-2, and SW48 colon cancer cell lines were generously provided by John Mariadason at the Olivia Newton-John Cancer Research Institute. For infection of MEFs and colon cancer cell lines, equal volume of virus-containing supernatant was added to target cells pre-incubated with 10 ng/μL polybrene, and centrifuged at 2500 rpm for 2 hours at 32° C. Following spin inoculation, cells were then incubated overnight at 37° C. Cells expressing the doxycycline-inducible constructs were then selected by sorting mCherry$^{+ve}$ cells. MEFs were maintained in DME Kelso medium supplemented with 10% (v/v) FBS, 250 mM L-asparagine and 50 mM 2-mercaptoethanol. Colon cancer cell lines were maintained in DMEM/F-12 supplemented with 10% (v/v) FBS.

For constitutive expression of αBCL2, αBCLXL, αBCLW, αMCL1 and αBFL1, genes were first codon optimized for human expression including a 5' Kozak sequence (GCCACC) and 3' FLAG tag, then cloned into the SparQ™ lentivector containing GFP reporter gene downstream of an internal ribosome entry site (QM530A-1; System Biosciences). Lentiviral particles were produced by transient transfection of 293T cells with plasmid DNA along with packaging constructs pMD2.G and psPAX using calcium chloride precipitation. Viral supernatants were harvested 48 or 72 hours after transfection, filtered and used immediately or stored in aliquots at −80° C.

MEF Cytochrome c Release Assay

Small molecule inhibitors used for cytochrome c release and survival assays were purchased from ChemiTek (ABT-263 and ABT-199) or prepared according to published methods (A-1331852; Leverson et al., 2015a; Wang et al., 2013). Mouse embryonic fibroblasts ($1 \times 10^6$) were pelleted and lysed in 0.05% (w/v) digitonin containing lysis buffer (20 mM Hepes-pH 7.2, 100 mM KCl, 5 mM MgCl$_2$, 1 mM EDTA, 1 mM EGTA, 250 mM Sucrose), supplemented with protease inhibitors (Roche) for 3 min on ice. Crude lysates containing the mitochondria were incubated with 10 μM ligand at 30° C. for 1 hour before pelleting. The supernatant was retained as the soluble fraction (S), while the pellet, containing the mitochondria (P), was solubilized in lysis buffer (20 mM Tris-pH 7.4, 135 mM NaCl, 1.5 mM MgCl$_2$, 1 mM EGTA, 10% (v/v) glycerol and 1% (v/v) Triton X-100. Both soluble and pellet fractions were subsequently analyzed by Western blotting using an anti-cytochrome c antibody (clone 7H8.2C12; BD Biosciences).

Short-Term Survival Assays

MEF and colon cancer cells were aliquoted in 96-well tissue culture plates in 50 culture media at 20,000 cells per mL. Cells were treated with doxycycline at a final concentration of 1 mg/mL to induce protein expression, and/or small molecule drugs at the indicated final concentrations and a final total volume of 100 μL per well. Viability was assayed after 24 hours with Cell Titer Glo (Promega). For drug titrations, ABT-263 and A-1331852 were serially diluted 2-fold from 250 nM to 2 nM (eight concentrations in total) and combined with doxycycline (to induce expression of αMCL1) or media (drug only). EC$_{50}$ values were determined with nonlinear regression.

HeLa, melanoma, and glioblastoma cell lines (maintained in DMEM with 10% [v/v] FBS) were seeded at 3,000-5,000 cells per well in 96 well plates in 100 μl culture medium. Cells were transduced the next day with 100 μl lentiviral supernatant to induce expression of each designed inhibitor. For experiments using combinations of three inhibitors, 75 µl media was removed before virus addition to accommodate the appropriate volume of virus. Viability was assayed at 72 hours post-infection with Cell Titer Glo (Promega). Expression of constructs was confirmed by flow cytometry (GFP) and western blotting (anti-FLAG).

Long-Term Survival Assays

MEF and colon cancers were seeded in 6-well tissue culture plates in 2 mL culture media at 150 cells per mL. The next day and every 48 hours following, doxycycline was added at a final concentration of 1 µg/mL to each well, while nothing was added to control wells. After seven to ten days, media was aspirated and colonies were stained (5:4:1 MeOH:$H_2O$:AcOH, 0.25% Coomassie Blue R-250) and counted.

Immunoprecipitation

Cells were harvested, washed with PBS, and extracted with ice-cold Chaps buffer (40 mM Tris-HCl, pH 7.5, 150 mM NaCl, 1 mM EDTA, 2% CHAPS, and Complete Protease Inhibitors [Roche]) for 20 minutes, on ice. Extracts were spun down at 10,000 g for 10 min and supernatants were removed and used for SDS-PAGE analysis. Expression of proteins of interest was analyzed using antibodies against Bcl-2, Bcl-xL, Mcl-1 (as above), Bfl-1 (ProSci, Inc.), Bim (BD Biosciences), and tubulin (SigmaAldrich). For immunoprecipitation experiments, 1,000 µg protein lysates were pre-cleared and then incubated with 3 µg Bim antibody for 2 hours at 4° C., followed by addition of Protein A/G Plus agarose beads (Santa Cruz Biotechnology) and overnight incubation with rotation at 4° C. Negative control reactions used normal IgG. Immunoprecipitates were washed four times with lysis buffer and eluted with loading buffer at 95° C., 2 times for 10 min, followed by SDS-PAGE analysis.

Discussion

By breaking free of the conformational constraints imposed by repurposing pre-existing scaffolds and instead building a new protein with structure tailored for the target surface, a remarkably tight and specific binder of the EBV apoptosis regulator BHRF1 was designed. The elevated toxicity of the engineered BINDI protein towards EBV-positive cancer lines supports the hypothesis that BHRF1 is necessary for survival in at least some EBV-associated cancers. BINDI should provide a useful tool for characterizing primary isolates of EBV-associated cancers in which the molecular mechanisms of cell transformation remain poorly understood, including EBV-positive BL, Hodgkin's lymphoma, and nasopharyngeal and gastric carcinomas (Young and Murray, 2003).

BINDI has a structure and amino acid sequence found after computationally filtering thousands of potential designed conformations for optimum interactions with BHRF1. The ability to custom-tailor the backbone conformation to the challenge at hand helped achieve very high affinity and specificity.

BINDI is an artificial polypeptide sequence that folds to a designed structure, with no identifiable homologues in nature. We demonstrate how sequence variants of BINDI (see FIGS. 2, 4, 6 and 14) can also bind BHRF1 with high affinity and specificity. Redesigning BINDI to bind other BCL2 family proteins yielded a set of related sequences (MINDI, 2-INDI, XINDI, 10-INDI, FINDI and WINDI), with any two differing by as many as 51 mutations (44% of the protein). Each of these redesigned BINDI variants were related to each other but not to any naturally occurring proteins. Saturation mutagenesis of all these designed proteins consistently revealed that significant sequence diversity is tolerated (FIG. 19 and Table 11-22). We have therefore designed a new family of proteins that share a common structure and architecture. We have shown that many sequence homologues can maintain our artificially designed structure and functional inhibition of BCL2 family proteins.

We demonstrate that BINDI can slow progression of EBV-positive B lymphoma and prolong survival in a human xenograft mouse model. More doses, higher dosage, alternative targeting antibodies, and copolymer optimization may all increase therapeutic efficacy. Intracellular delivery of BINDI, either of encoding nucleic acid or of the polypeptide, is expected to have therapeutic effects in Epstein-Barr related diseases generally. Quantitative analysis of mRNA expression has shown that different cancer lines overexpress different BCL2 family members. The designed proteins described herein can specifically inhibit BCL2 family members at the protein level, thereby demonstrating which BCL2 proteins are functionally important for preventing apoptosis in different cancers. This will lead to better tumor characterization and future diagnostics, in addition targeted therapies as described for BINDI delivery to EBV-positive cancer.

We demonstrate that the designed peptides targeting human pro-survival BCL2 proteins engage the BH3-binding grooves of only their specific target family members. The designs were used to determine the BCL2-dependence of different cancers, providing a more direct guide for therapy than knockdown/knockout strategies or mRNA analysis by mimicking the mechanism of action of BCL2-targeting small molecule drugs. While mRNA profiling suggests that Bfl-1 confers apoptotic resistance in SK-MEL-5 and LOX-IMVI melanomas (Hind et al., 2015), our combinatorial antagonism of pro-survival homologs indicates that Mcl-1 plays a more critical role and further discriminates between sensitive LOX-IMVI and resistant SK-MEL-5 We also provide further evidence that many colon cancers are generally dependent on Mcl-1 and Bcl-xL for survival; mRNA profiling indicates Mcl-1 and Bcl-xL are indeed more prevalent than other BCL2 homologs in many colon cancers, but resistant HCT-116 is indistinguishable from sensitive lines like Caco-2 and HT-29 (Placzek et al., 2010). Further, the detection of RKO sensitivity to Bfl-1 inhibition highlights the capacity of the designed inhibitors to determine unique BCL2-dependence profiles, even among cancers with similar general characteristics.

More generally, computationally designed inhibitors enable the investigation of the biological roles of specific protein interactions with the high spatio-temporal control that can be achieved with tissue-specific and inducible promoters. Competing approaches offer less control. The distribution of small molecules is difficult to spatially or temporally control in vivo, and broadly eliminating the protein of interest with CRISPR or RNAi cannot probe interactions with a specific interface or capture mechanistic intricacies. The designed peptide inhibitors presented here will thus provide a useful toolset for studying apoptotic regulation and dysfunction and treating associated pathologies.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

REFERENCES

Altmann, M., and Hammerschmidt, W. (2005). Epstein-Barr virus provides a new paradigm: a requirement for the immediate inhibition of apoptosis. PLoS Biol 3, e404.

Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. Nucleic Acids Res 25, 3389-3402.

Andersson, M., and Lindahl, T. (1976). Epstein-Barr virus DNA in human lymphoid cell lines: in vitro conversion. Virology 73, 96-105.

Azzarito, V., Long, K., Murphy, N. S., and Wilson, A. J. (2013). Inhibition of alpha-helix-mediated protein-protein interactions using designed molecules. Nat Chem 5, 161-173.

Carta, S., Chugh, S., Nhu, D., Lessene, G., and Kvansakul, M. (2012). Crystallization and preliminary X-ray characterization of Epstein-Barr virus BHRF1 in complex with benzoylurea peptidomimetic. Acta Crystallogr F Struct Biol Cryst Commun 1, 1521-1524.

Chao, G., Lau, W. L., Hackel, B. J., Sazinsky, S. L., Lippow, S. M., and Wittrup, K. D. (2006). Isolating and engineering human antibodies using yeast surface display. Nat Protoc 1, 755-768.

Chin, J. W., and Schepartz, A. (2001). Design and Evolution of a Miniature Bcl-2 Binding Protein. Angew Chem Int Ed Engl 40, 3806-3809.

Convertine, A. J., Diab, C., Prieve, M., Paschal, A., Hoffman, A. S., Johnson, P. H., and Stayton, P. S. (2010). pH-Responsive Polymeric Micelle Carriers for siRNA Drugs. Biomacromolecules.

Cooper, S., Khatib, F., Treuille, A., Barbero, J., Lee, J., Beenen, M., Leaver-Fay, A., Baker, D., Popovic, Z., and Players, F. (2010). Predicting protein structures with a multiplayer online game. Nature 466, 756-760.

Correia, B. E., Ban, Y. E., Holmes, M. A., Xu, H., Ellingson, K., Kraft, Z., Carrico, C., Boni, E., Sather, D. N., Zenobia, C., et al. (2010). Computational design of epitope-scaffolds allows induction of antibodies specific for a poorly immunogenic HIV vaccine epitope. Structure 18, 1116-1126.

Correia, B. E., Bates, J. T., Loomis, R. J., Baneyx, G., Carrico, C., Jardine, J. G., Rupert, P., Correnti, C., Kalyuzhniy, O., Vittal, V., et al. (2014). Proof of principle for epitope-focused vaccine design. Nature.

Czabotar, P. E., Lee, E. F., van Delft, M. F., Day, C. L., Smith, B. J., Huang, D. C., Fairlie, W. D., Hinds, M. G., and Colman, P. M. (2007). Structural insights into the degradation of Mcl-1 induced by BH3 domains. Proc Natl Acad Sci USA 104, 6217-6222.

Desbien, A. L., Kappler, J. W., and Marrack, P. (2009). The Epstein-Barr virus Bcl-2 homolog, BHRF1, blocks apoptosis by binding to a limited amount of Bim. Proc Natl Acad Sci USA 106, 5663-5668.

Dutta, S., Chen, T. S., and Keating, A. E. (2013). Peptide ligands for pro-survival protein Bfl-1 from computationally guided library screening. ACS Chem Biol 8, 778-788.

Dutta, S., Gulla, S., Chen, T. S., Fire, E., Grant, R. A., and Keating, A. E. (2010). Determinants of BH3 binding specificity for Mcl-1 versus Bcl-xL. J Mol Biol 398, 747-762.

Duvall, C. L., Convertine, A. J., Benoit, D. S., Hoffman, A. S., and Stayton, P. S. (2010). Intracellular delivery of a proapoptotic peptide via conjugation to a RAFT synthesized endosomolytic polymer. Mol Pharm 7, 468-476.

Flanagan, A. M., and Letai, A. (2008). BH3 domains define selective inhibitory interactions with BHRF-1 and KSHV BCL-2. Cell Death Differ 15, 580-588.

Fleishman, S. J., Leaver-Fay, A., Corn, J. E., Strauch, E. M., Khare, S. D., Koga, N., Ashworth, J., Murphy, P., Richter, F., Lemmon, G., et al. (2011a). RosettaScripts: a scripting language interface to the Rosetta macromolecular modeling suite. PLoS One 6, e20161.

Fleishman, S. J., Whitehead, T. A., Ekiert, D. C., Dreyfus, C., Corn, J. E., Strauch, E. M., Wilson, I. A., and Baker, D. (2011). Computational design of proteins targeting the conserved stem region of influenza hemagglutinin. Science 332, 816-821.

Fowler, D. M., Araya, C. L., Fleishman, S. J., Kellogg, E. H., Stephany, J. J., Baker, D., and Fields, S. (2010). High-resolution mapping of protein sequence-function relationships. Nat Methods 7, 741-746.

Fowler, D. M., Araya, C. L., Gerard, W., and Fields, S. (2011). Enrich: software for analysis of protein function by enrichment and depletion of variants. Bioinformatics 27, 3430-3431.

Gemperli, A. C., Rutledge, S. E., Maranda, A., and Schepartz, A. (2005). Paralog-selective ligands for bcl-2 proteins. J Am Chem Soc 127, 1596-1597.

Gront, D., Kulp, D. W., Vernon, R. M., Strauss, C. E., and Baker, D. (2011). Generalized fragment picking in Rosetta: design, protocols and applications. PLoS One 6, e23294.

Henderson, S., Huen, D., Rowe, M., Dawson, C., Johnson, G., and Rickinson, A. (1993). Epstein-Barr virus-coded BHRF1 protein, a viral homologue of Bcl-2, protects human B cells from programmed cell death. Proc Natl Acad Sci USA 90, 8479-8483.

Hind, C. K., Carter, M. J., Harris, C. L., Chan, H. T. C., James, S., and Cragg, M. S. (2015). Role of pro-survival molecule Bfl-1 in melanoma. Int J Biochem Cell B 59, 94-102.

Hoover, D. M., and Lubkowski, J. (2002). DNAWorks: an automated method for designing oligonucleotides for PCR-based gene synthesis. Nucleic Acids Res 30, e43.

Ishii, H. H., Etheridge, M. R., and Gobe, G. C. (1995). Cycloheximide-induced apoptosis in Burkitt lymphoma (BJA-B) cells with and without Epstein-Barr virus infection. Immunol Cell Biol 73, 463-468.

Jones, D. T. (1999). Protein secondary structure prediction based on position-specific scoring matrices. J Mol Biol 292, 195-202.

Leaver-Fay, A., Tyka, M., Lewis, S. M., Lange, O. F., Thompson, J., Jacak, R., Kaufman, K., Renfrew, P. D., Smith, C. A., Sheffler, W., et al. (2011). ROSETTA3: an object-oriented software suite for the simulation and design of macromolecules. Methods Enzymol 487, 545-574.

Kelly, G. L., Long, H. M., Stylianou, J., Thomas, W. A., Leese, A., Bell, A. I., Bornkamm, G. W., Mautner, J., Rickinson, A. B., and Rowe, M. (2009). An Epstein-Barr virus anti-apoptotic protein constitutively expressed in transformed cells and implicated in burkitt lymphomagenesis: the Wp/BHRF1 link. PLoS Pathog 5, e1000341.

Kelly, G. L., Stylianou, J., Rasaiyaah, J., Wei, W., Thomas, W., Croom-Carter, D., Kohler, C., Spang, R., Woodman, C., Kellam, P., et al. (2013). Different patterns of Epstein-Barr virus latency in endemic Burkitt lymphoma (BL)

lead to distinct variants within the BL-associated gene expression signature. J Virol 87, 2882-2894.

Koga, N., Tatsumi-Koga, R., Liu, G., Xiao, R., Acton, T. B., Montelione, G. T., and Baker, D. (2012). Principles for designing ideal protein structures. Nature 491, 222-227.

Kuhlman, B., Dantas, G., Ireton, G. C., Varani, G., Stoddard, B. L., and Baker, D. (2003). Design of a novel globular protein fold with atomic-level accuracy. Science 302, 1364-1368.

Kvansakul, M., Wei, A. H., Fletcher, J. I., Willis, S. N., Chen, L., Roberts, A. W., Huang, D. C., and Colman, P. M. (2010). Structural basis for apoptosis inhibition by Epstein-Barr virus BHRF1. PLoS Pathog 6, e1001236.

Lanci, C. J., MacDermaid, C. M., Kang, S. G., Acharya, R., North, B., Yang, X., Qiu, X. J., DeGrado, W. F., and Saven, J. G. (2012). Computational design of a protein crystal. Proc Natl Acad Sci USA 109, 7304-7309.

Leao, M., Anderton, E., Wade, M., Meekings, K., and Allday, M. J. (2007). Epstein-barr virus-induced resistance to drugs that activate the mitotic spindle assembly checkpoint in Burkitt's lymphoma cells. J Virol 81, 248-260.

Leaver-Fay, A., Tyka, M., Lewis, S. M., Lange, O. F., Thompson, J., Jacak, R., Kaufman, K., Renfrew, P. D., Smith, C. A., Sheffler, W., et al. (2011). ROSETTA3: an object-oriented software suite for the simulation and design of macromolecules. Methods Enzymol 487, 545-574.

Lessene, G., Czabotar, P. E., Sleebs, B. E., Zobel, K., Lowes, K. N., Adams, J. M., Baell, J. B., Colman, P. M., Deshayes, K., Fairbrother, W. J., et al. (2013). Structure-guided design of a selective BCL-X(L) inhibitor. Nat Chem Biol 9, 390-397.

Liu, X., Dai, S., Zhu, Y., Marrack, P., and Kappler, J. W. (2003). The structure of a Bcl-xL/Bim fragment complex: implications for Bim function. Immunity 19, 341-352.

Manganiello, M. J., Cheng, C., Convertine, A. J., Bryers, J. D., and Stayton, P. S. (2012). Diblock copolymers with tunable pH transitions for gene delivery. Biomaterials 33, 2301-2309.

Martinou, J. C., and Youle, R. J. (2011). Mitochondria in apoptosis: Bcl-2 family members and mitochondrial dynamics. Dev Cell 21, 92-101.

McLaughlin, R. N., Jr., Poelwijk, F. J., Raman, A., Gosal, W. S., and Ranganathan, R. (2012). The spatial architecture of protein function and adaptation. Nature 491, 138-142.

O'Connor, O. A., Smith, E. A., Toner, L. E., Teruya-Feldstein, J., Frankel, S., Rolfe, M., Wei, X., Liu, S., Marcucci, G., Chan, K. K., and Chanan-Khan, A. (2006). The combination of the proteasome inhibitor bortezomib and the bcl-2 antisense molecule oblimersen sensitizes human B-cell lymphomas to cyclophosphamide. Clin Cancer Res 12, 2902-2911.

Placzek, W. J., Wei, J., Kitada, S., Zhai, D., Reed, J. C., and Pellecchia, M. (2010). A survey of the anti-apoptotic Bcl-2 subfamily expression in cancer types provides a platform to predict the efficacy of Bcl-2 antagonists in cancer therapy. Cell Death and Disease 1, e40•e49.

Procko, E., Hedman, R., Hamilton, K., Seetharaman, J., Fleishman, S. J., Su, M., Aramini, J., Kornhaber, G., Hunt, J. F., Tong, L., et al. (2013). Computational Design of a Protein-Based Enzyme Inhibitor. J Mol Biol.

Sheffler, W., and Baker, D. (2009). RosettaHoles: rapid assessment of protein core packing for structure prediction, refinement, design, and validation. Protein Sci 18, 229-239.

Tse, C., Shoemaker, A. R., Adickes, J., Anderson, M. G., Chen, J., Jin, S., Johnson, E. F., Marsh, K. C., Mitten, M. J., Nimmer, P., et al. (2008). ABT-263: a potent and orally bioavailable Bcl-2 family inhibitor. Cancer Res 68, 3421-3428.

Watanabe, A., Maruo, S., Ito, T., Ito, M., Katsumura, K. R., and Takada, K. (2010). Epstein-Barr virus-encoded Bcl-2 homologue functions as a survival factor in Wp-restricted Burkitt lymphoma cell line P3HR-1. J Virol 84, 2893-2901.

Whitehead, T. A., Chevalier, A., Song, Y., Dreyfus, C., Fleishman, S. J., De Mattos, C., Myers, C. A., Kamisetty, H., Blair, P., Wilson, I. A., and Baker, D. (2012). Optimization of affinity, specificity and function of designed influenza inhibitors using deep sequencing. Nat Biotechnol 30, 543-548.

Young, L. S., and Murray, P. G. (2003). Epstein-Barr virus and oncogenesis: from latent genes to tumours. Oncogene 22, 5108-5121.

Figure 21:
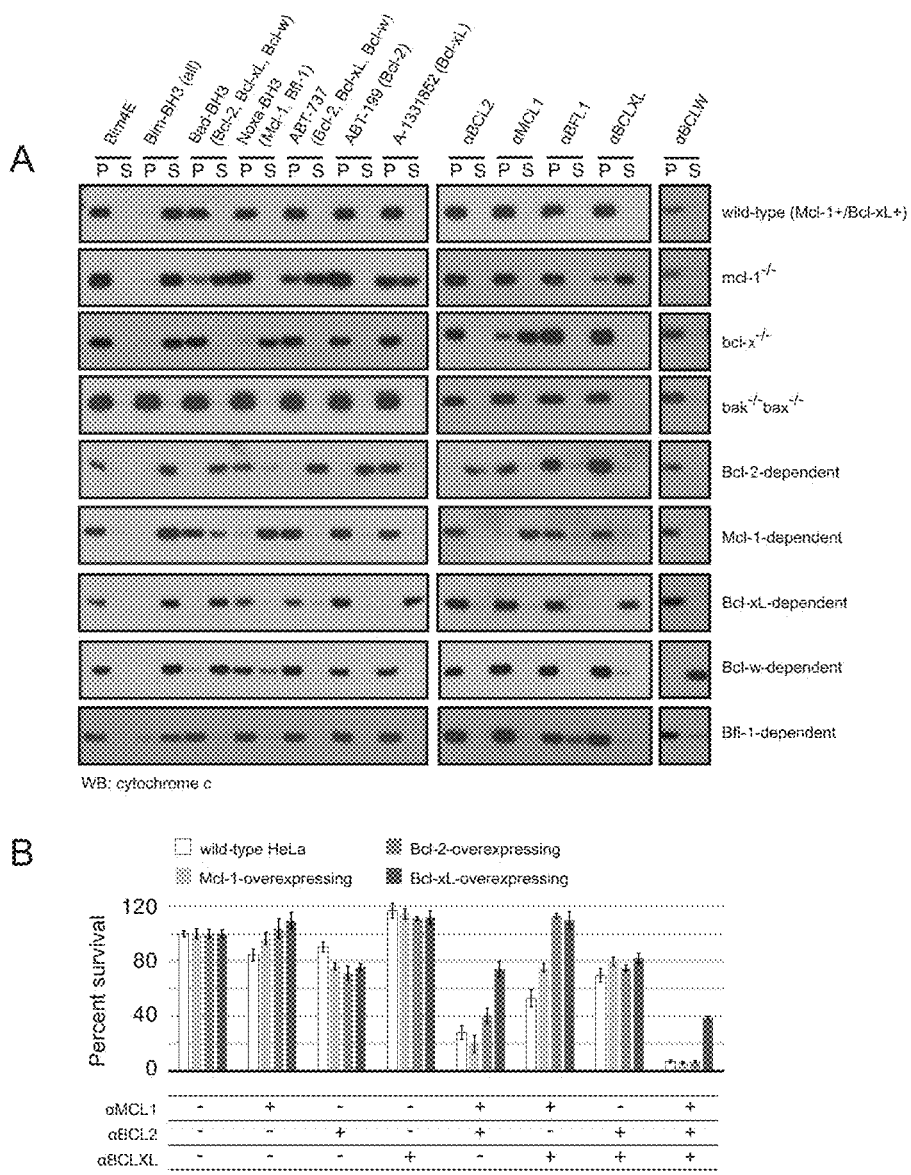
FIG. 21. Designed inhibitors induce apoptosis in vitro by engaging the BH3-binding grooves of specific pro-survival homologs. (A) Western blot for cytochrome c in pelleted (P) and soluble (S) fractions of engineered MEFs after permeabilization and treatment with 10 BCL2 inhibitors. Bim-BH3, which binds all pro-survival homologs, is a positive control. Bim-BH3 peptide with four mutations to glutamate at interface residues (Bim4E) is a negative control. BOPs Bad and Noxa, and small molecule drugs tested have the indicated binding specificities in parentheses. (B) HeLa cells were transduced with constructs for designed inhibitor expression, and viability was assayed after 72 hours (mean±SD; n=3).

Example 2. Validation of Binding Specificity and Mechanism in Engineered Cell Lines We investigated the BCL2 binding profiles and mechanism of action of the optimized inhibitors in mammalian cells, employing a suite of engineered mouse embryonic fibroblasts (MEFs). We first tested whether our inhibitors could selectively induce a hallmark of apoptosis by monitoring cytochrome c release from mitochondria into the cytosol of MEFs with engineered dependence on a single pro-survival BCL2 homolog. Strikingly, permeabilized MEFs treated with each designed inhibitor induced cytochrome c release only in the cell line dependent on the corresponding target BCL2 protein. No cytochrome c release was observed in $Bak^{-/-}Bax^{-/-}$ cells, confirming that mitochondrial outer membrane permeability following inhibitor treatment occurs specifically via the BCL2-regulated intrinsic pathway, as expected (FIG. 21A).

Figure 22:
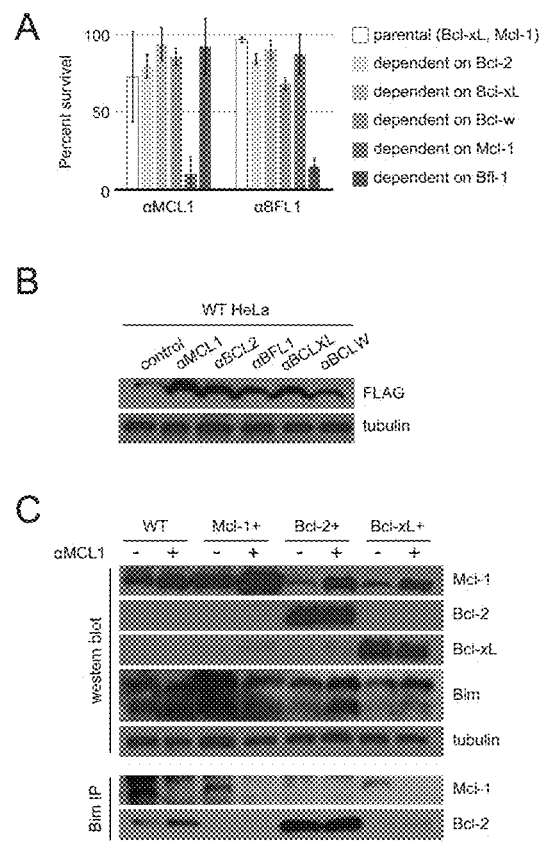
FIG. 22. Long-term MEF survival and HeLa co-immunoprecipitation studies. (A) Long-term survival of engineered MEFs (pro-survival protein dependence as indicated) was assayed by counting colonies after seven to ten days of doxycycline-induced expression of αMCL1 or αBFL1 (mean±SD, n=3). (B) Expression of FLAG-tagged designed inhibitors in transduced HeLa cells validated with Western blotting. (C) Bim coIP experiments in wild-type and engineered HeLa cells, with and without expression of αMCL1. Expression of αMCL1 caused a dramatic increase in the quantities of Mcl-1 protein present in all cell lines, consistent with previous studies showing increased Mcl-1 half-life in the presence of BH3-peptides (Lee et al., 2008). Bound αMCL1 may stabilize Mcl-1 or occlude Mule (Mcl-1 ubiquitin ligase E3), which binds and ubiquitinates Mcl-1 via a BH3 motif. Despite elevating Mcl-1 protein levels, αMCL1 expression potently induces apoptosis in the expected cell contexts (see FIG. 21A).

To further validate binding specificity we examined the effect of a subset of inhibitors (αMCL1 and αBFL1) on long-term (i.e. seven day) colony survival in MEFs engineered to inducibly express each inhibitor. Consistent with binding profiles and cytochrome c release data, large effects were only seen with αMCL1 in the Mcl-1-dependent line, causing a 90±11% decrease in survival, and with αBFL1 in the Bfl-1-dependent line, causing a 85±6% decrease in survival (FIG. 22A). Minimal effects on cell survival were observed in lines expressing non-cognate pro-survival proteins. These data validate the specificity of the designed proteins and their capacity to functionally engage BCL2 family members in a cellular milieu.

While engineered MEFs provided an excellent model system to study our designed proteins, we sought further mechanistic validation in a context relevant to their primary application: probing BCL2 family interactions and generating functional BCL2 dependency profiles in cancer. A representative cancer cell line (HeLa) was engineered to overexpress Mcl-1, Bcl-2 or Bcl-xL, and we assayed the activity of the designed inhibitors in each setting (FIG. 21B). Previous studies revealed that HeLa cells are resistant to expression of Noxa (which targets Mcl-1 and Bfl-1) and ABT-737 (Bcl-2 and Bcl-xL) independently, but are potently killed with the combination of Noxa with ABT-737 (van Delft et al., 2006). Likewise, single designed inhibitors had little effect on survival. However, the combination of αMCL1 with αBCL2 caused more substantial cell death (28±5% survival) than αMCL1 with αBCLXL (53±6%) and even more so than αBCL2 with αBCLXL (70±5%). These data, and similar results in Mcl-1-overexpressing (Mcl-1+) HeLa cells, suggest that Mcl-1 plays a more crucial role in wild-type HeLa survival than Bcl-2 or Bcl-xL, and Bcl-2 is a more important secondary target than Bcl-xL. Thus the designed inhibitors not only recapitulate the previous study's results, further validating their specificity and activity in vitro, but also offer improved sensitivity in delineating BCL2 dependencies.

Compared to wild-type and Mcl-1+HeLa cells, Bcl-xL-overexpressing (Bcl-xL+) cells are more resistant to the combination of αMCL1 with αBCL2, and likewise, Bcl-2-overexpressing (Bcl-2+) cells are more resistant to the combination of αMCL1 with αBCLXL. Thus, increased expression of a given BCL2 protein can compensate for the inhibition of others. The triple combination of αMCL1, αBCL2, and αBCLXL had greater efficacy than double combinations, indicating a contribution of each pro-survival protein to basal survival. Bcl-xL+ cells were generally more resistant than all other cell lines; the inability to completely inhibit Bcl-xL's survival function in Bcl-xL+ cells suggests that in this context, Bcl-xL may interact with proteins that are not displaced efficiently by αBCLXL.

To investigate potential mechanisms underlying these results, we assessed the binding profile of a representative BOP, Bim, to pro-survival homologs with co-immunoprecipitation (co-IP) experiments in wild-type and over-expressing cell lines, with and without added αMCL1 (FIG. 22C). In wild-type HeLa cells, Bim associated primarily with Mcl-1. Introduction of αMCL1 resulted in displacement of Bim from Mcl-1, with modest compensatory sequestration of Bim by Bcl-2. In Bcl-2+ cells, Bim is redistributed and preferentially binds Bcl-2 rather than Mcl-1, likely due to the stoichiometric excess of Bcl-2, and αMCL1 has no effect. The cell-killing activity of αMCL1 with αBCL2 in wild-type, Mcl-1+ and Bcl-2+ cells is consistent with these data; inhibition of both Mcl-1 and Bcl-2 in these settings likely overwhelms BOP sequestration, and a higher proportion of Bim and other activator BOPs may be free to interact with Bak and Bax, inducing apoptosis.

Designed Inhibitors Elucidate the Dependence of Human Cancer Cell Lines on Pro-Survival BCL2 Homologs Next, we set out to define functional BCL2 dependency profiles of other cancer cell lines using a larger set of our designed inhibitors. Apoptotic resistance in melanoma is thought to act via Bfl-1 (Hind et al., 2015), and likewise in glioblastoma via Bcl-2 (Weller et al., 1995) and Bcl-xL (Nagane et al., 2000). Further, oncogenic EGFR mutations in glioblastoma are associated with apoptotic resistance via increased Bcl-xL expression (Latha et al., 2012). Therefore, the selected melanoma and EGFR-modified series of glioblastoma cell lines provide diverse contexts to test the BCL2-profiling capacity of the designed proteins.

Figure 23:
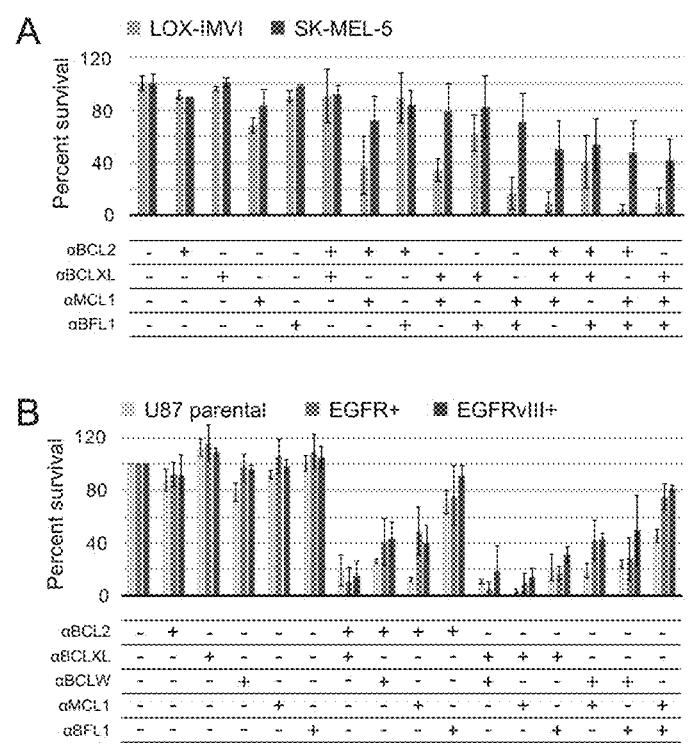
FIG. 23. Determination of functional BCL2 profiles in melanoma and glioblastoma cell lines. (A) Melanoma and (B) glioblastoma cell lines were transduced with constructs for designed inhibitor expression and viability was assayed after 72 hours (mean±SD; n=3).

In all cell lines, single inhibitors again were unable to induce apoptosis. While SK-MEL-5 were overall more resistant to apoptosis, LOX-IMVI melanoma cells were sensitive to double combinations that included αMCL1 and triple combinations (FIG. 23A). αBFL1 with αBCL2 or αBCLXL had less effect; thus, our results indicate that Mcl-1 plays a more critical role in survival than Bfl-1 in LOX-IMVI, in contrast to mRNA profiling suggesting the opposite (Hind et al., 2015). All glioblastoma cell lines showed similar trends in response to all combinations, while EGFR variants were in some instances more resistant than parental (FIG. 23B). Sensitivity to many different double combinations suggests that in these contexts, pro-survival homologs may resist apoptosis via "mode 1" interactions with the pan- or partially-specific BOPs (Llambi et al., 2011).

To more fully assess the capacity of the designed inhibitors to determine BCL2 profiles, we tested them alongside existing, selective BH3-mimetics in a larger number of cell lines from one type of cancer. Previously, colon cancers showed variable response to small-molecule-mediated Bcl-xL inhibition, and RNAi experiments identified Mcl-1 as a resistance factor (Zhang et al., 2015). To determine whether Mcl-1 antagonism could render colon cancers sensitive to Bcl-xL neutralization and assess the influence of other pro-survival homologs on survival, we modified a panel of seven colon cancer lines to inducibly express either αMCL1 or αBFL1, and treated them with small molecules to selectively inhibit Bcl-2 (ABT-199), Bcl-xL (A-1331852), or Bcl-2 and Bcl-xL simultaneously (ABT-263).

Figure 24:
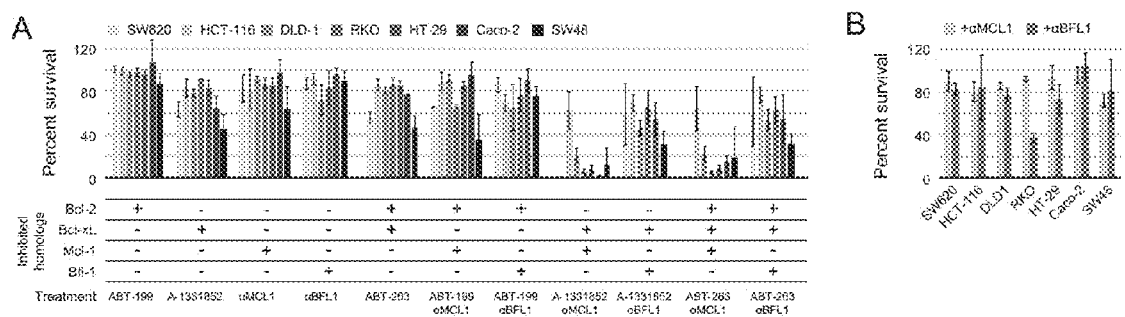
FIG. 24. Determination of functional BCL2 profiles in colon cancer cell lines. (A) Colon cancers were treated with small molecule drugs and/or doxycycline to induce expression of designed inhibitors, as indicated, and viability was assayed after 24 hours (mean±SD; n=3). (B) Long-term survival was assessed after expression of αMCL1 (mean±SD; n=3) or αBFL1 (mean±SD; n=3 for Bfl-1-dependent cell line, n=2 for all others).
Figure 25:
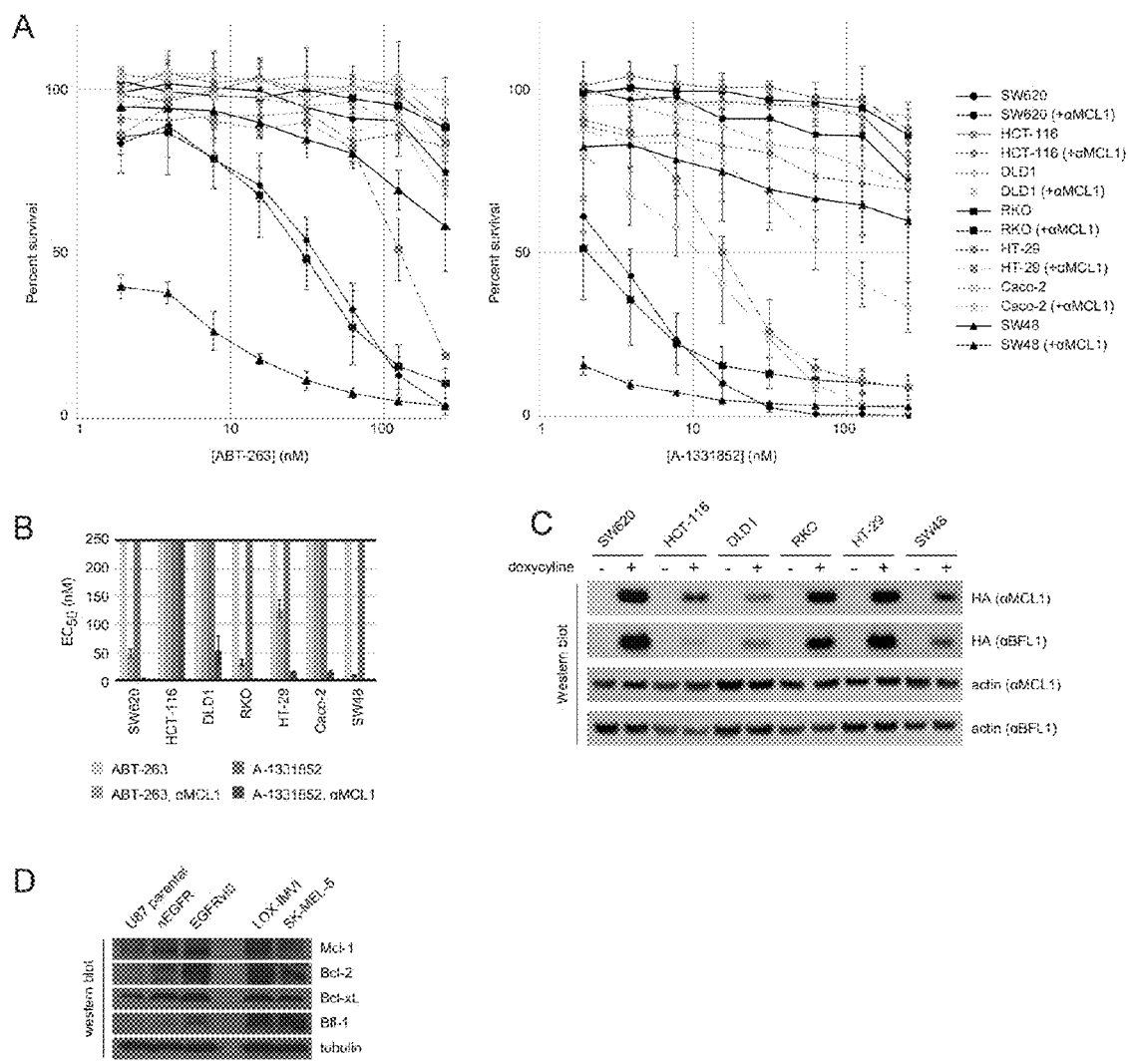
FIG. 25. Drug titration assays in colon cancers. (A) Drug titrations for $EC_{50}$ determination of ABT-263 and A-1331852 in colon cancer lines, with (dotted lines) and without (solid lines) expression of αMCL1 (mean±SD, n=3). (B) EC50 values were determined from titration data using linear regression. (C) Western blotting confirms expression of HA-tagged αMCL1 and αBFL1 in transformed cell lines (actin loading control). (D) Western blotting assays expression of pro-survival proteins in glioblastoma and melanoma cell lines.

Inhibiting a single pro-survival homolog had little effect on short-term survival; only SW48 cells showed greater than a 50% decrease in viability after treatment with A-1331852, consistent with the previous study showing SW48 is sensitive to Bcl-xL inhibition (Zhang et al., 2015; FIG. 24A). Combined inhibition of both Mcl-1 and Bcl-xL caused nearly complete cell death after 24 hours in all colon cancers except HCT-116; further analyses showed that αMCL1-mediated Mcl-1 inhibition strongly sensitizes most colon cancers to A-1331852 (and to a lesser extent ABT-263), with a 4.6-fold or greater decrease in $EC_{50}$ values observed in all cell lines except HCT-116 (FIG. 25A-B). All other combinations had much smaller effects. Thus, inhibition of two pro-survival proteins was required and sufficient for cell killing, contrasting glioblastoma in which pro-survival proteins appeared largely redundant. These results suggest that in context of colon cancer, pro-survival proteins may resist apoptosis primarily via "mode 2" inhibition of the direct effector Bak, which interacts preferentially with Mcl-1 and Bcl-xL (Llambi et al., 2011). As αMCL1 targets Mcl-1 in a manner more akin to a drug (i.e. antagonism) compared to RNAi, our data provide further evidence that treatment strategies involving Mcl-1 and Bcl-xL inhibition could be effective in these malignancies.

In long-term survival assays, αMCL1 had negligible effect, but remarkably, αBFL1 caused a significant (63±4%) decrease in RKO cell survival (FIG. 24B). Thus, long-term assays detect sensitivities that short-term assays miss, on a timescale that may provide a more informative preview of therapy. Overall, these data show the utility and sensitivity of the inhibitors in establishing the critical survival factors in colon cancer.

We claim:

1. A polypeptide comprising an amino acid sequence having at least 50% amino acid sequence identity over its length relative to the amino acid sequence of SEQ ID NO. 1, wherein the polypeptide selectively binds to a protein selected from the group consisting of Epstein Barr protein BHFR1, and B cell lymphoma family proteins selected from the group consisting of myeloid cell leukemia 1 (Mcl-1), B-cell lymphoma 2 (Bcl-2), Bcl-2-like protein 1 (BCL2L1/Bcl-XL), Bcl-2-like protein 10 (BCL2L10/Bcl-B), Bcl-2-like protein A1 (A1/Bfl-1), and Bcl-w.

2. The polypeptide of claim 1, comprising an amino acid sequence having at least 66% identity over its length relative to the amino acid sequence of SEQ ID NO. 1.

3. The polypeptide of claim 1, wherein the polypeptide comprises an amino acid sequence having at least 50% amino acid sequence identity over its length relative to the amino acid sequence selected from the group consisting of SEQ ID NOS:2-6 and 265.

4. The polypeptide of claim 3, wherein the polypeptide comprises an amino acid sequence having at least 66% amino acid sequence identity over its length relative to the amino acid sequence selected from the group.

5. The polypeptide of claim 1, wherein the polypeptide is selected from the group consisting of:
   (a) a polypeptide that comprises an amino acid sequence according to SEQ ID NO: 7, wherein the polypeptide binds to BHFR1;
   (b) a polypeptide that comprises an amino acid sequence according to SEQ ID NO: 8, wherein the polypeptide binds to Bcl-2;
   (c) a polypeptide that comprises an amino acid sequence according to SEQ ID NO:9, wherein the polypeptide binds to binds to Bcl-2-like protein 1 (BCL2L1/Bcl-xL);
   (d) a polypeptide that comprises an amino acid sequence according to SEQ ID NO: 10, wherein the polypeptide binds to Bcl-2-like protein 10 (BCL2L10/Bcl-B);
   (e) a polypeptide that comprises an amino acid sequence according to SEQ ID NO: 11, wherein the polypeptide binds to Bcl-2-like protein A1 (A1/Bfl-1);
   (f) a polypeptide that comprises an amino acid sequence according to SEQ ID NO: 12, wherein the polypeptide binds to Bcl-2-like protein Mcl-1;
   (g) a polypeptide that comprises an amino acid sequence according to SEQ ID NO: 276, wherein the polypeptide binds to Bcl-2-like protein 2 (BCL2L2/Bcl-w).

6. The polypeptide of claim 1, wherein the polypeptide comprises the amino acid sequence selected from the group consisting of SEQ ID NOS: 1-6 and 262-273.

7. The polypeptide of claim 1, wherein the polypeptide comprises an amino acid sequence having at least 50% identity over its length relative to the amino acid sequence of SEQ ID NO:13.

8. The polypeptide of claim 7, comprising at least one conservative substitution corresponding to residues 3, 13, 21, 28, 31, 33, 46, 48, 49, 61, 62, 65, 79, 84, 103, and 104 of the amino acid sequence of SEQ ID NO: 13.

9. The polypeptide of claim 8, comprising the substitutions K31E, E48R, and E65R.

10. The polypeptide of claim 9, further comprising the substitutions I21L, Q79L, L84Q, and H104R.

11. The polypeptide of claim 1, further comprising a cell-penetrating peptide.

12. A pharmaceutical composition, comprising the polypeptide of claim 1 and a pharmaceutically acceptable carrier.

13. The pharmaceutical composition of claim 12 further comprising an antibody.

14. The pharmaceutical composition of claim 12, wherein the carrier comprises a polymer.

15. The pharmaceutical composition of claim 14, wherein the polymer comprises a hydrophilic block and an endosomolytic block.

16. The pharmaceutical composition of claim 15, wherein the hydrophilic block comprises polyethylene glycol methacrylate, and wherein the endosomolytic block comprises a diethylaminoethyl methacrylate-butyl methacrylate copolymer.

17. The pharmaceutical composition of claim 14, wherein the polymer is a stimuli-responsive polymer that responds to one or more stimuli selected from the group consisting of pH, temperature, UV-visible light, photo-irradiation, exposure to an electric field, ionic strength, and the concentration of certain chemicals by exhibiting a property change.

18. A recombinant nucleic acid encoding the polypeptide of claim 1.

19. A recombinant expression vector comprising the nucleic acid of claim 18 operatively linked to a promoter.

20. A recombinant host cell comprising the recombinant expression vector of claim 19.

21. A method of treating an Epstein-Barr virus-related disease comprising administering to a subject in need thereof a therapeutically effective amount of one or more of the polypeptide of claim 1, or salts thereof, pharmaceutical compositions thereof, a recombinant nucleic acid encoding the one or more polypeptide, a recombinant expression vector comprising the recombinant nucleic acids, and/or a recombinant host cells comprising the recombinant expression vector, to treat and/or limit Epstein-Barr virus related diseases wherein the polypeptide or encoded polypeptide selectively inhibits BHRF 1.

22. A method for treating cancer, comprising administering to a subject in need thereof a therapeutically effective amount of one or more of the polypeptide of claim 1, or salts thereof, to treat cancer, wherein the or encoded polypeptide selectively inhibits one or more of Mcl-1, Bcl-2, BCL2L1/Bcl-XL, BCL2L10/Bci-B, A1/Bfl-1, and Bci-w.

23. A method for determining the Bcl-2 phenotype of a tumor, comprising contacting tumor cells, tumor cell lysates or tumor cellular components with one or more polypeptides selected from the group consisting of SEQ ID NOS: 1-6, 8-12, 262-273 and 276, under conditions suitable to promote apoptosis signaling in cells of the tumor that express a bcl-2 homologue targeted by the one or more polypeptides; and determining BCL2 dependency of the tumor based on the polypeptide.

* * * * *